US012674181B2

(12) United States Patent
Daigle et al.

(10) Patent No.: US 12,674,181 B2
(45) Date of Patent: Jul. 7, 2026

(54) ARTIFICIAL EXPRESSION CONSTRUCTS FOR MODULATING GENE EXPRESSION IN CHANDELIER CELLS

(71) Applicant: Allen Institute, Seattle, WA (US)

(72) Inventors: Tanya Daigle, Seattle, WA (US); Lucas T. Graybuck, Seattle, WA (US); Brian Edward Kalmbach, Poulsbo, WA (US); Edward Sebastian Lein, Seattle, WA (US); John K. Mich, Seattle, WA (US); Boaz P. Levi, Seattle, WA (US); Adriana Estela Sedeño Cortés, Seattle, WA (US); Bosiljka Tasic, Seattle, WA (US); Jonathan Ting, Seattle, WA (US); Hongkui Zeng, Seattle, WA (US)

(73) Assignee: Allen Institute, Seattle, WA (US)

( * ) Notice: Subject to any disclaimer, the term of this patent is extended or adjusted under 35 U.S.C. 154(b) by 497 days.

(21) Appl. No.: 18/252,498

(22) PCT Filed: Nov. 10, 2021

(86) PCT No.: PCT/US2021/058812
§ 371 (c)(1),
(2) Date: May 10, 2023

(87) PCT Pub. No.: WO2022/103859
PCT Pub. Date: May 19, 2022

(65) Prior Publication Data
US 2024/0018543 A1      Jan. 18, 2024

Related U.S. Application Data

(60) Provisional application No. 63/112,102, filed on Nov. 10, 2020.

(51) Int. Cl.
*C12N 15/86*          (2006.01)

(52) U.S. Cl.
CPC .... *C12N 15/86* (2013.01); *C12N 2750/14143* (2013.01); *C12N 2750/14171* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 5,399,363 A | 3/1995 | Liversidge et al. | |
| 5,543,158 A | 8/1996 | Gref et al. | |
| 5,614,515 A | 3/1997 | Rodgers et al. | |

FOREIGN PATENT DOCUMENTS

| | | | | |
|---|---|---|---|---|
| WO | WO2012087983 A1 | 6/2012 | | |
| WO | WO-2020097121 A1 * | 5/2020 | ......... | A01K 67/0275 |
| WO | WO2020168279 A2 | 8/2020 | | |

OTHER PUBLICATIONS

Howard, et al., "Lighting the chandelier: new vistas for axo-axonic cells", Trends in Neurosciences, vol. 28, No. 6, Jun. 1, 2005, pp. 310-316.

Mich, et al., "Functional enhancer elelments drive subclass-selective expression from mouse to primate neocortex", retrieved on Nov. 10, 2024 at <<http://doi.org/10.1101/555318>>, bioRxiv, Apr. 21, 2020, pp. 1-43.

Search Report for European Application No. 21892744.0, Dated Nov. 21, 2024, 7 pages.

Daigle, et al., "A Suite of Transgenic Driver and Reporter Mouse Lines with Enhanced Brain-Cell-Type Targeting and Functionality," Cell, vol. 174, No. 2, 2018, pp. 465-480.

Fiskerstrand, et al., "An intronic polymorphic domain often associated with susceptibility to affective disorders has allele dependent differential enhancer activity in embryonic stem cells," FEBS Lett., vol. 458, No. 2, 1999, pp. 171-174.

Gong, et al., "Targeting Cre recombinase to specific neuron populations with bacterial artificial chromosome constructs," J. Neurosci., vol. 27, No. 37, 2007, pp. 9817-9823.

Hodge, et al., "Conserved cell types with divergent features in human versus mouse cortex," Nature., vol. 573, No. 7772, 2019, pp. 61-68.

MacKenzie and Quinn, "A serotonin transporter gene intron 2 polymorphic region, correlated with affective disorders, has allele-dependent differential enhancer-like properties in the mouse embryo," PNAS USA, vol. 96, No. 26, 1999, pp. 15251-152515.

Taniguchi, et al., "A resource of Cre driver lines for genetic targeting of GABAergic neurons in cerebral cortex," Neuron, vol. 71, No. 6, 2011, pp. 995-1013.

Tasic, Bosiljka, "Single cell transcriptomics in neuroscience: cell classification and beyond," Curr. Opin. Neurobiol, vol. 50, 2018, pp. 242-249.

Tasic, et al., "Shared and distinct transcriptomic cell types across neocortical areas," Nature, vol. 563, No. 7729, 2018, pp. 72-78.

Wang, et al., "Chandelier Cells in Functional and Dysfunctional Neural Circuits," Front Neural Circuits, vol. 10, No. 33, 2016, 8 pages.

Zeng and Sanes, "Neuronal cell-type classification: challenges, opportunities and the path forward," Nat. Rev. Neurosci., vol. 18, No. 9, 2017, pp. 530-546.

Choi, et al., "Optimization of AAV expression cassettes to improve packaging capacity and transgene expression on neurons", Molecular brain, vol. 7, No. 17, 2014, 10 pages.

GenBank submission AC123673.8, May 23, 2006, retrieved from <<https://cipweb.cardinal-ip.com/pctsrs/PCTSRS_DATA/PCT-US% 2021-58812/20220311_075435_PCT-US21-58812-6RGE.TXT> 5 pages.

(Continued)

*Primary Examiner* — Anna Skibinsky
*Assistant Examiner* — Catherine L McCormick
(74) *Attorney, Agent, or Firm* — C. Rachal Winger; Chrystal Quisenberry; Lee & Hayes PC

(57)          ABSTRACT

Artificial expression constructs for modulating gene expression in targeted central nervous system cell types are described. The artificial expression constructs can be used to express synthetic genes or modify gene expression in chandelier cells. Chandelier cells are a subtype of GABAergic interneurons that that have been implicated in disorders such as epilepsy and schizophrenia.

12 Claims, 71 Drawing Sheets

Specification includes a Sequence Listing.

(56)          References Cited

OTHER PUBLICATIONS

GenBank submission FR242253/c, Sep. 12, 2009, retrieved from <<https://www.ncbi.nim.nih.gov/nuccore/258063011>, 2 pages.
Invitation to Pay Additional Fees Dated Jan. 24, 2033 for International Application No. PCT/US2021/058812, 2 pages.
Search Report and Written Opinion Dated Mar. 30, 2022 for International Application No. PCT/US2021/058812, 16 pages.

* cited by examiner

CN2320 labeled cells from mouse VISp mapping to the mouse VISp cell type taxonomy CN2320 labeled cells from macaque frontal cortex with mapping to the human middle temporal cortex cell type taxonomy Mapping score 100/100 to the
chandelier cluster (Inh L2–5 PVALB SCUBE3)

20 mV
250 ms

20 µm

FIG. 14 eHGT_297m (907 bp):
ACTATTCCAGCCACGAGGTATAAACACTGGGAAGGAAAGTCCTGGCTCTGTATTGTCCACA
AAGACCCGAAGCTGCAGCAAAGTTGGCAAAAGAGAAACAAAAAGAGCAGAGAAGGCTCAG
CTTTCAACAGCTAGGCTCACCCAAACATCAAGAGGTGGACAAATATTTACAGTGTGAACCT
TAACCCAAAGAACGGCAGTGCGGTCATGCTGCACAGAGTCAACTTCAGAACCAAGACTGT
GACCAGGGCTGGAGCAAGAGACACTTCACGCTAATAAATAGGCCACTTAATCAAGAAGCT
GTCACAGTCCTAAATATGTATGCACCGAGCATTAGCACTTCCAAGTAGAGTGGAACAGCTA
AAGATAGAGGCAAGAAGCAAGCAGACAAATCTTCGGTGATTGTTGGAAATCACAGCATTTC
TCTCAGCAATTGTCAGGACACAGAAAATCAGCGAGAAGACAGAAGAGTCTCACAATAGTCC
CCATCAACTTGACCTAATTGACATTTATGGAGCTTGGCATCCAACAGCCGTGGAGCGCATG
CGCTCTTTAAGGCAGAATACAGACCATCAAACAAAACCAGGGAGACCAAAGTCACAGAAAA
TATGCTCTGTGAACATGACATAATAAAGTGGAAATCGATAACAGAGAGATCGCTGCAAAAT
CCCCCAAGTGATTGGTAATTAAATGCTCTACTCCTGAATGAATGATGGGCGAGAAGGAAA
GCCACGGGGGAAAGCAGATTTCTGCGTTGAAAGAGCATGGAGACAGACTTCGTCAAGATG
AGAGAGCACGTGGGGCTGGAGGGATGGCTCAGCACTTCAGAGGCACTCACGCTCTTCCAT
AGGACCTAGGTTCACTTCTCAGCACACACATGGCAACTCACACCTGTGATGCAGAGAA
(SEQ ID NO: 1)

eHGT_303m (392 bp):
TCCTTCTCAGAACCTAGGTAAGGTAAGTTCCTTTCAAGGCTGGCTATATAAATAATCATCTC
AGTTAGGATGCTTGGTGGGACCAAAGAACCAAAACTGCCGAGCAGGCATGATCTGACTTG
GAGTGGTTCCAGGACCTTCCTGTGAATGCTGGAGTCATTCAGTGTAGAGCTCTCCTCTGTG
ACTGGGTCAAGGTTGCCCCACTGTAAACCCAGGGAAGCTAGCCCAGCCTTCCTCTCAGGG
AATGTGTATGCTTCCCTTACACCTGACCCTGGCACAGACCTGGTGGTTGTTTTTCAGAAGC
ATCAGTGTCTTTGCCTTAGGCATTTGTCCTCAAAGGGCAGCGACACTGTCTACTGACTGCT
TTGTACAGGGTAACTGCTTAACTAATT (SEQ ID NO: 2)

eHGT_307m (339 bp):
AAATGGAGACTGCCAAGGGCTGAAACGGGGTGCGGGAACCAGGGACCGAGCCCCCCCCC
TCCCCACATGAGAATCTGTCACATTGCTGCTCCAGTGGCCTGAAAGACCAGCACAGCCCC
AGCTGGAGCCTCTCCCCTCTGGATCTTGTCAATGTGGCTTTGCTTTGCTGCTTGGGCAGCC
GGGAGTGGTGACAAGCAGGGAGAGAGCGCCCAAGGCATCTGGCTGTGCCACTCCAGCCT
GACTGCCAGCTCACCCATCAGTGCCCATCTCATCATCGAGAGGGACCCAGATGAGACCGG
GGATCAGCACTGTCCTTACCTTGAAGGGACGTGTCAGGAA (SEQ ID NO: 3)

eHGT_308m (408 bp):
TCTGCTTTCTCTTCCCTTGGCCTCCTGCTGGGATAGAAGGGGTTGGTGTGAGTGTGTATGG
TGGGGTGCTGTGAGATTAATTAGCAGCCGTGCCAGGCAGCAGGCGGTGGGGTGCAGAGT
AGGCTGGCTTTCCCTGCTATAGATCCATGCTCTCTGGGAGAGGCACTAGCCGGCTGCTTT
GGGCTCTGGCTCAGCTATTTTAGGAATATTCTTAACCCTTCCAGAACCGCTGCCATTGCCA
GATCTCTCTCCCAGAACACAGGCCAGCTCCAGATTGCCCCTCCTTTCTGCCCCCGCCCTG
CACCCCACCTAGCCTCTGCTCTTCCTCCCTACAAGTTGAGAAGGTCAAGGTTTGACTTTTA
CCAAAGAAACTCCTGGCTCCTGATCCCACTCTCTGTGCTTTACCT (SEQ ID NO: 4)

eHGT_472m (713 bp):
GGGATGCGATGCAGTGGCATGGTAAAAATGCCGTACCTAATGATGCAGTTTCAGCCATCAT
GACGTATGGATGGAATGAAAAGATGACAAAGCTACTAGCGGATCTGTTCACAAAGGAAAAG
AGGCTCAGTTTCCAACAGTCTCTGGCATTTCATCTTTGGAAAACTTGTCAAAGCTAAGATGA
TTTGTGAGAGTCCTAACTCATTTTCCTAAATATGAAGTCGCTATTATGGATAAAGAAAGGTT

FIG. 14 cont'd

ACAATGGAGCATCCATTTCCACTCTAGTCATTCTGCTTGATTGCACCAATTAGCCCTGCATT
CACTGTGCATTTTAACTTCATAATGGTCTATTATTTGGACCACTGACCATAATGATGCAATTC
TTTCCTTGACGAAAATAAATGCTTAGTGATAAATAAGTAATCATAATTAAAGCTTTCATAGTA
CTTATAGTACCACAATTGGTATTTAGCCCATTGATTATAATTTAAACACATTTTAATTAATATG
TAACTATATTACTTCCCTATTTTTCTTTTCTTTCCTCCAAAATGCCTCATGTCTCCTTCTATCA
ACACCCCCATACCCCCCAGACACTCCTTGTCAAATTGATGGCCTTTTAAAATTATTATTAT
TGTAACATGAAGAAATAGTTGAACAAATATATAAATACAGTACAATGAGTCTGTTTATGGTG
GCTCCTATGGGTATGATTTGGGGGCCT (SEQ ID NO: 5)

eHGT_475m (627 bp):
TATCTTAGAGTGGGAAGATTTGAGAAGTGCCATGGTTAATATGACTGACTTTTTATTCTTATT
TCTTTTAATTTCATGGTTCTAAATCCGAATTTAATCATAGTACCCAGAAAAGCAGAGGTGTA
GAGGTTCACAGTGGGAGTTGTAATCTAGCCCTATTCATTTTGACCTCAAAACCCAAATTATT
TATAACAAATTATTTCCTATTCTTTCCTTCACTATTCAGGAACATCTGTCCACCACTTACATG
ATCACTTATCTTGCTATTGTGTCATTTTGATGAAAAGAATTTTTTCTAAATATCTAAATACAA
GGCCCCATATTAACAGTGCTTTTTAAATCCCCACAGATGTGGGAGATGACCCCTTTCCATC
CCTGAAGATTGTAATTGGGCCAGTCTTTAGTACAGTTTGTTCCAATAAAGAGATACAATTTT
ATTCATTAATTTGTGTATTCATTTAGCAAATCACTTTAGAGTCTTATTATATCAGGATTTTGG
GGTCTATTTTAGTATATCTTTTTGTATTCTTGGAACCTCTCCAATTATTCTAGACTCTTTCAA
AGGTTGGTGATCAATATTAGACATTATTATGAAAAGAATCTTACTTGCTAAAGGGTTAGAT
G (SEQ ID NO: 6)

eHGT_476m (486 bp):
TATGATGTGCCAGGCTTGGGAGAAACACCACAAGCAAAGCCAAAATAGGTGGCCTAGAAC
TTCCAGCTTGAAATATGGGAGAGAATGAGGGAGGCACTGTAGAGCAGCTGCCGGGTGCC
GCATGAGAACAATTCTCCCTGCTCATAATTAATCCTACCTATTTCTGATGACAGCTGGCTCT
TCACTTTGAACAAGCTAGTTAACAACTTTCTTCTCACATTGAGCAAATAATTCATATTTAATT
ACTTAACCACCAGTTACAAAATGAGAATCATCAAGGAATCACAATTAATTTGCTATTGACAA
ACTCATACTTTTAGCAGGCTGATTTCTACTTTATACTTAGATTGGTAATGAAAAATGAAGCTT
ATTTTAGTTGATTGGTTGGACTTGTGTATGAATATTATCTATTATTTGAAAAGCCAAACTTGA
ATGCAAAAAAATATTGAATATGAAAAGAAAAACATTTGCAGTAAAGCTTGTTCT (SEQ ID NO:
7)

eHGT_476m core (439 bp):
AGAAACACCACAAGCAAAGCCAAAATAGGTGGCCTAGAACTTCCAGCTTGAAATATGGGAG
AGAATGAGGGAGGCACTGTAGAGCAGCTGCCGGGTGCCGCATGAGAACAATTCTCCCTGC
TCATAATTAATCCTACCTATTTCTGATGACAGCTGGCTCTTCACTTTGAACAAGCTAGTTAAC
AACTTTCTTCTCACATTGAGCAAATAATTCATATTTAATTACTTAACCACCAGTTACAAAATG
AGAATCATCAAGGAATCACAATTAATTTGCTATTGACAAACTCATACTTTTAGCAGGCTGATT
TCTACTTTATACTTAGATTGGTAATGAAAAATGAAGCTTATTTTAGTTGATTGGTTGGACTTG
TGTATGAATATTATCTATTATTTGAAAAGCCAAACTTGAATGCAAAAAAATATTGAATATGAA
AAG (SEQ ID NO: 8)

3x_eHGT_476m core (1317 bp):
AGAAACACCACAAGCAAAGCCAAAATAGGTGGCCTAGAACTTCCAGCTTGAAATATGGGAG
AGAATGAGGGAGGCACTGTAGAGCAGCTGCCGGGTGCCGCATGAGAACAATTCTCCCTGC
TCATAATTAATCCTACCTATTTCTGATGACAGCTGGCTCTTCACTTTGAACAAGCTAGTTAAC
AACTTTCTTCTCACATTGAGCAAATAATTCATATTTAATTACTTAACCACCAGTTACAAAATG

FIG. 14 cont'd

AGAATCATCAAGGAATCACAATTAATTTGCTATTGACAAACTCATACTTTTAGCAGGCTGATT
TCTACTTTATACTTAGATTGGTAATGAAAAATGAAGCTTATTTTAGTTGATTGGTTGGACTTG
TGTATGAATATTATCTATTATTTGAAAAGCCAAACTTGAATGCAAAAAAATATTGAATATGAA
AAGAGAAACACCACAAGCAAAGCCAAAATAGGTGGCCTAGAACTTCCAGCTTGAAATATGG
GAGAGAATGAGGGAGGCACTGTAGAGCAGCTGCCGGGTGCCGCATGAGAACAATTCTCC
CTGCTCATAATTAATCCTACCTATTTCTGATGACAGCTGGCTCTTCACTTTGAACAAGCTAG
TTAACAACTTTCTTCTCACATTGAGCAAATAATTCATATTTAATTACTTAACCACCAGTTACAA
AATGAGAATCATCAAGGAATCACAATTAATTTGCTATTGACAAACTCATACTTTTAGCAGGC
TGATTTCTACTTTATACTTAGATTGGTAATGAAAAATGAAGCTTATTTTAGTTGATTGGTTGG
ACTTGTGTATGAATATTATCTATTATTTGAAAAGCCAAACTTGAATGCAAAAAAATATTGAAT
ATGAAAAGAGAAACACCACAAGCAAAGCCAAAATAGGTGGCCTAGAACTTCCAGCTTGAAA
TATGGGAGAGAATGAGGGAGGCACTGTAGAGCAGCTGCCGGGTGCCGCATGAGAACAAT
TCTCCCTGCTCATAATTAATCCTACCTATTTCTGATGACAGCTGGCTCTTCACTTTGAACAA
GCTAGTTAACAACTTTCTTCTCACATTGAGCAAATAATTCATATTTAATTACTTAACCACCAG
TTACAAAATGAGAATCATCAAGGAATCACAATTAATTTGCTATTGACAAACTCATACTTTTAG
CAGGCTGATTTCTACTTTATACTTAGATTGGTAATGAAAAATGAAGCTTATTTTAGTTGATTG
GTTGGACTTGTGTATGAATATTATCTATTATTTGAAAAGCCAAACTTGAATGCAAAAAAATAT
TGAATATGAAAAG (SEQ ID NO: 9)

eHGT_503m (988 bp):
AAAGCTACATCTCTGGGCTCCATTATTAAAGCTGCTTTCCTTCCTTTCTCTCTCTCGCTC
TCTCTCTCTCTCTCTTTCTTTCTTTCTTTTTCCTGAGATGGGTCTCATGTAGCCCAGGCTGG
CCTCAAGCTTGCCACATAGCCAAGGAGCCAAGGATGGCATTGAACTCCTAGATCCTCCAG
CCTCTGCCTCCTGTTAGGATTAGAGGTGAGCTACAATCCCAAGGGCCTTTAGTGTAACAGT
CAAAAGCTACTGGGAGTCAGGCAATTGGCTCAGTATAACCCTGATTCTCCTTTTGTGCCCA
GGCACGTTGGTCAGGAGTCTGTCTTCAGCCTGTCATGGCAGCAGCTCAGCTTCAGTGACC
AATCTATACTCACTCACAGGAGACTCTGAAATCCCAGATTCTGTGCTATAAAGTCCCCGCTC
GAGTGAGTCGTGACTGCTCCAAACAGCCTGGGCAGCTGCGAACCCTCATGGCATCTAGGT
GACCCTGTTCATCCTACAGCTGTTCTCACTGAGGGGAGGGGAGCTTTTGAGTGAGCCAGT
CAAAACTCTGTGCTCGGTGATCCTGTGAGGCTCGGAACGGTGGCACCCGAAGCCATGGGT
GCACACACAAACAGGGCTCTAATCGGTGGGATCACAATCCATGAACAAGCATGAGACCTC
CCTTCTTCTCACACACACACACACACACACACACACACACACTCACTCACATACATGAG
CTGGTTTCCACAACTGTGGGGTTAGCCTGGAAGGTGTCTGTCCTATATAGTACTCCAGTAC
CAGTGTTGCAGACTCTAGGCCCAGGAAAAGGTTTTTGATGTTTGCTGGTGTTTTTGATGAC
CTTCATCGTGGGTAGAGCAGGCTGCGCTGGTTCATAAAGAGAAGACAAGACCTAGAGTGC
TGTGACCCTTTAAGGCATCATGGTGTGATGACCCCCAACCATAAAGTTATTTTCGCTGCTG
CTTTGTAACTGTAAGT (SEQ ID NO: 10)

eHGT_571m (428 bp):
TGAATCTTCATGGAGAAACATCATGAATAGAGAATGAAGAAGTAAAGATGAACAAGTGAG
AATTCAGATCATCAGAGGGTTTTCTAGGATTTCTGTAAATTTCTCTGTGTTTTGGAATGCAAT
AGGAATGCCAGCCCAAAGCCATATAGGTCACAGCTGCCCAAGAACAGTTACCAATACAGTA
TAAATAACGTCCTAAACTTAGAATATTGTGAAATTCTTTTTATAACTCAGCCATTTAATTCTTG
AGTGTAAATTTTGTAGATGGAGTCATGTTGTAATGTTAGACACATTTGCTAGTGATGTGACA
ACATAATATTCCCATGAACTGATGTCAAATGTTGTATTGTACTTTGACCAGGTATATAAGGTT
TATTATCTTCTTGACCTTGGAGTAATTTCAGTCCCAACTTAAATCCCTAGTGGT (SEQ ID NO: 11)

FIG. 14 cont'd eHGT_706m (352 bp):
TATGTAGATACAGGTCATAGAACTTGCCCTGGGGAATGGCTCCATTTGGTACCAACAGGCT
GACCCCTAGGGAGGAAGGAAGGCTATCAGCAAGAGGAGGAGGAGGTAGCAGAGATGAGA
AAGATGGGGTAGACTCTGGCTCCAACCTAGGGAAGGGAAAGACTCTAGACTCGGGGGTAT
GGGGGTGGATAGATACAGGGAGCACACAGGCTACTTGGCCTGGTCTGCCCATGAATACAG
GGGGCCTCTAACATTGCTGGGGTAGGAGGGTCAGAATGCTCCAGTGCTAGCCCTCATGCT
GGCTCAGGACAGGACTCTGAAAAGCCACCAGCTGCCACTTTCACAAGCTGAG (SEQ ID
NO: 12)

eHGT_710m (382 bp):
AGTGACTTGGTGCTATGAGCCATATTTTGCTGTTGCTGTTGTTACTGGTAGTTTTTGTAATT
CTGGGGCTAAAACTTGGGGTCTGGTATGCTGTCATTTACCAGTGAGCTATACCCTGGATAT
TATGATTTAGATGAATGTGAAATATCACCCCAGACATACATATACTAAACACTTGGCCCTTG
GCCCATGATGCTAAATGGAGGAGATAGAAGCTTTTGGGGCACAGCCTAGTGGAAGGAAAT
GAGGTCAAATGACATGTACTCTGAAAGGAATATGGGTATTCTGGGCTTGCGTTATTCTCTCT
CTCCCTCTCTCTCCCTCTCTCTCCCTCTCCCTCTCTCTTTCTCCTTTTCTCTTTCTCTCCTCG
CCTTGTTTTCCA (SEQ ID NO: 13)

eHGT_296m (912 bp):
TCCAGCTACCACCAGCCTGTCCAAAAGGGGACACCAAAGGAGAGGAGGAAGTCTGAGAGA
CACCTCTCTGCACCATGGCCATCTTAGTAGTCAGACCCAGAACAAAACTCTCTGATGAGTG
TGCGGAGCGTCGCTTCTGGTCTTTGCTCAAACTATTCACTGAAGATTTAAAGCAATCCCGT
GAGTGATACATTTGGGTGAATTTGTTCTCTAGAAGGTATCACAGAAATCTGGTCACTGGGC
CACCCGAGACATCCTGATAGGCCCTCTGGTAACCCATCACATGCTGCAGACTGACTCTGG
GGGCCTAGAACCCAGATCAGAAGCAACCTTGACCCCGGCCCACCCGCCACGGAAGCACC
ATCATCTCTCTGATTAAAAACCTCGATCACGGACCCGGGGGCGTGCCCGGAAGAGCTAAG
ATAATCAGCGTCAGCACTTTGCCTTCGCCGTCCAAGACTGCAGACGGCCTTCATTTGACCT
GATTCGTGGTGTTAATGACAGCAGAGCAATTTTGAGAGGCAGCTTGCTCTCGGCATCTATA
AGGAGAGGAAAAGCACTGAGGGCTGGGGACCAAGCTCCTTGCAGAGGCGGCAGCTGCAG
TCACCCTCCCCCTCCACCCCTGCCCCTCCCCTCCCCTCCAGAGGCACTTTGAGTAAGTGC
TGCCCTCCGATCTGCCCTGATACGATGGGAGAAAGCTGATGTGAGGGCTGGAGCCAGAGT
GTGCAAGGGGACAGTGTGTGCATGTGCGTGTGTCGGGGAGAGGTACCCGTGCTATACCT
GAGAACATTGCTGGGTGAACACAGCCTTGGACCTGGAAGAGCGCATAGCTTACTTAGAGG
CATGGGCTGCACATGAGCTGCCCATTTACCTGCTCATTTAGAAGCTACTATGAAGGCTGGT
GAGATGGCT (SEQ ID NO: 14)

eHGT_299m (481 bp):
ACCAGAAGTTCAGTGAGCAGAAGATGGGCTAAAATGAAAAGGGTACTGTCTTGAACTGAAG
ATGGAATCCTGCAGCTTCATTCTGGCCAAAAGAAGATCTATTCCCAGGAGGAGGGTAAAGG
CTTTGTTCTTAAGAGATGCTGAGGCTGGCCCTGTGAATCTGATGTCAAGATGTCCCTTGTC
ACTCTGCAGAAGCGTATGTCTCTTGCATTTCCTTCTTATTTCCTTGGGTGAAATTGCTGTGG
CATTGTGTCACTCATCCTAATGGGTCATGTCTAACATCTGCGTGCTTACAAATCAGGCATGC
TCATTTCTGGGCTTATGGAGCTTGTATAACACCAGGACAGGCAAGACATGTTGCCCACTCA
GGAAGAATAGAAGCTGGGCACAGCTGGAGTGCAAAGTAGGTCAGTTCAGAGAGCAAAGG
GAGTTGATGGAGCAATGAGTTGTTAGTGGGAAAGTTCTAACCAACTGTCCCAGA (SEQ ID
NO: 15)

FIG. 14 cont'd eHGT_300m (990 bp):
TGTCTTAGACTGAGTTGCTGTAACAAAAATCTGGGATGAGGTCATTTCTAAAGCACAGCAAT
TTATTTCCCACAGTCTGAAGGCTGCAGATTCCAAGATCACTGGCAAGATCAGTTGTAAAGG
CTTCGTCCTCCAGAGGCGGGGATGCTGCATACTCCCTGGGCAGAGAGACAGGAAAACTCC
GTAACTGCATGTGTCCTTCCTGATGCCTCTTCTATATAGGCCTGGATCCCAATCACCCTGT
GAACCTCTCCCTGCTTCGTGGCCCCCACCTCTTAACACTACCACATTGGCAACTCCTGAAA
TTTGAAGGGGACACACTGAACCATGGCACAACAGCTTTCTGACTGATGCAGTAACCCAATG
GCAGTGCAGAAGGGGCCAGCTAAAGCCCAAATGGTTAGCTCAAAATTCGCTGTCTCTTCC
GAGTGTCTGAACCCTTAGTCCTGGTATGTAAAGACATCAGAACATTTCCCCTTGTGTCCATC
AGATTTCTGTCTAGTGAAACGATGACACTGTAACCTCCAAGATCTCACACGAAATGATCTTT
TCTCCTTTGTGGAAGGAAACCAGCATTTAGCTCATCTCTCCTTCGTAGCAGCTCAGAATGT
CCACAGTGACCCAGTTACCATAGCTAAAGGCTTCCTTTTCAAAACACAGAGCAGAGGCAGC
CAATTCAGTATGTGCTGCTGCCATCCTCTGATTCTTTCCTGCTTCCATAGACACCAACTCTA
TTGTAACTAAGCCTTATACATTGTGTCTTCCTCCTTTACATTAGCTTGTGCTGGGGTGGTTC
ATGAGGCCCGCTGAGTAGTTTCAGTGACAGCCTATCCCTCTGCCAGTGCTGCTTTGAGCC
ATCTTATTGGTGAGGCTGTAAGAGAAGCCTGAAGTCACAGGGTAAAGCTATGTTGAAGGCA
GCCCCAGAACCAAGTTTCCCTATTTCTATCTCCTTACGCTGTTTGAGCCTCAGGGGTAGAT
CAGGTGCCTGT (SEQ ID NO: 16)

eHGT_306m (860 bp):
AGATGAGTCTGCAGCTGGGTACAGTGACCTTTCAGTCCATGTTTATTTGGAAATGACCTTTA
AGCAGCAATCAGCAAGAATAAAATGCTTCAAAGGAATACATTAGATAATGCAGAAGTCCCC
CAGAGGTAAGTTACACCCAAGGCACCCAGCTGACAATGAAAGTGGCCCTGCCCTGGGAAG
CCAAGGACTAGGCCACCCATTAGACTAACAAGTGAACACAGGGTCCCCAGAGTTTGGTCT
AATAGACAATGGGGAGTCTGAAGACAGGGTGACCTGGGCAAGACACAAGAGCAGTTCCAA
AATTAAACCTCTGTCGTAATGAAGGATGCCTAGTTGTGCTTTTTCCATCCTAGGATGGGGAA
TCCTCAAGGGCAGGGCACAGCTGTGCCAGGGGAACTGTACGGGCTCCATCCTGCCTCCC
TCCCATGGGGTGAGCTGATAGTCTTCCTCATACTGAGCTCTTGTCTCTGCTGTGTGCTGGG
GAGTCTGAAATGCTAGAGAAACTAAGCCTTCCCACTCAAAGACAGAGAAAGAGCTGGCCC
ATGGCTCCGTGCCCTCTCCTCTCTCTGTGCGTGTCTTTAACTCTGTATGTTCTATTTTCCCC
CTCCTCGTCCCCTGCTTCGCGCTCACAGAGTCACTCCTAGTAGCACCAAAGAGAGATGCTT
GGCAGTTCACTAACCCCTTGAGCTGAAATAGAAATAAATATCCCAAAAGAGAAATCAGAAAA
GCAGGGTGTCGCGCTGGAGAAGAGGCAGGAAGATCAGAAATACAAGGTCATCTGTGGCTA
CACATCTAGTCCAAGTCCCAGCCTGGGCTATGTGAGATGGAGGGGAATCGCTCAGAAACA
AGGCTGTACA (SEQ ID NO: 17)

eHGT_309m (778 bp):
TTCACCCACCTGACACTTGGGTTAGACCTGAATGTCGTTTCTTTAACTCACACTGCTCATCC
CACTGGCCTTTGCTGTGCTTCTCTGTGCCTCCTCAGAGATACATGAAACTGTCCCATCCCC
CTAACGATGCTGGATGGATGGCTCCAACAGCTCACTGCTCTCACCTTGACACAAAGTCCTA
GCGTCTGCATCTGTGAGACAAGTTGGAATTTATATATTTCCAGTGGAGATTAATAATTCATT
AGATGCTGAAGTAGAAAACAAAGTACCGATTAATCAAGGCTCTGCTGAGGCCTGCTTTGC
AGCCACCAGTCTGTGGGGATTGGCAGTGCTTTTACACTGGAAGTAGGTCAGGACCACAGA
AAAGCAGCTCTCATGCACTAGCATCTGTTCGCACTAATCACTGTACACAGCTTTGGGTCTTA
CTATAGTTTTTATTAGTTATCCCAGCTGGGATTTATGTCTCAGGAATAAAGAGCCAAGAATG
GGAGGAGTTACCCTCGAAAGATCCAGGTCATGTGGTGCAGGGCAGGGAATATGGCTGACT
CAATCTCTTTGCCCATAGAGCCTCAGAGTATCAGATCTTAGCACTCTAAGGAGGGAGACTC
AGAGGGTACAAGTCTTAGAAGTCTCCCTAGGGCTTGGTGCCCAGCAAATATATGCTGTTTG

FIG. 14 cont'd

TGACTTCCCTAATACCAGGTACAGGCCAACACAAAGGACCTGTCCAAGGGAAACTCACGG
CTCAGACCTGATCTATTTACAGGTTGAGTTTGGGTGAAGCCAAGA (SEQ ID NO: 18)

eHGT_310m (549 bp):
ATCCCTGGAGATGAGGAGTCCTCTCTGGCAGGGTCCCCTCACTCTAGAGCAGCCCCTATC
CCAGGCCCCCTAGGAGTCTCTAATTAAAGGGCCGGCACGCCCCTCTGGGACTCATTAGGC
CCGCTGTGCAGAGAACATTTAATCATTGCTCAGAGCATCGATTGGAAAATCAATTTCTTTGT
CTCTTCGCACGAGGCGCGCTGGAGAAGTGGGGGGAGTGCTGACCTCCTTCTGCTGCCGT
GTAAAGCGCTGCACATTTAATCAGGGAACAGAAATCAATTAGCCACTTACGAGGTTGGCTT
TAGTTACCGAGTCGGCAAGGCCCGCGCCACAGCTCAGCCGCTGACAGTAGCGAATCTCCT
CCTCTCGGCCCTGCTGCATGGCTCTGTCTCCCTCCCTGTATCTCTCTGGCTTCCTTCTTTC
CCAGAGTGCTCTGGGTTCTCACCATCTTGGCAGATCCTCACAGAACTCCAAACAAGTCCCG
AGAAGCCTTCCTAATGCCCAGTCTCCTCGGCCACCTTCTTGTTCTCAGCTCTAGACGTTTC
AAGA (SEQ ID NO: 19)

eHGT_890m (575 bp):
TGAGCTTCAACCAAATCAGGCATTGATGGATTTTATAGTTTGATTAACAAAGATAATAGCAA
ACCCCAGATTTAGTTTAAACATAAAAAGTATTAAGGTTGTATCCTGCTTGTATAGCATATGCA
AATGACCTCGTTTCTGCTACTGCATTTGGAAATGTAGCAGAAGAAAAAAAAAGGCACTTCA
ATTGCAGCTCTCATCAGTTATTCACTGTATCCAGGCCTCTCAATTGTGTTCTTTTCTTTAATG
CAATAGCAAGCAGCAATCACCCAGCTGTGCTTGGTAGAGTGAACTATATACACATCTATATT
GAGATTTCATACACACATAACATAAAAGCGAGAGAAAAAGCCTCAAGAATGTTTGGCCCATT
GCAAATCACACAAAGGACTAATGAATCTCTCTCCAAATGGATCTGTAGTGACCATCTGTAA
GCCTTGATTGATTCATATTCCATAACGGTATCAGCATCCAGGAAGTGATTACTTCAAGGTGC
AACACAACTTCCCCTATGAAAGCTCAGTCTCTTTAATCATACCTAGTCAGTATCTGTCACGG
GGATAAACTAAGGCA (SEQ ID NO: 20)

eHGT_891m (611 bp):
ACATTTGCAGTAAAGCTTGTTCTTTTTCTTGAAGTATATTTTAAGATTTTGAGTTCTACTATCA
TTAAAGACAGATAATTAATAGTTTATTTTTATTTACTTTTGTTAGTAGTGACTTGGTGCTATGA
GCCATATTTTGCTGTTGCTGTTGTTACTGGTAGTTTTTGTAATTCTGGGGCTAAAACTTGGG
GTCTGGTATGCTGTCATTTACCAGTGAGCTATACCCTGGATATTATGATTTAGATGAATGTG
AAATATCACCCCAGACATACATATACTAAACACTTGGCCCTTGGCCCATGATGCTAAATGGA
GGAGATAGAAGCTTTTGGGGCACAGCCTAGTGGAAGGAAATGAGGTCAAATGACATGTAC
TCTGAAAGGAATATGGGTATTCTGGGCTTGCGTTATTCTCTCTCTCCCTCTCTCTCCCTCTC
TCTCCCTCTCCCTCTCTCTTTCTCCTTTTCTCTTTCTCTCCTCGCCTTGTTTCCAGCTGCCA
GAAGGTAGGCCTCTTCTCTGCTGAATATCTGTGTCATGTTATGCACCAACACAGTACTAACT
GTCATGTTATACCTAGTGGCCAGGTAACCATGGACCAAAATGGCAGAGCA (SEQ ID NO:
21)

eHGT_892m (661 bp):
TGCAAAATAAAGATTTCTTGGGATACAGAGAAAAAAACAAATCTGACAGGAGAGGAAGAAG
CACCCGGTGGGCTATAACGGTGCAATTCAGCTGATTATATGTTACAAGTAACAAGGACGAG
AAAAAATGTTATTTCTTTGAAAATAAAACTAACCAGGCCATACATATTTAACAGGACTGCATG
AGAGAAGAAGAAGCCAGCTGCAGGAGTGACTGTGGGGGGGAGGGGGAACTTGACAAAAA
AAGCAAATGGCAGTCCTGCTTCCAAAGTCCTCAAGGTCACAGTTATTTGGGCATTCTTGC
GGGCACTGCTTATACAAGAATGTGCTTTCAGTCAAGGCTTTCTAATAGATTCTCAAAATTTG
GGACAAATGTTATTTTTGTATCTGTAGAAATGTACTGATTCAGAAAGATCTTTGAGCAATACA

FIG. 14 cont'd

GATGTTAAAACATTTAAGTCACAAAATGGGTCTATTTAATCAATGCGACTAGTTTGGAACATT
ATTCAAACTGCCAGAAATACAATGTAAATGAAACCTCAGGCCAATATTTTGGAGCCCTAAAA
GATTTGATGGCTAATTTTATCGTAGACACTAATTATAAATAGGAGACCCCAGGATGGGACTA
GAAAACCAAGCCAGCTTTTTAATTTACCCCTCCAGGACTTTGCT (SEQ ID NO: 22)

eHGT_476m (1316 bp):
AGAAACACCACAAGCAAAGCCAAAATAGGTGGCCTAGAACTTCCAGCTTGAAATATGGGAG
AGAATGAGGGAGGCACTGTAGAGCAGCTGCCGGGTGCCGCATGAGAACAATTCTCCCTGC
TCATAATTAATCCTACCTATTTCTGATGACAGCTGGCTCTTCACTTTGAACAAGCTAGTTAAC
AACTTTCTTCTCACATTGAGCAAATAATTCATATTTAATTACTTAACCACCAGTTACAAAATG
AGAATCATCAAGGAATCACAATTAATTTGCTATTGACAAACTCATACTTTTAGCAGGCTGATT
TCTACTTTATACTTAGATTGGTAATGAAAAATGAAGCTTATTTTAGTTGATTGGTTGGACTTG
TGTATGAATATTATCTATTATTTGAAAAGCCAAACTTGAATGCAAAAAAATATTGAATATGAA
AAGAGAAACACCACAAGCAAAGCCAAAATAGGTGGCCTAGAACTTCCAGCTTGAAATATGG
GAGAGAATGAGGGAGGCACTGTAGAGCAGCTGCCGGGTGCCGCATGAGAACAATTCTCC
CTGCTCATAATTAATCCTACCTATTTCTGATGACAGCTGGCTCTTCACTTTGAACAAGCTAG
TTAACAACTTTCTTCTCACATTGAGCAAATAATTCATATTTAATTACTTAACCACCAGTTACAA
AATGAGAATCATCAAGGAATCACAATTAATTTGCTATTGACAAACTCATACTTTTAGCAGGC
TGATTTCTACTTTATACTTAGATTGGTAATGAAAAATGAAGCTTATTTTAGTTGATTGGTTGG
ACTTGTGTATGAATATTATCTATTATTTGAAAAGCCAAACTTGAATGCAAAAAAATATTGAAT
ATGAAAAGAGAAACACCACAAGCAAAGCCAAAATAGGTGGCCTAGAACTTCCAGCTTGAAA
TATGGGAGAGAATGAGGGAGGCACTGTAGAGCAGCTGCCGGGTGCCGCATGAGAACAAT
TCTCCCTGCTCATAATTAATCCTACCTATTTCTGATGACAGCTGGCTCTTCACTTTGAACAA
GCTAGTTAACAACTTTCTTCTCACATTGAGCAAATAATTCATATTTAATTACTTAACCACCAG
TTACAAAATGAGAATCATCAAGGAATCACAATTAATTTGCTATTGACAAACTCATACTTTTAG
CAGGCTGATTTCTACTTTATACTTAGATTGGTAATGAAAAATGAAGCTTATTTTAGTTGATTG
GTTGGACTTGTGTATGAATATTATCTATTATTTGAAAAGCCAAACTTGAATGCAAAAAAATAT
TGAATATGAAAA (SEQ ID NO: 23)

eHGT_1022m (505 bp):
CAGTTTCCAGCGTGGTTGTTGATGAGGCTCAGAGAAAAGACTCTAAAGTTATGATGGGAAA
TTACCATGCCATTCATCATCATACACATTCACCTCACACTTTCTGAGTCTCCTATACAAAGTC
AGTTCTCTGCCAAGGGCATGGAAGAGCGAGGAACAGGATGTTAGGAAGGGCTGACAGCG
CTGTTTTAGCCTGACAGGCAGATTTACAACAGGAGAATGAATGTACCACTTGTATAAGAAG
GCCATGCGGCACTGCTAATGCACAAGTTGGCAGTACATCAACATCTCTATCGTCCTCATAT
TCATGAAGCAGAGAACGGAAATGGCACACTGCTTGTACCGGCGAATAACCAAAGTGAACG
CCCTACGGCTGCCATTCACTGTGTCCTTCCAAAAGCATTTTCTACTGAGCTCTTCCCAGA
GATTTAGGGTTTGCTTAGACAGGTCTTATGACGCCACGTGATAGGTCATTCTTCTGTTCTGA
GGAGCTTGGAGAAGATC (SEQ ID NO: 24)

eHGT_1023m (439 bp):
GTAGAACATACTTATTAACACATTCGTACATAAAATAAAATTCTACTCTCCCGACCTTTTCCT
CACCATCTTGCTTTTCAACGTATGGCGTTAGACCTAACAGCGAGTCCACTTCTTCCCCTTTC
ATTCTGTAGCAAGAACACACGGCTCACTGTAACAGGGACTTGGCTGTGGGTTGCAGACTG
GCTTCCTGCTGCCTCCACTTGAGCCCCACACAGCTGTGGCTTTGTGTTTACAACCCTCCAG
GCTGCCATTCATTCGGTGCTGTGGGCTCATGTACTGGAAGACAGCTTCCATCACAACCTTC
CCGTCCCAGCAGGAGAACTCCCTTGCTTCCTTGGGGAACATTTGCTTGCTCCTGCTGCTTG

FIG. 14 cont'd

GCTCTTCCCACTTTTGCCTCACTCTGGAGTTTCTCTCTCCCGTTTTGAATTCTAGTAGTAAA
CACATGGCC (SEQ ID NO: 25)

eHGT_1024m (507 bp):
CCAGTGAGATCTTCCACCAGCAGAACTCATGGACACAAACTAGACAGCTCACTTCTTGCCT
GTATTCCAGGAGTGGCTTTTTCTCTACTCCTGTACTGATGCCAGTCATTCAGAGTGCACTCA
AGACACTTGACCCACATCAGTTAAGAGAATGAAAATCAAGCTCTGAAAGCCATTAGCTTCTA
TTGCACACCCAGAAAACAGGCTCATCAAACACCTTCTTATGGTAATGCCTTTGATCAAAAGG
AGGGTTAATTCAACAAATGGTTTGCACCGTGACCCCATCAAAGCCTGAGCACCAGTGTCCT
CATTTCCTTTCCCCTGGTGTATAATGAGTTGTTAGTCTGGCTCACCTTGTCATCCCCATCAT
ACTGCCATAATCCACATCTCTAAAGAGTGGATTACAACAGTCCCGTCTGTGACACTCAGGA
CTGGCATCAAGGTTCCCAAGCTCTAGTCTATTGTGACATTGATACAAATAGGGCTCAGAGT
CTCACTGATCACACC (SEQ ID NO: 26)

Beta-Globin Minimal Promoter (pBGmin/minBGlobin/minBGprom):
GGGCTGGGCATAAAAGTCAGGGCAGAGCCATCTATTGCTTACATTTGCTTCTG (SEQ ID
NO: 27)

minCMV Promoter:
GAGGTAGGCGTGTACGGTGGGAGGCCTATATAAGCAGAGCTCGTTTAGTGAACCGTCAGA
TCGCCTGG (SEQ ID NO: 28)

Mutated minCMV Promoter (SacI RE site removed):
GAGGTAGGCGTGTACGGTGGGAGGCCTATATAAGCAGAGCTGGTTTAGTGAACCGTCAGA
TCGCCTGG (SEQ ID NO: 29)

minRho Promoter:
GATTCAGCCGGGAGCTTAGGGAGGGGAGGTCACTTCATAAGGGCCTGGGGGGGGGAGTTG
GAGCCACGAGTCGTCCAGCCGGAGCCCCGTGTGGCTGAGCTCCGGCCTCAGAAGCATCC
CC (SEQ ID NO: 30)

**minRho* Promoter:**
GATTCAGCCGGGAGCTTAGGGAGGGGAGGTCACTTCATAAGGGCTTGGGGGGGGGAGTTG
GAGCCACGAGTCGTCCAGCCGGAGCCCCGTGTGGCTGTGCTCCGGCCTCAGAAGCATCC
CC (SEQ ID NO: 31)

Hsp68 minimal Promoter (proHsp68):
CAGGAACATCCAAACTGAGCAGCCGGGGTCCCCCCCACCCCCCACCCCGCCCCACGCGG
CAACTTTGAGCCTGTGCTGGGACAGAGCCTCTAGTTCCTAAATTAGTCCATGAGGTCAGAG
GCAGCACTGCCATTGTAACGCGATTGGAGAGGATCACGTCACCGGACACGCCCCCAGGC
ATCTCCCTGGGTCTCCTAAACTTGGCGGGGAGAAGTTTTAGCCCTTAAGTTTTAGCCTTTAA
CCCCCATATTCAGAACTGTGCGAGTTGGCGAAACCCCACAAATCACAACAAACTGTACACA
ACACCGAGCTAGAGGTGATCTTTCTTGTCCATTCCACACAGGCCTTAGTAATGCGTCGCCA
TAGCAACAGTGTCACTAGTAGCACCAGCACTTCCCCACACCCTCCCCCTCAGGAATCCGTA
CTCTCCAGTGAACCCCAGAAACCTCTGGAGAGTTCTGGACAAGGGCGGAACCCACAACTC
CGATTACTCAAGGGAGGCGGGGAAGCTCCACCAGACGCGAAACTGCTGGAAGATTCCTG
GCCCCAAGGCCTCCTCCGGCTCGCTGATTGGCCCAGCGGAGAGTGGGCGGGGCCGGTG
AAGACTCCTTAAAGGCGCAGGGCGGCGAGCAGGTCACCAGACGCTGACAGCTACTCAGA

FIG. 14 cont'd

ACCAAATCTGGTTCCATCCAGAGACAAGCGAAGACAAGAGAAGCAGAGCGAGCGGCGCGT
TCCCGATCCTCGGCCAGGACCAGCCTTCCCCAGAGCATCCCTGCCGCGGAGCGCAACCT
TCCCAGGAGCATCCCTGCCGCGGAGCGCAACTTTCCCCGGAGCATCCACGCCGCGGAGC
GCAGCCTTCCAGAAGCAGAGCGCGGCGCC (SEQ ID NO: 32)

SYFP2:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAA (SEQ ID NO: 33)

EGFP:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAA (SEQ ID NO: 34)

Optimized Flp recombinase (FlpO):
ATGGCTCCTAAGAAGAAGAGGAAGGTGATGAGCCAGTTCGACATCCTGTGCAAGACCCCC
CCCAAGGTGCTGGTGCGGCAGTTCGTGGAGAGATTCGAGAGGCCCAGCGGCGAGAAGAT
CGCCAGCTGTGCCGCCGAGCTGACCTACCTGTGCTGGATGATCACCCACAACGGCACCG
CCATCAAGAGGGCCACCTTCATGAGCTACAACACCATCATCAGCAACAGCCTGAGCTTCGA
CATCGTGAACAAGAGCCTGCAGTTCAAGTACAAGACCCAGAAGGCCACCATCCTGGAGGC
CAGCCTGAAGAAGCTGATCCCCGCCTGGGAGTTCACCATCATCCCTTACAACGGCCAGAA
GCACCAGAGCGACATCACCGACATCGTGTCCAGCCTGCAGCTGCAGTTCGAGAGCAGCG
AGGAGGCCGACAAGGGCAACAGCCACAGCAAGAAGATGCTGAAGGCCCTGCTGTCCGAG
GGCGAGAGCATCTGGGAGATCACCGAGAAGATCCTGAACAGCTTCGAGTACACCAGCAGG
TTCACCAAGACCAAGACCCTGTACCAGTTCCTGTTCCTGGCCACATTCATCAACTGCGGCA
GGTTCAGCGACATCAAGAACGTGGACCCCAAGAGCTTCAAGCTGGTGCAGAACAAGTACC
TGGGCGTGATCATTCAGTGCCTGGTGACCGAGACCAAGACAAGCGTGTCCAGGCACATCT

FIG. 14 cont'd

ACTTTTTCAGCGCCAGAGGCAGGATCGACCCCCTGGTGTACCTGGACGAGTTCCTGAGGA
ACAGCGAGCCCGTGCTGAAGAGAGTGAACAGGACCGGCAACAGCAGCAGCAACAAGCAG
GAGTACCAGCTGCTGAAGGACAACCTGGTGCGCAGCTACAACAAGGCCCTGAAGAAGAAC
GCCCCCTACCCCATCTTCGCTATCAAGAACGGCCCTAAGAGCCACATCGGCAGGCACCTG
ATGACCAGCTTTCTGAGCATGAAGGGCCTGACCGAGCTGACAAACGTGGTGGGCAACTGG
AGCGACAAGAGGGCCTCCGCCGTGGCCAGGACCACCTACACCCACCAGATCACCGCCAT
CCCCGACCACTACTTCGCCCTGGTGTCCAGGTACTACGCCTACGACCCCATCAGCAAGGA
GATGATCGCCCTGAAGGACGAGACCAACCCCATCGAGGAGTGGCAGCACATCGAGCAGC
TGAAGGGCAGCGCCGAGGGCAGCATCAGATACCCCGCCTGGAACGGCATCATCAGCCAG
GAGGTGCTGGACTACCTGAGCAGCTACATCAACAGGCGGATCTGA (SEQ ID NO: 35)

Improved Cre recombinase (iCre):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCAGGGACATGGCCAGGGCTGGTGTGTCCATCCCTGAAATCATGCAGG
CTGGTGGCTGGACCAATGTGAACATTGTGATGAACTACATCAGAAACCTGGACTCTGAGAC
TGGGGCCATGGTGAGGCTGCTCGAGGATGGGGACTAA (SEQ ID NO: 36)

iCre(R297T):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCACCGACATGGCCAGGGCTGGTGTGTCCATCCCTGAAATCATGCAGGC

FIG. 14 cont'd

TGGTGGCTGGACCAATGTGAACATTGTGATGAACTACATCAGAAACCTGGACTCTGAGACT
GGGGCCATGGTGAGGCTGCTCGAAGATGGGGACTGA (SEQ ID NO: 37)

CreN-inteinN:
ATGACGAGTGATGAGGTTCGCAAGAACCTGATGGACATGTTCAGGGATCGCCAGGCGTTT
TCTGAGCATACCTGGAAAATGCTTCTGTCCGTTTGCCGGTCGTGGGCGGCATGGTGCAAG
TTGAATAAATTTGCGGAATATTGCCTCAGTTTTGGCACCGAAATTTTAACCGTTGAGTACGG
CCCATTGCCCATTGGCAAAATTGTGAGTGAAGAAATTAATTGTTCTGTGTACAGTGTTGATC
CAGAAGGGAGAGTTTACACCCAGGCGATCGCCCAATGGCATGACCGGGGAGAGCAGGAA
GTATTGGAATATGAATTGGAAGATGGTTCAGTAATCCGAGCTACCTCTGACCACCGCTTTTT
AACCACCGATTATCAACTGTTGGCGATCGAAGAAATTTTTGCTAGGCAACTGGACTTGTTG
ACTTTAGAAAATATTAAGCAAACTGAAGAAGCTCTTGACAACCATCGTCTTCCCTTTCCATT
ACTTGACGCTGGGACAATTAAATAA (SEQ ID NO: 38)

inteinC-CreC:
ATGGTTAAAGTTATCGGTCGTCGTTCCCTCGGAGTGCAAAGAATATTTGATATTGGTCTTCC
CCAAGACCATAATTTTCTGCTAGCCAATGGGGCGATCGCCGCCAATTGTTTTAACAAATCC
AACCGGAAATGGTTTCCCGCAGAACCTGAAGATGTTCGCGATTATCTTCTATATCTTCAGG
CGCGCGGTCTGGCAGTAAAAACTATCCAGCAACATTTGGGCCAGCTAAACATGCTTCATCG
TCGGTCCGGGCTGCCACGACCAAGTGACAGCAATGCTGTTTCACTGGTTATGCGGCGGAT
CCGAAAAGAAACGTTGATGCCGGTGAACGTGCAAAACAGGCTCTAGCGTTCGAACGCAC
TGATTTCGACCAGGTTCGTTCACTCATGGAAAATAGCGATCGCTGCCAGGATATACGTAAT
CTGGCATTTCTGGGGATTGCTTATAACACCCTGTTACGTATAGCCGAAATTGCCAGGATCA
GGGTTAAAGATATCTCACGTACTGACGGTGGGAGAATGTTAATCCATATTGGCAGAACGAA
AACGCTGGTTAGCACCGCAGGTGTAGAGAAGGCACTTAGCCTGGGGGTAACTAAACTGGT
CGAGCGATGGATTTCCGTCTCTGGTGTAGCTGATGATCCGAATAACTACCTGTTTTGCCGG
GTCAGAAAAAATGGTGTTGCCGCGCCATCTGCCACCAGCCAGCTATCAACTCGCGCCCTG
GAAGGGATTTTTGAAGCAACTCATCGATTGATTTACGGCGCTAAGGATGACTCTGGTCAGA
GATACCTGGCCTGGTCTGGACACAGTGCCCGTGTCGGAGCCGCGCGAGATATGGCCCGC
GCTGGAGTTTCAATACCGGAGATCATGCAAGCTGGTGGCTGGACCAATGTAAATATTGTCA
TGAACTATATCCGTAACCTGGATAGTGAAACAGGGGCAATGGTGCGCCTGCTGGAAGATG
GCGATTAG (SEQ ID NO: 39)

SP10 insulator (SP10ins):
GAAGCTACCCCTAACACACTATTCTACACACAGAAAATGCTCTTCACTAG (SEQ ID NO: 40)

3xSP10ins:
GAAGCTACCCCTAACACACTATTCTACACACAGAAAATGCTCTTCACTAGGAAGCTACCCC
TAACACACTATTCTACACACAGAAAATGCTCTTCACTAGGAAGCTACCCCTAACACACTATT
CTACACACAGAAAATGCTCTTCACTAG (SEQ ID NO: 41)

FIG. 14 cont'd

4X2C:
GCGGCCTT<u>AAAGAGACCGGTTCACTGTGA</u>CAGT<u>AAAAGAGACCGGTTCACTGTGA</u>GAATG
<u>AAAGAGACCGGTTCACTGTGA</u>TCGGA<u>AAAGAGACCGGTTCACTGTGA</u>GCGGCCTT**GAAAC
CCAGCAGACAATGTAGCTCAGTAGAAACCCAGCAGACAATGTAGCTGAATGGAAACCCA
GCAGACAATGTAGCTTCGGAGAAACCCAGCAGACAATGTAGCT**GTCGAC (SEQ ID NO:
42)
In this sequence, the miR128 recognition sequences are underlined and the miR221 recognition
sequences are in bold.

miR128 Recognition Sequence:
AAAGAGACCGGTTCACTGTGA (SEQ ID NO: 136)

miR221 Recognition Sequence:
GAAACCCAGCAGACAATGTAGCT (SEQ ID NO: 137)

3XFLAG:
GACTACAAAGACCATGACGGAGATTATAAAGATCATGACATCGATTACAAGGATGACGATG
ACAAG (SEQ ID NO: 43)

10 aa:
TCCGGACTCAGATCTGGAGGCTCCGGAGGC (SEQ ID NO: 44)

H2B:
CCAGAGCCAGCGAAGTCTGCTCCCGCCCCGAAAAAGGGCTCCAAGAAGGCGGTGACTAA
GGCGCAGAAGAAAGGCGGCAAGAAGCGCAAGCGCAGCCGCAAGGAGAGCTATTCCATCT
ATGTGTATAAGGTTCTGAAGCAGGTCCACCCTGACACCGGCATTTCGTCCAAGGCCATGG
GCATCATGAACTCGTTTGTGAACGACATTTTCGAGCGCATCGCAGGTGAGGCTTCCCGCCT
GGCGCATTACAACAAGCGCTCGACCATCACCTCCAGGGAGATCCAGACGGCCGTGCGCC
TGCTGCTGCCTGGGGAGTTGGCCAAGCACGCCGTGTCCGAGGGTACTAAGGCCATCACC
AAGTACACCAGCGCTAAGTAATGA (SEQ ID NO: 135)

CCAGAGCCAGCGAAGTCTGCTCCCGCCCCGAAAAAGGGCTCCAAGAAGGCGGTGACTAA
GGCGCAGAAGAAAGGCGGCAAGAAGCGCAAGCGCAGCCGCAAGGAGAGCTATTCCATCT
ATGTGTACAAGGTTCTGAAGCAGGTCCACCCTGACACCGGCATTTCGTCCAAGGCCATGG
GCATCATGAATTCGTTTGTGAACGACATTTTCGAGCGCATCGCAGGAGAGGCTTCCCGCCT
GGCGCATTACAACAAGCGCTCGACCATCACCTCCCGGGAGATCCAGACGGCCGTGCGCC
TGCTGCTGCCTGGGGAGTTGGCCAAGCACGCCGTGTCCGAGGGTACTAAGGCCATCACC
AAGTACACCAGCGCTAAGTAA (SEQ ID NO: 45)

WPRE3:
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
(SEQ ID NO: 46)

FIG. 14 cont'd

WPRE:
GCTTATCGATAATCAACCTCTGGATTACAAAATTTGTGAAAGATTGACTGGTATTCTTAACTA
TGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGC
TCGCCTATGTTGCCACCTGGATTCTGCGCGGGACGTCCTTCTGCTACGTCCTTCGGCCC
TCAATCCAGCGGACCTTCCTTCCCGCGGCCTGCTGCCGGCTCTGCGGCCTCTTCCGCGTC
TTCGCCTTCGCCCTCAGACGAGTCGGATCTCCCTTTGGGCCGCCTCCCCGCATCGATACC
G (SEQ ID NO: 47)

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 48)

HGHpA:
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCC
TTCTATAATATTATGGGGTGGAGGGGGGTGGTATGGAGCAAGGGGCAAGTTGGGAAGACA
ACCTGTAGGGCCTGCGGGGTCTATTGGGAACCAAGCTGGAGTGCAGTGGCACAATCTTGG
CTCACTGCAATCTCCGCCTCCTGGGTTCAAGCGATTCTCCTGCCTCAGCCTCCCGAGTTGT
TGGGATTCCAGGCATGCATGACCAGGCTCAGCTAATTTTTGTTTTTTTGGTAGAGACGGGG
TTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTT (SEQ ID
NO: 49)

P2A:
GGCAGCGGCGCCACCAACTTCAGCCTGCTGAAGCAGGCCGGCGACGTGGAGGAGAACCC
CGGCCCCGGAGCTAGCGGA (SEQ ID NO: 50)

GGCTCTGGTGCTACCAACTTCTCACTGTTGAAACAGGCAGGGGATGTAGAGGAGAATCCA
GGGCCTGGTGCTAGTGGA (SEQ ID NO: 51)

T2A:
(GSG)EGRGSLLTCGDVEENPGP (SEQ ID NO: 52)

E2A:
(GSG)QCTNYALLKLAGDVESNPGPP (SEQ ID NO: 53)

F2A:
(GSG)VKQTLNFDLLKLAGDVESNPGP (SEQ ID NO: 54)

FIG. 14 cont'd

Exemplary Plasmid Backbone 1 – Left ITR:
CCTGCAGGCAGCTGCGCGCTCGCTCGCTCACTGAGGCCGCCCGGGCGTCGGGCGACCTT
TGGTCGCCCGGCCTCAGTGAGCGAGCGAGCGCGCAGAGAGGGAGTGGCCAACTCCATCA
CTAGGGGTTCCT (SEQ ID NO: 55)

Exemplary Plasmid Backbone 1 – Right ITR:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCT (SEQ ID NO: 56)

Exemplary Plasmid Backbone 2 – Left ITR:
CATGTCCTGCAGGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAGGG
AGTGGCCAACTCCATCACTAGGGGTTCCT (SEQ ID NO: 57)

Exemplary Plasmid Backbone 2 – Right ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGCTGCCTGCAGGGGCGCCTG (SEQ ID NO: 58)

PHP.eB capsid:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQS<u>DGTLAVPFK</u>AQAQTGWVQNQGILPGMVWQDRDV
YLQGPIWAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLTRNL
(SEQ ID NO: 59)

AAV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE

FIG. 14 cont'd

WELQKENSKRWNPEIQYTSNYYKSNNVEFAVNTEGVYSEPRPIGTRYLTRNL (SEQ ID NO: 60)

tet-Transactivator version 2 (tTA2):
ATGTCTAGACTGGACAAGAGCAAAGTCATAAACTCTGCTCTGGAATTACTCAATGAAGTCG
GTATCGAAGGCCTGACGACAAGGAAACTCGCTCAAAAGCTGGGAGTTGAGCAGCCTACCC
TGTACTGGCACGTGAAGAACAAGCGGGCCCTGCTCGATGCCCTGGCAATCGAGATGCTGG
ACAGGCATCATACCCACTTCTGCCCCCTGGAAGGCGAGTCATGGCAAGACTTTCTGCGGA
ACAACGCCAAGTCATTCCGCTGTGCTCTCCTCTCACATCGCGACGGGGCTAAAGTGCATCT
CGGCACCCGCCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGGCCACTTTAC
ACTGGGCTGCGTATTGGAGGATCAGGAGCATCAAGTAGCAAAGAGGAAAGAGAGACACC
TACCACCGATTCTATGCCCCCACTTCTGAGACAAGCAATTGAGCTGTTCGACCATCAGGGA
GCCGAACCTGCCTTCCTTTTCGGCCTGGAACTAATCATATGTGGCCTGGAGAAACAGCTAA
AGTGCGAAAGCGGCGGGCCGGCCGACGCCCTTGACGATTTTGACTTAGACATGCTCCCAG
CCGATGCCCTTGACGACTTTGACCTTGATATGCTGCCTGCTGACGCTCTTGACGATTTTGA
CCTTGACATGCTCCCCGGGTAA (SEQ ID NO: 61)

GTPase HRas [Homo sapiens]:
MTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHQYREQIKRVKDSDDVPMVLVGNKCDLAARTVESR
QAQDLARSYGIPYIETSAKTRQGVEDAFYTLVREIRQHKLRKLNPPDESGPGCMSCKCVLS
(SEQ ID NO: 62)

Substance P is position 58-68 of Protachykinin-1 [Homo sapiens]:
RPKPQQFFGLM (SEQ ID NO: 63)

Oxytocin is position 20-28 of Oxytocin-neurophysin 1 [Homo sapiens]:
CYIQNCPLG (SEQ ID NO: 64)

GCaMP6m:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC

FIG. 14 cont'd

GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAGGGA
GCTACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 65)

GCaMP6s:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCCACATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 66)

GCaMP6f:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG

FIG. 14 cont'd

AGTACAACCTGCCGGACCAACTGACTGAAGAGCAGATCGCAGAATTTAAAGAGGAATTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 67)

CN1917 (length between ITRs: 2495 bp):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTACTATTC
CAGCCACGAGGTATAAACACTGGGAAGGAAAGTCCTGGCTCTGTATTGTCCACAAAGACC
CGAAGCTGCAGCAAAGTTGGCAAAAGAGAAACAAAAGAGCAGAGAAGGCTCAGCTTTCA
ACAGCTAGGCTCACCCAAACATCAAGAGGTGGACAAATATTTACAGTGTGAACCTTAACCC
AAAGAACGGCAGTGCGGTCATGCTGCACAGAGTCAACTTCAGAACCAAGACTGTGACCAG
GGCTGGAGCAAGAGACACTTCACGCTAATAAATAGGCCACTTAATCAAGAAGCTGTCACAG
TCCTAAATATGTATGCACCGAGCATTAGCACTTCCAAGTAGAGTGGAACAGCTAAAGATAG
AGGCAAGAAGCAAGCAGACAAATCTTCGGTGATTGTTGGAAATCACAGCATTTCTCTCAGC
AATTGTCAGGACACAGAAAATCAGCGAGAAGACAGAAGAGTCTCACAATAGTCCCCATCAA
CTTGACCTAATTGACATTTATGGAGCTTGGCATCCAACAGCCGTGGAGCGCATGCGCTCTT
TAAGGCAGAATACAGACCATCAAACAAAACCAGGGAGACCAAAGTCACAGAAAATATGCTC
TGTGAACATGACATAATAAAGTGGAAATCGATAACAGAGAGATCGCTGCAAAATCCCCCAA
GTGATTGGTAATTAAATGCTCTACTCCTGAATGAATGATGGGCGAGAAAGGAAAGCCACGG
GGGAAAGCAGATTTCTGCGTTGAAAGAGCATGGAGACAGACTTCGTCAAGATGAGAGAGC
ACGTGGGGCTGGAGGGATGGCTCAGCACTTCAGAGGCACTCACGCTCTTCCATAGGACCT
AGGTTCACTTCTCAGCACACACATGGCAACTCACACCTGTGATGCAGAGAAGAGCTCGATT
CAGCCGGGAGCTTAGGGAGGGGAGGTCACTTCATAAGGGCTTGGGGGGGGAGTTGGAGC
CACGAGTCGTCCAGCCGGAGCCCCGTGTGGCTGTGCTCCGGCCTCAGAAGCATCCCCGG
ATCCAGATCTTTCGAAGCTAGCGCTACCGGTCGCCACCATGGTGAGCAAGGGCGAGGAGC
TGTTCACCGGGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGACCCTGAAGCT
GATCTGCACCACCGGCAAGCTGCCCGTGCCCTGGCCCACCCTCGTGACCACCCTGGGCT
ACGGCGTGCAGTGCTTCGCCCGCTACCCCGACCACATGAAGCAGCACGACTTCTTCAAGT
CCGCCATGCCCGAAGGCTACGTCCAGGAGCGCACCATCTTCTTCAAGGACGACGGCAACT
ACAAGACCCGCGCCGAGGTGAAGTTCGAGGGCGACACCCTGGTGAACCGCATCGAGCTG
AAGGGCATCGACTTCAAGGAGGACGGCAACATCCTGGGGCACAAGCTGGAGTACAACTAC
AACAGCCACAACGTCTATATCACCGCCGACAAGCAGAAGAACGGCATCAAGGCCAACTTC
AAGATCCGCCACAACATCGAGGACGGCGGCGTGCAGCTCGCCGACCACTACCAGCAGAA
CACCCCCATCGGCGACGGCCCCGTGCTGCTGCCCGACAACCACTACCTGAGCTACCAGT
CCAAGCTGAGCAAAGACCCCAACGAGAAGCGCGATCACATGGTCCTGCTGGAGTTCGTGA
CCGCCGCCGGGATCACTCTCGGCATGGACGAGCTGTACAAGTAAGTCGACGGCGCGCCG
CGGCCGCGAATTCGATATCATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTAGTTCTTGC
CACGGCGGAACTCATCGCCGCCTGCCTTGCCCGCTGCTGGACAGGGGCTCGGCTGTTGG
GCACTGACAATTCCGTGGCTCGAGAGATCTTCGACTGTGCCTTCTAGTTGCCAGCCATCTG

FIG. 14 cont'd

TTGTTTGCCCCTCCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGAGATCTC
ACGTGCGGACCGAGCGGCCGC (SEQ ID NO: 68)

CN2047 (length between ITRs: 1986 bp):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTTCCTTCT
CAGAACCTAGGTAAGGTAAGTTCCTTTCAAGGCTGGCTATATAAATAATCATCTCAGTTAGG
ATGCTTGGTGGGACCAAAGAACCAAAACTGCCGAGCAGGCATGATCTGACTTGGAGTGGT
TCCAGGACCTTCCTGTGAATGCTGGAGTCATTCAGTGTAGAGCTCTCCTCTGTGACTGGGT
CAAGGTTGCCCCACTGTAAACCCAGGGAAGCTAGCCCAGCCTTCCTCTCAGGGAATGTGT
ATGCTTCCCTTACACCTGACCCTGGCACAGACCTGGTGGTTGTTTTTCAGAAGCATCAGTG
TCTTTGCCTTAGGCATTTGTCCTCAAAGGGCAGCGACACTGTCTACTGACTGCTTTGTACA
GGGTAACTGCTTAACTAATTCTTAAGGAGCTCGATTCAGCCGGGAGCTTAGGGAGGGGAG
GTCACTTCATAAGGGCTTGGGGGGGGAGTTGGAGCCACGAGTCGTCCAGCCGGAGCCCC
GTGTGGCTGTGCTCCGGCCTCAGAAGCATCCCCGGATCCAGATCTTTCGAAGCTAGCGCT
ACCGGTCGCCACCATGGTGAGCAAGGGCGAGGAGCTGTTCACCGGGGTGGTGCCCATCC
TGGTCGAGCTGGACGGCGACGTAAACGGCCACAAGTTCAGCGTGTCCGGCGAGGGCGAG
GGCGATGCCACCTACGGCAAGCTGACCCTGAAGCTGATCTGCACCACCGGCAAGCTGCC
CGTGCCCTGGCCCACCCTCGTGACCACCCTGGGCTACGGCGTGCAGTGCTTCGCCCGCT
ACCCCGACCACATGAAGCAGCACGACTTCTTCAAGTCCGCCATGCCCGAAGGCTACGTCC
AGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCACC
GCCGACAAGCAGAAGAACGGCATCAAGGCCAACTTCAAGATCCGCCACAACATCGAGGAC
GGCGGCGTGCAGCTCGCCGACCACTACCAGCAGAACACCCCCATCGGCGACGGCCCCGT
GCTGCTGCCCGACAACCACTACCTGAGCTACCAGTCCAAGCTGAGCAAAGACCCCAACGA
GAAGCGCGATCACATGGTCCTGCTGGAGTTCGTGACCGCCGCCGGGATCACTCTCGGCAT
GGACGAGCTGTACAAGTAAGTCGACGGCGCGCCGCGGCCGCGAATTCGATATCATAATCA
ACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCA
TTTTCTCCTCCTTGTATAAATCCTGGTTAGTTCTTGCCACGGCGGAACTCATCGCCGCCTG
CCTTGCCCGCTGCTGGACAGGGGCTCGGCTGTTGGGCACTGACAATTCCGTGGCTCGAG
AGATCTTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGG
GGGAGGATTGGGAAGACAATAGCAGGCATGAGATCTCACGTGCGGACCGAGCGGCCGC
(SEQ ID NO: 69)

CN2048 (length between ITRs: 1927 bp):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTAAATGGA
GACTGCCAAGGGCTGAAACGGGGGTGCGGGAACCAGGGACCGAGCCCCCCCCCTCCCCA
CATGAGAATCTGTCACATTGCTGCTCCAGTGGCCTGAAAGACCAGCACAGCCCCAGCTGG
AGCCTCTCCCCTCTGGATCTTGTCAATGTGGCTTTGCTTTGCTGCTTGGGCAGCCGGGAGT

FIG. 14 cont'd

GGTGACAAGCAGGGAGAGAGCGCCCAAGGCATCTGGCTGTGCCACTCCAGCCTGACTGC
CAGCTCACCCATCAGTGCCCATCTCATCATCGAGAGGGACCCAGATGAGACCGGGGATCA
GCACTGTCCTTACCTTGAAGGGACGTGTCAGGAAGAGCTCGATTCAGCCGGGAGCTTAGG
GAGGGGAGGTCACTTCATAAGGGCTTGGGGGGGGAGTTGGAGCCACGAGTCGTCCAGCC
GGAGCCCCGTGTGGCTGTGCTCCGGCCTCAGAAGCATCCCCGGATCCAGATCTTTCGAAG
CTAGCGCTACCGGTCGCCACCATGGTGAGCAAGGGCGAGGAGCTGTTCACCGGGGTGGT
GCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGCTGATCTGCACCACCGGC
AAGCTGCCCGTGCCCTGGCCCACCCTCGTGACCACCCTGGGCTACGGCGTGCAGTGCTT
CGCCCGCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGCGCCGA
GGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTA
TATCACCGCCGACAAGCAGAAGAACGGCATCAAGGCCAACTTCAAGATCCGCCACAACAT
CGAGGACGGCGGCGTGCAGCTCGCCGACCACTACCAGCAGAACACCCCCATCGGCGACG
GCCCCGTGCTGCTGCCCGACAACCACTACCTGAGCTACCAGTCCAAGCTGAGCAAAGACC
CCAACGAGAAGCGCGATCACATGGTCCTGCTGGAGTTCGTGACCGCCGCCGGGATCACT
CTCGGCATGGACGAGCTGTACAAGTAAGTCGACGGCGCGCCGCGGCCGCGAATTCGATA
TCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTA
TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGAGATCTTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGAGATCTCACGTGCGGACCGAGC
GGCCGC (SEQ ID NO: 70)

CN2049 (length between ITRs: 1996 bp):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTTCTGCTT
TCTCTTCCCTTGGCCTCCTGCTGGGATAGAAGGGGGTTGGTGTGAGTGTGTATGGTGGGGT
GCTGTGAGATTAATTAGCAGCCGTGCCAGGCAGCAGGCGGTGGGGTGCAGAGTAGGCTG
GCTTTCCCTGCTATAGATCCATGCTCTCTGGGAGAGGCACTAGCCGGCTGCTTTGGGCTC
TGGCTCAGCTATTTTAGGAATATTCTTAACCCTTCCAGAACCGCTGCCATTGCCAGATCTCT
CTCCCAGAACACAGGCCAGCTCCAGATTGCCCCTCCTTTCTGCCCCCGCCCTGCACCCCA
CCTAGCCTCTGCTCTTCCTCCCTACAAGTTGAGAAGGTCAAGGTTTGACTTTTACCAAAGAA
AACTCCTGGCTCCTGATCCCACTCTCTGTGCTTTACCTGAGCTCGATTCAGCCGGGAGCTT
AGGGAGGGGAGGTCACTTCATAAGGGCTTGGGGGGGGAGTTGGAGCCACGAGTCGTCCA
GCCGGAGCCCCGTGTGGCTGTGCTCCGGCCTCAGAAGCATCCCCGGATCCAGATCTTTC
GAAGCTAGCGCTACCGGTCGCCACCATGGTGAGCAAGGGCGAGGAGCTGTTCACCGGGG
TGGTGCCCATCCTGGTCGAGCTGGACGGCGACGTAAACGGCCACAAGTTCAGCGTGTCC
GGCGAGGGCGAGGGCGATGCCACCTACGGCAAGCTGACCCTGAAGCTGATCTGCACCAC
CGGCAAGCTGCCCGTGCCCTGGCCCACCCTCGTGACCACCCTGGGCTACGGCGTGCAGT
GCTTCGCCCGCTACCCCGACCACATGAAGCAGCACGACTTCTTCAAGTCCGCCATGCCCG
AAGGCTACGTCCAGGAGCGCACCATCTTCTTCAAGGACGACGGCAACTACAAGACCCGCG
CCGAGGTGAAGTTCGAGGGCGACACCCTGGTGAACCGCATCGAGCTGAAGGGCATCGAC

FIG. 14 cont'd

TTCAAGGAGGACGGCAACATCCTGGGGCACAAGCTGGAGTACAACTACAACAGCCACAAC
GTCTATATCACCGCCGACAAGCAGAAGAACGGCATCAAGGCCAACTTCAAGATCCGCCAC
AACATCGAGGACGGCGGCGTGCAGCTCGCCGACCACTACCAGCAGAACACCCCCATCGG
CGACGGCCCCGTGCTGCTGCCCGACAACCACTACCTGAGCTACCAGTCCAAGCTGAGCAA
AGACCCCAACGAGAAGCGCGATCACATGGTCCTGCTGGAGTTCGTGACCGCCGCCGGGA
TCACTCTCGGCATGGACGAGCTGTACAAGTAAGTCGACGGCGCGCCGCGGCCGCGAATT
CGATATCATAATCAACCTCTGGATTACAAAATTTGTGAAAGATTGACTGGTATTCTTAACTAT
GTTGCTCCTTTTACGCTATGTGGATACGCTGCTTAATGCCTTTGTATCATGCTATTGCTTC
CCGTATGGCTTTCATTTTCTCCTCCTTGTATAAATCCTGGTTAGTTCTTGCCACGGCGGAAC
TCATCGCCGCCTGCCTTGCCCGCTGCTGGACAGGGGCTCGGCTGTTGGGCACTGACAATT
CCGTGGCTCGAGAGATCTTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGAGATCTCACGTGCGGACC
GAGCGGCCGC (SEQ ID NO: 71)

CN2427 (length between ITRs: 2071 bp):
GCGGCCGCACGCGTGGGATGCGATGCAGTGGCATGGTAAAAATGCCGTACCTAATGATGC
AGTTTCAGCCATCATGACGTATGGATGGAATGAAAAGATGACAAAGCTACTAGCGGATCTG
TTCACAAAGGAAAAGAGGCTCAGTTTCCAACAGTCTCTGGCATTTCATCTTTGGAAAACTTG
TCAAAGCTAAGATGATTTGTGAGAGTCCTAACTCATTTTCCTAAATATGAAGTCGCTATTAT
GGATAAAGAAAGGTTACAATGGAGCATCCATTTCCACTCTAGTCATTCTGCTTGATTGCACC
AATTAGCCCTGCATTCACTGTGCATTTTAACTTCATAATGGTCTATTATTTGGACCACTGAC
CATAATGATGCAATTCTTTCCTTGACGAAAATAAATGCTTAGTGATAAATAAGTAATCATAAT
TAAAGCTTTCATAGTACTTATAGTACCACAATTGGTATTTAGCCCATTGATTATAATTTAAAC
ACATTTTAATTAATATGTAACTATATTACTTCCCTATTTTTCTTTTCTTTCCTCCAAAATGCCT
CATGTCTCCTTCTATCAACACCCCCCATACCCCCCAGACACTCCTTGTCAAATTGATGGCC
TTTTAAAATTATTATTATTGTAACATGAAGAAATAGTTGAACAAATATATAAATACAGTACAAT
GAGTCTGTTTATGGTGGCTCCTATGGGTATGATTTGGGGGCCTGAGCTCGGGCTGGGCAT
AAAAGTCAGGGCAGAGCCATCTATTGCTTACATTTGCTTCTGGGATCCAGATCTTTCGAAG
CTAGCGCTACCGGTCGCCACCATGGTGAGCAAGGGCGAGGAGCTGTTCACCGGGGTGGT
GCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGCTGATCTGCACCACCGGC
AAGCTGCCCGTGCCCTGGCCCACCCTCGTGACCACCCTGGGCTACGGCGTGCAGTGCTT
CGCCCGCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGCGCCGA
GGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTA
TATCACCGCCGACAAGCAGAAGAACGGCATCAAGGCCAACTTCAAGATCCGCCACAACAT
CGAGGACGGCGGCGTGCAGCTCGCCGACCACTACCAGCAGAACACCCCCATCGGCGACG
GCCCCGTGCTGCTGCCCGACAACCACTACCTGAGCTACCAGTCCAAGCTGAGCAAAGACC
CCAACGAGAAGCGCGATCACATGGTCCTGCTGGAGTTCGTGACCGCCGCCGGGATCACT
CTCGGCATGGACGAGCTGTACAAGTAAGTCGACGGCGCGCCGCGGCCGCGAATTCGATA
TCATAATCAACCTCTGGATTACAAAATTTGTGAAAGATTGACTGGTATTCTTAACTATGTTGC
TCCTTTTACGCTATGTGGATACGCTGCTTAATGCCTTTGTATCATGCTATTGCTTCCCGTA
TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGAGATCTTCGACTGTGCCTTCTAGTTGCCAGCCATCTGTTGTTTGCCCCTCCCC

FIG. 14 cont'd

CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGAGATCTCACGTGCGGACCGAGC
GGCCGC (SEQ ID NO: 72)

CN2320 (length between ITRs: 1985 bp):
GCGGCCGCACGCGTTATCTTAGAGTGGGAAGATTTGAGAAGTGCCATGGTTAATATGACT
GACTTTTTATTCTTATTTCTTTTAATTTCATGGTTCTAAATCCGAATTTAATCATAGTACCCAG
AAAAGCAGAGGTGTAGAGGTTCACAGTGGGAGTTGTAATCTAGCCCTATTCATTTTGACCT
CAAAACCCAAATTATTTATAACAAATTATTTCCTATTCTTTCCTTCACTATTCAGGAACATCTG
TCCACCACTTACATGATCACTTATCTTGCTATTGTGTCATTTTGATGAAAAGAATTTTTTCT
AAATATCTAAATACAAGGCCCCATATTAACAGTGCTTTTTAAATCCCCACAGATGTGGGAGA
TGACCCCTTTCCATCCCTGAAGATTGTAATTGGGCCAGTCTTTAGTACAGTTTGTTCCAATA
AAGAGATACAATTTTATTCATTAATTTGTGTATTCATTTAGCAAATCACTTTAGAGTCTTATTA
TATCAGGATTTTGGGGTCTATTTTAGTATATCTTTTTGTATTTCTTGGAACCTCTCCAATTATT
CTAGACTCTTTCAAAGGTTGGTGATCAATATTAGACATTATTATGAAAAGAATCTTACTTGCT
AAAAGGGTTAGATGGAGCTCGGGCTGGGCATAAAAGTCAGGGCAGAGCCATCTATTGCTT
ACATTTGCTTCTGGGATCCAGATCTTTCGAAGCTAGCGCTACCGGTCGCCACCATGGTGAG
CAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAG
CTGACCCTGAAGCTGATCTGCACCACCGGCAAGCTGCCCGTGCCCTGGCCCACCCTCGT
GACCACCCTGGGCTACGGCGTGCAGTGCTTCGCCCGCTACCCCGACCACATGAAGCAGC
ACGACTTCTTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACCCTGGTGA
ACCGCATCGAGCTGAAGGGCATCGACTTCAAGGAGGACGGCAACATCCTGGGGCACAAG
CTGGAGTACAACTACAACAGCCACAACGTCTATATCACCGCCGACAAGCAGAAGAACGGC
ATCAAGGCCAACTTCAAGATCCGCCACAACATCGAGGACGGCGGCGTGCAGCTCGCCGA
CCACTACCAGCAGAACACCCCCATCGGCGACGGCCCCGTGCTGCTGCCCGACAACCACT
ACCTGAGCTACCAGTCCAAGCTGAGCAAAGACCCCAACGAGAAGCGCGATCACATGGTCC
TGCTGGAGTTCGTGACCGCCGCCGGGATCACTCTCGGCATGGACGAGCTGTACAAGTAAG
TCGACGGCGCGCCGCGGCCGCGAATTCGATATCATAATCAACCTCTGGATTACAAAATTTG
TGAAAGATTGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTTGTATAAAT
CCTGGTTAGTTCTTGCCACGGCGGAACTCATCGCCGCCTGCCTTGCCCGCTGCTGGACAG
GGGCTCGGCTGTTGGGCACTGACAATTCCGTGGCTCGAGAGATCTTCGACTGTGCCTTCT
AGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATA
GCAGGCATGAGATCTCACGTGCGGACCGAGCGGCCGC (SEQ ID NO: 73)

CN2321 (length between ITRs: 1844 bp):
GCGGCCGCACGCGTTATGATGTGCCAGGCTTGGGAGAAACACCACAAGCAAAGCCAAAAT
AGGTGGCCTAGAACTTCCAGCTTGAAATATGGGAGAGAATGAGGGAGGCACTGTAGAGCA
GCTGCCGGGTGCCGCATGAGAACAATTCTCCCTGCTCATAATTAATCCTACCTATTTCTGAT
GACAGCTGGCTCTTCACTTTGAACAAGCTAGTTAACAACTTTCTTCTCACATTGAGCAAATA
ATTCATATTTAATTACTTAACCACCAGTTACAAAATGAGAATCATCAAGGAATCACAATTAAT
TTGCTATTGACAAACTCATACTTTTAGCAGGCTGATTTCTACTTTATACTTAGATTGGTAATG
AAAAATGAAGCTTATTTTAGTTGATTGGTTGGACTTGTGTATGAATATTATCTATTATTTGAA

FIG. 14 cont'd

AAGCCAAACTTGAATGCAAAAAAATATTGAATATGAAAAGAAAAACATTTGCAGTAAAGCTT
GTTCTGAGCTCGGGCTGGGCATAAAAGTCAGGGCAGAGCCATCTATTGCTTACATTTGCTT
CTGGGATCCAGATCTTTCGAAGCTAGCGCTACCGGTCGCCACCATGGTGAGCAAGGGCGA
GGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTG
AAGCTGATCTGCACCACCGGCAAGCTGCCCGTGCCCTGGCCCACCCTCGTGACCACCCT
GGGCTACGGCGTGCAGTGCTTCGCCCGCTACCCCGACCACATGAAGCAGCACGACTTCTT
CAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTAC
AACTACAACAGCCACAACGTCTATATCACCGCCGACAAGCAGAAGAACGGCATCAAGGCC
AACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGC (SEQ ID NO: 74)

CN2719 (length between ITRs: 2346 bp):
GCGGCCGCACGCGTAAAGCTACATCTCTGGGCTCCATTATTAAAGCTGCTTTCCTTCCTTT
CTCTCTCTCGCTCTCTCTCTCTCTCTTTCTTTCTTTCTTTTTCCTGAGATGGGTCTCAT
GTAGCCCAGGCTGGCCTCAAGCTTGCCACATAGCCAAGGAGCCAAGGATGGCATTGAACT
CCTAGATCCTCCAGCCTCTGCCTCCTGTTAGGATTAGAGGTGAGCTACAATCCCAAGGGC
CTTTAGTGTAACAGTCAAAAGCTACTGGGAGTCAGGCAATTGGCTCAGTATAACCCTGATT
CTCCTTTTGTGCCCAGGCACGTTGGTCAGGAGTCTGTCTTCAGCCTGTCATGGCAGCAGC
TCAGCTTCAGTGACCAATCTATACTCACTCACAGGAGACTCTGAAATCCCAGATTCTGTGCT
ATAAAGTCCCCGCTCGAGTGAGTCGTGACTGCTCCAAACAGCCTGGGCAGCTGCGAACCC
TCATGGCATCTAGGTGACCCTGTTCATCCTACAGCTGTTCTCACTGAGGGGAGGGGAGCT
TTTGAGTGAGCCAGTCAAAACTCTGTGCTCGGTGATCCTGTGAGGCTCGGAACGGTGGCA
CCCGAAGCCATGGGTGCACACACAAACAGGGCTCTAATCGGTGGGATCACAATCCATGAA
CAAGCATGAGACCTCCCTTCTTCTCACACACACACACACACACACACACACACACACACTC
ACTCACATACATGAGCTGGTTTCCACAACTGTGGGGTTAGCCTGGAAGGTGTCTGTCCTAT
ATAGTACTCCAGTACCAGTGTTGCAGACTCTAGGCCCAGGAAAAGGTTTTTGATGTTTGCT
GGTGTTTTTGATGACCTTCATCGTGGGTAGAGCAGGCTGCGCTGGTTCATAAAGAGAAGAC
AAGACCTAGAGTGCTGTGACCCTTTAAGGCATCATGGTGTGATGACCCCCAACCATAAAGT
TATTTTCGCTGCTGCTTTGTAACTGTAAGTGAGCTCGGGCTGGGCATAAAAGTCAGGGCAG
AGCCATCTATTGCTTACATTTGCTTCTGGGATCCAGATCTTTCGAAGCTAGCGCTACCGGT
CGCCACCATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGAT
GCCACCTACGGCAAGCTGACCCTGAAGCTGATCTGCACCACCGGCAAGCTGCCCGTGCC
CTGGCCCACCCTCGTGACCACCCTGGGCTACGGCGTGCAGTGCTTCGCCCGCTACCCCG

FIG. 14 cont'd

ACCACATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAAC
ATCCTGGGGCACAAGCTGGAGTACAACTACAACAGCCACAACGTCTATATCACCGCCGAC
AAGCAGAAGAACGGCATCAAGGCCAACTTCAAGATCCGCCACAACATCGAGGACGGCGGC
GTGCAGCTCGCCGACCACTACCAGCAGAACACCCCCATCGGCGACGGCCCCGTGCTGCT
GCCCGACAACCACTACCTGAGCTACCAGTCCAAGCTGAGCAAAGACCCCAACGAGAAGCG
CGATCACATGGTCCTGCTGGAGTTCGTGACCGCCGCCGGGATCACTCTCGGCATGGACGA
GCTGTACAAGTAAGTCGACGGCGCGCCGCGGCCGCGAATTCGATATCATAATCAACCTCT
GGATTACAAAATTTGTGAAAGATTGACTGGTATTCTTAACTATGTTGCTCCTTTTACGCTATG
TGGATACGCTGCTTTAATGCCTTTGTATCATGCTATTGCTTCCCGTATGGCTTTCATTTTCTC
CTCCTTGTATAAATCCTGGTTAGTTCTTGCCACGGCGGAACTCATCGCCGCCTGCCTTGCC
CGCTGCTGGACAGGGGCTCGGCTGTTGGGCACTGACAATTCCGTGGCTCGAGAGATCTTC
GACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGAT
TGGGAAGACAATAGCAGGCATGAGATCTCACGTGCGGACCGAGCGGCCGC (SEQ ID NO:
75)

CN2707 (length between ITRs: 1786 bp):
GCGGCCGCACGCGTTGAATCTTCATGGAGAAAACATCATGAATAGAGAATGAAGAAGTAAA
GATGAACAAGTGAGAATTCAGATCATCAGAGGGTTTTCTAGGATTTCTGTAAATTTCTCTGT
GTTTTGGAATGCAATAGGAATGCCAGCCCAAAGCCATATAGGTCACAGCTGCCCAAGAACA
GTTACCAATACAGTATAAATAACGTCCTAAACTTAGAATATTGTGAAATTCTTTTTATAACTC
AGCCATTTAATTCTTGAGTGTAAATTTTGTAGATGGAGTCATGTTGTAATGTTAGACACATTT
GCTAGTGATGTGACAACATAATATTCCCATGAACTGATGTCAAATGTTGTATTGTACTTTGA
CCAGGTATATAAGGTTTATTATCTTCTTGACCTTGGAGTAATTTCAGTCCCAACTTAAATCCC
TAGTGGTGAGCTCGGGCTGGGCATAAAAGTCAGGGCAGAGCCATCTATTGCTTACATTTG
CTTCTGGGATCCAGATCTTTCGAAGCTAGCGCTACCGGTCGCCACCATGGTGAGCAAGGG
CGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACC
CTGAAGCTGATCTGCACCACCGGCAAGCTGCCCGTGCCCTGGCCCACCCTCGTGACCAC
CCTGGGCTACGGCGTGCAGTGCTTCGCCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAG
TACAACTACAACAGCCACAACGTCTATATCACCGCCGACAAGCAGAAGAACGGCATCAAG
GCCAACTTCAAGATCCGCCACAACATCGAGGACGGCGGCGTGCAGCTCGCCGACCACTA
CCAGCAGAACACCCCCATCGGCGACGGCCCCGTGCTGCTGCCCGACAACCACTACCTGA
GCTACCAGTCCAAGCTGAGCAAAGACCCCAACGAGAAGCGCGATCACATGGTCCTGCTGG
AGTTCGTGACCGCCGCCGGGATCACTCTCGGCATGGACGAGCTGTACAAGTAAGTCGACG
GCGCGCCGCGGCCGCGAATTCGATATCATAATCAACCTCTGGATTACAAAATTTGTGAAAG
ATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGT
TAGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT

FIG. 14 cont'd

TCTGGGGGGTGGGGTGGGGCAGGACAGCAAGGGGGAGGATTGGGAAGACAATAGCAGG
CATGAGATCTCACGTGCGGACCGAGCGGCCGC (SEQ ID NO: 76)

CN2713 (length between ITRs: 1710 bp):
GCGGCCGCACGCGTTATGTAGATACAGGTCATAGAACTTGCCCTGGGGAATGGCTCCATT
TGGTACCAACAGGCTGACCCCTAGGGAGGAAGGAAGGCTATCAGCAAGAGGAGGAGGAG
GTAGCAGAGATGAGAAAGATGGGGTAGACTCTGGCTCCAACCTAGGGAAGGGAAAGACTC
TAGACTCGGGGGGTATGGGGGTGGATAGATACAGGGAGCACACAGGCTACTTGGCCTGGT
CTGCCCATGAATACAGGGGGCCTCTAACATTGCTGGGGTAGGAGGGTCAGAATGCTCCAG
TGCTAGCCCTCATGCTGGCTCAGGACAGGACTCTGAAAAGCCACCAGCTGCCACTTTCAC
AAGCTGAGGAGCTCGGGCTGGGCATAAAAGTCAGGGCAGAGCCATCTATTGCTTACATTT
GCTTCTGGGATCCAGATCTTTCGAAGCTAGCGCTACCGGTCGCCACCATGGTGAGCAAGG
GCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGAC
CCTGAAGCTGATCTGCACCACCGGCAAGCTGCCCGTGCCCTGGCCCACCCTCGTGACCA
CCCTGGGCTACGGCGTGCAGTGCTTCGCCCGCTACCCCGACCACATGAAGCAGCACGAC
TTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGTAAGTCGAC
GGCGCGCCGCGGCCGCGAATTCGATATCATAATCAACCTCTGGATTACAAAATTTGTGAAA
GATTGACTGGTATTCTTAACTATGTTGCTCCTTTTACGCTATGTGGATACGCTGCTTTAATG
CCTTTGTATCATGCTATTGCTTCCCGTATGGCTTTCATTTTCTCCTCCTTGTATAAATCCTGG
TTAGTTCTTGCCACGGCGGAACTCATCGCCGCCTGCCTTGCCCGCTGCTGGACAGGGGCT
CGGCTGTTGGGCACTGACAATTCCGTGGCTCGAGAGATCTTCGACTGTGCCTTCTAGTTG
CCAGCCATCTGTTGTTTGCCCCTCCCCCGTGCCTTCCTTGACCCTGGAAGGTGCCACTCC
CACTGTCCTTTCCTAATAAAATGAGGAAATTGCATCGCATTGTCTGAGTAGGTGTCATTCTA
TTCTGGGGGGTGGGGTGGGGCAGGACAGCAAGGGGGAGGATTGGGAAGACAATAGCAG
GCATGAGATCTCACGTGCGGACCGAGCGGCCGC (SEQ ID NO: 77)

CN2717 (length between ITRs: 1740 bp):
GCGGCCGCACGCGTAGTGACTTGGTGCTATGAGCCATATTTTGCTGTTGCTGTTGTTACTG
GTAGTTTTTGTAATTCTGGGGCTAAAACTTGGGGTCTGGTATGCTGTCATTTACCAGTGAG
CTATACCCTGGATATTATGATTTAGATGAATGTGAAATATCACCCCAGACATACATATACTAA
ACACTTGGCCCTTGGCCCATGATGCTAAATGGAGGAGATAGAAGCTTTTGGGGCACAGCC
TAGTGGAAGGAAATGAGGTCAAATGACATGTACTCTGAAAGGAATATGGGTATTCTGGGCT
TGCGTTATTCTCTCTCTCCCTCTCTCTCCCTCTCTCTCCCTCTCCCTCTCTCTTTCTCCTTTT
CTCTTTCTCTCCTCGCCTTGTTTCCAGAGCTCGGGCTGGGCATAAAAGTCAGGGCAGAGC
CATCTATTGCTTACATTTGCTTCTGGGATCCAGATCTTTCGAAGCTAGCGCTACCGGTCGC
CACCATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCGATGCC
ACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA

FIG. 14 cont'd

CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA
TCACATGGTCCTGCTGGAGTTCGTGACCGCCGCCGGGATCACTCTCGGCATGGACGAGCT
GTACAAGTAAGTCGACGGCGCGCCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGAGATCTCACGTGCGGACCGAGCGGCCGC (SEQ ID NO: 78)

AiP1104 (length between ITRs: 3455 bp):
GCGGCCGCACGCGTTCCAGCTACCACCAGCCTGTCCAAAAGGGGACACCAAAGGAGAGG
AGGAAGTCTGAGAGACACCTCTCTGCACCATGGCCATCTTAGTAGTCAGACCCAGAACAAA
ACTCTCTGATGAGTGTGCGGAGCGTCGCTTCTGGTCTTTGCTCAAACTATTCACTGAAGAT
TTAAAGCAATCCCGTGAGTGATACATTTGGGTGAATTTGTTCTCTAGAAGGTATCACAGAAA
TCTGGTCACTGGGCCACCCGAGACATCCTGATAGGCCCTCTGGTAACCCATCACATGCTG
CAGACTGACTCTGGGGGCCTAGAACCCAGATCAGAAGCAACCTTGACCCCGGCCCACCC
GCCACGGAAGCACCATCATCTCTCTGATTAAAAACCTCGATCACGGACCCGGGGGCGTGC
CCGGAAGAGCTAAGATAATCAGCGTCAGCACTTTGCCTTCGCCGTCCAAGACTGCAGACG
GCCTTCATTTGACCTGATTCGTGGTGTTAATGACAGCAGAGCAATTTTGAGAGGCAGCTTG
CTCTCGGCATCTATAAGGAGAGGAAAAGCACTGAGGGCTGGGGACCAAGCTCCTTGCAGA
GGCGGCAGCTGCAGTCACCCTCCCCCTCCACCCCTGCCCCTCCCCTCCCCTCCAGAGGC
ACTTTGAGTAAGTGCTGCCCTCCGATCTGCCCTGATACGATGGGAGAAAGCTGATGTGAG
GGCTGGAGCCAGAGTGTGCAAGGGGACAGTGTGTGCATGTGCGTGTGTCGGGGAGAGGT
ACCCGTGCTATACCTGAGAACATTGCTGGGTGAACACAGCCTTGGACCTGGAAGAGCGCA
TAGCTTACTTAGAGGCATGGGCTGCACATGAGCTGCCCATTTACCTGCTCATTTAGAAGCT
ACTATGAAGGCTGGTGAGATGGCTGAGCTCGGGCTGGGCATAAAAGTCAGGGCAGAGCC
ATCTATTGCTTACATTTGCTTCTGGCGTGGCCACCATGGCTCCTAAGAAGAAGAGGAAGGT
GATGAGCCAGTTCGACATCCTGTGCAAGACCCCCCCCAAGGTGCTGGTGCGGCAGTTCGT
GGAGAGATTCGAGAGGCCCAGCGGCGAGAAGATCGCCAGCTGTGCCGCCGAGCTGACCT
ACCTGTGCTGGATGATCACCCACAACGGCACCGCCATCAAGAGGGCCACCTTCATGAGCT
ACAACACCATCATCAGCAACAGCCTGAGCTTCGACATCGTGAACAAGAGCCTGCAGTTCAA
GTACAAGACCCAGAAGGCCACCATCCTGGAGGCCAGCCTGAAGAAGCTGATCCCCGCCT
GGGAGTTCACCATCATCCCTTACAACGGCCAGAAGCACCAGAGCGACATCACCGACATCG
TGTCCAGCCTGCAGCTGCAGTTCGAGAGCAGCGAGGAGGCCGACAAGGGCAACAGCCAC
AGCAAGAAGATGCTGAAGGCCCTGCTGTCCGAGGGCGAGAGCATCTGGGAGATCACCGA
GAAGATCCTGAACAGCTTCGAGTACACCAGCAGGTTCACCAAGACCAAGACCCTGTACCA
GTTCCTGTTCCTGGCCACATTCATCAACTGCGGCAGGTTCAGCGACATCAAGAACGTGGA
CCCCAAGAGCTTCAAGCTGGTGCAGAACAAGTACCTGGGCGTGATCATTCAGTGCCTGGT
GACCGAGACCAAGACAAGCGTGTCCAGGCACATCTACTTTTTCAGCGCCAGAGGCAGGAT
CGACCCCCTGGTGTACCTGGACGAGTTCCTGAGGAACAGCGAGCCCGTGCTGAAGAGAG

FIG. 14 cont'd

TGAACAGGACCGGCAACAGCAGCAGCAACAAGCAGGAGTACCAGCTGCTGAAGGACAAC
CTGGTGCGCAGCTACAACAAGGCCCTGAAGAAGAACGCCCCCTACCCCATCTTCGCTATC
AAGAACGGCCCTAAGAGCCACATCGGCAGGCACCTGATGACCAGCTTTCTGAGCATGAAG
GGCCTGACCGAGCTGACAAACGTGGTGGGCAACTGGAGCGACAAGAGGGCCTCCGCCGT
GGCCAGGACCACCTACACCCACCAGATCACCGCCATCCCCGACCACTACTTCGCCCTGGT
GTCCAGGTACTACGCCTACGACCCCATCAGCAAGGAGATGATCGCCCTGAAGGACGAGAC
CAACCCCATCGAGGAGTGGCAGCACATCGAGCAGCTGAAGGGCAGCGCCGAGGGCAGCA
TCAGATACCCCGCCTGGAACGGCATCATCAGCCAGGAGGTGCTGGACTACCTGAGCAGCT
ACATCAACAGGCGGATCTGAGAATTCGATATCAAGCTTATCGATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCCACCACCTGTC
AGCTCCTTTCCGGGACTTTCGCTTTCCCCCTCCCTATTGCCACGGCGGAACTCATCGCCG
CCTGCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTATGTTGCCACCTGGATTCTGCG
CGGGACGTCCTTCTGCTACGTCCCTTCGGCCCTCAATCCAGCGGACCTTCCTTCCCGCGG
CCTGCTGCCGGCTCTGCGGCCTCTTCCGCGTCTTCGCCTTCGCCCTCAGACGAGTCGGAT
CTCCCTTTGGGCCGCCTCCCCGCATCGATACCGAGCGCTGCTCGAGAGATCTACGGGTG
GCATCCCTGTGACCCCTCCCCAGTGCCTCTCCTGGCCCTGGAAGTTGCCACTCCAGTGCC
CACCAGCCTTGTCCTAATAAAATTAAGTTGCATCATTTTGTCTGACTAGGTGTCCTTCTATAA
TATTATGGGGTGGAGGGGGGTGGTATGGAGCAAGGGGCAAGTTGGGAAGACAACCTGTA
GGGCCTGCGGGGTCTATTGGGAACCAAGCTGGAGTGCAGTGGCACAATCTTGGCTCACTG
CAATCTCCGCCTCCTGGGTTCAAGCGATTCTCCTGCCTCAGCCTCCCGAGTTGTTGGGATT
CCAGGCATGCATGACCAGGCTCAGCTAATTTTTGTTTTTTTGGTAGAGACGGGGTTTCACC
ATATTGGCCAGGCTGGTCTCCAACTCCTAATCTCAGGTGATCTACCCACCTTGGCCTCCCA
AATTGCTGGGATTACAGGCGTGAACCACTGCTCCCTTCCCTGTCCTTCTGATTTTGTAGGT
AACCACGTGCGGACCGAGCGGCCGC (SEQ ID NO: 79)

AiP1089 (length between ITRs: 3450 bp):
GCGGCCGCACGCGTACTATTCCAGCCACGAGGTATAAACACTGGGAAGGAAAGTCCTGGC
TCTGTATTGTCCACAAAGACCCGAAGCTGCAGCAAAGTTGGCAAAAGAGAAACAAAAAGAG
CAGAGAAGGCTCAGCTTTCAACAGCTAGGCTCACCCAAACATCAAGAGGTGGACAAATATT
TACAGTGTGAACCTTAACCCAAAGAACGGCAGTGCGGTCATGCTGCACAGAGTCAACTTCA
GAACCAAGACTGTGACCAGGGCTGGAGCAAGAGACACTTCACGCTAATAAATAGGCCACT
TAATCAAGAAGCTGTCACAGTCCTAAATATGTATGCACCGAGCATTAGCACTTCCAAGTAGA
GTGGAACAGCTAAAGATAGAGGCAAGAAGCAAGCAGACAAATCTTCGGTGATTGTTGGAAA
TCACAGCATTTCTCTCAGCAATTGTCAGGACACAGAAAATCAGCGAGAAGACAGAAGAGTC
TCACAATAGTCCCCATCAACTTGACCTAATTGACATTTATGGAGCTTGGCATCCAACAGCC
GTGGAGCGCATGCGCTCTTTAAGGCAGAATACAGACCATCAAACAAAACCAGGGAGACCA
AAGTCACAGAAAATATGCTCTGTGAACATGACATAATAAAGTGGAAATCGATAACAGAGAG
ATCGCTGCAAAATCCCCCAAGTGATTGGTAATTAAATGCTCTACTCCTGAATGAATGATGG
GCGAGAAAGGAAAGCCACGGGGGAAAGCAGATTTCTGCGTTGAAAGAGCATGGAGACAG
ACTTCGTCAAGATGAGAGAGCACGTGGGGCTGGAGGGATGGCTCAGCACTTCAGAGGCA
CTCACGCTCTTCCATAGGACCTAGGTTCACTTCTCAGCACACACATGGCAACTCACACCTG
TGATGCAGAGAAGAGCTCGGGCTGGGCATAAAGTCAGGGCAGAGCCATCTATTGCTTAC
ATTTGCTTCTGGCGTGGCCACCATGGCTCCTAAGAAGAAGAGGAAGGTGATGAGCCAGTT
CGACATCCTGTGCAAGACCCCCCCCAAGGTGCTGGTGCGGCAGTTCGTGGAGAGATTCGA

FIG. 14 cont'd

GAGGCCCAGCGGCGAGAAGATCGCCAGCTGTGCCGCCGAGCTGACCTACCTGTGCTGGA
TGATCACCCACAACGGCACCGCCATCAAGAGGGCCACCTTCATGAGCTACAACACCATCA
TCAGCAACAGCCTGAGCTTCGACATCGTGAACAAGAGCCTGCAGTTCAAGTACAAGACCC
AGAAGGCCACCATCCTGGAGGCCAGCCTGAAGAAGCTGATCCCCGCCTGGGAGTTCACC
ATCATCCCTTACAACGGCCAGAAGCACCAGAGCGACATCACCGACATCGTGTCCAGCCTG
CAGCTGCAGTTCGAGAGCAGCGAGGAGGCCGACAAGGGCAACAGCCACAGCAAGAAGAT
GCTGAAGGCCCTGCTGTCCGAGGGCGAGAGCATCTGGGAGATCACCGAGAAGATCCTGA
ACAGCTTCGAGTACACCAGCAGGTTCACCAAGACCAAGACCCTGTACCAGTTCCTGTTCCT
GGCCACATTCATCAACTGCGGCAGGTTCAGCGACATCAAGAACGTGGACCCCAAGAGCTT
CAAGCTGGTGCAGAACAAGTACCTGGGCGTGATCATTCAGTGCCTGGTGACCGAGACCAA
GACAAGCGTGTCCAGGCACATCTACTTTTTCAGCGCCAGAGGCAGGATCGACCCCCTGGT
GTACCTGGACGAGTTCCTGAGGAACAGCGAGCCCGTGCTGAAGAGAGTGAACAGGACCG
GCAACAGCAGCAGCAACAAGCAGGAGTACCAGCTGCTGAAGGACAACCTGGTGCGCAGC
TACAACAAGGCCCTGAAGAAGAACGCCCCCTACCCCATCTTCGCTATCAAGAACGGCCCT
AAGAGCCACATCGGCAGGCACCTGATGACCAGCTTTCTGAGCATGAAGGGCCTGACCGAG
CTGACAAACGTGGTGGGCAACTGGAGCGACAAGAGGGCCTCCGCCGTGGCCAGGACCAC
CTACACCCACCAGATCACCGCCATCCCCGACCACTACTTCGCCCTGGTGTCCAGGTACTA
CGCCTACGACCCCATCAGCAAGGAGATGATCGCCCTGAAGGACGAGACCAACCCCATCGA
GGAGTGGCAGCACATCGAGCAGCTGAAGGGCAGCGCCGAGGGCAGCATCAGATACCCCG
CCTGGAACGGCATCATCAGCCAGGAGGTGCTGGACTACCTGAGCAGCTACATCAACAGGC
GGATCTGAGAATTCGATATCAAGCTTATCGATAATCAACCTCTGGATTACAAAATTTGTGAA
AGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCAC
TGTGTTTGCTGACGCAACCCCCACTGGTTGGGGCATTGCCACCACCTGTCAGCTCCTTTCC
GGGACTTTCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTCGGGGAA
ATCATCGTCCTTTCCTTGGCTGCTCGCCTATGTTGCCACCTGGATTCTGCGCGGGACGTCC
TTCTGCTACGTCCCTTCGGCCCTCAATCCAGCGGACCTTCCTTCCCGCGGCCTGCTGCCG
GCTCTGCGGCCTCTTCCGCGTCTTCGCCTTCGCCCTCAGACGAGTCGGATCTCCCTTTGG
GCCGCCTCCCCGCATCGATACCGAGCGCTGCTCGAGAGATCTACGGGTGGCATCCCTGT
GACCCCTCCCCAGTGCCTCTCCTGGCCCTGGAAGTTGCCACTCCAGTGCCCACCAGCCTT
GTCCTAATAAAATTAAGTTGCATCATTTTGTCTGACTAGGTGTCCTTCTATAATATTATGGGG
TGGAGGGGGGTGGTATGGAGCAAGGGGCAAGTTGGGAAGACAACCTGTAGGGCCTGCGG
GGTCTATTGGGAACCAAGCTGGAGTGCAGTGGCACAATCTTGGCTCACTGCAATCTCCGC
CTCCTGGGTTCAAGCGATTCTCCTGCCTCAGCCTCCCGAGTTGTTGGGATTCCAGGCATG
CATGACCAGGCTCAGCTAATTTTTGTTTTTTTGGTAGAGACGGGGTTTCACCATATTGGCCA
GGCTGGTCTCCAACTCCTAATCTCAGGTGATCTACCCACCTTGGCCTCCCAAATTGCTGGG
ATTACAGGCGTGAACCACTGCTCCCTTCCCTGTCCTTCTGATTTTGTAGGTAACCACGTGC
GGACCGAGCGGCCGC (SEQ ID NO: 80)

AiP1105 (length between ITRs: 3024 bp):
GCGGCCGCACGCGTACCAGAAGTTCAGTGAGCAGAAGATGGGCTAAAATGAAAAGGGTAC
TGTCTTGAACTGAAGATGGAATCCTGCAGCTTCATTCTGGCCAAAAGAAGATCTATTCCCA
GGAGGAGGGTAAAGGCTTTGTTCTTAAGAGATGCTGAGGCTGGCCCTGTGAATCTGATGT
CAAGATGTCCCTTGTCACTCTGCAGAAGCGTATGTCTCTTGCATTTCCTTCTTATTTCCTTG
GGTGAAATTGCTGTGGCATTGTGTCACTCATCCTAATGGGTCATGTCTAACATCTGCGTGC
TTACAAATCAGGCATGCTCATTTCTGGGCTTATGGAGCTTGTATAACACCAGGACAGGCAA

FIG. 14 cont'd

GACATGTTGCCCACTCAGGAAGAATAGAAGCTGGGCACAGCTGGAGTGCAAAGTAGGTCA
GTTCAGAGAGCAAAGGGAGTTGATGGAGCAATGAGTTGTTAGTGGGAAAGTTCTAACCAAC
TGTCCCAGAGAGCTCGGGCTGGGCATAAAAGTCAGGGCAGAGCCATCTATTGCTTACATTT
GCTTCTGGCGTGGCCACCATGGCTCCTAAGAAGAAGAGGAAGGTGATGAGCCAGTTCGAC
ATCCTGTGCAAGACCCCCCCCAAGGTGCTGGTGCGGCAGTTCGTGGAGAGATTCGAGAG
GCCCAGCGGCGAGAAGATCGCCAGCTGTGCCGCCGAGCTGACCTACCTGTGCTGGATGA
TCACCCACAACGGCACCGCCATCAAGAGGGCCACCTTCATGAGCTACAACACCATCATCA
GCAACAGCCTGAGCTTCGACATCGTGAACAAGAGCCTGCAGTTCAAGTACAAGACCCAGA
AGGCCACCATCCTGGAGGCCAGCCTGAAGAAGCTGATCCCCGCCTGGGAGTTCACCATCA
TCCCTTACAACGGCCAGAAGCACCAGAGCGACATCACCGACATCGTGTCCAGCCTGCAGC
TGCAGTTCGAGAGCAGCGAGGAGGCCGACAAGGGCAACAGCCACAGCAAGAAGATGCTG
AAGGCCCTGCTGTCCGAGGGCGAGAGCATCTGGGAGATCACCGAGAAGATCCTGAACAG
CTTCGAGTACACCAGCAGGTTCACCAAGACCAAGACCCTGTACCAGTTCCTGTTCCTGGCC
ACATTCATCAACTGCGGCAGGTTCAGCGACATCAAGAACGTGGACCCCAAGAGCTTCAAG
CTGGTGCAGAACAAGTACCTGGGCGTGATCATTCAGTGCCTGGTGACCGAGACCAAGACA
AGCGTGTCCAGGCACATCTACTTTTTCAGCGCCAGAGGCAGGATCGACCCCCTGGTGTAC
CTGGACGAGTTCCTGAGGAACAGCGAGCCCGTGCTGAAGAGAGTGAACAGGACCGGCAA
CAGCAGCAGCAACAAGCAGGAGTACCAGCTGCTGAAGGACAACCTGGTGCGCAGCTACAA
CAAGGCCCTGAAGAAGAACGCCCCCTACCCCATCTTCGCTATCAAGAACGGCCCTAAGAG
CCACATCGGCAGGCACCTGATGACCAGCTTTCTGAGCATGAAGGGCCTGACCGAGCTGAC
AAACGTGGTGGGCAACTGGAGCGACAAGAGGGCCTCCGCCGTGGCCAGGACCACCTACA
CCCACCAGATCACCGCCATCCCCGACCACTACTTCGCCCTGGTGTCCAGGTACTACGCCT
ACGACCCCATCAGCAAGGAGATGATCGCCCTGAAGGACGAGACCAACCCCATCGAGGAGT
GGCAGCACATCGAGCAGCTGAAGGGCAGCGCCGAGGGCAGCATCAGATACCCCGCCTGG
AACGGCATCATCAGCCAGGAGGTGCTGGACTACCTGAGCAGCTACATCAACAGGCGGATC
TGAGAATTCGATATCAAGCTTATCGATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTGC
TGTCTCTTTATGAGGAGTTGTGGCCCGTTGTCAGGCAACGTGGCGTGGTGTGCACTGTGT
TTGCTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCGCT
GCTGGACAGGGGCTCGGCTGTTGGGCACTGACAATTCCGTGGTGTTGTCGGGGAAATCAT
CGTCCTTTCCTTGGCTGCTCGCCTATGTTGCCACCTGGATTCTGCGCGGGACGTCCTTCTG
CTACGTCCCTTCGGCCCTCAATCCAGCGGACCTTCCTTCCCGCGGCCTGCTGCCGGCTCT
GCGGCCTCTTCCGCGTCTTCGCCTTCGCCCTCAGACGAGTCGGATCTCCCTTTGGGCCGC
CTCCCCGCATCGATACCGAGCGCTGCTCGAGAGATCTACGGGTGGCATCCCTGTGACCCC
TCCCCAGTGCCTCTCCTGGCCCTGGAAGTTGCCACTCCAGTGCCCACCAGCCTTGTCCTA
ATAAAATTAAGTTGCATCATTTTGTCTGACTAGGTGTCCTTCTATAATATTATGGGGTGGAG
GGGGGTGGTATGGAGCAAGGGGCAAGTTGGGAAGACAACCTGTAGGGCCTGCGGGGTCT
ATTGGGAACCAAGCTGGAGTGCAGTGGCACAATCTTGGCTCACTGCAATCTCCGCCTCCT
GGGTTCAAGCGATTCTCCTGCCTCAGCCTCCCGAGTTGTTGGGATTCCAGGCATGCATGA
CCAGGCTCAGCTAATTTTTGTTTTTTTGGTAGAGACGGGGTTTCACCATATTGGCCAGGCT
GGTCTCCAACTCCTAATCTCAGGTGATCTACCCACCTTGGCCTCCCAAATTGCTGGGATTA
CAGGCGTGAACCACTGCTCCCTTCCCTGTCCTTCTGATTTTGTAGGTAACCACGTGCGGAC
CGAGCGGCCGC (SEQ ID NO: 81)

FIG. 14 cont'd

AiP1090 (length between ITRs: 3533 bp):
GCGGCCGCACGCGTTGTCTTAGACTGAGTTGCTGTAACAAAAATCTGGGATGAGGTCATTT
CTAAAGCACAGCAATTTATTTCCCACAGTCTGAAGGCTGCAGATTCCAAGATCACTGGCAA
GATCAGTTGTAAAGGCTTCGTCCTCCAGAGGCGGGGATGCTGCATACTCCCTGGGCAGAG
AGACAGGAAAACTCCGTAACTGCATGTGTCCTTCCTGATGCCTCTTCTATATAGGCCTGGA
TCCCAATCACCCTGTGAACCTCTCCCTGCTTCGTGGCCCCCACCTCTTAACACTACCACAT
TGGCAACTCCTGAAATTTGAAGGGGACACACTGAACCATGGCACAACAGCTTTCTGACTGA
TGCAGTAACCCAATGGCAGTGCAGAAGGGGCCAGCTAAAAGCCCAAATGGTTAGCTCAAA
ATTCGCTGTCTCTTCCGAGTGTCTGAACCCTTAGTCCTGGTATGTAAAGACATCAGAACATT
TCCCCTTGTGTCCATCAGATTTCTGTCTAGTGAAACGATGACACTGTAACCTCCAAGATCTC
ACACGAAATGATCTTTCTCCTTTGTGGAAGGAAACCAGCATTTAGCTCATCTCTCCTTCGT
AGCAGCTCAGAATGTCCACAGTGACCCAGTTACCATAGCTAAAGGCTTCCTTTTCAAAACA
CAGAGCAGAGGCAGCCAATTCAGTATGTGCTGCTGCCATCCTCTGATTCTTTCCTGCTTCC
ATAGACACCAACTCTATTGTAACTAAGCCTTATACATTGTGTCTTCCTCCTTTACATTAGCTT
GTGCTGGGGTGGTTCATGAGGCCCGCTGAGTAGTTTCAGTGACAGCCTATCCCTCTGCCA
GTGCTGCTTTGAGCCATCTTATTGGTGAGGCTGTAAGAGAAGCCTGAAGTCACAGGGTAAA
GCTATGTTGAAGGCAGCCCCAGAACCAAGTTTCCCTATTTCTATCTCCTTACGCTGTTTGAG
CCTCAGGGGTAGATCAGGTGCCTGTGAGCTCGGGCTGGGCATAAAAGTCAGGGCAGAGC
CATCTATTGCTTACATTTGCTTCTGGCGTGGCCACCATGGCTCCTAAGAAGAAGAGGAAGG
TGATGAGCCAGTTCGACATCCTGTGCAAGACCCCCCCCAAGGTGCTGGTGCGGCAGTTCG
TGGAGAGATTCGAGAGGCCCAGCGGCGAGAAGATCGCCAGCTGTGCCGCCGAGCTGACC
TACCTGTGCTGGATGATCACCCACAACGGCACCGCCATCAAGAGGGCCACCTTCATGAGC
TACAACACCATCATCAGCAACAGCCTGAGCTTCGACATCGTGAACAAGAGCCTGCAGTTCA
AGTACAAGACCCAGAAGGCCACCATCCTGGAGGCCAGCCTGAAGAAGCTGATCCCCGCCT
GGGAGTTCACCATCATCCCTTACAACGGCCAGAAGCACCAGAGCGACATCACCGACATCG
TGTCCAGCCTGCAGCTGCAGTTCGAGAGCAGCGAGGAGGCCGACAAGGGCAACAGCCAC
AGCAAGAAGATGCTGAAGGCCCTGCTGTCCGAGGGCGAGAGCATCTGGGAGATCACCGA
GAAGATCCTGAACAGCTTCGAGTACACCAGCAGGTTCACCAAGACCAAGACCCTGTACCA
GTTCCTGTTCCTGGCCACATTCATCAACTGCGGCAGGTTCAGCGACATCAAGAACGTGGA
CCCCAAGAGCTTCAAGCTGGTGCAGAACAAGTACCTGGGCGTGATCATTCAGTGCCTGGT
GACCGAGACCAAGACAAGCGTGTCCAGGCACATCTACTTTTTCAGCGCCAGAGGCAGGAT
CGACCCCCTGGTGTACCTGGACGAGTTCCTGAGGAACAGCGAGCCCGTGCTGAAGAGAG
TGAACAGGACCGGCAACAGCAGCAGCAACAAGCAGGAGTACCAGCTGCTGAAGGACAAC
CTGGTGCGCAGCTACAACAAGGCCCTGAAGAAGAACGCCCCCTACCCCATCTTCGCTATC
AAGAACGGCCCTAAGAGCCACATCGGCAGGCACCTGATGACCAGCTTTCTGAGCATGAAG
GGCCTGACCGAGCTGACAAACGTGGTGGGCAACTGGAGCGACAAGAGGGCCTCCGCCGT
GGCCAGGACCACCTACACCCACCAGATCACCGCCATCCCCGACCACTACTTCGCCCTGGT
GTCCAGGTACTACGCCTACGACCCCATCAGCAAGGAGATGATCGCCCTGAAGGACGAGAC
CAACCCCATCGAGGAGTGGCAGCACATCGAGCAGCTGAAGGGCAGCGCCGAGGGCAGCA
TCAGATACCCCGCCTGGAACGGCATCATCAGCCAGGAGGTGCTGGACTACCTGAGCAGCT
ACATCAACAGGCGGATCTGAGAATTCGATATCAAGCTTATCGATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCCACCACCTGTC
AGCTCCTTTCCGGGACTTTCGCTTTCCCCCTCCCTATTGCCACGGCGGAACTCATCGCCG
CCTGCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTATGTTGCCACCTGGATTCTGCG

FIG. 14 cont'd

CGGGACGTCCTTCTGCTACGTCCCTTCGGCCCTCAATCCAGCGGACCTTCCTTCCCGCGG
CCTGCTGCCGGCTCTGCGGCCTCTTCCGCGTCTTCGCCTTCGCCCTCAGACGAGTCGGAT
CTCCCTTTGGGCCGCCTCCCCGCATCGATACCGAGCGCTGCTCGAGAGATCTACGGGTG
GCATCCCTGTGACCCCTCCCCAGTGCCTCTCCTGGCCCTGGAAGTTGCCACTCCAGTGCC
CACCAGCCTTGTCCTAATAAAATTAAGTTGCATCATTTTGTCTGACTAGGTGTCCTTCTATAA
TATTATGGGGTGGAGGGGGGTGGTATGGAGCAAGGGGCAAGTTGGGAAGACAACCTGTA
GGGCCTGCGGGGTCTATTGGGAACCAAGCTGGAGTGCAGTGGCACAATCTTGGCTCACTG
CAATCTCCGCCTCCTGGGTTCAAGCGATTCTCCTGCCTCAGCCTCCCGAGTTGTTGGGATT
CCAGGCATGCATGACCAGGCTCAGCTAATTTTTGTTTTTTTGGTAGAGACGGGGTTTCACC
ATATTGGCCAGGCTGGTCTCCAACTCCTAATCTCAGGTGATCTACCCACCTTGGCCTCCCA
AATTGCTGGGATTACAGGCGTGAACCACTGCTCCCTTCCCTGTCCTTCTGATTTTGTAGGT
AACCACGTGCGGACCGAGCGGCCGC (SEQ ID NO: 82)

AiP1106 (length between ITRs: 3409 bp):
GCGGCCGCACGCGTAGATGAGTCTGCAGCTGGGTACAGTGACCTTTCAGTCCATGTTTAT
TTGGAAATGACCTTTAAGCAGCAATCAGCAAGAATAAAATGCTTCAAAGGAATACATTAGAT
AATGCAGAAGTCCCCCAGAGGTAAGTTACACCCAAGGCACCCAGCTGACAATGAAAGTGG
CCCTGCCCTGGGAAGCCAAGGACTAGGCCACCCATTAGACTAACAAGTGAACACAGGGTC
CCCAGAGTTTGGTCTAATAGACAATGGGGAGTCTGAAGACAGGGTGACCTGGGCAAGACA
CAAGAGCAGTTCCAAAATTAAACCTCTGTCGTAATGAAGGATGCCTAGTTGTGCTTTTTCCA
TCCTAGGATGGGGAATCCTCAAGGGCAGGGCACAGCTGTGCCAGGGGAACTGTACGGGC
TCCATCCTGCCTCCCTCCCATGGGGTGAGCTGATAGTCTTCCTCATACTGAGCTCTTGTCT
CTGCTGTGTGCTGGGGAGTCTGAAATGCTAGAGAAACTAAGCCTTCCCACTCAAAGACAGA
GAAAGAGCTGGCCCATGGCTCCGTGCCCTCTCCTCTCTGTGCGTGTCTTTAACTCTGTA
TGTTCTATTTTCCCCCTCCTCGTCCCCTGCTTCGCGCTCACAGAGTCACTCCTAGTAGCAC
CAAAGAGAGATGCTTGGCAGTTCACTAACCCCTTGAGCTGAAATAGAAATAAATATCCCAA
AAGAGAAATCAGAAAAGCAGGGTGTCGCGCTGGAGAAGAGGCAGGAAGATCAGAAATACA
AGGTCATCTGTGGCTACACATCTAGTCCAAGTCCCAGCCTGGGCTATGTGAGATGGAGGG
GAATCGCTCAGAAACAAGGCTGTACACTTAAGGAGCTCGGGCTGGGCATAAAAGTCAGGG
CAGAGCCATCTATTGCTTACATTTGCTTCTGGCGTGGCCACCATGGCTCCTAAGAAGAAGA
GGAAGGTGATGAGCCAGTTCGACATCCTGTGCAAGACCCCCCCCAAGGTGCTGGTGCGG
CAGTTCGTGGAGAGATTCGAGAGGCCCAGCGGCGAGAAGATCGCCAGCTGTGCCGCCGA
GCTGACCTACCTGTGCTGGATGATCACCCACAACGGCACCGCCATCAAGAGGGCCACCTT
CATGAGCTACAACACCATCATCAGCAACAGCCTGAGCTTCGACATCGTGAACAAGAGCCTG
CAGTTCAAGTACAAGACCCAGAAGGCCACCATCCTGGAGGCCAGCCTGAAGAAGCTGATC
CCCGCCTGGGAGTTCACCATCATCCCTTACAACGGCCAGAAGCACCAGAGCGACATCACC
GACATCGTGTCCAGCCTGCAGCTGCAGTTCGAGAGCAGCGAGGAGGCCGACAAGGGCAA
CAGCCACAGCAAGAAGATGCTGAAGGCCCTGCTGTCCGAGGGCGAGAGCATCTGGGAGA
TCACCGAGAAGATCCTGAACAGCTTCGAGTACACCAGCAGGTTCACCAAGACCAAGACCC
TGTACCAGTTCCTGTTCCTGGCCACATTCATCAACTGCGGCAGGTTCAGCGACATCAAGAA
CGTGGACCCCAAGAGCTTCAAGCTGGTGCAGAACAAGTACCTGGGCGTGATCATTCAGTG
CCTGGTGACCGAGACCAAGACAAGCGTGTCCAGGCACATCTACTTTTTCAGCGCCAGAGG
CAGGATCGACCCCCTGGTGTACCTGGACGAGTTCCTGAGGAACAGCGAGCCCGTGCTGA
AGAGAGTGAACAGGACCGGCAACAGCAGCAGCAACAAGCAGGAGTACCAGCTGCTGAAG
GACAACCTGGTGCGCAGCTACAACAAGGCCCTGAAGAAGAACGCCCCCTACCCCATCTTC
GCTATCAAGAACGGCCCTAAGAGCCACATCGGCAGGCACCTGATGACCAGCTTTCTGAGC
ATGAAGGGCCTGACCGAGCTGACAAACGTGGTGGGCAACTGGAGCGACAAGAGGGCCTC
CGCCGTGGCCAGGACCACCTACACCCACCAGATCACCGCCATCCCCGACCACTACTTCGC

FIG. 14 cont'd

CCTGGTGTCCAGGTACTACGCCTACGACCCCATCAGCAAGGAGATGATCGCCCTGAAGGA
CGAGACCAACCCCATCGAGGAGTGGCAGCACATCGAGCAGCTGAAGGGCAGCGCCGAGG
GCAGCATCAGATACCCCGCCTGGAACGGCATCATCAGCCAGGAGGTGCTGGACTACCTGA
GCAGCTACATCAACAGGCGGATCTGAGAATTCGATATCAAGCTTATCGATAATCAACCTCT
GGATTACAAAATTTGTGAAAGATTGACTGGTATTCTTAACTATGTTGCTCCTTTTACGCTATG
TGGATACGCTGCTTTAATGCCTTTGTATCATGCTATTGCTTCCCGTATGGCTTTCATTTTCTC
CTCCTTGTATAAATCCTGGTTGCTGTCTCTTTATGAGGAGTTGTGGCCCGTTGTCAGGCAA
CGTGGCGTGGTGTGCACTGTGTTTGCTGACGCAACCCCCACTGGTTGGGGCATTGCCACC
ACCTGTCAGCTCCTTTCCGGGACTTTCGCTTTCCCCCTCCCTATTGCCACGGCGGAACTCA
TCGCCGCCTGCCTTGCCCGCTGCTGGACAGGGGCTCGGCTGTTGGGCACTGACAATTCC
GTGGTGTTGTCGGGGAAATCATCGTCCTTTCCTTGGCTGCTCGCCTATGTTGCCACCTGGA
TTCTGCGCGGGACGTCCTTCTGCTACGTCCCTTCGGCCCTCAATCCAGCGGACCTTCCTT
CCCGCGGCCTGCTGCCGGCTCTGCGGCCTCTTCCGCGTCTTCGCCTTCGCCCTCAGACG
AGTCGGATCTCCCTTTGGGCCGCCTCCCCGCATCGATACCGAGCGCTGCTCGAGAGATCT
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCC
TTCTATAATATTATGGGGTGGAGGGGGGTGGTATGGAGCAAGGGGCAAGTTGGGAAGACA
ACCTGTAGGGCCTGCGGGGTCTATTGGGAACCAAGCTGGAGTGCAGTGGCACAATCTTGG
CTCACTGCAATCTCCGCCTCCTGGGTTCAAGCGATTCTCCTGCCTCAGCCTCCCGAGTTGT
TGGGATTCCAGGCATGCATGACCAGGCTCAGCTAATTTTTGTTTTTTGGTAGAGACGGGG
TTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTTCTGATTT
TGTAGGTAACCACGTGCGGACCGAGCGGCCGC (SEQ ID NO: 83)

AiP1091 (length between ITRs: 3320 bp):
GCGGCCGCACGCGTTTCACCCACCTGACACTTGGGTTAGACCTGAATGTCGTTTCTTTAAC
TCACACTGCTCATCCCACTGGCCTTTGCTGTGCTTCTCTGTGCCTCCTCAGAGATACATGA
AACTGTCCCATCCCCCTAACGATGCTGGATGGATGGCTCCAACAGCTCACTGCTCTCACCT
TGACACAAAGTCCTAGCGTCTGCATCTGTGAGACAAGTTGGAATTTATATATTTCCAGTGGA
GATTAATAATTCATTAGATGCTGAAGTAGAAAAACAAAGTACCGATTAATCAAGGCTCTGCT
GAGGCCTGCTTTGCAGCCACCAGTCTGTGGGGATTGGCAGTGCTTTTACACTGGAAGTAG
GTCAGGACCACAGAAAAGCAGCTCTCATGCACTAGCATCTGTTCGCACTAATCACTGTACA
CAGCTTTGGGTCTTACTATAGTTTTTATTAGTTATCCCAGCTGGGATTTATGTCTCAGGAAT
AAAGAGCCAAGAATGGGAGGAGTTACCCTCGAAAGATCCAGGTCATGTGGTGCAGGGCAG
GGAATATGGCTGACTCAATCTCTTTGCCCATAGAGCCTCAGAGTATCAGATCTTAGCACTC
TAAGGAGGGAGACTCAGAGGGTACAAGTCTTAGAAGTCTCCCTAGGGCTTGGTGCCCAGC
AAATATATGCTGTTTGTGACTTCCCTAATACCAGGTACAGGCCAACACAAAGGACCTGTCC
AAGGGAAACTCACGGCTCAGACCTGATCTATTTACAGGTTGAGTTTGGGTGAAGCCAAGAG
AGCTCGGGCTGGGCATAAAGTCAGGGCAGAGCCATCTATTGCTTACATTTGCTTCTGGC
GTGGCCACCATGGCTCCTAAGAAGAAGAGGAAGGTGATGAGCCAGTTCGACATCCTGTGC
AAGACCCCCCCCAAGGTGCTGGTGCGGCAGTTCGTGGAGAGATTCGAGAGGCCCAGCGG
CGAGAAGATCGCCAGCTGTGCCGCCGAGCTGACCTACCTGTGCTGGATGATCACCCACAA
CGGCACCGCCATCAAGAGGGCCACCTTCATGAGCTACAACACCATCATCAGCAACAGCCT
GAGCTTCGACATCGTGAACAAGAGCCTGCAGTTCAAGTACAAGACCCAGAAGGCCACCAT
CCTGGAGGCCAGCCTGAAGAAGCTGATCCCCGCCTGGGAGTTCACCATCATCCCTTACAA
CGGCCAGAAGCACCAGAGCGACATCACCGACATCGTGTCCAGCCTGCAGCTGCAGTTCGA
GAGCAGCGAGGAGGCCGACAAGGGCAACAGCCACAGCAAGAAGATGCTGAAGGCCCTGC
TGTCCGAGGGCGAGAGCATCTGGGAGATCACCGAGAAGATCCTGAACAGCTTCGAGTACA

FIG. 14 cont'd

CCAGCAGGTTCACCAAGACCAAGACCCTGTACCAGTTCCTGTTCCTGGCCACATTCATCAA
CTGCGGCAGGTTCAGCGACATCAAGAACGTGGACCCCAAGAGCTTCAAGCTGGTGCAGAA
CAAGTACCTGGGCGTGATCATTCAGTGCCTGGTGACCGAGACCAAGACAAGCGTGTCCAG
GCACATCTACTTTTTCAGCGCCAGAGGCAGGATCGACCCCCTGGTGTACCTGGACGAGTT
CCTGAGGAACAGCGAGCCCGTGCTGAAGAGAGTGAACAGGACCGGCAACAGCAGCAGCA
ACAAGCAGGAGTACCAGCTGCTGAAGGACAACCTGGTGCGCAGCTACAACAAGGCCCTGA
AGAAGAACGCCCCCTACCCCATCTTCGCTATCAAGAACGGCCCTAAGAGCCACATCGGCA
GGCACCTGATGACCAGCTTTCTGAGCATGAAGGGCCTGACCGAGCTGACAAACGTGGTGG
GCAACTGGAGCGACAAGAGGGCCTCCGCCGTGGCCAGGACCACCTACACCCACCAGATC
ACCGCCATCCCCGACCACTACTTCGCCCTGGTGTCCAGGTACTACGCCTACGACCCCATC
AGCAAGGAGATGATCGCCCTGAAGGACGAGACCAACCCCATCGAGGAGTGGCAGCACAT
CGAGCAGCTGAAGGGCAGCGCCGAGGGCAGCATCAGATACCCCGCCTGGAACGGCATCA
TCAGCCAGGAGGTGCTGGACTACCTGAGCAGCTACATCAACAGGCGGATCTGAGAATTCG
ATATCAAGCTTATCGATAATCAACCTCTGGATTACAAAATTTGTGAAAGATTGACTGGTATTC
TTAACTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTGCTGTCTCTTTATG
AGGAGTTGTGGCCCGTTGTCAGGCAACGTGGCGTGGTGTGCACTGTGTTTGCTGACGCAA
CCCCCACTGGTTGGGGCATTGCCACCACCTGTCAGCTCCTTTCCGGGACTTTCGCTTTCC
CCCTCCCTATTGCCACGGCGGAACTCATCGCCGCCTGCCTTGCCCGCTGCTGGACAGGG
GCTCGGCTGTTGGGCACTGACAATTCCGTGGTGTTGTCGGGGAAATCATCGTCCTTTCCTT
GGCTGCTCGCCTATGTTGCCACCTGGATTCTGCGCGGGACGTCCTTCTGCTACGTCCCTT
CGGCCCTCAATCCAGCGGACCTTCCTTCCCGCGGCCTGCTGCCGGCTCTGCGGCCTCTTC
CGCGTCTTCGCCTTCGCCCTCAGACGAGTCGGATCTCCCTTTGGGCCGCCTCCCCGCATC
GATACCGAGCGCTGCTCGAGAGATCTACGGGTGGCATCCCTGTGACCCCTCCCCAGTGCC
TCTCCTGGCCCTGGAAGTTGCCACTCCAGTGCCCACCAGCCTTGTCCTAATAAAATTAAGT
TGCATCATTTTGTCTGACTAGGTGTCCTTCTATAATATTATGGGGTGGAGGGGGGTGGTAT
GGAGCAAGGGGCAAGTTGGGAAGACAACCTGTAGGGCCTGCGGGGTCTATTGGGAACCA
AGCTGGAGTGCAGTGGCACAATCTTGGCTCACTGCAATCTCCGCCTCCTGGGTTCAAGCG
ATTCTCCTGCCTCAGCCTCCCGAGTTGTTGGGATTCCAGGCATGCATGACCAGGCTCAGC
TAATTTTTGTTTTTTTGGTAGAGACGGGGTTTCACCATATTGGCCAGGCTGGTCTCCAACTC
CTAATCTCAGGTGATCTACCCACCTTGGCCTCCCAAATTGCTGGGATTACAGGCGTGAACC
ACTGCTCCCTTCCCTGTCCTTCTGATTTTGTAGGTAACCACGTGCGGACCGAGCGGCCG
(SEQ ID NO: 84)

AiP1092 (length between ITRs: 3092 bp):
GCGGCCGCACGCGTATCCCTGGAGATGAGGAGTCCTCTCTGGCAGGGTCCCCTCACTCTA
GAGCAGCCCCTATCCCAGGCCCCCTAGGAGTCTCTAATTAAAGGGCCGGCACGCCCCTCT
GGGACTCATTAGGCCCGCTGTGCAGAGAACATTTAATCATTGCTCAGAGCATCGATTGGAA
AATCAATTTCTTTGTCTCTTCGCACGAGGCGCGCTGGAGAAGTGGGGGGAGTGCTGACCT
CCTTCTGCTGCCGTGTAAAGCGCTGCACATTTAATCAGGGAACAGAAATCAATTAGCCACT
TACGAGGTTGGCTTTAGTTACCGAGTCGGCAAGGCCCGCGCCACAGCTCAGCCGCTGACA
GTAGCGAATCTCCTCCTCTCGGCCCTGCTGCATGGCTCTGTCTCCCTCCCTGTATCTCTCT
GGCTTCCTTCTTTCCCAGAGTGCTCTGGGTTCTCACCATCTTGGCAGATCCTCACAGAACT
CCAAACAAGTCCCGAGAAGCCTTCCTAATGCCCAGTCTCCTCGGCCACCTTCTTGTTCTCA
GCTCTAGACGTTTCAAGAGAGCTCGGGCTGGGCATAAAAGTCAGGGCAGAGCCATCTATT
GCTTACATTTGCTTCTGGCGTGGCCACCATGGCTCCTAAGAAGAAGAGGAAGGTGATGAG
CCAGTTCGACATCCTGTGCAAGACCCCCCCCAAGGTGCTGGTGCGGCAGTTCGTGGAGA
GATTCGAGAGGCCCAGCGGCGAGAAGATCGCCAGCTGTGCCGCCGAGCTGACCTACCTG

FIG. 14 cont'd

TGCTGGATGATCACCCACAACGGCACCGCCATCAAGAGGGCCACCTTCATGAGCTACAAC
ACCATCATCAGCAACAGCCTGAGCTTCGACATCGTGAACAAGAGCCTGCAGTTCAAGTACA
AGACCCAGAAGGCCACCATCCTGGAGGCCAGCCTGAAGAAGCTGATCCCCGCCTGGGAG
TTCACCATCATCCCTTACAACGGCCAGAAGCACCAGAGCGACATCACCGACATCGTGTCCA
GCCTGCAGCTGCAGTTCGAGAGCAGCGAGGAGGCCGACAAGGGCAACAGCCACAGCAAG
AAGATGCTGAAGGCCCTGCTGTCCGAGGGCGAGAGCATCTGGGAGATCACCGAGAAGAT
CCTGAACAGCTTCGAGTACACCAGCAGGTTCACCAAGACCAAGACCCTGTACCAGTTCCT
GTTCCTGGCCACATTCATCAACTGCGGCAGGTTCAGCGACATCAAGAACGTGGACCCCAA
GAGCTTCAAGCTGGTGCAGAACAAGTACCTGGGCGTGATCATTCAGTGCCTGGTGACCGA
GACCAAGACAAGCGTGTCCAGGCACATCTACTTTTTCAGCGCCAGAGGCAGGATCGACCC
CCTGGTGTACCTGGACGAGTTCCTGAGGAACAGCGAGCCCGTGCTGAAGAGAGTGAACA
GGACCGGCAACAGCAGCAGCAACAAGCAGGAGTACCAGCTGCTGAAGGACAACCTGGTG
CGCAGCTACAACAAGGCCCTGAAGAAGAACGCCCCCTACCCCATCTTCGCTATCAAGAAC
GGCCCTAAGAGCCACATCGGCAGGCACCTGATGACCAGCTTTCTGAGCATGAAGGGCCTG
ACCGAGCTGACAAACGTGGTGGGCAACTGGAGCGACAAGAGGGCCTCCGCCGTGGCCAG
GACCACCTACACCCACCAGATCACCGCCATCCCCGACCACTACTTCGCCCTGGTGTCCAG
GTACTACGCCTACGACCCCATCAGCAAGGAGATGATCGCCCTGAAGGACGAGACCAACCC
CATCGAGGAGTGGCAGCACATCGAGCAGCTGAAGGGCAGCGCCGAGGGCAGCATCAGAT
ACCCCGCCTGGAACGGCATCATCAGCCAGGAGGTGCTGGACTACCTGAGCAGCTACATCA
ACAGGCGGATCTGAGAATTCGATATCAAGCTTATCGATAATCAACCTCTGGATTACAAAATT
TGTGAAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGTATAA
ATCCTGGTTGCTGTCTCTTTATGAGGAGTTGTGGCCCGTTGTCAGGCAACGTGGCGTGGT
GTGCACTGTGTTTGCTGACGCAACCCCCACTGGTTGGGGCATTGCCACCACCTGTCAGCT
CCTTTCCGGGACTTTCGCTTTCCCCCTCCCTATTGCCACGGCGGAACTCATCGCCGCCTG
CCTTGCCCGCTGCTGGACAGGGGCTCGGCTGTTGGGCACTGACAATTCCGTGGTGTTGTC
GGGGAAATCATCGTCCTTTCCTTGGCTGCTCGCCTATGTTGCCACCTGGATTCTGCGCGG
GACGTCCTTCTGCTACGTCCCTTCGGCCCTCAATCCAGCGGACCTTCCTTCCCGCGGCCT
GCTGCCGGCTCTGCGGCCTCTTCCGCGTCTTCGCCTTCGCCCTCAGACGAGTCGGATCTC
CCTTTGGGCCGCCTCCCCGCATCGATACCGAGCGCTGCTCGAGAGATCTACGGGTGGCAT
CCCTGTGACCCCTCCCCAGTGCCTCTCCTGGCCCTGGAAGTTGCCACTCCAGTGCCCACC
AGCCTTGTCCTAATAAAATTAAGTTGCATCATTTTGTCTGACTAGGTGTCCTTCTATAATATT
ATGGGGTGGAGGGGGGTGGTATGGAGCAAGGGGCAAGTTGGGAAGACAACCTGTAGGGC
CTGCGGGGTCTATTGGGAACCAAGCTGGAGTGCAGTGGCACAATCTTGGCTCACTGCAAT
CTCCGCCTCCTGGGTTCAAGCGATTCTCCTGCCTCAGCCTCCCGAGTTGTTGGGATTCCA
GGCATGCATGACCAGGCTCAGCTAATTTTTGTTTTTTTGGTAGAGACGGGGTTTCACCATAT
TGGCCAGGCTGGTCTCCAACTCCTAATCTCAGGTGATCTACCCACCTTGGCCTCCCAAATT
GCTGGGATTACAGGCGTGAACCACTGCTCCCTTCCCTGTCCTTCTGATTTTGTAGGTAACC
ACGTGCGGACCGAGCGGCCGC (SEQ ID NO: 85)

CN2581 (length between ITRs: 2307 bp):
GCGGCCGCACGCGTTATGATGTGCCAGGCTTGGGAGAAACACCACAAGCAAAGCCAAAAT
AGGTGGCCTAGAACTTCCAGCTTGAAATATGGGAGAGAATGAGGGAGGCACTGTAGAGCA
GCTGCCGGGTGCCGCATGAGAACAATTCTCCCTGCTCATAATTAATCCTACCTATTTCTGAT
GACAGCTGGCTCTTCACTTTGAACAAGCTAGTTAACAACTTTCTTCTCACATTGAGCAAATA
ATTCATATTTAATTACTTAACCACCAGTTACAAAATGAGAATCATCAAGGAATCACAATTAAT
TTGCTATTGACAAACTCATACTTTTAGCAGGCTGATTTCTACTTTATACTTAGATTGGTAATG
AAAAATGAAGCTTATTTTAGTTGATTGGTTGGACTTGTGTATGAATATTATCTATTATTTGAA

FIG. 14 cont'd

AAGCCAAACTTGAATGCAAAAAAATATTGAATATGAAAAGAAAAACATTTGCAGTAAAGCTT
GTTCTGAGCTCGATTCAGCCGGGAGCTTAGGGAGGGGAGGTCACTTCATAAGGGCTTGGG
GGGGGAGTTGGAGCCACGAGTCGTCCAGCCGGAGCCCCGTGTGGCTGTGCTCCGGCCTC
AGAAGCATCCCCGGATCCTTCGAAGCTAGCGCTACCGGTCGCCACCATGGTGAGCAAGG
GCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGAC
CCTGAAGCTGATCTGCACCACCGGCAAGCTGCCCGTGCCCTGGCCCACCCTCGTGACCA
CCCTGGGCTACGGCGTGCAGTGCTTCGCCCGCTACCCCGACCACATGAAGCAGCACGAC
TTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGTCCGGACT
CAGATCTGGAGGCTCCGGAGGCCCAGAGCCAGCGAAGTCTGCTCCCGCCCCGAAAAAGG
GCTCCAAGAAGGCGGTGACTAAGGCGCAGAAGAAAGGCGGCAAGAAGCGCAAGCGCAGC
CGCAAGGAGAGCTATTCCATCTATGTGTATAAGGTTCTGAAGCAGGTCCACCCTGACACCG
GCATTTCGTCCAAGGCCATGGGCATCATGAACTCGTTTGTGAACGACATTTTCGAGCGCAT
CGCAGGTGAGGCTTCCCGCCTGGCGCATTACAACAAGCGCTCGACCATCACCTCCAGGGA
GATCCAGACGGCCGTGCGCCTGCTGCTGCCTGGGGAGTTGGCCAAGCACGCCGTGTCCG
AGGGTACTAAGGCCATCACCAAGTACACCAGCGCTAAGTAATGAGTCGACGGCGCGCCCC
TGCAGGGAATTCGATATCATAATCAACCTCTGGATTACAAAATTTGTGAAAGATTGACTGGT
ATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTAGTTCTTGCC
ACGGCGGAACTCATCGCCGCCTGCCTTGCCCGCTGCTGGACAGGGGCTCGGCTGTTGGG
CACTGACAATTCCGTGGCTCGAGAGATCTTCGACTGTGCCTTCTAGTTGCCAGCCATCTGT
TGTTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGCACGTGC
GGACCGAGCGGCCGC (SEQ ID NO: 86)

CN2782 (length between ITRs: 2675 bp):
GCGGCCGCACGCGTAGAAACACCACAAGCAAAGCCAAAATAGGTGGCCTAGAACTTCCAG
CTTGAAATATGGGAGAGAATGAGGGAGGCACTGTAGAGCAGCTGCCGGGTGCCGCATGA
GAACAATTCTCCCTGCTCATAATTAATCCTACCTATTTCTGATGACAGCTGGCTCTTCACTTT
GAACAAGCTAGTTAACAACTTTCTTCTCACATTGAGCAAATAATTCATATTTAATTACTTAAC
CACCAGTTACAAAATGAGAATCATCAAGGAATCACAATTAATTTGCTATTGACAAACTCATA
CTTTTAGCAGGCTGATTTCTACTTTATACTTAGATTGGTAATGAAAAATGAAGCTTATTTTAG
TTGATTGGTTGGACTTGTGTATGAATATTATCTATTATTTGAAAAGCCAAACTTGAATGCAAA
AAAATATTGAATATGAAAAGAGAAACACCACAAGCAAAGCCAAAATAGGTGGCCTAGAACT
TCCAGCTTGAAATATGGGAGAGAATGAGGGAGGCACTGTAGAGCAGCTGCCGGGTGCCG
CATGAGAACAATTCTCCCTGCTCATAATTAATCCTACCTATTTCTGATGACAGCTGGCTCTT
CACTTTGAACAAGCTAGTTAACAACTTTCTTCTCACATTGAGCAAATAATTCATATTTAATTA
CTTAACCACCAGTTACAAAATGAGAATCATCAAGGAATCACAATTAATTTGCTATTGACAAA
CTCATACTTTTAGCAGGCTGATTTCTACTTTATACTTAGATTGGTAATGAAAAATGAAGCTTA
TTTTAGTTGATTGGTTGGACTTGTGTATGAATATTATCTATTATTTGAAAAGCCAAACTTGAA

FIG. 14 cont'd

TGCAAAAAAATATTGAATATGAAAAGAGAAACACCACAAGCAAAGCCAAAATAGGTGGCCT
AGAACTTCCAGCTTGAAATATGGGAGAGAATGAGGGAGGCACTGTAGAGCAGCTGCCGGG
TGCCGCATGAGAACAATTCTCCCTGCTCATAATTAATCCTACCTATTTCTGATGACAGCTGG
CTCTTCACTTTGAACAAGCTAGTTAACAACTTTCTTCTCACATTGAGCAAATAATTCATATTT
AATTACTTAACCACCAGTTACAAAATGAGAATCATCAAGGAATCACAATTAATTTGCTATTGA
CAAACTCATACTTTTAGCAGGCTGATTTCTACTTTATACTTAGATTGGTAATGAAAAATGAAG
CTTATTTTAGTTGATTGGTTGGACTTGTGTATGAATATTATCTATTATTTGAAAGCCAAACT
TGAATGCAAAAAAATATTGAATATGAAAAGGAGCTCGGGCTGGGCATAAAAGTCAGGGCAG
AGCCATCTATTGCTTACATTTGCTTCTGGGATCCAGATCTTTCGAAGCTAGCGCTACCGGT
CGCCACCATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGAT
GCCACCTACGGCAAGCTGACCCTGAAGCTGATCTGCACCACCGGCAAGCTGCCCGTGCC
CTGGCCCACCCTCGTGACCACCCTGGGCTACGGCGTGCAGTGCTTCGCCCGCTACCCCG
ACCACATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAAC
ATCCTGGGGCACAAGCTGGAGTACAACTACAACAGCCACAACGTCTATATCACCGCCGAC
AAGCAGAAGAACGGCATCAAGGCCAACTTCAAGATCCGCCACAACATCGAGGACGGCGGC
GTGCAGCTCGCCGACCACTACCAGCAGAACACCCCCATCGGCGACGGCCCCGTGCTGCT
GCCCGACAACCACTACCTGAGCTACCAGTCCAAGCTGAGCAAAGACCCCAACGAGAAGCG
CGATCACATGGTCCTGCTGGAGTTCGTGACCGCCGCCGGGATCACTCTCGGCATGGACGA
GCTGTACAAGTAAGTCGACGGCGCGCCGCGGCCGCGAATTCGATATCATAATCAACCTCT
GGATTACAAAATTTGTGAAAGATTGACTGGTATTCTTAACTATGTTGCTCCTTTTACGCTATG
TGGATACGCTGCTTTAATGCCTTTGTATCATGCTATTGCTTCCCGTATGGCTTTCATTTTCTC
CTCCTTGTATAAATCCTGGTTAGTTCTTGCCACGGCGGAACTCATCGCCGCCTGCCTTGCC
CGCTGCTGGACAGGGGCTCGGCTGTTGGGCACTGACAATTCCGTGGCTCGAGAGATCTTC
GACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGAT
TGGGAAGACAATAGCAGGCATGAGATCTCACGTGCGGACCGAGCGGCCGC (SEQ ID NO:
87)

CN3407 (length between ITRs: 2479 bp):
GCGGCCGCACGCGTTGAGCTTCAACCAAATCAGGCATTGATGGATTTTATAGTTTGATTAA
CAAAGATAATAGCAAACCCCAGATTTAGTTTAAACATAAAAAGTATTAAGGTTGTATCCTGC
TTGTATAGCATATGCAAATGACCTCGTTTCTGCTACTGCATTTGGAAATGTAGCAGAAGAAA
AAAAAAAGGCACTTCAATTGCAGCTCTCATCAGTTATTCACTGTATCCAGGCCTCTCAATTG
TGTTCTTTTCTTTAATGCAATAGCAAGCAGCAATCACCCAGCTGTGCTTGGTAGAGTGAACT
ATATACACATCTATATTGAGATTTCATACACACATAACATAAAAGCGAGAGAAAAAGCCTCA
AGAATGTTTGGCCCATTGCAAATCACACAAAAGGACTAATGAATCTCTCTCCAAATGGATCT
GTAGTGACCATCTGTAAGCCTTGATTGATTCATATTCCATAACGGTATCAGCATCCAGGAAG
TGATTACTTCAAGGTGCAACACAACTTCCCCTATGAAAGCTCAGTCTCTTTAATCATACCTA
GTCAGTATCTGTCACGGGGATAAACTAAGGCAGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTCTCCAAGGGCGAGGAGCTGTTCACCGGGGTGGTGCCCATCCTGG
TCGAGCTGGACGGCGATGTCAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC

FIG. 14 cont'd

CGACCACATGAAGCAGCACGACTTCTTCAAGTCCGCCATGCCCGAAGGCTACGTCCAGGA
GCGCACCATCTTCTTCAAAGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGGGCTCTGGTGCTACCAACTTCTCACTGTTGAAACAGGCAGGGGATGT
AGAGGAGAATCCAGGGCCTGGTGCTAGTGGAGACTACAAAGACCATGACGGAGATTATAA
AGATCATGACATCGATTACAAGGATGACGATGACAAGTCCGGACTCAGATCTGGAGGCTC
CGGAGGCCCAGAGCCAGCGAAGTCTGCTCCCGCCCCGAAAAAGGGCTCCAAGAAGGCGG
TGACTAAGGCGCAGAAGAAAGGCGGCAAGAAGCGCAAGCGCAGCCGCAAGGAGAGCTAT
TCCATCTATGTGTACAAGGTTCTGAAGCAGGTCCACCCTGACACCGGCATTTCGTCCAAGG
CCATGGGCATCATGAATTCGTTTGTGAACGACATTTTCGAGCGCATCGCAGGAGAGGCTTC
CCGCCTGGCGCATTACAACAAGCGCTCGACCATCACCTCCCGGGAGATCCAGACGGCCG
TGCGCCTGCTGCTGCCTGGGGAGTTGGCCAAGCACGCCGTGTCCGAGGGTACTAAGGCC
ATCACCAAGTACACCAGCGCTAAGTAATGAGGCGCGCCGCGGCCGCGAATTCGATATCAT
AATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGC
TTTCATTTTCTCCTCCTTGTATAAATCCTGGTTAGTTCTTGCCACGGCGGAACTCATCGCCG
CCTGCCTTGCCCGCTGCTGGACAGGGGCTCGGCTGTTGGGCACTGACAATTCCGTGGCT
CGAGAGATCTTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCA
AGGGGGAGGATTGGGAAGACAATAGCAGGCATGAGATCTCACGTGCGGACCGAGCGGCC
GC (SEQ ID NO: 88)

CN3408 (length between ITRs: 2515 bp):
GCGGCCGCACGCGTACATTTGCAGTAAAGCTTGTTCTTTTTCTTGAAGTATATTTTAAGATT
TTGAGTTCTACTATCATTAAAGACAGATAATTAATAGTTTATTTTTATTTACTTTTGTTAGTAG
TGACTTGGTGCTATGAGCCATATTTTGCTGTTGCTGTTGTTACTGGTAGTTTTTGTAATTCT
GGGGCTAAAACTTGGGGTCTGGTATGCTGTCATTTACCAGTGAGCTATACCCTGGATATTA
TGATTTAGATGAATGTGAAATATCACCCCAGACATACATATACTAAACACTTGGCCCTTGGC
CCATGATGCTAAATGGAGGAGATAGAAGCTTTTGGGGCACAGCCTAGTGGAAGGAAATGA
GGTCAAATGACATGTACTCTGAAAGGAATATGGGTATTCTGGGCTTGCGTTATTCTCTCT
CCCTCTCTCTCCCTCTCTCTCCCTCTCCCTCTCTCTTTCTCCTTTTCTCTTTCTCTCCTCGCC
TTGTTTTCCAGCTGCCAGAAGGTAGGCCTCTTCTCTGCTGAATATCTGTGTCATGTTATGCA
CCAACACAGTACTAACTGTCATGTTATACCTAGTGGCCAGGTAACCATGGACCAAAATGGC
AGAGCAGAGCTCGGGCTGGGCATAAAAGTCAGGGCAGAGCCATCTATTGCTTACATTTGC
TTCTGGGATCCAGATCTTTCGAAGCTAGCGCTACCGGTCGCCACCATGGTCTCCAAGGGC
GAGGAGCTGTTCACCGGGGTGGTGCCCATCCTGGTCGAGCTGGACGGCGATGTCAACGG
CCACAAGTTCAGCGTGTCCGGCGAGGGCGAGGGCGATGCCACCTACGGCAAGCTGACCC
TGAAGCTGATCTGCACCACCGGCAAGCTGCCCGTGCCCTGGCCCACCCTCGTGACCACC
CTGGGCTACGGCGTGCAGTGCTTCGCCCGCTACCCCGACCACATGAAGCAGCACGACTTC
TTCAAGTCCGCCATGCCCGAAGGCTACGTCCAGGAGCGCACCATCTTCTTCAAAGACGAC
GGCAACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGT

FIG. 14 cont'd

ACAACTACAACAGCCACAACGTCTATATCACCGCCGACAAGCAGAAGAACGGCATCAAGG
CCAACTTCAAGATCCGCCACAACATCGAGGACGGCGGCGTGCAGCTCGCCGACCACTACC
AGCAGAACACCCCCATCGGCGACGGCCCCGTGCTGCTGCCCGACAACCACTACCTGAGC
TACCAGTCCAAGCTGAGCAAAGACCCCAACGAGAAGCGCGATCACATGGTCCTGCTGGAG
TTCGTGACCGCCGCCGGGATCACTCTCGGCATGGACGAGCTGTACAAGGGCTCTGGTGCT
ACCAACTTCTCACTGTTGAAACAGGCAGGGGATGTAGAGGAGAATCCAGGGCCTGGTGCT
AGTGGAGACTACAAAGACCATGACGGAGATTATAAAGATCATGACATCGATTACAAGGATG
ACGATGACAAGTCCGGACTCAGATCTGGAGGCTCCGGAGGCCCAGAGCCAGCGAAGTCT
GCTCCCGCCCCGAAAAAGGGCTCCAAGAAGGCGGTGACTAAGGCGCAGAAGAAAGGCGG
CAAGAAGCGCAAGCGCAGCCGCAAGGAGAGCTATTCCATCTATGTGTACAAGGTTCTGAA
GCAGGTCCACCCTGACACCGGCATTTCGTCCAAGGCCATGGGCATCATGAATTCGTTTGT
GAACGACATTTTCGAGCGCATCGCAGGAGAGGCTTCCCGCCTGGCGCATTACAACAAGCG
CTCGACCATCACCTCCCGGGAGATCCAGACGGCCGTGCGCCTGCTGCTGCCTGGGGAGT
TGGCCAAGCACGCCGTGTCCGAGGGTACTAAGGCCATCACCAAGTACACCAGCGCTAAGT
AATGAGGCGCGCCGCGGCCGCGAATTCGATATCATAATCAACCTCTGGATTACAAAATTTG
TGAAAGATTGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTTGTATAAAT
CCTGGTTAGTTCTTGCCACGGCGGAACTCATCGCCGCCTGCCTTGCCCGCTGCTGGACAG
GGGCTCGGCTGTTGGGCACTGACAATTCCGTGGCTCGAGAGATCTTCGACTGTGCCTTCT
AGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATA
GCAGGCATGAGATCTCACGTGCGGACCGAGCGGCCGC (SEQ ID NO: 89)

CN3409 (length between ITRs: 2565 bp):
GCGGCCGCACGCGTTGCAAAATAAAGATTTCTTGGGATACAGAGAAAAAAACAAATCTGAC
AGGAGAGGAAGAAGCACCCGGTGGGCTATAACGGTGCAATTCAGCTGATTATATGTTACAA
GTAACAAGGACGAGAAAAAATGTTATTTCTTTGAAAATAAAACTAACCAGGCCATACATATT
TAACAGGACTGCATGAGAGAAGAAGAAGCCAGCTGCAGGAGTGACTGTGGGGGGGAGGG
GGAACTTGACAAAAAAAGCAAAATGGCAGTCCTGCTTCCAAAGTCCTCAAGGTCACAGTTA
TTTGGGCATTCTTGCGGGCACTGCTTATACAAGAATGTGCTTTCAGTCAAGGCTTTCTAATA
GATTCTCAAAATTTGGGACAAATGTTATTTTTGTATCTGTAGAAATGTACTGATTCAGAAAGA
TCTTTGAGCAATACAGATGTTAAAACATTTAAGTCACAAAATGGGTCTATTTAATCAATGCGA
CTAGTTTGGAACATTATTCAAACTGCCAGAAATACAATGTAAATGAAACCTCAGGCCAATAT
TTTGGAGCCCTAAAAGATTTGATGGCTAATTTTATCGTAGACACTAATTATAAATAGGAGAC
CCCAGGATGGGACTAGAAAACCAAGCCAGCTTTTTAATTTACCCCTCCAGGACTTTGCTGA
GCTCGGGCTGGGCATAAAAGTCAGGGCAGAGCCATCTATTGCTTACATTTGCTTCTGGGAT
CCAGATCTTTCGAAGCTAGCGCTACCGGTCGCCACCATGGTCTCCAAGGGCGAGGAGCTG
TTCACCGGGGTGGTGCCCATCCTGGTCGAGCTGGACGGCGATGTCAACGGCCACAAGTT
CAGCGTGTCCGGCGAGGGCGAGGGCGATGCCACCTACGGCAAGCTGACCCTGAAGCTGA
TCTGCACCACCGGCAAGCTGCCCGTGCCCTGGCCCACCCTCGTGACCACCCTGGGCTAC
GGCGTGCAGTGCTTCGCCCGCTACCCCGACCACATGAAGCAGCACGACTTCTTCAAGTCC
GCCATGCCCGAAGGCTACGTCCAGGAGCGCACCATCTTCTTCAAAGACGACGGCAACTAC
AAGACCCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACAACTACAA
CAGCCACAACGTCTATATCACCGCCGACAAGCAGAAGAACGGCATCAAGGCCAACTTCAA
GATCCGCCACAACATCGAGGACGGCGGCGTGCAGCTCGCCGACCACTACCAGCAGAACA
CCCCCATCGGCGACGGCCCCGTGCTGCTGCCCGACAACCACTACCTGAGCTACCAGTCC

FIG. 14 cont'd

AAGCTGAGCAAAGACCCCAACGAGAAGCGCGATCACATGGTCCTGCTGGAGTTCGTGACC
GCCGCCGGGATCACTCTCGGCATGGACGAGCTGTACAAGGGCTCTGGTGCTACCAACTTC
TCACTGTTGAAACAGGCAGGGGATGTAGAGGAGAATCCAGGGCCTGGTGCTAGTGGAGAC
TACAAAGACCATGACGGAGATTATAAAGATCATGACATCGATTACAAGGATGACGATGACA
AGTCCGGACTCAGATCTGGAGGCTCCGGAGGCCCAGAGCCAGCGAAGTCTGCTCCCGCC
CCGAAAAAGGGCTCCAAGAAGGCGGTGACTAAGGCGCAGAAGAAAGGCGGCAAGAAGCG
CAAGCGCAGCCGCAAGGAGAGCTATTCCATCTATGTGTACAAGGTTCTGAAGCAGGTCCA
CCCTGACACCGGCATTTCGTCCAAGGCCATGGGCATCATGAATTCGTTTGTGAACGACATT
TTCGAGCGCATCGCAGGAGAGGCTTCCCGCCTGGCGCATTACAACAAGCGCTCGACCATC
ACCTCCCGGGAGATCCAGACGGCCGTGCGCCTGCTGCTGCCTGGGGAGTTGGCCAAGCA
CGCCGTGTCCGAGGGTACTAAGGCCATCACCAAGTACACCAGCGCTAAGTAATGAGGCGC
GCCGCGGCCGCGAATTCGATATCATAATCAACCTCTGGATTACAAAATTTGTGAAAGATTG
ACTGGTATTCTTAACTATGTTGCTCCTTTTACGCTATGTGGATACGCTGCTTTAATGCCTTT
GTATCATGCTATTGCTTCCCGTATGGCTTTCATTTTCTCCTCCTTGTATAAATCCTGGTTAGT
TCTTGCCACGGCGGAACTCATCGCCGCCTGCCTTGCCCGCTGCTGGACAGGGGCTCGGC
TGTTGGGCACTGACAATTCCGTGGCTCGAGAGATCTTCGACTGTGCCTTCTAGTTGCCAGC
CATCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGG
GGGGTGGGGTGGGGCAGGACAGCAAGGGGGAGGATTGGGAAGACAATAGCAGGCATGA
GATCTCACGTGCGGACCGAGCGGCCGC (SEQ ID NO: 90)

CN2580 (length between ITRs: 2378 bp):
GCGGCCGCACGCGTTATGATGTGCCAGGCTTGGGAGAAACACCACAAGCAAAGCCAAAAT
AGGTGGCCTAGAACTTCCAGCTTGAAATATGGGAGAGAATGAGGGAGGCACTGTAGAGCA
GCTGCCGGGTGCCGCATGAGAACAATTCTCCCTGCTCATAATTAATCCTACCTATTTCTGAT
GACAGCTGGCTCTTCACTTTGAACAAGCTAGTTAACAACTTTCTTCTCACATTGAGCAAATA
ATTCATATTTAATTACTTAACCACCAGTTACAAAATGAGAATCATCAAGGAATCACAATTAAT
TTGCTATTGACAAACTCATACTTTTAGCAGGCTGATTTCTACTTTATACTTAGATTGGTAATG
AAAAATGAAGCTTATTTTAGTTGATTGGTTGGACTTGTGTATGAATATTATCTATTATTTGAA
AAGCCAAACTTGAATGCAAAAAAATATTGAATATGAAAAGAAAAACATTTGCAGTAAAGCTT
GTTCTGAGCTCGGGCTGGGCATAAAGTCAGGGCAGAGCCATCTATTGCTTACATTTGCTT
CTGGGATCCAGATCTTTCGAAGCTAGCACCATGGTGCCCAAGAAGAAGAGGAAAGTCTCC
AACCTGCTGACTGTGCACCAAAACCTGCCTGCCCTCCCTGTGGATGCCACCTCTGATGAA
GTCAGGAAGAACCTGATGGACATGTTCAGGGACAGGCAGGCCTTCTCTGAACACACCTGG
AAGATGCTCCTGTCTGTGTGCAGATCCTGGGCTGCCTGGTGCAAGCTGAACAACAGGAAA
TGGTTCCCTGCTGAACCTGAGGATGTGAGGGACTACCTCCTGTACCTGCAAGCCAGAGGC
CTGGCTGTGAAGACCATCCAACAGCACCTGGGCCAGCTCAACATGCTGCACAGGAGATCT
GGCCTGCCTCGCCCTTCTGACTCCAATGCTGTGTCCCTGGTGATGAGGAGAATCAGAAAG
GAGAATGTGGATGCTGGGGAGAGAGCCAAGCAGGCCCTGGCCTTTGAACGCACTGACTTT
GACCAAGTCAGATCCCTGATGGAGAACTCTGACAGATGCCAGGACATCAGGAACCTGGCC
TTCCTGGGCATTGCCTACAACACCCTGCTGCGCATTGCCGAAATTGCCAGAATCAGAGTGA
AGGACATCTCCCGCACCGATGGTGGGAGAATGCTGATCCACATTGGCAGGACCAAGACCC
TGGTGTCCACAGCTGGTGTGGAGAAGGCCCTGTCCCTGGGGGTTACCAAGCTGGTGGAG
AGATGGATCTCTGTGTCTGGTGTGGCTGATGACCCCAACAACTACCTGTTCTGCCGGGTCA
GAAAGAATGGTGTGGCTGCCCCTTCTGCCACCTCCCAACTGTCCACCCGGGCCCTGGAAG
GGATCTTTGAGGCCACCCACCGCCTGATCTATGGTGCCAAGGATGACTCTGGGCAGAGAT
ACCTGGCCTGGTCTGGCCACTCTGCCAGAGTGGGTGCTGCCAGGGACATGGCCAGGGCT
GGTGTGTCCATCCCTGAAATCATGCAGGCTGGTGGCTGGACCAATGTGAACATTGTGATG

FIG. 14 cont'd

AACTACATCAGAAACCTGGACTCTGAGACTGGGGCCATGGTGAGGCTGCTCGAGGATGGG
GACTAATGAGGCGCGCCGCGGCCTTAAAGAGACCGGTTCACTGTGACAGTAAAAGAGACC
GGTTCACTGTGAGAATGAAAGAGACCGGTTCACTGTGATCGGAAAAGAGACCGGTTCACT
GTGAGCGGCCTTGAAACCCAGCAGACAATGTAGCTCAGTAGAAACCCAGCAGACAATGTA
GCTGAATGGAAACCCAGCAGACAATGTAGCTTCGGAGAAACCCAGCAGACAATGTAGCTG
TCGACGAATTCGATATCATAATCAACCTCTGGATTACAAAATTTGTGAAAGATTGACTGGTA
TTCTTAACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTAGTTCTTGCCA
CGGCGGAACTCATCGCCGCCTGCCTTGCCCGCTGCTGGACAGGGGCTCGGCTGTTGGGC
ACTGACAATTCCGTGGCTCGAGAGATCTTCGACTGTGCCTTCTAGTTGCCAGCCATCTGTT
GTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCACGTGCG
GACCGAGCGGCCGC (SEQ ID NO: 91)

CN2825 (length between ITRs: 2625 bp):
GCGGCCGCACGCGTTATGATGTGCCAGGCTTGGGAGAAACACCACAAGCAAAGCCAAAAT
AGGTGGCCTAGAACTTCCAGCTTGAAATATGGGAGAGAATGAGGGAGGCACTGTAGAGCA
GCTGCCGGGTGCCGCATGAGAACAATTCTCCCTGCTCATAATTAATCCTACCTATTTCTGAT
GACAGCTGGCTCTTCACTTTGAACAAGCTAGTTAACAACTTTCTTCTCACATTGAGCAAATA
ATTCATATTTAATTACTTAACCACCAGTTACAAAATGAGAATCATCAAGGAATCACAATTAAT
TTGCTATTGACAAACTCATACTTTTAGCAGGCTGATTTCTACTTTATACTTAGATTGGTAATG
AAAAATGAAGCTTATTTTAGTTGATTGGTTGGACTTGTGTATGAATATTATCTATTATTTGAA
AAGCCAAACTTGAATGCAAAAAAATATTGAATATGAAAAGAAAAACATTTGCAGTAAAGCTT
GTTCTGAGCTCGGGCTGGGCATAAAAGTCAGGGCAGAGCCATCTATTGCTTACATTTGCTT
CTGGGATCCAGATCTTTCGAAGCTAGCCACCATGGCTCCTAAGAAGAAGAGGAAGGTGAT
GAGCCAGTTCGACATCCTGTGCAAGACCCCCCCCAAGGTGCTGGTGCGGCAGTTCGTGG
AGAGATTCGAGAGGCCCAGCGGCGAGAAGATCGCCAGCTGTGCCGCCGAGCTGACCTAC
CTGTGCTGGATGATCACCCACAACGGCACCGCCATCAAGAGGGCCACCTTCATGAGCTAC
AACACCATCATCAGCAACAGCCTGAGCTTCGACATCGTGAACAAGAGCCTGCAGTTCAAGT
ACAAGACCCAGAAGGCCACCATCCTGGAGGCCAGCCTGAAGAAGCTGATCCCCGCCTGG
GAGTTCACCATCATCCCTTACAACGGCCAGAAGCACCAGAGCGACATCACCGACATCGTG
TCCAGCCTGCAGCTGCAGTTCGAGAGCAGCGAGGAGGCCGACAAGGGCAACAGCCACAG
CAAGAAGATGCTGAAGGCCCTGCTGTCCGAGGGCGAGAGCATCTGGGAGATCACCGAGA
AGATCCTGAACAGCTTCGAGTACACCAGCAGGTTCACCAAGACCAAGACCCTGTACCAGTT
CCTGTTCCTGGCCACATTCATCAACTGCGGCAGGTTCAGCGACATCAAGAACGTGGACCC
CAAGAGCTTCAAGCTGGTGCAGAACAAGTACCTGGGCGTGATCATTCAGTGCCTGGTGAC
CGAGACCAAGACAAGCGTGTCCAGGCACATCTACTTTTTCAGCGCCAGAGGCAGGATCGA
CCCCCTGGTGTACCTGGACGAGTTCCTGAGGAACAGCGAGCCCGTGCTGAAGAGAGTGA
ACAGGACCGGCAACAGCAGCAGCAACAAGCAGGAGTACCAGCTGCTGAAGGACAACCTG
GTGCGCAGCTACAACAAGGCCCTGAAGAAGAACGCCCCCTACCCCATCTTCGCTATCAAG
AACGGCCCTAAGAGCCACATCGGCAGGCACCTGATGACCAGCTTTCTGAGCATGAAGGGC
CTGACCGAGCTGACAAACGTGGTGGGCAACTGGAGCGACAAGAGGGCCTCCGCCGTGGC
CAGGACCACCTACACCCACCAGATCACCGCCATCCCCGACCACTACTTCGCCCTGGTGTC
CAGGTACTACGCCTACGACCCCATCAGCAAGGAGATGATCGCCCTGAAGGACGAGACCAA
CCCCATCGAGGAGTGGCAGCACATCGAGCAGCTGAAGGGCAGCGCCGAGGGCAGCATCA
GATACCCCGCCTGGAACGGCATCATCAGCCAGGAGGTGCTGGACTACCTGAGCAGCTACA
TCAACAGGCGGATCTGAGTCGACGGCGCGCCGCGGCCTTAAAGAGACCGGTTCACTGTG

FIG. 14 cont'd

ACAGTAAAAGAGACCGGTTCACTGTGAGAATGAAAGAGACCGGTTCACTGTGATCGGAAAA
GAGACCGGTTCACTGTGAGCGGCCTTGAAACCCAGCAGACAATGTAGCTCAGTAGAAACC
CAGCAGACAATGTAGCTGAATGGAAACCCAGCAGACAATGTAGCTTCGGAGAAACCCAGC
AGACAATGTAGCTGTCGACGAATTCGATATCATAATCAACCTCTGGATTACAAAATTTGTGA
AAGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTAGTTCTTGCCACGGCGGAACTCATCGCCGCCTGCCTTGCCCGCTGCTGGACAGGGG
CTCGGCTGTTGGGCACTGACAATTCCGTGGCTCGAGAGATCTTCGACTGTGCCTTCTAGTT
GCCAGCCATCTGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCA
GGCATGCACGTGCGGACCGAGCGGCCGC (SEQ ID NO: 92)

CN3270 (length between ITRs: 2205 bp):
GCGGCCGCACGCGTTATCTTAGAGTGGGAAGATTTGAGAAGTGCCATGGTTAATATGACT
GACTTTTTATTCTTATTTCTTTTAATTTCATGGTTCTAAATCCGAATTTAATCATAGTACCCAG
AAAAGCAGAGGTGTAGAGGTTCACAGTGGGAGTTGTAATCTAGCCCTATTCATTTTGACCT
CAAAACCCAAATTATTTATAACAAATTATTTCCTATTCTTTCCTTCACTATTCAGGAACATCTG
TCCACCACTTACATGATCACTTATCTTGCTATTGTGTCATTTTGATGAAAAGAATTTTTTCT
AAATATCTAAATACAAGGCCCCATATTAACAGTGCTTTTTAAATCCCCACAGATGTGGGAGA
TGACCCCTTTCCATCCCTGAAGATTGTAATTGGGCCAGTCTTTAGTACAGTTTGTTCCAATA
AAGAGATACAATTTTATTCATTAATTTGTGTATTCATTTAGCAAATCACTTTAGAGTCTTATTA
TATCAGGATTTTGGGGTCTATTTTAGTATATCTTTTTGTATTTCTTGGAACCTCTCCAATTATT
CTAGACTCTTTCAAAGGTTGGTGATCAATATTAGACATTATTATGAAAAGAATCTTACTTGCT
AAAAGGGTTAGATGGAGCTCGGGCTGGGCATAAAAGTCAGGGCAGAGCCATCTATTGCTT
ACATTTGCTTCTGGGATCCAGATCTTTCGAAGCTAGCGCTACCGGTCGCCACCATGGTGAG
CAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAG
CTGACCCTGAAGCTGATCTGCACCACCGGCAAGCTGCCCGTGCCCTGGCCCACCCTCGT
GACCACCCTGGGCTACGGCGTGCAGTGCTTCGCCCGCTACCCCGACCACATGAAGCAGC
ACGACTTCTTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACCCTGGTGA
ACCGCATCGAGCTGAAGGGCATCGACTTCAAGGAGGACGGCAACATCCTGGGGCACAAG
CTGGAGTACAACTACAACAGCCACAACGTCTATATCACCGCCGACAAGCAGAAGAACGGC
ATCAAGGCCAACTTCAAGATCCGCCACAACATCGAGGACGGCGGCGTGCAGCTCGCCGA
CCACTACCAGCAGAACACCCCCATCGGCGACGGCCCCGTGCTGCTGCCCGACAACCACT
ACCTGAGCTACCAGTCCAAGCTGAGCAAAGACCCCAACGAGAAGCGCGATCACATGGTCC
TGCTGGAGTTCGTGACCGCCGCCGGGATCACTCTCGGCATGGACGAGCTGTACAAGTAAG
TCGACGGCGCGCCGCGGCCTTAAAGAGACCGGTTCACTGTGACAGTAAAAGAGACCGGTT
CACTGTGAGAATGAAAGAGACCGGTTCACTGTGATCGGAAAAGAGACCGGTTCACTGTGA
GCGGCCTTGAAACCCAGCAGACAATGTAGCTCAGTAGAAACCCAGCAGACAATGTAGCTG
AATGGAAACCCAGCAGACAATGTAGCTTCGGAGAAACCCAGCAGACAATGTAGCTGTCGA
CGAATTCGATATCATAATCAACCTCTGGATTACAAAATTTGTGAAAGATTGACTGGTATTCTT
AACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA

FIG. 14 cont'd

AAATGAGGAAATTGCATCGCATTGTCTGAGTAGGTGTCATTCTATTCTGGGGGGGTGGGGGTG
GGGCAGGACAGCAAGGGGGAGGATTGGGAAGACAATAGCAGGCATGAGATCTCACGTGC
GGACCGAGCGGCCGC (SEQ ID NO: 93)

CN3316 (length between ITRs: 1960 bp):
GCGGCCGCACGCGTAGTGACTTGGTGCTATGAGCCATATTTTGCTGTTGCTGTTGTTACTG
GTAGTTTTTGTAATTCTGGGGCTAAAACTTGGGGTCTGGTATGCTGTCATTTACCAGTGAG
CTATACCCTGGATATTATGATTTAGATGAATGTGAAATATCACCCCAGACATACATATACTAA
ACACTTGGCCCTTGGCCCATGATGCTAAATGGAGGAGATAGAAGCTTTTGGGGCACAGCC
TAGTGGAAGGAAATGAGGTCAAATGACATGTACTCTGAAAGGAATATGGGTATTCTGGGCT
TGCGTTATTCTCTCTCTCCCTCTCTCTCCCTCTCTCTCCCTCTCCCTCTCTCTTTCTCCTTTT
CTCTTTCTCTCCTCGCCTTGTTTTCCAGAGCTCGGGCTGGGCATAAAAGTCAGGGCAGAGC
CATCTATTGCTTACATTTGCTTCTGGGATCCAGATCTTTCGAAGCTAGCGCTACCGGTCGC
CACCATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCGATGCC
ACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA
TCACATGGTCCTGCTGGAGTTCGTGACCGCCGCCGGGATCACTCTCGGCATGGACGAGCT
GTACAAGTAAGTCGACGGCGCGCCGCGGCCTTAAAGAGACCGGTTCACTGTGACAGTAAA
AGAGACCGGTTCACTGTGAGAATGAAAGAGACCGGTTCACTGTGATCGGAAAAGAGACCG
GTTCACTGTGAGCGGCCTTGAAACCCAGCAGACAATGTAGCTCAGTAGAAACCCAGCAGA
CAATGTAGCTGAATGGAAACCCAGCAGACAATGTAGCTTCGGAGAAACCCAGCAGACAAT
GTAGCTGTCGACGAATTCGATATCATAATCAACCTCTGGATTACAAAATTTGTGAAAGATTG
ACTGGTATTCTTAACTATGTTGCTCCTTTTACGCTATGTGGATACGCTGCTTTAATGCCTTT
GTATCATGCTATTGCTTCCCGTATGGCTTTCATTTTCTCCTCCTTGTATAAATCCTGGTTAGT
TCTTGCCACGGCGGAACTCATCGCCGCCTGCCTTGCCCGCTGCTGGACAGGGGCTCGGC
TGTTGGGCACTGACAATTCCGTGGCTCGAGAGATCTTCGACTGTGCCTTCTAGTTGCCAGC
CATCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGG
GGGGTGGGGTGGGGCAGGACAGCAAGGGGGAGGATTGGGAAGACAATAGCAGGCATGA
GATCTCACGTGCGGACCGAGCGGCCGC (SEQ ID NO: 94)

CN3271 (length between ITRs: 2895 bp):
GCGGCCGCACGCGTAGAAACACCACAAGCAAAGCCAAAATAGGTGGCCTAGAACTTCCAG
CTTGAAATATGGGAGAGAATGAGGGAGGCACTGTAGAGCAGCTGCCGGGTGCCGCATGA
GAACAATTCTCCCTGCTCATAATTAATCCTACCTATTTCTGATGACAGCTGGCTCTTCACTTT
GAACAAGCTAGTTAACAACTTTCTTCTCACATTGAGCAAATAATTCATATTTAATTACTTAAC
CACCAGTTACAAAATGAGAATCATCAAGGAATCACAATTAATTTGCTATTGACAAACTCATA
CTTTTAGCAGGCTGATTTCTACTTTATACTTAGATTGGTAATGAAAATGAAGCTTATTTTAG
TTGATTGGTTGGACTTGTGTATGAATATTATCTATTATTTGAAAAGCCAAACTTGAATGCAAA
AAAATATTGAATATGAAAAGAGAAACACCACAAGCAAAGCCAAAATAGGTGGCCTAGAACT

FIG. 14 cont'd

TCCAGCTTGAAATATGGGAGAGAATGAGGGAGGCACTGTAGAGCAGCTGCCGGGTGCCG
CATGAGAACAATTCTCCCTGCTCATAATTAATCCTACCTATTTCTGATGACAGCTGGCTCTT
CACTTTGAACAAGCTAGTTAACAACTTTCTTCTCACATTGAGCAAATAATTCATATTTAATTA
CTTAACCACCAGTTACAAAATGAGAATCATCAAGGAATCACAATTAATTTGCTATTGACAAA
CTCATACTTTTAGCAGGCTGATTTCTACTTTATACTTAGATTGGTAATGAAAAATGAAGCTTA
TTTTAGTTGATTGGTTGGACTTGTGTATGAATATTATCTATTATTTGAAAAGCCAAACTTGAA
TGCAAAAAAATATTGAATATGAAAAGAGAAACACCACAAGCAAAGCCAAAATAGGTGGCCT
AGAACTTCCAGCTTGAAATATGGGAGAGAATGAGGGAGGCACTGTAGAGCAGCTGCCGGG
TGCCGCATGAGAACAATTCTCCCTGCTCATAATTAATCCTACCTATTTCTGATGACAGCTGG
CTCTTCACTTTGAACAAGCTAGTTAACAACTTTCTTCTCACATTGAGCAAATAATTCATATTT
AATTACTTAACCACCAGTTACAAAATGAGAATCATCAAGGAATCACAATTAATTTGCTATTGA
CAAACTCATACTTTTAGCAGGCTGATTTCTACTTTATACTTAGATTGGTAATGAAAAATGAAG
CTTATTTTAGTTGATTGGTTGGACTTGTGTATGAATATTATCTATTATTTGAAAAGCCAAACT
TGAATGCAAAAAAATATTGAATATGAAAAGGAGCTCGGGCTGGGCATAAAAGTCAGGGCAG
AGCCATCTATTGCTTACATTTGCTTCTGGGATCCAGATCTTTCGAAGCTAGCGCTACCGGT
CGCCACCATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGAT
GCCACCTACGGCAAGCTGACCCTGAAGCTGATCTGCACCACCGGCAAGCTGCCCGTGCC
CTGGCCCACCCTCGTGACCACCCTGGGCTACGGCGTGCAGTGCTTCGCCCGCTACCCCG
ACCACATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAAC
ATCCTGGGGCACAAGCTGGAGTACAACTACAACAGCCACAACGTCTATATCACCGCCGAC
AAGCAGAAGAACGGCATCAAGGCCAACTTCAAGATCCGCCACAACATCGAGGACGGCGGC
GTGCAGCTCGCCGACCACTACCAGCAGAACACCCCCATCGGCGACGGCCCCGTGCTGCT
GCCCGACAACCACTACCTGAGCTACCAGTCCAAGCTGAGCAAAGACCCCAACGAGAAGCG
CGATCACATGGTCCTGCTGGAGTTCGTGACCGCCGCCGGGATCACTCTCGGCATGGACGA
GCTGTACAAGTAAGTCGACGGCGCGCCGCGGCCTTAAAGAGACCGGTTCACTGTGACAGT
AAAAGAGACCGGTTCACTGTGAGAATGAAAGAGACCGGTTCACTGTGATCGGAAAAGAGA
CCGGTTCACTGTGAGCGGCCTTGAAACCCAGCAGACAATGTAGCTCAGTAGAAACCCAGC
AGACAATGTAGCTGAATGGAAACCCAGCAGACAATGTAGCTTCGGAGAAACCCAGCAGAC
AATGTAGCTGTCGACGAATTCGATATCATAATCAACCTCTGGATTACAAAATTTGTGAAAGA
TTGACTGGTATTCTTAACTATGTTGCTCCTTTTACGCTATGTGGATACGCTGCTTTAATGCC
TTTGTATCATGCTATTGCTTCCCGTATGGCTTTCATTTTCTCCTCCTTGTATAAATCCTGGTT
AGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGG
CATGAGATCTCACGTGCGGACCGAGCGGCCGC (SEQ ID NO: 95)

CN3793 (length between ITRs: 2409 bp):
GCGGCCGCACGCGTCAGTTTCCAGCGTGGTTGTTGATGAGGCTCAGAGAAAAGACTCTAA
AGTTATGATGGGAAATTACCATGCCATTCATCATCATACACATTCACCTCACACTTTCTGAG
TCTCCTATACAAAGTCAGTTCTCTGCCAAGGGCATGGAAGAGCGAGGAACAGGATGTTAG
GAAGGGCTGACAGCGCTGTTTTAGCCTGACAGGCAGATTTACAACAGGAGAATGAATGTA
CCACTTGTATAAGAAGGCCATGCGGCACTGCTAATGCACAAGTTGGCAGTACATCAACATC
TCTATCGTCCTCATATTCATGAAGCAGAGAACGGAAATGGCACACTGCTTGTACCGGCGAA

FIG. 14 cont'd

TAACCAAAGTGAACGCCCTACGGCTGCCATTCACTGTGTCCTTCCAAAAGCATTTTTCTACT
GAGCTCTTCCCAGAGATTTAGGGTTTGCTTAGACAGGTCTTATGACGCCACGTGATAGGTC
ATTCTTCTGTTCTGAGGAGCTTGGAGAAGATCGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTCTCCAAGGGCGAGGAGCTGTTCACCGGGGTGGTGCCCATCCTGG
TCGAGCTGGACGGCGATGTCAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAAGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGGGCTCTGGTGCTACCAACTTCTCACTGTTGAAACAGGCAGGGGATGT
AGAGGAGAATCCAGGGCCTGGTGCTAGTGGAGACTACAAAGACCATGACGGAGATTATAA
AGATCATGACATCGATTACAAGGATGACGATGACAAGTCCGGACTCAGATCTGGAGGCTC
CGGAGGCCCAGAGCCAGCGAAGTCTGCTCCCGCCCCGAAAAAGGGCTCCAAGAAGGCGG
TGACTAAGGCGCAGAAGAAAGGCGGCAAGAAGCGCAAGCGCAGCCGCAAGGAGAGCTAT
TCCATCTATGTGTACAAGGTTCTGAAGCAGGTCCACCCTGACACCGGCATTTCGTCCAAGG
CCATGGGCATCATGAATTCGTTTGTGAACGACATTTTCGAGCGCATCGCAGGAGAGGCTTC
CCGCCTGGCGCATTACAACAAGCGCTCGACCATCACCTCCCGGGAGATCCAGACGGCCG
TGCGCCTGCTGCTGCCTGGGGAGTTGGCCAAGCACGCCGTGTCCGAGGGTACTAAGGCC
ATCACCAAGTACACCAGCGCTAAGTAATGAGGCGCGCCGCGGCCGCGAATTCGATATCAT
AATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGC
TTTCATTTTCTCCTCCTTGTATAAATCCTGGTTAGTTCTTGCCACGGCGGAACTCATCGCCG
CCTGCCTTGCCCGCTGCTGGACAGGGGCTCGGCTGTTGGGCACTGACAATTCCGTGGCT
CGAGAGATCTTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCA
AGGGGGAGGATTGGGAAGACAATAGCAGGCATGAGATCTCACGTGCGGACCGAGCGGCC
GC (SEQ ID NO: 96)

CN3794 (length between ITRs: 2343 bp):
GCGGCCGCACGCGTGTAGAACATACTTATTAACACATTCGTACATAAAATAAAATTCTACTC
TCCCGACCTTTTCCTCACCATCTTGCTTTTCAACGTATGGCGTTAGACCTAACAGCGAGTC
CACTTCTTCCCCTTTCATTCTGTAGCAAGAACACACGGCTCACTGTAACAGGGACTTGGCT
GTGGGTTGCAGACTGGCTTCCTGCTGCCTCCACTTGAGCCCCACACAGCTGTGGCTTTGT
GTTTACAACCCTCCAGGCTGCCATTCATTCGGTGCTGTGGGCTCATGTACTGGAAGACAGC
TTCCATCACAACCTTCCCGTCCCAGCAGGAGAACTCCCTTGCTTCCTTGGGGAACATTTGC
TTGCTCCTGCTGCTTGGCTCTTCCCACTTTTGCCTCACTCTGGAGTTTCTCTCTCCCGTTTT
GAATTCTAGTAGTAAACACATGGCCGAGCTCGGGCTGGGCATAAAAGTCAGGGCAGAGCC
ATCTATTGCTTACATTTGCTTCTGGGATCCAGATCTTTCGAAGCTAGCGCTACCGGTCGCC
ACCATGGTCTCCAAGGGCGAGGAGCTGTTCACCGGGGTGGTGCCCATCCTGGTCGAGCT
GGACGGCGATGTCAACGGCCACAAGTTCAGCGTGTCCGGCGAGGGCGAGGGCGATGCCA

FIG. 14 cont'd

CCTACGGCAAGCTGACCCTGAAGCTGATCTGCACCACCGGCAAGCTGCCCGTGCCCTGG
CCCACCCTCGTGACCACCCTGGGCTACGGCGTGCAGTGCTTCGCCCGCTACCCCGACCA
CATGAAGCAGCACGACTTCTTCAAGTCCGCCATGCCCGAAGGCTACGTCCAGGAGCGCAC
CATCTTCTTCAAAGACGACGGCAACTACAAGACCCGCGCCGAGGTGAAGTTCGAGGGCGA
CACCCTGGTGAACCGCATCGAGCTGAAGGGCATCGACTTCAAGGAGGACGGCAACATCCT
GGGGCACAAGCTGGAGTACAACTACAACAGCCACAACGTCTATATCACCGCCGACAAGCA
GAAGAACGGCATCAAGGCCAACTTCAAGATCCGCCACAACATCGAGGACGGCGGCGTGC
AGCTCGCCGACCACTACCAGCAGAACACCCCCATCGGCGACGGCCCCGTGCTGCTGCCC
GACAACCACTACCTGAGCTACCAGTCCAAGCTGAGCAAAGACCCCAACGAGAAGCGCGAT
CACATGGTCCTGCTGGAGTTCGTGACCGCCGCCGGGATCACTCTCGGCATGGACGAGCT
GTACAAGGGCTCTGGTGCTACCAACTTCTCACTGTTGAAACAGGCAGGGGATGTAGAGGA
GAATCCAGGGCCTGGTGCTAGTGGAGACTACAAAGACCATGACGGAGATTATAAAGATCAT
GACATCGATTACAAGGATGACGATGACAAGTCCGGACTCAGATCTGGAGGCTCCGGAGGC
CCAGAGCCAGCGAAGTCTGCTCCCGCCCCGAAAAAGGGCTCCAAGAAGGCGGTGACTAA
GGCGCAGAAGAAAGGCGGCAAGAAGCGCAAGCGCAGCCGCAAGGAGAGCTATTCCATCT
ATGTGTACAAGGTTCTGAAGCAGGTCCACCCTGACACCGGCATTTCGTCCAAGGCCATGG
GCATCATGAATTCGTTTGTGAACGACATTTTCGAGCGCATCGCAGGAGAGGCTTCCCGCCT
GGCGCATTACAACAAGCGCTCGACCATCACCTCCCGGGAGATCCAGACGGCCGTGCGCC
TGCTGCTGCCTGGGGAGTTGGCCAAGCACGCCGTGTCCGAGGGTACTAAGGCCATCACC
AAGTACACCAGCGCTAAGTAATGAGGCGCGCCGCGGCCGCGAATTCGATATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGG
GGAGGATTGGGAAGACAATAGCAGGCATGAGATCTCACGTGCGGACCGAGCGGCCGC
(SEQ ID NO: 97)

CN3795 (length between ITRs: 2411 bp):
GCGGCCGCACGCGTCCAGTGAGATCTTCCACCAGCAGAACTCATGGACACAAACTAGACA
GCTCACTTCTTGCCTGTATTCCAGGAGTGGCTTTTTCTCTACTCCTGTACTGATGCCAGTCA
TTCAGAGTGCACTCAAGACACTTGACCCACATCAGTTAAGAGAATGAAAATCAAGCTCTGA
AAGCCATTAGCTTCTATTGCACACCCAGAAAACAGGCTCATCAAACACCTTCTTATGGTAAT
GCCTTTGATCAAAAGGAGGGTTAATTCAACAAATGGTTTGCACCGTGACCCCATCAAAGCC
TGAGCACCAGTGTCCTCATTTCCTTTCCCCTGGTGTATAATGAGTTGTTAGTCTGGCTCACC
TTGTCATCCCCATCATACTGCCATAATCCACATCTCTAAAGAGTGGATTACAACAGTCCCGT
CTGTGACACTCAGGACTGGCATCAAGGTTCCCAAGCTCTAGTCTATTGTGACATTGATACA
AATAGGGCTCAGAGTCTCACTGATCACACCGAGCTCGGGCTGGGCATAAAAGTCAGGGCA
GAGCCATCTATTGCTTACATTTGCTTCTGGGATCCAGATCTTTCGAAGCTAGCGCTACCGG
TCGCCACCATGGTCTCCAAGGGCGAGGAGCTGTTCACCGGGGTGGTGCCCATCCTGGTC
GAGCTGGACGGCGATGTCAACGGCCACAAGTTCAGCGTGTCCGGCGAGGGCGAGGGCG
ATGCCACCTACGGCAAGCTGACCCTGAAGCTGATCTGCACCACCGGCAAGCTGCCCGTGC
CCTGGCCCACCCTCGTGACCACCCTGGGCTACGGCGTGCAGTGCTTCGCCCGCTACCCC
GACCACATGAAGCAGCACGACTTCTTCAAGTCCGCCATGCCCGAAGGCTACGTCCAGGAG
CGCACCATCTTCTTCAAAGACGACGGCAACTACAAGACCCGCGCCGAGGTGAAGTTCGAG
GGCGACACCCTGGTGAACCGCATCGAGCTGAAGGGCATCGACTTCAAGGAGGACGGCAA

FIG. 14 cont'd

CATCCTGGGGCACAAGCTGGAGTACAACTACAACAGCCACAACGTCTATATCACCGCCGA
CAAGCAGAAGAACGGCATCAAGGCCAACTTCAAGATCCGCCACAACATCGAGGACGGCGG
CGTGCAGCTCGCCGACCACTACCAGCAGAACACCCCCATCGGCGACGGCCCCGTGCTGC
TGCCCGACAACCACTACCTGAGCTACCAGTCCAAGCTGAGCAAAGACCCCAACGAGAAGC
GCGATCACATGGTCCTGCTGGAGTTCGTGACCGCCGCCGGGATCACTCTCGGCATGGAC
GAGCTGTACAAGGGCTCTGGTGCTACCAACTTCTCACTGTTGAAACAGGCAGGGGATGTA
GAGGAGAATCCAGGGCCTGGTGCTAGTGGAGACTACAAAGACCATGACGGAGATTATAAA
GATCATGACATCGATTACAAGGATGACGATGACAAGTCCGGACTCAGATCTGGAGGCTCC
GGAGGCCCAGAGCCAGCGAAGTCTGCTCCCGCCCCGAAAAAGGGCTCCAAGAAGGCGGT
GACTAAGGCGCAGAAGAAAGGCGGCAAGAAGCGCAAGCGCAGCCGCAAGGAGAGCTATT
CCATCTATGTGTACAAGGTTCTGAAGCAGGTCCACCCTGACACCGGCATTTCGTCCAAGGC
CATGGGCATCATGAATTCGTTTGTGAACGACATTTTCGAGCGCATCGCAGGAGAGGCTTCC
CGCCTGGCGCATTACAACAAGCGCTCGACCATCACCTCCCGGGAGATCCAGACGGCCGT
GCGCCTGCTGCTGCCTGGGGAGTTGGCCAAGCACGCCGTGTCCGAGGGTACTAAGGCCA
TCACCAAGTACACCAGCGCTAAGTAATGAGGCGCGCCGCGGCCGCGAATTCGATATCATA
ATCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTAGTTCTTGCCACGGCGGAACTCATCGCCGC
CTGCCTTGCCCGCTGCTGGACAGGGGCTCGGCTGTTGGGCACTGACAATTCCGTGGCTC
GAGAGATCTTCGACTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAA
GGGGGAGGATTGGGAAGACAATAGCAGGCATGAGATCTCACGTGCGGACCGAGCGGCCG
C (SEQ ID NO: 98)

CN3790 (length between ITRs: 2043 bp):
GCGGCCGCACGCGTTATCTTAGAGTGGGAAGATTTGAGAAGTGCCATGGTTAATATGACT
GACTTTTTATTCTTATTTCTTTTAATTTCATGGTTCTAAATCCGAATTTAATCATAGTACCCAG
AAAAGCAGAGGTGTAGAGGTTCACAGTGGGAGTTGTAATCTAGCCCTATTCATTTTGACCT
CAAAACCCAAATTATTTATAACAAATTATTTCCTATTCTTTCCTTCACTATTCAGGAACATCTG
TCCACCACTTACATGATCACTTATCTTGCTATTGTGTCATTTTGATGAAAAGAATTTTTTCT
AAATATCTAAATACAAGGCCCCATATTAACAGTGCTTTTTAAATCCCCACAGATGTGGGAGA
TGACCCCTTTCCATCCCTGAAGATTGTAATTGGGCCAGTCTTTAGTACAGTTTGTTCCAATA
AAGAGATACAATTTTATTCATTAATTTGTGTATTCATTTAGCAAATCACTTTAGAGTCTTATTA
TATCAGGATTTTGGGGTCTATTTTAGTATATCTTTTGTATTTCTTGGAACCTCTCCAATTATT
CTAGACTCTTTCAAAGGTTGGTGATCAATATTAGACATTATTATGAAAAGAATCTTACTTGCT
AAAAGGGTTAGATGGAGCTCGGGCTGGGCATAAAAGTCAGGGCAGAGCCATCTATTGCTT
ACATTTGCTTCTGGGATCCAGATCTTTCCAAGCTAGCCACCATGGTGCCCAAGAAGAAGAG
GAAAGTCTCCAACCTGCTGACTGTGCACCAAAACCTGCCTGCCCTCCCTGTGGATGCCAC
CTCTGATGAAGTCAGGAAGAACCTGATGGACATGTTCAGGGACAGGCAGGCCTTCTCTGA
ACACACCTGGAAGATGCTCCTGTCTGTGTGCAGATCCTGGGCTGCCTGGTGCAAGCTGAA
CAACAGGAAATGGTTCCCTGCTGAACCTGAGGATGTGAGGGACTACCTCCTGTACCTGCA
AGCCAGAGGCCTGGCTGTGAAGACCATCCAACAGCACCTGGGCCAGCTCAACATGCTGCA
CAGGAGATCTGGCCTGCCTCGCCCTTCTGACTCCAATGCTGTGTCCCTGGTGATGAGGAG
AATCAGAAGGAGAATGTGGATGCTGGGGAGAGAGCCAAGCAGGCCCTGGCCTTTGAAC
GCACTGACTTTGACCAAGTCAGATCCCTGATGGAGAACTCTGACAGATGCCAGGACATCA
GGAACCTGGCCTTCCTGGGCATTGCCTACAACACCCTGCTGCGCATTGCCGAAATTGCCA
GAATCAGAGTGAAGGACATCTCCCGCACCGATGGTGGGAGAATGCTGATCCACATTGGCA

FIG. 14 cont'd

GGACCAAGACCCTGGTGTCCACAGCTGGTGTGGAGAAGGCCCTGTCCCTGGGGGTTACC
AAGCTGGTGGAGAGATGGATCTCTGTGTCTGGTGTGGCTGATGACCCCAACAACTACCTG
TTCTGCCGGGTCAGAAAGAATGGTGTGGCTGCCCCTTCTGCCACCTCCCAACTGTCCACC
CGGGCCCTGGAAGGGATCTTTGAGGCCACCCACCGCCTGATCTATGGTGCCAAGGATGAC
TCTGGGCAGAGATACCTGGCCTGGTCTGGCCACTCTGCCAGAGTGGGTGCTGCCACCGA
CATGGCCAGGGCTGGTGTGTCCATCCCTGAAATCATGCAGGCTGGTGGCTGGACCAATGT
GAACATTGTGATGAACTACATCAGAAACCTGGACTCTGAGACTGGGGCCATGGTGAGGCT
GCTCGAAGATGGGGACTGAGGCGCGCCGAATTCAAGCTTCTCGAGAGATCTTCGACTGTG
CCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGCACGTGCGGACCGAGCGGCCGC (SEQ ID NO: 99)

CN3751 (length between ITRs: 1747 bp):
GCGGCCGCACGCGTTATCTTAGAGTGGGAAGATTTGAGAAGTGCCATGGTTAATATGACT
GACTTTTTATTCTTATTTCTTTTAATTTCATGGTTCTAAATCCGAATTTAATCATAGTACCCAG
AAAAGCAGAGGTGTAGAGGTTCACAGTGGGAGTTGTAATCTAGCCCTATTCATTTTGACCT
CAAAACCCAAATTATTTATAACAAATTATTTCCTATTCTTTCCTTCACTATTCAGGAACATCTG
TCCACCACTTACATGATCACTTATCTTGCTATTGTGTCATTTTGATGAAAAGAATTTTTTCT
AAATATCTAAATACAAGGCCCCATATTAACAGTGCTTTTTAAATCCCCACAGATGTGGGAGA
TGACCCCTTTCCATCCCTGAAGATTGTAATTGGGCCAGTCTTTAGTACAGTTTGTTCCAATA
AAGAGATACAATTTTATTCATTAATTTGTGTATTCATTTAGCAAATCACTTTAGAGTCTTATTA
TATCAGGATTTTGGGGTCTATTTTAGTATATCTTTTTGTATTTCTTGGAACCTCTCCAATTATT
CTAGACTCTTTCAAAGGTTGGTGATCAATATTAGACATTATTATGAAAAGAATCTTACTTGCT
AAAAGGGTTAGATGGAGCTCGGGCTGGGCATAAAAGTCAGGGCAGAGCCATCTATTGCTT
ACATTTGCTTCTGGGATCCAGATCTTTCGAAGCTAGCAATTCGCCACCATGACGAGTGATG
AGGTTCGCAAGAACCTGATGGACATGTTCAGGGATCGCCAGGCGTTTTCTGAGCATACCT
GGAAAATGCTTCTGTCCGTTTGCCGGTCGTGGGCGGCATGGTGCAAGTTGAATAAATTTGC
GGAATATTGCCTCAGTTTTGGCACCGAAATTTTAACCGTTGAGTACGGCCCATTGCCCATT
GGCAAAATTGTGAGTGAAGAAATTAATTGTTCTGTGTACAGTGTTGATCCAGAAGGGAGAG
TTTACACCCAGGCGATCGCCCAATGGCATGACCGGGGAGAGCAGGAAGTATTGGAATATG
AATTGGAAGATGGTTCAGTAATCCGAGCTACCTCTGACCACCGCTTTTTAACCACCGATTAT
CAACTGTTGGCGATCGAAGAAATTTTTGCTAGGCAACTGGACTTGTTGACTTTAGAAAATAT
TAAGCAAACTGAAGAAGCTCTTGACAACCATCGTCTTCCCTTTCCATTACTTGACGCTGGG
ACAATTAAATAACTCGAATCATAATCAACCTCTGGATTACAAAATTTGTGAAAGATTGACTG
GTATTCTTAACTATGTTGCTCCTTTTACGCTATGTGGATACGCTGCTTTAATGCCTTTGTATC
ATGCTATTGCTTCCCGTATGGCTTTCATTTTCTCCTCCTTGTATAAATCCTGGTTAGTTCTTG
CCACGGCGGAACTCATCGCCGCCTGCCTTGCCCGCTGCTGGACAGGGGCTCGGCTGTTG
GGCACTGACAATTCCGTGGCTCGAGAGATCTTCGACTGTGCCTTCTAGTTGCCAGCCATCT
GTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGG
TGGGGTGGGGCAGGACAGCAAGGGGGAGGATTGGGAAGACAATAGCAGGCATGAGATCT
CACGTGCGGACCGAGCGGCCGC (SEQ ID NO: 100)

CN3752 (length between ITRs: 2071 bp):
GCGGCCGCACGCGTTATGATGTGCCAGGCTTGGGAGAAACACCACAAGCAAAGCCAAAAT
AGGTGGCCTAGAACTTCCAGCTTGAAATATGGGAGAGAATGAGGGAGGCACTGTAGAGCA
GCTGCCGGGTGCCGCATGAGAACAATTCTCCCTGCTCATAATTAATCCTACCTATTTCTGAT

FIG. 14 cont'd

GACAGCTGGCTCTTCACTTTGAACAAGCTAGTTAACAACTTTCTTCTCACATTGAGCAAATA
ATTCATATTTAATTACTTAACCACCAGTTACAAAATGAGAATCATCAAGGAATCACAATTAAT
TTGCTATTGACAAACTCATACTTTTAGCAGGCTGATTTCTACTTTATACTTAGATTGGTAATG
AAAAATGAAGCTTATTTTAGTTGATTGGTTGGACTTGTGTATGAATATTATCTATTATTTGAA
AAGCCAAACTTGAATGCAAAAAAATATTGAATATGAAAAGAAAAACATTTGCAGTAAAGCTT
GTTCTGAGCTCGGGCTGGGCATAAAAGTCAGGGCAGAGCCATCTATTGCTTACATTTGCTT
CTGGGATCCAGATCTTTCGAAGCTAGCAATTCGCCACCATGGTTAAAGTTATCGGTCGTCG
TTCCCTCGGAGTGCAAAGAATATTTGATATTGGTCTTCCCCAAGACCATAATTTTCTGCTAG
CCAATGGGGCGATCGCCGCCAATTGTTTTAACAAATCCAACCGGAAATGGTTTCCCGCAGA
ACCTGAAGATGTTCGCGATTATCTTCTATATCTTCAGGCGCGCGGTCTGGCAGTAAAAACT
ATCCAGCAACATTTGGGCCAGCTAAACATGCTTCATCGTCGGTCCGGGCTGCCACGACCA
AGTGACAGCAATGCTGTTTCACTGGTTATGCGGCGGATCCGAAAAGAAAACGTTGATGCC
GGTGAACGTGCAAAACAGGCTCTAGCGTTCGAACGCACTGATTTCGACCAGGTTCGTTCA
CTCATGGAAAATAGCGATCGCTGCCAGGATATACGTAATCTGGCATTTCTGGGGATTGCTT
ATAACACCCTGTTACGTATAGCCGAAATTGCCAGGATCAGGGTTAAAGATATCTCACGTAC
TGACGGTGGGAGAATGTTAATCCATATTGGCAGAACGAAAACGCTGGTTAGCACCGCAGG
TGTAGAGAAGGCACTTAGCCTGGGGGGTAACTAAACTGGTCGAGCGATGGATTTCCGTCTC
TGGTGTAGCTGATGATCCGAATAACTACCTGTTTTGCCGGGTCAGAAAAAATGGTGTTGCC
GCGCCATCTGCCACCAGCCAGCTATCAACTCGCGCCCTGGAAGGGATTTTTGAAGCAACT
CATCGATTGATTTACGGCGCTAAGGATGACTCTGGTCAGAGATACCTGGCCTGGTCTGGA
CACAGTGCCCGTGTCGGAGCCGCGCGAGATATGGCCCGCGCTGGAGTTTCAATACCGGA
GATCATGCAAGCTGGTGGCTGGACCAATGTAAATATTGTCATGAACTATATCCGTAACCTG
GATAGTGAAACAGGGGCAATGGTGCGCCTGCTGGAAGATGGCGATTAGCTCGAATCATAA
TCAACCTCTGGATTACAAAATTTGTGAAAGATTGACTGGTATTCTTAACTATGTTGCTCCTTT
TACGCTATGTGGATACGCTGCTTTAATGCCTTTGTATCATGCTATTGCTTCCCGTATGGCTT
TCATTTTCTCCTCCTTGTATAAATCCTGGTTAGTTCTTGCCACGGCGGAACTCATCGCCGCC
TGCCTTGCCCGCTGCTGGACAGGGGCTCGGCTGTTGGGCACTGACAATTCCGTGGCTCG
AGAGATCTTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCAT
CGCATTGTCTGAGTAGGTGTCATTCTATTCTGGGGGGTGGGGTGGGGCAGGACAGCAAG
GGGGAGGATTGGGAAGACAATAGCAGGCATGAGATCTCACGTGCGGACCGAGCGGCCGC
(SEQ ID NO: 101)

1

ARTIFICIAL EXPRESSION CONSTRUCTS FOR MODULATING GENE EXPRESSION IN CHANDELIER CELLS

CROSS-REFERENCE TO RELATED APPLICATION

This application is a U.S. National Phase Patent Application based on International Patent Application No. PCT/US2021/058812, filed on Nov. 10, 2021, which claims priority to U.S. Provisional Patent Application No. 63/112,102 filed on Nov. 10, 2020, each of which is incorporated herein by reference in its entirety as if fully set forth herein.

STATEMENT REGARDING FEDERALLY SPONSORED RESEARCH OR DEVELOPMENT

This invention was made with government support under MH114126 and DA036909 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2WO2329_ST25.txt. The text file is 184 KB, was created on May 4, 2023, and is being submitted electronically via Patent Center.

FIELD OF THE DISCLOSURE

The current disclosure provides artificial expression constructs for modulating gene expression in targeted central nervous system cell types. The artificial expression constructs can be used to express synthetic genes or modify gene expression in chandelier cells.

BACKGROUND OF THE DISCLOSURE

To fully understand the biology of the brain, different cell types need to be distinguished and defined and, to further study them, artificial expression constructs that can label and perturb them need to be identified. In mouse, recombinase driver lines have been used to great effect to label cell populations that share marker gene expression. However, the creation, maintenance, and use of such lines that label cell types with high specificity can be costly, frequently requiring double or triple transgenic crosses, which yield a low frequency of experimental animals. Furthermore, those tools require germline transgenic animals and thus are not applicable to humans.

Chandelier cells are a subtype of GABAergic interneurons that were discovered in the 1970s and that have been implicated in disorders such as epilepsy and schizophrenia. While significant information has been learned about this cell type, many questions regarding their function and brain-wide effects remain.

SUMMARY OF THE DISCLOSURE

The current disclosure provides artificial expression constructs that drive gene expression in chandelier cells. Particular embodiments of the artificial expression constructs utilize the enhancers eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, and eHGT_1024m to drive gene expression within chandelier cells. Additional embodiments utilize the enhancer eHGT_503m to drive gene expression in chandelier cells and VIP cells. Additional embodiments utilize enhancer eHGT_710m to drive gene expression in chandelier cells, glutamatergic neurons in the thalamus, and/or molecular layer GABAergic interneurons in the cerebellum.

Particular embodiments provide artificial expression constructs including the features of vectors described herein including vectors: CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and CN3752.

BRIEF DESCRIPTION OF THE FIGURES

Some of the drawings submitted herein may be better understood in color. Applicant considers the color versions of the drawings as part of the original submission and reserves the right to present color images of the drawings in later proceedings.

FIG. 14. Sequences supporting the disclosure, including eHGT_297m (SEQ ID NO: 1); eHGT_303m (SEQ ID NO: 2); eHGT_307m (SEQ ID NO: 3); eHGT_308m (SEQ ID NO: 4); eHGT_472m (SEQ ID NO: 5); eHGT_475m (SEQ ID NO: 6); eHGT_476m (SEQ ID NO: 7); eHGT_476m core (SEQ ID NO: 8); 3×_eHGT_476m core (SEQ ID NO: 9); eHGT_503m (SEQ ID NO: 10); eHGT_571m (SEQ ID NO: 11); eHGT_706m (SEQ ID NO: 12); eHGT_710m (SEQ ID NO: 13); eHGT_296m (SEQ ID NO: 14); eHGT_299m (SEQ ID NO: 15); eHGT_300m (SEQ ID NO: 16); eHGT_306m (SEQ ID NO: 17); eHGT_309m (SEQ ID NO: 18); eHGT_310m (SEQ ID NO: 19); eHGT_890m (SEQ ID NO: 20); eHGT_891m (SEQ ID NO: 21); eHGT_892m (SEQ ID NO: 22); eHGT_476m (SEQ ID NO: 23); eHGT_1022m (SEQ ID NO: 24); eHGT_1023m (SEQ ID NO: 25); eHGT_1024m (SEQ ID NO: 26); Beta-Globin Minimal Promoter (SEQ ID NO: 27); minCMV Promoter (SEQ ID NO: 28); Mutated minCMV Promoter (SEQ ID NO: 29); minRho Promoter (SEQ ID NO: 30); minRho* Promoter (SEQ ID NO: 31); Hsp68 minimal Promoter (SEQ ID NO: 32); SYFP2 (SEQ ID NO: 33); EGFP (SEQ ID NO:

Figure 1:
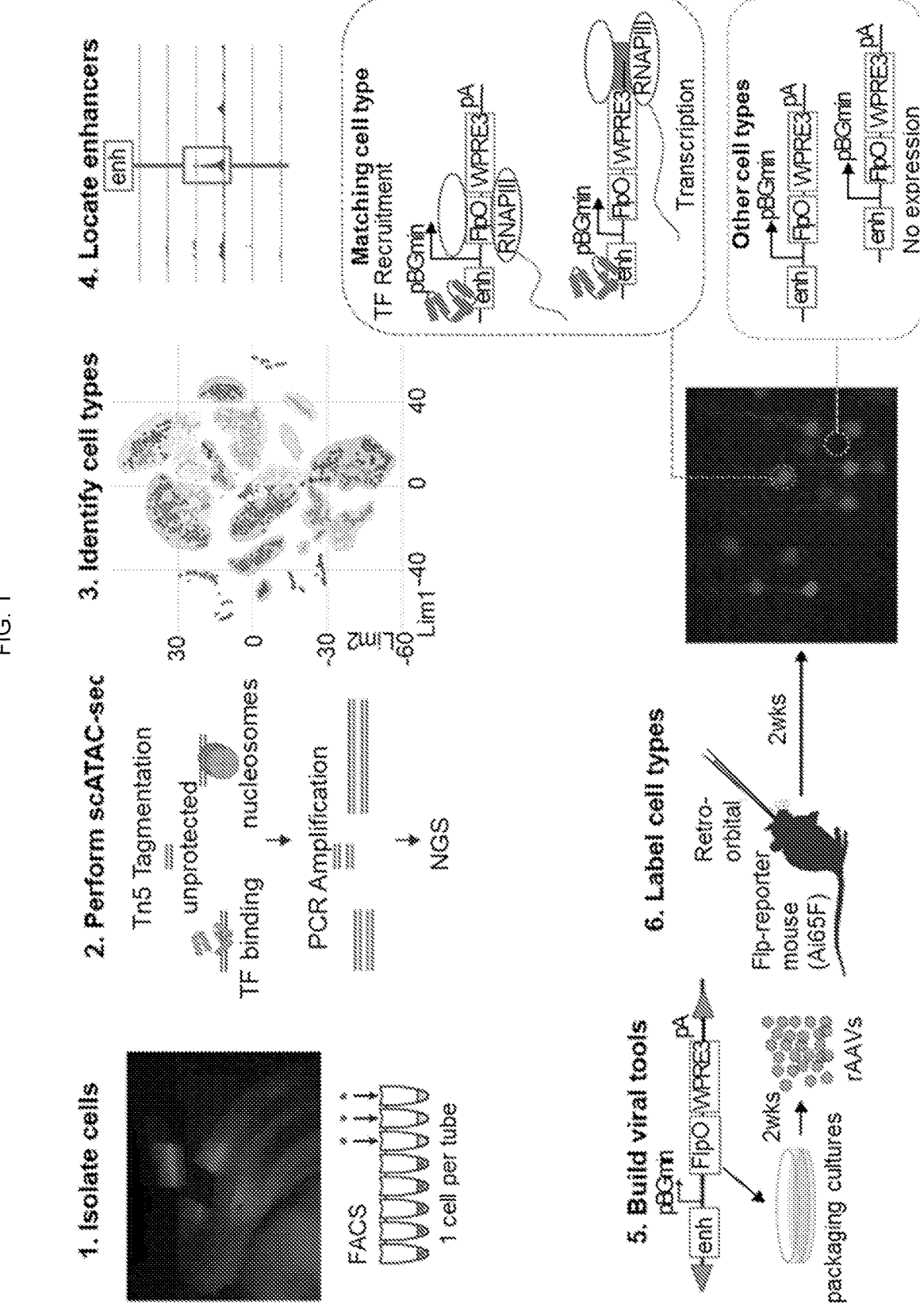
FIG. 1: Overview of enhancer discovery for viral tools. To build cell type-specific labeling tools, cells from adult mouse cortex were isolated and a single cell assay for transposase-accessible chromatin using sequencing (scATAC-seq) was performed. Samples were clustered and compared to single cell RNA sequencing (scRNA-seq) datasets to identify the clusters. Single cells matching the same transcriptomic types were then pooled and the genome was searched for type-specific putative enhancers. These regions were cloned upstream of a minimal promoter in an AAV genomic backbone, which was used to generate self-complementary adeno-associated viral vectors (scAAVs), recombinant adeno-associated viral vectors (rAAVs), plasmid adeno-associated virus vectors (pAAVs). These viral tools were delivered retro-orbitally to label specific cortical populations. In cells with a matching cell type, enhancers recruit their cognate transcription factors to drive cell type-specific expression. In other cells, viral genomes are present, but transcripts are not expressed.
Figure 2A:
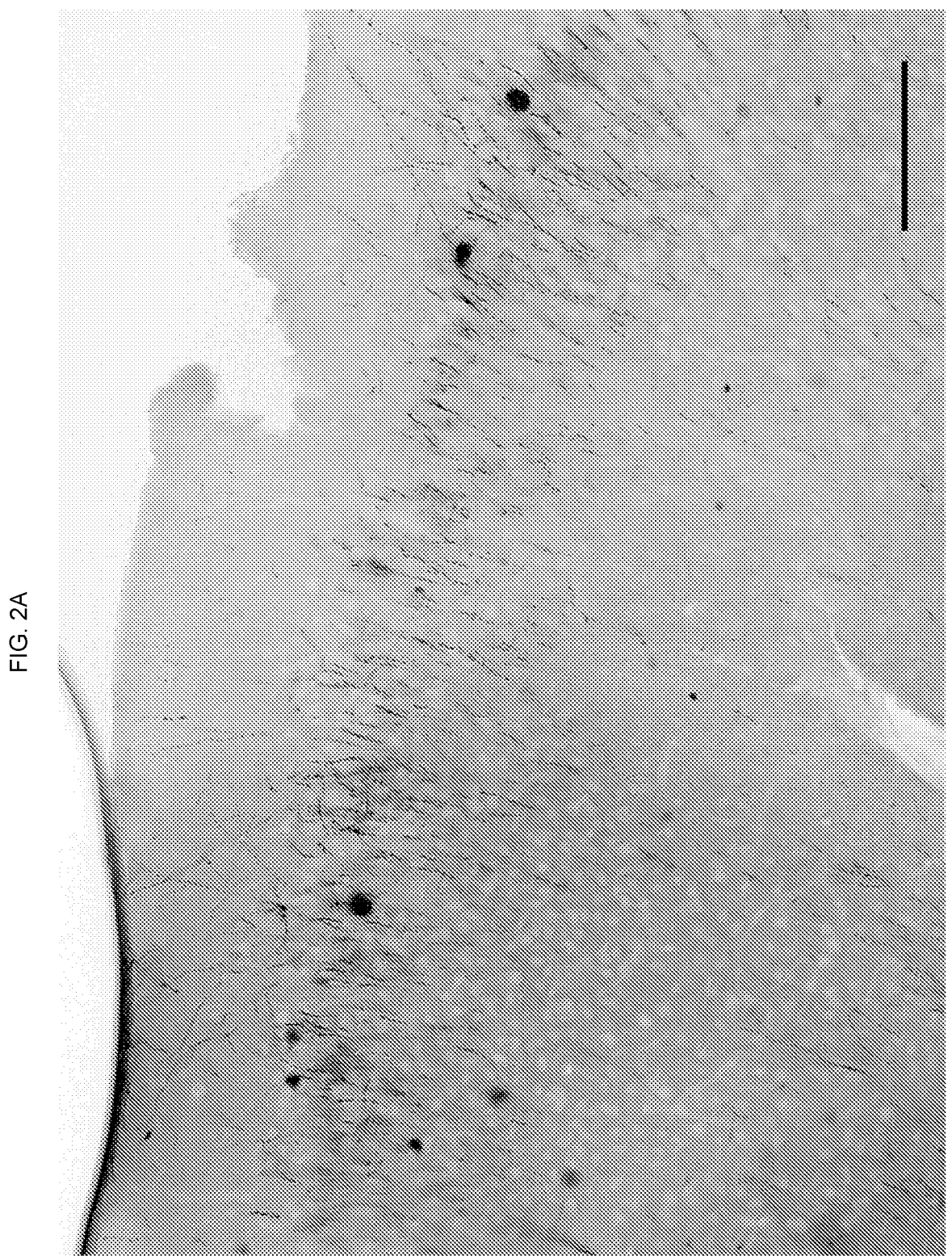
FIGS. 2A,2B. CN2320 (eHGT_475m) in mouse neocortex. (2A) Epifluorescence micrograph image (inverted) showing native SYFP2 expression in the neocortex 28 days after intracerebroventricular injection of 8.0E10 viral genome copies of AAV vector #CN2320 (eHGT_475m) in 2-day old mouse pup. Scale bar: 100 microns. (2B) Higher magnification view showing a cell body and signature chandelier cell axon cartridges. Scale bar: 50 microns.
Figure 2B:
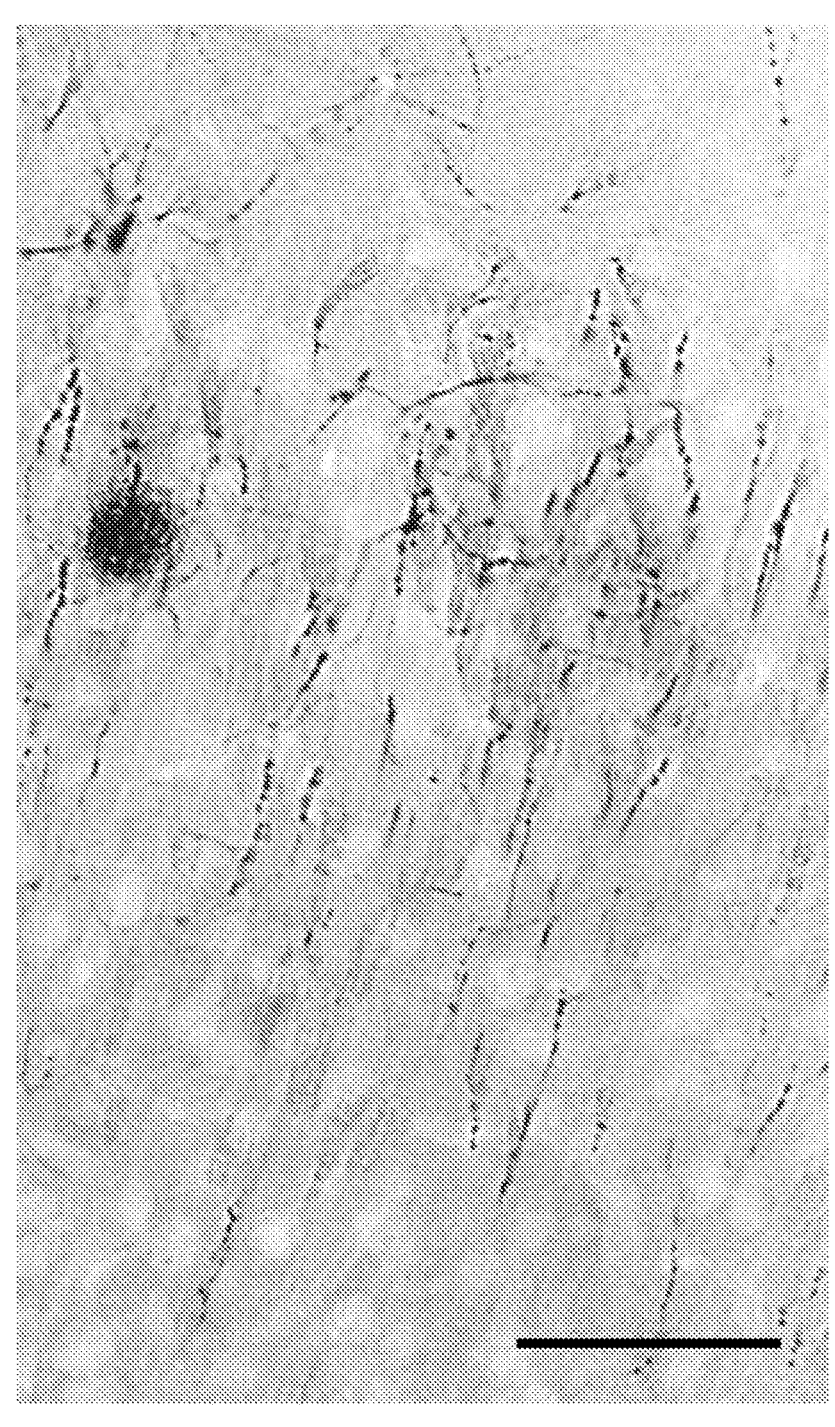

34); Optimized Flp recombinase (SEQ ID NO: 35); Improved Cre recombinase (iCre) (SEQ ID NO: 36); iCre (R297T) (SEQ ID NO: 37); CreN-inteinN (SEQ ID NO: 38); inteinC-CreC (SEQ ID NO: 39); SP10 insulator (SP10ins) (SEQ ID NO: 40); 3×SP10ins (SEQ ID NO: 41); 4×2C (SEQ ID NO: 42); miR128 Recognition Sequence (SEQ ID NO: 136); miR221 Recognition Sequence (SEQ ID NO: 137); 3×FLAG (SEQ ID NO: 43); 10 aa (SEQ ID NO: 44); H2B (SEQ ID NOs: 135 and 45); WPRE3 (SEQ ID NO: 46); WPRE (SEQ ID NO: 47); BGHpA (SEQ ID NO: 48); HGHpA (SEQ ID NO: 49); P2A (SEQ ID NOs: 50 and 51); T2A (SEQ ID NO: 52); E2A (SEQ ID NO: 53); F2A (SEQ ID NO: 54); Exemplary Plasmid Backbone 1—Left ITR (SEQ ID NO: 55); Exemplary Plasmid Backbone 1—Right ITR (SEQ ID NO: 56); Exemplary Plasmid Backbone 2—Left ITR (SEQ ID NO: 57); Exemplary Plasmid Backbone 2—Right ITR (SEQ ID NO: 58); PHP.eB capsid (SEQ ID NO: 59); AAV9 VP1 capsid protein (SEQ ID NO: 60); tet-Transactivator version 2 (tTA2) (SEQ ID NO: 61); GTPase HRas [Homo sapiens] (SEQ ID NO: 62); Substance P is position 58-68 of Protachykinin-1 [Homo sapiens] (SEQ ID NO: 63); Oxytocin is position 20-28 of Oxytocin-neurophysin 1 [Homo sapiens](SEQ ID NO: 64); GCaMP6m (SEQ ID NO: 65); GCaMP6s (SEQ ID NO: 66); GCaMP6f (SEQ ID NO: 67); CN1917 (SEQ ID NO: 68); CN2047 (SEQ ID NO: 69); CN2048 (SEQ ID NO: 70); CN2049 (SEQ ID NO: 71); CN2427 (SEQ ID NO: 72); CN2320 (SEQ ID NO: 73); CN2321 (SEQ ID NO: 74); CN2719 (SEQ ID NO: 75); CN2707 (SEQ ID NO: 76); CN2713 (SEQ ID NO: 77); CN2717 (SEQ ID NO: 78); AiP1104 (SEQ ID NO: 79); AiP1089 (SEQ ID NO: 80); AiP1105 (SEQ ID NO: 81); AiP1090 (SEQ ID NO: 82); AiP1106 (SEQ ID NO: 83); AiP1091 (SEQ ID NO: 84); AiP1092 (SEQ ID NO: 85); CN2581 (SEQ ID NO: 86); CN2782 (SEQ ID NO: 87); CN3407 (SEQ ID NO: 88); CN3408 (SEQ ID NO: 89); CN3409 (SEQ ID NO: 90); CN2580 (SEQ ID NO: 91); CN2825 (SEQ ID NO: 92); CN3270 (SEQ ID NO: 93); CN3316 (SEQ ID NO: 94); CN3271 (SEQ ID NO: 95); CN3793 (SEQ ID NO: 96); CN3794 (SEQ ID NO: 97); CN3795 (SEQ ID NO: 98); CN3790 (SEQ ID NO: 99); CN3751 (SEQ ID NO: 100); and CN3752 (SEQ ID NO: 101).

DETAILED DESCRIPTION

To fully understand the biology of the brain, different cell types need to be distinguished and defined and, to further study them, artificial expression constructs that can label and perturb them need to be identified (Tasic, Curr. Opin. Neurobiol. 50, 242-249 (2018); Zeng & Sanes, Nat. Rev. Neurosci. 18, 530-546 (2017)). In mouse, recombinase driver lines have been used to great effect to label cell populations that share marker gene expression (Daigle et al., Cell 174, 465-480.e22 (2018); Taniguchi, et al., Neuron 71, 995-1013 (2011); Gong et al., J. Neurosci. 27, 9817-9823 (2007)). However, the creation, maintenance, and use of such lines that label cell types with high specificity can be costly, frequently requiring double or triple transgenic crosses, which yield a low frequency of experimental animals. Furthermore, those tools require germline transgenic animals and thus are not applicable to humans or non-human primates.

Chandelier cells are a subtype of GABAergic interneurons that were discovered in the 1970s and that have been implicated in disorders such as epilepsy and schizophrenia. Chandelier cells (also referred to as axo-axonic cells) selectively innervate pyramidal neurons at the axon initial segment where action potentials are generated. This innervation occurs in cortical layers 2, 3, 5a, and 5b. Chandelier cells have a distinct morphology resembling candlesticks on a chandelier due to axonal arborization patterns. These cells express the markers Cpne5 and Vipr2 in mouse, and NOG in human. Putative conserved cross-species marker genes for mouse, monkey, and human chandelier cells include UNC5B and C1QL1. For more information regarding chandelier cells, see Wang, et al., Chandelier Cells in Functional and Dysfunctional Neural Circuits, Frontiers in Neural Circuits, doi:10.3389/fncir.2016.00044. While significant information has been learned about this cell type, many questions regarding their function and brain-wide effects remain.

The current disclosure provides artificial expression constructs that drive gene expression in chandelier cells. Particular embodiments of the artificial expression constructs utilize the enhancers eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, and eHGT_1024m to drive gene expression within chandelier cells. Additional embodiments utilize the enhancer eHGT_503m to drive gene expression in chandelier cells and VIP cells. Additional embodiments utilize enhancer eHGT_710m to drive gene expression in chandelier cells, glutamatergic neurons in the thalamus, and molecular layer GABAergic interneurons in the cerebellum.

Particular embodiments provide artificial expression constructs including the features of vectors described herein including vectors: CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and CN3752.

Aspects of the disclosure are now described with the following additional options and detail: (i) Artificial Expression Constructs & Vectors for Targeted Expression of Genes in Targeted Cell Types; (ii) Compositions for Administration (iii) Cell Lines Including Artificial Expression Constructs; (iv) Transgenic Animals; (v) Methods of Use; (vi) Kits and Commercial Packages; (vii) Exemplary Embodiments; and (viii) Closing Paragraphs. These headings are provided for organization purposes only and do not limit the scope or interpretation of the disclosure.

(i) Artificial Expression Constructs & Vectors for Targeted Expression of Genes in Targeted Cell Types Artificial expression constructs disclosed herein include (i) an enhancer sequence that leads to targeted expression of a coding sequence within a targeted central nervous system cell type, (ii) a coding sequence that is expressed, and (iii) a promoter. The artificial expression construct can also include other regulatory elements if necessary or beneficial.

In particular embodiments, an "enhancer" or an "enhancer element" is a cis-acting sequence that increases the level of transcription associated with a promoter and can function in either orientation relative to the promoter and the coding sequence that is to be transcribed and can be located upstream or downstream relative to the promoter or the coding sequence to be transcribed. There are art-recognized methods and techniques for measuring function(s) of enhancer element sequences. Particular examples of enhancer sequences utilized within artificial expression constructs disclosed herein include eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, and eHGT_503m.

In particular embodiments, a targeted central nervous system cell type enhancer is an enhancer that is uniquely or predominantly utilized by the targeted central nervous system cell type. A targeted central nervous system cell type enhancer enhances expression of a gene in the targeted central nervous system. In certain embodiments, a targeted central nervous system cell type enhancer is also a selective targeted central nervous system type enhancer that enhances expression of a gene in the targeted central nervous system and does not substantially direct expression of genes in other non-targeted cell types, thus having cell type specific transcriptional activity.

When a heterologous coding sequence operatively linked to an enhancer disclosed herein leads to expression in a targeted cell type, it leads to expression of the administered heterologous coding sequence in the intended cell type. When a heterologous coding sequence is selectively expressed in selected cells, it leads to expression of the administered heterologous coding sequence in the intended cell type and is not substantially expressed in other cell types, as explained in additional detail below. In particular embodiments, not substantially expressed in other cell types is less than 50% expression in a reference cell type as compared to an intended cell type; less than 40% expression in a reference cell type as compared to an intended cell type; less than 30% expression in a reference cell type as compared to an intended cell type; less than 20% expression in a reference cell type as compared to an intended cell type; or less than 10% expression in a reference cell type as compared to an intended cell type. In particular embodiments, a reference cell type refers to non-targeted cells. The non-targeted cells can be within the same anatomical structure as the targeted cells and/or can project to a common anatomical area. In particular embodiments, a reference cell type is within an anatomical structure that is adjacent to an anatomical structure that includes the targeted cell type. In particular embodiments, a reference cell type is a non-targeted cell with a different gene expression profile than targeted cells.

In particular embodiments, the product of the coding sequence may be expressed at low levels in non-targeted cell types, for example at less than 1% or 1%, 2%, 3%, 5%, 10%, 15% or 20% of the levels at which the product is expressed in targeted cells. In particular embodiments, the targeted central nervous system cell type is the only cell type that expresses the right combination of transcription factors that bind an enhancer disclosed herein to drive gene expression. Thus, in particular embodiments, expression occurs exclusively within the targeted cell type.

In particular embodiments, targeted cell types (e.g. neuronal, and/or non-neuronal) can be identified based on transcriptional profiles, such as those described in Tasic et al., Nature 563, 72-78 (2018) and Hodge et al., Nature 573, 61-68 (2019). For reference, the following description of cell types and distinguishing features is also provided:

Neocortical GABAergic neuron Subclasses:

All: Express GABA synthesis genes Gad1/GAD1 and Gad2/GAD2.

Sst and Pvalb GABAergic neurons: Developmentally derived from neuronal progenitors in the medial ganglionic eminence (MGE).

Lamp5_Lhx6 GABAergic neurons: A subset of Lamp5 GABAergic neurons that co-express Lamp5 and Lhx6.

Sncg GABAergic neurons: Found in many neocortical layers, and have molecular overlaps with Lamp5 and Vip cells, but inconsistent expression of Lamp5 or Vip, with more consistent expression of Sncg.

Serpinf1 GABAergic neurons: Found in many neocortical layers, and have molecular overlaps with Sncg and Vip cells, but inconsistent expression of Sncg or Vip, with more consistent expression of Serpinf1.

Vip GABAergic neurons: Found in many neocortical layers, but especially frequent in upper layers (L1-L4), and highly express the neurotransmitter vasoactive intestinal peptide (Vip).

Sst GABAergic neurons: Found in many neocortical layers, but especially frequent in lower layers (L5-L6). They highly express the neurotransmitter somatostatin (Sst), and frequently block dendritic inputs to postsynaptic neurons. Included in this subclass are sleep-active Sst ChodI neurons (which also express Nos1 and Tacr1) that are highly distinct from other Sst neurons but express some shared marker genes including Sst. In human, SST gene expression is often detected in layer 1 LAMP5+ GABAergic neuron subtypes.

Pvalb GABAergic neurons: Found in many neocortical layers, but especially frequent in lower layers (L5-L6). They highly express the calcium-binding protein parvalbumin (Pvalb), express neuropeptide Tac1, and frequently dampen the output of postsynaptic neurons.

Most fast-spiking GABAergic neurons express Pvalb strongly. Included in this subclass are chandelier cells, which have distinct, chandelier-like morphology and express the markers Clq11, Cpne5, Unc5b and Vipr2 in mouse, and NOG, C1QL1, and UNC5B in human. Notably, Pvalb expression is not always detected in all chandelier cells in the adult brain.

Meis2: A distinct subclass defined by a single type, only neocortical GABAergic neuron type that expresses Meis2 gene, and does not express some other genes that are expressed by all other neocortical GABAergic neuron types (for example, Thy1 and Scn2b). This type is found in L6b and subcortical white matter.

Neocortical glutamatergic neuron subclasses:

All: Express glutamate transmitters Slc17a6 and/or Slc17a7. They all express Snap25 and lack expression of Gad1/Gad2.

L2/3 IT glutamatergic neurons: Primarily reside in Layer 2/3 and have mainly intratelencephalic (cortico-cortical) projections.

L4 IT glutamatergic neurons: Primarily reside in Layer 4 and mainly have either local or intratelencephalic (cortico-cortical) projections.

L5 IT glutamatergic neurons: Primarily reside in Layer 5 and have mainly intratelencephalic (cortico-cortical) projections. Also called L5a.

L5 PT glutamatergic neurons: Primarily reside in Layer 5 and have mainly cortico-subcortical (pyramidal tract or corticofugal) projections. Also called L5b or L5 CF (corticofugal) or L5 ET (extratelencephalic). This subclass includes cells that are located in the primary motor cortex and neighboring areas and are corticospinal projection neurons, which are associated with motor neuron/movement disorders, such as ALS. This subclass includes thick-tufted pyramidal neurons, including distinctive subtypes found only in specialized regions, e.g. Betz cells, Meynert cells, and von Economo cells.

L5 NP glutamatergic neurons: Primarily reside in Layer 5 and have mainly nearby projections.

L6 CT glutamatergic neurons: Primarily reside in Layer 6 and have mainly cortico-thalamic projections.

L6 IT glutamatergic neurons: Primarily reside in Layer 6 and have mainly intratelencephalic (cortico-cortical) projections. Included in this subclass are L6 IT Car3 cells, which are highly similar to intracortical-projecting cells in the claustrum.

L6b glutamatergic neurons: Primarily reside in the neocortical subplate (L6b), with local (near the cell body) projections and some cortico-cortical projections from VISp to anterior cingulate, and cortico-subcortical projections to the thalamus.

CR neurons: A distinct subclass defined by a single type in L1, Cajal-Retzius cells express distinct molecular markers Lhx5 and Trp73.

Cerebellar Purkinje cells: large GABAergic neurons that are the only projection neurons and the sole output from the cerebellum. Their cell bodies form a single layer, so called 'Purkinje cell layer', and they express parvalbumin.

Deep cerebellar nucleus neurons: neurons located in the deep cerebellar nuclei structures. These include glutamatergic and GABAergic cells that express the gene Pvalb.

Non-neuronal Subclasses:

Astrocytes: Neuroectoderm-derived glial cells which express the marker Aqp4 and often GFAP, but do not express neuronal marker SNAP25. They can have a distinct star-shaped morphology and are involved in metabolic support of other cells in the brain. Multiple astrocyte morphologies are observed in mouse and human Oligodendrocytes: Neuroectoderm-derived glial cells, which express the marker Sox10. This category includes oligodendrocyte precursor cells (OPCs). Oligodendrocytes are the subclass that is primarily responsible for myelination of neurons.

VLMCs: Vascular leptomeningeal cells (VLMCs) are part of the meninges that surround the outer layer of the cortex and express the marker genes Lum and Col1a1.

Pericytes: Blood vessel-associated cells that express the marker genes Kcnj8 and Abcc9. Pericytes wrap around endothelial cells and are important for regulation of capillary blood flow and are involved in blood-brain barrier permeability.

SMCs: Specialized smooth-muscle cells which are blood vessel-associated cells that express the marker gene Acta2. SMCs cover arterioles in the brain and are involved in blood-brain barrier permeability.

Endothelial cells: Cells that line blood vessels of the brain. Endothelial cells express the markers Tek and PDGF-B.

Microglia: hematopoietic-derived immune cells, which are brain-resident macrophages, and perivascular macrophages (PVMs) that may be transitionally associated with brain tissue or included as a biproduct of brain dissection methods. Microglia are known to express Cx3cr1, Tmem119, and PTPRC (CD45).

In particular embodiments, a coding sequence is a heterologous coding sequence that encodes an effector element. An effector element is a sequence that is expressed to achieve, and that in fact achieves, an intended effect. Examples of effector elements include reporter genes/proteins and functional genes/proteins.

Exemplary reporter genes/proteins include those expressed by Addgene ID #s 83894 (pAAV-hDIx-Flex-dTomato-Fishell_7), 83895 (pAAV-hDIx-Flex-GFP-Fishell_6), 83896 (pAAV-hDIx-GiDREADD-dTomato-Fishell-5), 83898 (pAAV-mDIx-ChR2-mCherry-Fishell-3), 83899 (pAAV-mDIx-GCaMP6f-Fishell-2), 83900 (pAAV-mDIx-GFP-Fishell-1), and 89897 (pcDNA3-FLAG-mTET2 (N500)). Exemplary reporter genes particularly can include those which encode an expressible fluorescent protein, or expressible biotin; blue fluorescent proteins (e.g. eBFP, eBFP2, Azurite, mKalama1, GFPuv, Sapphire, T-sapphire); cyan fluorescent proteins (e.g. eCFP, Cerulean, CyPet, AmCyan1, Midoriishi-Cyan, mTurquoise); green fluorescent proteins (e.g. GFP, GFP-2, tagGFP, turboGFP, EGFP, Emerald, Azami Green, Monomeric Azami Green (mAzami-green), CopGFP, AceGFP, avGFP, ZsGreen1, Oregon Green™ (Thermo Fisher Scientific)); Luciferase; orange fluorescent proteins (mOrange, mKO, Kusabira-Orange, Monomeric Kusabira-Orange, mTangerine, tdTomato, dTomato); red fluorescent proteins (mKate, mKate2, mPlum, DsRed monomer, mCherry, mRuby, mRFP1, DsRed-Express, DsRed2, DsRed-Monomer, HcRed-Tandem, HcRed1, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellow1); and tandem conjugates.

GFP is composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of $9.13 \times 10^{-21}$ $m^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

Exemplary functional molecules include functioning ion transporters, cellular trafficking proteins, enzymes, transcription factors, neurotransmitters, calcium reporters, channelrhodopsins, guide RNA, nucleases, microRNA, or designer receptors exclusively activated by designer drugs (DREADDs).

Ion transporters are transmembrane proteins that mediate transport of ions across cell membranes. These transporters are pervasive throughout most cell types and important for regulating cellular excitability and homeostasis. Ion transporters participate in numerous cellular processes such as action potentials, synaptic transmission, hormone secretion, and muscle contraction. Many important biological processes in living cells involve the translocation of cations, such as calcium (Ca2+), potassium (K+), and sodium (Na+) ions, through such ion channels. In particular embodiments, ion transporters include voltage gated sodium channels (e.g., SCN1A), potassium channels (e.g., KCNQ2), and calcium channels (e.g. CACNA1C)).

Exemplary enzymes, transcription factors, receptors, membrane proteins, cellular trafficking proteins, signaling molecules, and neurotransmitters include enzymes such as lactase, lipase, helicase, alpha-glucosidase, amylase; transcription factors such as SP1, AP-1, Heat shock factor protein 1, C/EBP (CCAA-T/enhancer binding protein), and Oct-1; receptors such as transforming growth factor receptor beta 1, platelet-derived growth factor receptor, epidermal growth factor receptor, vascular endothelial growth factor receptor, and interleukin 8 receptor alpha; membrane proteins, cellular trafficking proteins such as clathrin, dynamin, caveolin, Rab-4A, and Rab-11A; signaling molecules such as nerve growth factor (NGF), platelet-derived growth factor (PDGF), transforming growth factor β (TGFβ), epidermal growth factor (EGF), GTPase and HRas; and neurotransmitters such as cocaine and amphetamine regulated transcript, substance P, oxytocin, and somatostatin.

In particular embodiments, functional molecules include reporters of cell function and states such as calcium reporters. Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are efficient and widely used tools. The GCaMPs are formed by fusion of M13 and calmodulin protein to N- and C-termini of circularly permutated GFP. Some GCaMPs yield distinct fluorescence emission spectra (Zhao et al., Science, 2011, 333(6051): 1888-1891). Exemplary GECIs with green fluorescence include GCaMP3, GCaMP5G, GCaMP6s, GCaMP6m, GCaMP6f, jGCaMP7s, jGCaMP7c, jGCaMP7b, and jGCaMP7f. Furthermore, GECIs with red fluorescence include jRGECO1a and jRGECO1b. AAV products containing GECIs are commercially available. For example, Vigene Biosciences provides AAV products including AAV8-CAG-GCaMP3 (Cat. No:BS4-CX3AAV8), AAV8-Syn-FLEX-GCaMP6s-WPRE (Cat. No:BS1-NXSAAV8), AAV8-Syn-FLEX-GCaMP6s-WPRE (Cat. No:BS1-NXSAAV8), AAV9-CAG-FLEX-GCaMP6m-WPRE (Cat. No:BS2-CXMAAV9), AAV9-Syn-FLEX-jGCaMP7s-WPRE (Cat. No:BS12-NXSAAV9), AAV9-CAG-FLEX-jGCaMP7f-WPRE (Cat. No:BS12-CXFAAV9), AAV9-Syn-FLEX-jGCaMP7b-WPRE (Cat. No:BS12-NXBAAV9), AAV9-Syn-FLEX-jGCaMP7c-WPRE (Cat. No:BS12-NXCAAV9), AAV9-Syn-FLEX-NES-jRGECO1a-WPRE (Cat. No:BS8-NXAAAV9), and AAV8-Syn-FLEX-NES-jRCaMP1b-WPRE (Cat. No:BS7-NXBAAV8).

In particular embodiments calcium reporters include the genetically encoded calcium indicators GECI, NTnC; Myosin light chain kinase, GFP, Calmodulin chimera; Calcium indicator TN-XXL; BRET-based auto-luminescent calcium indicator; and/or Calcium indicator protein OeNL(Ca2+)-18u).

In particular embodiments, functional molecules include modulators of neuronal activity like channelrhodopsins (e.g., channelrhodopsin-1, channelrhodopsin-2, and variants thereof). Channelrhodopsins are a subfamily of retinylidene proteins (rhodopsins) that function as light-gated ion channels. In addition to channelrhodopsin 1 (ChR1) and channelrhodopsin 2 (ChR2), several variants of channelrhodopsins have been developed. For example, Lin et al. (*Biophys J*, 2009, 96(5): 1803-14) describe making chimeras of the transmembrane domains of ChR1 and ChR2, combined with site-directed mutagenesis. Zhang et al. (*Nat Neurosci*, 2008, 11(6): 631-3) describe VChR1, which is a red-shifted channelrhodopsin variant. VChR1 has lower light sensitivity and poor membrane trafficking and expression. Other known channelrhodopsin variants include the ChR2 variant described in Nagel, et al., *Proc Natl Acad Sci USA*, 2003, 100(24): 13940-5), ChR2/H134R (Nagel, G., et al., *Curr Biol*, 2005, 15(24): 2279-84), and ChD/ChEF/ChIEF (Lin, J. Y., et al., *Biophys J*, 2009, 96(5): 1803-14), which are activated by blue light (470 nm) but show no sensitivity to orange/red light. Additional variants are described in Lin, Experimental Physiology, 2010, 96.1: 19-25 and Knopfel et al., *The Journal of Neuroscience*, 2010, 30(45): 14998-15004).

In particular embodiments, functional molecules include DNA and RNA editing tools such CRISPR/CAS (e.g., guide RNA and a nuclease, such as Cas, Cas9 or cpf1). Functional molecules can also include engineered Cpf1s such as those described in US 2018/0030425, US 2016/0208243, WO/2017/184768 and Zetsche et al. (2015) *Cell* 163: 759-771; single gRNA (see e.g., Jinek et al. (2012) *Science* 337:816-821; Jinek et al. (2013) eLife 2:e00471; Segal (2013) eLife 2:e00563) or editase, guide RNA molecules, microRNA, or homologous recombination donor cassettes.

Sequences are publicly-available. As examples, lactase (e.g., GenBank: EAX11622.1), lipase (e.g., GenBank: AAA60129.1), helicase (e.g., GenBank: AMD82207.1), amylase (e.g., GenBank: AAA51724.1), alpha-glucosidase (e.g., GenBank: AB153718.1), transcription factor SP1 (e.g., UniProtKB/Swiss-Prot: P08047.3), transcription factor AP-1 (e.g., NP_002219.1), heat shock factor protein 1 (e.g., UniProtKB/Swiss-Prot: Q00613.1), CCAAT/enhancer-binding protein (C/EBP) beta isoform a (e.g., NP_005185.2), Oct-1 (e.g., UniProtKB/Swiss-Prot: P14859.2), TGFβ (e.g., GenBank: CAF02096.2), platelet-derived growth factor receptor (e.g., GenBank: AAA60049.1), epidermal growth factor receptor (e.g., GenBank: CAA25240.1), vascular endothelial growth factor receptor (e.g., GenBank: AAC16449.2), interleukin 8 receptor alpha (e.g., GenBank: AAB59436.1), caveolin (e.g., GenBank: CAA79476.1), dynamin (e.g., GenBank: AAA88025.1), clathrin heavy chain 1 isoform 1 (e.g., NP_004850.1), clathrin heavy chain 2 isoform 1 (e.g., NP_009029.3), clathrin light chain A isoform a (e.g., NP_001824.1), clathrin light chain B isoform a (e.g., NP_001825.1), ras-related protein Rab-4A isoform 1 (e.g., NP_004569.2), ras-related protein Rab-11A (e.g., UniProtKB/Swiss-Prot: P62491.3), platelet-derived growth factor (e.g., GenBank: AAA60552.1), transforming growth factor-beta3 (e.g., GenBank: AAA61161.1), nerve growth factor (e.g., GenBank: CAA37703.1), EGF (e.g., GenBank: CAA34902.2), cocaine and amphetamine regulated transcript (Chain A) (e.g., PDB: 1HY9_A), protachykinin-1 (e.g., UniProtKB—P20366), oxytocin-neurophysin 1 (e.g., UniProtKB—P01178), somatostatin (e.g., GenBank: AAH32625.1), genetically-encoded green calcium indicator NTnC (chain A) [synthetic construct] (e.g., PDB: 5MWC_A), calcium indicator TN-XXL [synthetic construct], (e.g., GenBank: ACF93133.1), BRET-based auto-luminescent calcium indicator [synthetic construct] (e.g., GenBank ADF42668.1), calcium indicator protein OeNL (Ca2+)-18u [synthetic construct], ((e.g., GenBank BBB18812.1), myosin light chain kinase, Green fluorescent protein, Calmodulin chimera (Chain A) [synthetic construct] ((e.g., PDB: 3EKJ_A), channelopsin 1 (e.g., UniProtKB—F8UV15), channelopsin 1 (e.g., GenBank: AER58217.1), channelrhodopsin-2 ((e.g., UniProtKB—B4Y105), channel rhodopsin 2 [synthetic construct] ((e.g., GenBank: AB064386.1), CRISPR-associated protein (Cas) (e.g., GenBank: AKG27598.1), Cas9 [synthetic construct] (e.g., GenBank: AST09977.1), CRISPR-associated endonuclease Cpf1 (e.g., UniProtKB/Swiss-Prot: U2UMQ6.1), ribonuclease 4 or ribonuclease L (e.g., UniProtKB/Swiss-Prot: Q05823.2), deoxyribonuclease II beta (e.g., GenBank: AAF76893.1), sodium channel protein type 1 subunit alpha (e.g., UniProtKB—P35498), potassium voltage-gated channel subfamily KQT member 2 (e.g., UniProtKB—O43526), and voltage-dependent L-type calcium channel subunit alpha-1C (e.g., UniProtKB—Q13936).

In particular embodiments, a functional molecule includes intein-mediated protein splicing elements. Intein-mediated protein splicing is a process whereby an intein catalyzes its removal from a protein precursor, permitting synthesis of a mature, active protein. When a pair of split inteins are involved in the splicing process, the mature and active protein is formed from two separate protein precursors. An intein is an in-frame intervening sequence in a protein precursor. The intein disrupts the coding region of a gene, until it catalyzes its own excision from the protein precursor through a post-translational protein splicing process to yield the free intein and a mature protein. A "split intein" is made up of two distinct polypeptides or proteins, referred to as the "N-terminal" or inteinN and the "C-terminal" or inteinC because of their homology to the N-terminal and C-terminal regions of non-split inteins, respectively. Together inteinN and inteinC polypeptides, when operably linked to foreign polypeptides, possess all necessary functionality to complete a trans-protein splicing reaction, whereby the two foreign "extein" fragments are ligated together by formation of a peptide bond. DNA sequences encoding inteinN and inteinC may be separated by many kilobases of nucleotides in a genome or on different chromosomes. In particular embodiments, the extein is a split Cre gene. In particular embodiments, intein-mediated protein splicing elements include CreN-inteinN and inteinC-CreC.

Additional effector elements include Cre, iCre, dgCre, FlpO, and tTA2. iCre refers to a codon-improved Cre. iCre includes the sequence as set forth in SEQ ID NOs: 36 and 37. dgCre refers to an enhanced GFP/Cre recombinase fusion gene with an N terminal fusion of the first 159 amino acids of the *Escherichia coli* K-12 strain chromosomal dihydrofolate reductase gene (DHFR or folA) harboring a G67S mutation and modified to also include the R12Y/Y1001 destabilizing domain mutation. FlpO refers to a codon-optimized form of FLPe that greatly increases protein expression and FRT recombination efficiency in mouse cells. Like the Cre/LoxP system, the FLP/FRT system has been widely used for gene expression (and generating conditional knockout mice, mediated by the FLP/FRT system). tTA2 refers to tetracycline transactivator.

Exemplary expressible elements are expression products that do not include effector elements, for example, a non-functioning or defective protein. In particular embodiments, expressible elements can provide methods to study the effects of their functioning counterparts. In particular embodiments, expressible elements are non-functioning or defective based on an engineered mutation that renders them non-functioning. In these aspects, non-expressible elements are as similar in structure as possible to their functioning counterparts.

In particular embodiments, artificial expression constructs include tag cassettes. Exemplary tag cassettes encode a His tag (HHHHHH; SEQ ID NO: 123), Flag tag (DYKDDDDK; SEQ ID NO: 124), Xpress tag (DLYDDDDK; SEQ ID NO: 125), Avi tag (GLNDIFEAQKIEWHE; SEQ ID NO: 126), Calmodulin tag (KRRWKKNFIAVSAANRFKKISSSGAL; SEQ ID NO: 127), Polyglutamate tag, HA tag (YPYDVPDYA; SEQ ID NO: 128), Myc tag (EQKLI-SEEDL; SEQ ID NO: 129), Strep tag (which refers the original STREP® tag (WRHPQFGG; SEQ ID NO: 130), STREP® tag II (WSHPQFEK SEQ ID NO: 131 (IBA Institut fur Bioanalytik, Germany); see, e.g., U.S. Pat. No. 7,981,632), Softag 1 (SLAELLNAGLGGS; SEQ ID NO: 132), Softag 3 (TQDPSRVG; SEQ ID NO: 133), and V5 tag (GKPIPNPLLGLDST; SEQ ID NO: 134). In particular embodiments, artificial expression constructs include three tandem FLAG tag epitopes including 3×FLAG (SEQ ID NO: 43). In particular embodiments, artificial expression constructs include miRNA-guided neuron tags (mAG-NETs). Exemplary mAGNETs include 4×2C, 4×3C, and 8×2C. In particular embodiments, artificial expression constructs include 4×2C (SEQ ID NO: 42). In particular embodiments artificial expression constructs includes 10 aa (SEQ ID NO: 44).

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the artificial expression constructs include an internal ribosome entry site (IRES) sequence. IRES (e.g. IRES2) allow ribosomes to initiate translation at a second internal site on a mRNA molecule, leading to production of two proteins from one mRNA.

Coding sequences encoding molecules (e.g., RNA, proteins) described herein can be obtained from publicly available databases and publications. Coding sequences can further include various sequence polymorphisms, mutations, and/or sequence variants wherein such alterations do not affect the function of the encoded molecule. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, insulators, and/or post-regulatory elements, such as termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin, CMV, minCMV, minCMV* (minCMV* is minCMV with a SacI restriction site removed), minRho, minRho* (minRho* is minRho with a SacI restriction site removed), SV40 immediately early promoter, the Hsp68 minimal promoter (proHSP68), and the Rous Sarcoma Virus (RSV) long-terminal repeat (LTR) promoter. Minimal promoters have no activity to drive gene expression on their own but can be activated to drive gene expression when linked to a proximal enhancer element.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived components that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus vectors refer to those constructs containing adenovirus sequences sufficient to (a) support packaging of an artificial expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and because their capsids and genomes can be tailored to allow expression in targeted cell populations. scAAV refers to a self-complementary AAV. pAAV refers to a plasmid adeno-associated virus. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV), Rous Sarcoma Virus (RSV), and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

A safety enhancement for the use of some vectors can be provided by replacing the U3 region of the 5' LTR with a heterologous promoter to drive transcription of the viral genome during production of viral particles. Examples of heterologous promoters which can be used for this purpose include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In particular embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include one or more chemical compounds or the physiological conditions such as temperature or pH, in which the host cells are cultured.

In particular embodiments, viral vectors include a TAR element. The term "TAR" refers to the "trans-activation response" genetic element located in the R region of lentiviral LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid. Examples include the woodchuck hepatitis virus posttranscriptional regulatory element (WPRE; Zufferey et al., 1999, J. Virol., 73:2886); the posttranscriptional regulatory element present in hepatitis B virus (HPRE) (Smith et al., Nucleic Acids Res. 26(21):4818-4827, 1998); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation signal 3' of a polynucleotide encoding a molecule (e.g., protein) to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA, HGHpA, or SV40 pA. In particular embodiments, a preferred embodiment of an expression construct includes a terminator element. These elements can serve to enhance transcript levels and to minimize read through from the construct into other plasmid sequences.

In particular embodiments, a viral vector further includes one or more insulator elements. Insulators elements may contribute to protecting viral vector-expressed sequences, e.g., effector elements or expressible elements, from integration site effects, which may be mediated by cis-acting elements present in genomic DNA and lead to deregulated expression of transferred sequences (i.e., position effect; see, e.g., Burgess-Beusse et al., *PNAS., USA*, 99:16433, 2002; and Zhan et al., *Hum. Genet.*, 109:471, 2001). In particular embodiments, viral transfer vectors include one or more insulator elements at the 3' LTR and upon integration of the provirus into the host genome, the provirus includes the one or more insulators at both the 5' LTR and 3' LTR, by virtue of duplicating the 3' LTR. Suitable insulators for use in particular embodiments include the chicken β-globin insulator (see Chung et al., *Cell* 74:505, 1993; Chung et al., *PNAS USA* 94:575, 1997; and Bell et al., *Cell* 98:387, 1999), SP10 insulator (Abhyankar et al., *JBC* 282:36143, 2007), or other small CTCF recognition sequences that function as enhancer blocking insulators (Liu et al., *Nature Biotechnology*, 33:198, 2015).

Artificial expression constructs can encode linker segments between other components. A particular example of a protein linker sequence includes SGLRSGGSGG (SEQ ID NO: 102). Examples of Gly-Ser linkers include sets of glycine and serine repeats such as from one to ten repeats of $(Gly_xSer_y)_n$, wherein x and y are independently an integer from 0 to 10 provided that x and y are not both 0 and wherein n is an integer of 1, 2, 3, 4, 5, 6, 7, 8, 9 or 10). Particular examples include $(Gly_4Ser)_n$ (SEQ ID NO: 103), $(Gly_3Ser)_n(Gly_4Ser)_n$ (SEQ ID NO: 104), $(Gly_3Ser)_n(Gly_2Ser)_n$ (SEQ ID NO: 105), and $(Gly_3Ser)_n(Gly_4Ser)_1$ (SEQ ID NO: 106). In particular embodiments, the linker is $(Gly_4Ser)_4$ (SEQ ID NO: 107), $(Gly_4Ser)_3$ (SEQ ID NO: 108), $(Gly_4Ser)_2$ (SEQ ID NO: 109), $(Gly_4Ser)_1$ (SEQ ID NO: 110), $(Gly_3Ser)_2$ (SEQ ID NO: 111), $(Gly_3Ser)_1$ (SEQ ID NO: 112), $(Gly_2Ser)_2$ (SEQ ID NO: 113) or $(Gly_2Ser)_1$, GGSGGGSGGSG (SEQ ID NO: 114), GGSGGGSGSG (SEQ ID NO: 115), and GGSGGGSG (SEQ ID NO: 116).

Artificial expression constructs can encode nuclear localization proteins, such as Histone H1, Histone H2A, Histone H2B, Histone H3, Histone H4, histone-like protein HPhA.

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

Particular embodiments of vectors disclosed herein include:

| Expression Construct Name | Expression Construct Features |
|---|---|
| CN1917 | rAAV-3xSP10ins-eHGT__297m-minRho*-SYFP2-WPRE3-BGHpA |
| CN2047 | rAAV-3xSP10ins-eHGT__303m-minRho*-SYFP2-WPRE3-BGHpA |
| CN2048 | rAAV-3xSP10ins-eHGT__307m-minRho*-SYFP2-WPRE3-BGHpA |
| CN2049 | rAAV-3xSP10ins-eHGT__308m-minRho*-SYFP2-WPRE3-BGHpA |
| CN2427 | rAAV-eHGT__472m-minBglobin-SYFP2-WPRE3-BGHpA |
| CN2320 | rAAV-eHGT__475m-minBglobin-SYFP2-WPRE3-BGHpA |
| CN2321 | rAAV-eHGT__476m-minBglobin-SYFP2-WPRE3-BGHpA |
| CN2719 | rAAV-eHGT__503m-minBglobin-SYFP2-WPRE3-BGHpA |
| CN2707 | rAAV-eHGT__571m-minBglobin-SYFP2-WPRE3-BGHpA |
| CN2713 | rAAV-eHGT__706m-minBglobin-SYFP2-WPRE3-BGHpA |
| CN2717 | rAAV-eHGT__710m-minBglobin-SYFP2-WPRE3-BGHpA |
| AiP1104 | rAAV-eHGT__296m-minBglobin-FlpO-WPRE-HGHpA |
| AiP1089 | rAAV-eHGT__297m-minBglobin-FlpO-WPRE-HGHpA |
| AiP1105 | rAAV-eHGT__299m-minBglobin-FlpO-WPRE-HGHpA |
| AiP1090 | rAAV-eHGT__300m-minBglobin-FlpO-WPRE-HGHpA |
| AiP1106 | rAAV-eHGT__306m-minBglobin-FlpO-WPRE-HGHpA |
| AiP1091 | rAAV-eHGT__309m-minBglobin-FlpO-WPRE-HGHpA |
| AiP1092 | rAAV-eHGT__310m-minBglobin-FlpO-WPRE-HGHpA |
| CN2581 | rAAV-eHGT__476m-minRho*-SYFP2-10aa-H2B-WPRE3-BGHpA |
| CN2782 | pAAV-eHGT__3x_eHGT__476m-minBGlobin-SYFP2-WPRE3-BGHpA |
| CN3407 | pAAV-eHGT__890m-minBGlobin-SYFP2-P2A-3XFLAG-10aa-H2B-WPRE3-BGHpA |
| CN3408 | pAAV-eHGT__891m-minBGlobin-SYFP2-P2A-3XFLAG-10aa-H2B-WPRE3-BGHpA |
| CN3409 | pAAV-eHGT__892m-minBGlobin-SYFP2-P2A-3XFLAG-10aa-H2B-WPRE3-BGHpA |
| CN2580 | rAAV-eHGT__476m-minBGlobin-iCre-4X2C-WPRE3-BGHpA |
| CN2825 | rAAV-eHGT__476m-minBGlobin-FlpO-4X2C-WPRE3-BGHpA |
| CN3270 | rAAV-eHGT__475m-minBglobin-SYFP2-4X2C-WPRE3-BGHpA |
| CN3316 | rAAV-eHGT__710m-minBglobin-SYFP2-4X2C-WPRE3-BGHpA |
| CN3271 | pAAV-eHGT__3x_eHGT__476m- minBGlobin -SYFP2-4X2C-WPRE3-BGHpA |
| CN3793 | pAAV-eHGT__1022m-minBGlobin-SYFP2-P2A-3XFLAG-10aa-H2B-WPRE3-BGHpA |
| CN3794 | pAAV-eHGT__1023m- minBGlobin -SYFP2-P2A-3XFLAG-10aa-H2B-WPRE3-BGHpA |
| CN3795 | pAAV-eHGT__1024m- minBGlobin -SYFP2-P2A-3XFLAG-10aa-H2B-WPRE3-BGHpA |
| CN3790 | rAAV-eHGT__475m- minBGlobin -iCre(R297T)-BGHpA |

-continued

| Expression Construct Name | Expression Construct Features |
| --- | --- |
| CN3751 | rAAV-eHGT_475m- minBGlobin -CreN-inteinN-WPRE3-BGHpA |
| CN3752 | rAAV-eHGT_476m- minBGlobin -inteinC-CreC-WPRE3-BGHpA |

Figure 3:
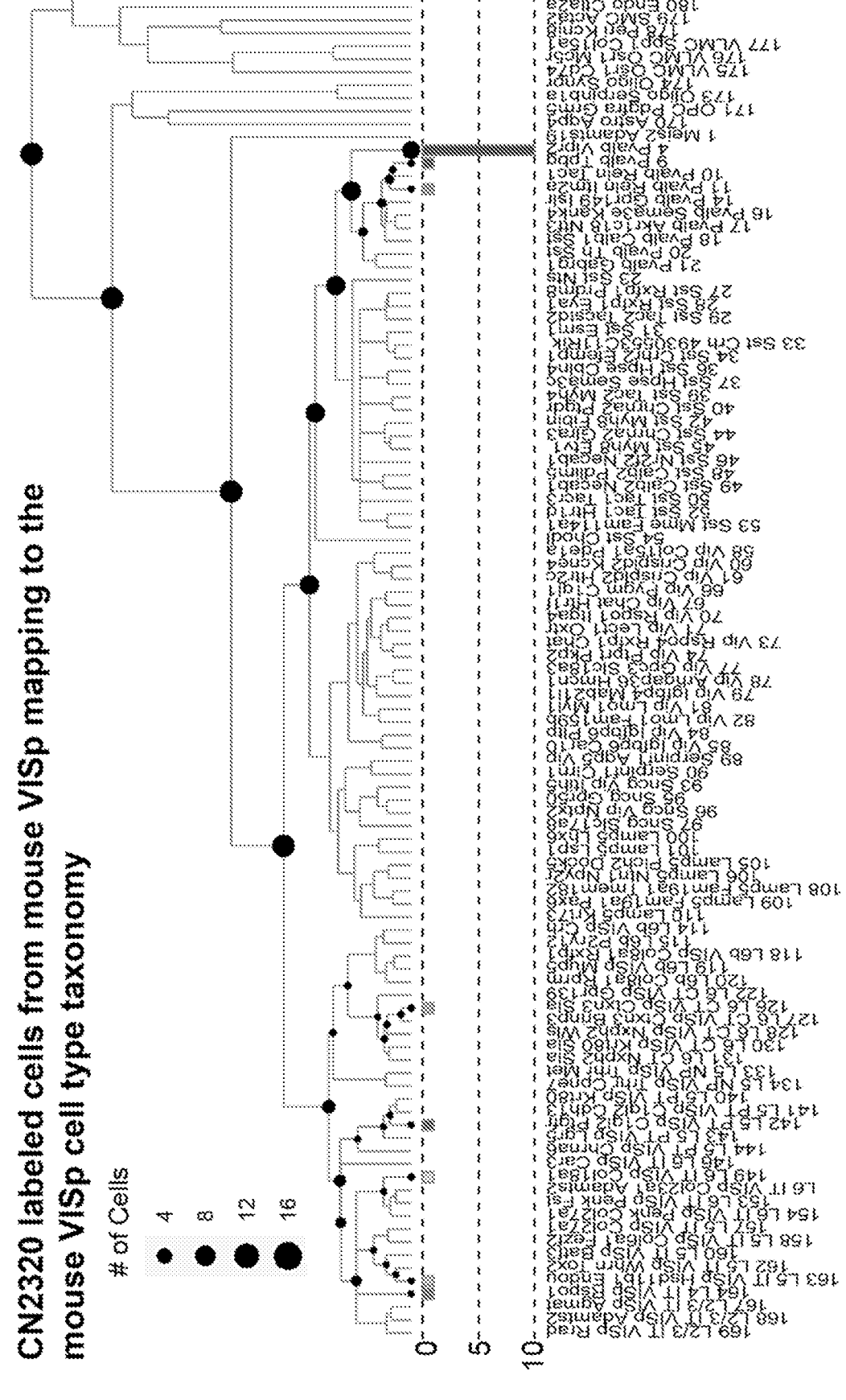
FIG. 3. CN2320 (eHGT_475m) in VISp of 554420 and 584422 animals. Mapping of single cell transcriptomic profiles of SYPF2+ cells sorted from the VISp region of the mouse neocortex after retro-orbital injection of CN2320 virus packaged with the PHP.eB capsid. Number of cells mapped to the final leaf are shown on the bar plot below the dendrogram. This data shows eHGT_475m enhancer-driven reporter expression is enriched in chandelier cells (Pvalb Vipr2 cells) when mouse VISp is evaluated. Transcriptomic cell types are shown on the bottom and read (from left to right): 169 L2/3 IT VISp Rrad, 168 L2/3 IT VISp Adamts2, 167 L2/3 IT VISp Agmat, 164 L4 IT VISp Rspo1, 163 L5 IT VISp Hsd11b1 Endou, 162 L5 IT VISp Whrn Tox2, 160 L5 IT VISp Batf3, 158 L5 IT VISp Col6a1 Fezf2, 157 L5 IT VISp Col27a1, 154 L6 IT VISp Penk Col27a1, 153 L6 IT VISp Penk Fst, L6 IT VISp Col23a1 Adamts2, 149 L6 IT VISp Col18a1, 146 L6 IT VISp Car3, 144 L5 PT VISp Chrna6, 143 L5 PT VISp Lgr5, 142 L5 PT VISp Clql2 Ptgfr, 141 L5 PT VISp Clql2 Cdh13, 140 L5 PT VISp Krt80, 134 L5 NP VISp Trhr Cpne7, 133 L5 NP VISp Trhr Met, 131 L6 CT Nxph2 Sla, 130 L6 CT VISp Krt80 Sla, 128 L6 CT VISp Nxph2 Wls, 127 L6 CT VISp Ctxn3 Brinp3, 126 L6 CT VISp Ctxn3 Sla, 122 L6 CT VISp Gpr139, 120 L6b Col8a1 Rprm, 119 L6b VISp Mup5, 118 L6b Col8a1 Rxfp1, 115 L6b P2ry12, 114 L6b VISp Crh, 110 Lamp5 Krt73, 109 Lamp5 Fam19a1 Pax6, 108 Lamp5 Fam19a1 Tmem182, 106 Lamp5 Ntn1 Npy2r, 105 Lamp5 Plch2 Dock5, 101 Lamp5 Lsp1, 100 Lamp5 Lhx6, 97 Sncg Slc17a8, 96 Sncg Vip Nptx2, 95 Sncg Gpr50, 93 Sncg Vip Itih5, 90 Serpinf1 CIrn1, 89 Serpinf1 Agp5 Vip, 85 Vip Igfbp6 Car10, 84 Vip Igfbp6 Pltp, 82 Vip Lmo1 Fam159b, 81 Vip Lmo1 My11, 79 Vip Igfbp4 Mab21l1, 78 Vip Arhgap36 Hmcn1, 77 Vip Gpc3 Slc18a3, 74 Vip Ptprt Pkp2, 73 Vip Rspo4 Rxfp1 Chat, 71 Vip Lect Oxtr, 70 Vip Rspo1 Itga4, 67 Vip Chat Htr1f, 66 Vip Pygm ClqIl1, 61 Vip CrispId2 Htr2c, 60 Vip CrispId2 Kcne4, 58 Vip Col15a1 Pde1a, 54 Sst ChodI, 53 Sst Mme Fam114a1, 52 Sst Tac1 Htr1d, 50 Sst Tac1 Tacr3, 49 Sst Calb2 Necab1, 48 Sst Calb2 Pdlim5, 46 Sst Nr2f2 Necab1, 45 Sst Myh8 Etv1, 44 Sst Chrna2 Glra3, 42 Sst Myh8 Fibin, 40 Sst Chrna2 Ptgdr, 37 Sst Tac2 Myh4, 36 Sst Hpse Sema3c, 34 Sst Crhr2 Efemp1, 33 Sst Crh 4930553C11Rik, 31 Sst Esm1, 29 Sst Tac2 Tacstd2, 28 Sst Rxfp1 Eya1, 27 Sst Rxfp1 Prdm8, 23 Sst Nts, 21 Pvalb Gabrg1, 20 Pvalb Th Sst, 18 Pvalb Calb1 Sst, 17 Pvalb Akr1c18 Ntf3, 16 Pvalb Sema3e Kank4, 14 Pvalb Gpr149 IsIr, 11 Pvalb Reln Itm2a, 10 Pvalb Reln Tac1, 9 Pvalb Tpbg, 4 Pvalb Vipr2, 1 Meis2 Adamts19, 170 Astro Aqp4, 171 OPC Pdgfra Grm5, 173 Oligo Serpinb1a, 174 Oligo Synpr, 175 VLMC Osr1 Cd74, 176 VLMC Osr1 Mc5r, 177 VLMC Spp1 Col15a1, 178 Peri Kcnj8, 179 SMC Acta2, 180 Endo Ctla2a, and 181 Microglia Siglech.
Figure 4A:
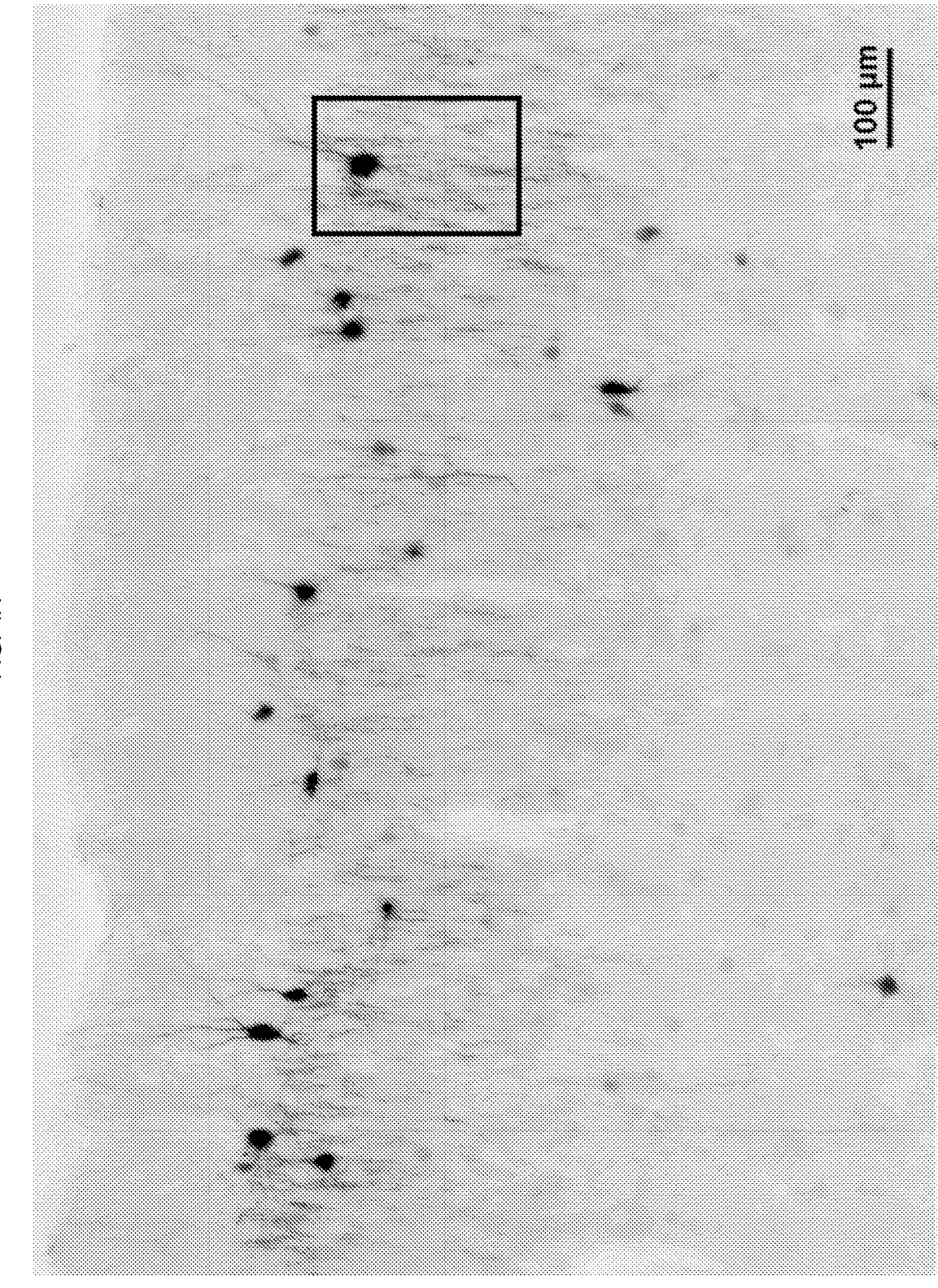
FIGS. 4A, 4B. CN2320 (eHGT_475m) in rat neocortex. (4A) Epifluorescence micrograph image (inverted) showing native SYFP2 expression in the neocortex 18 days after intracerebroventricular injection of 1.5E11 viral genome copies of AAV vector #CN2320 (eHGT_475m) in 1-day old rat pup. Scale bar: 100 microns. (4B) Higher magnification view showing a cell body and signature chandelier cell axon cartridges. Scale bar: 25 microns.
Figure 4B:
Figure 5A:
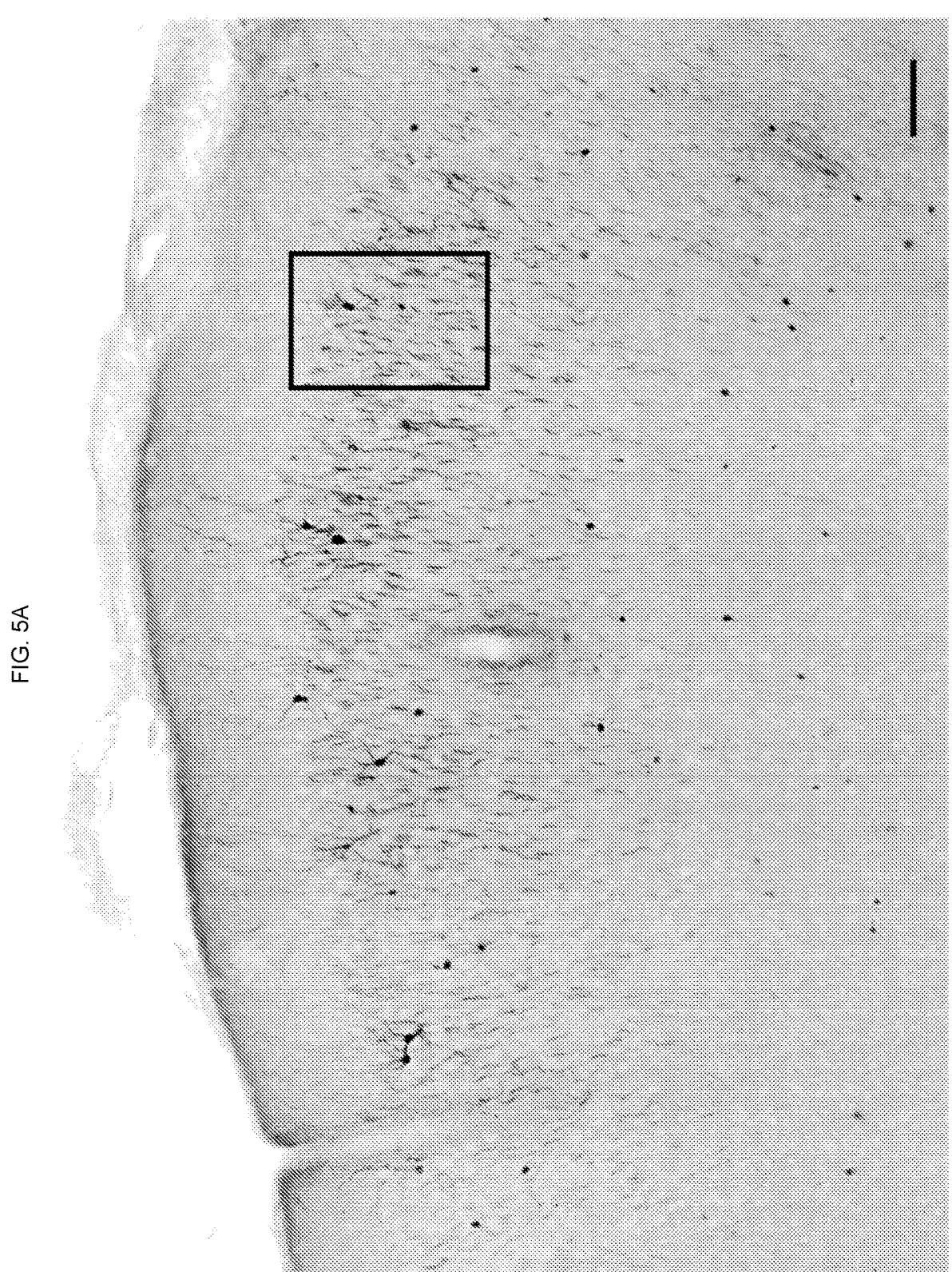
FIGS. 5A, 5B. CN2320 (eHGT_475m) in macaque frontal cortex. (5A) Epifluorescence micrograph image (inverted) showing native SYFP2 expression in the superior frontal cortex region 64 days after stereotaxic injection of 8.0E10 viral genome copies of AAV vector #CN2320 (eHGT_475m) in adult macaque in vivo. Scale bar: 100 microns. (5B) Higher magnification view showing a cell body and signature chandelier cell axon cartridges. Scale bar: 50 microns.
Figure 5B:
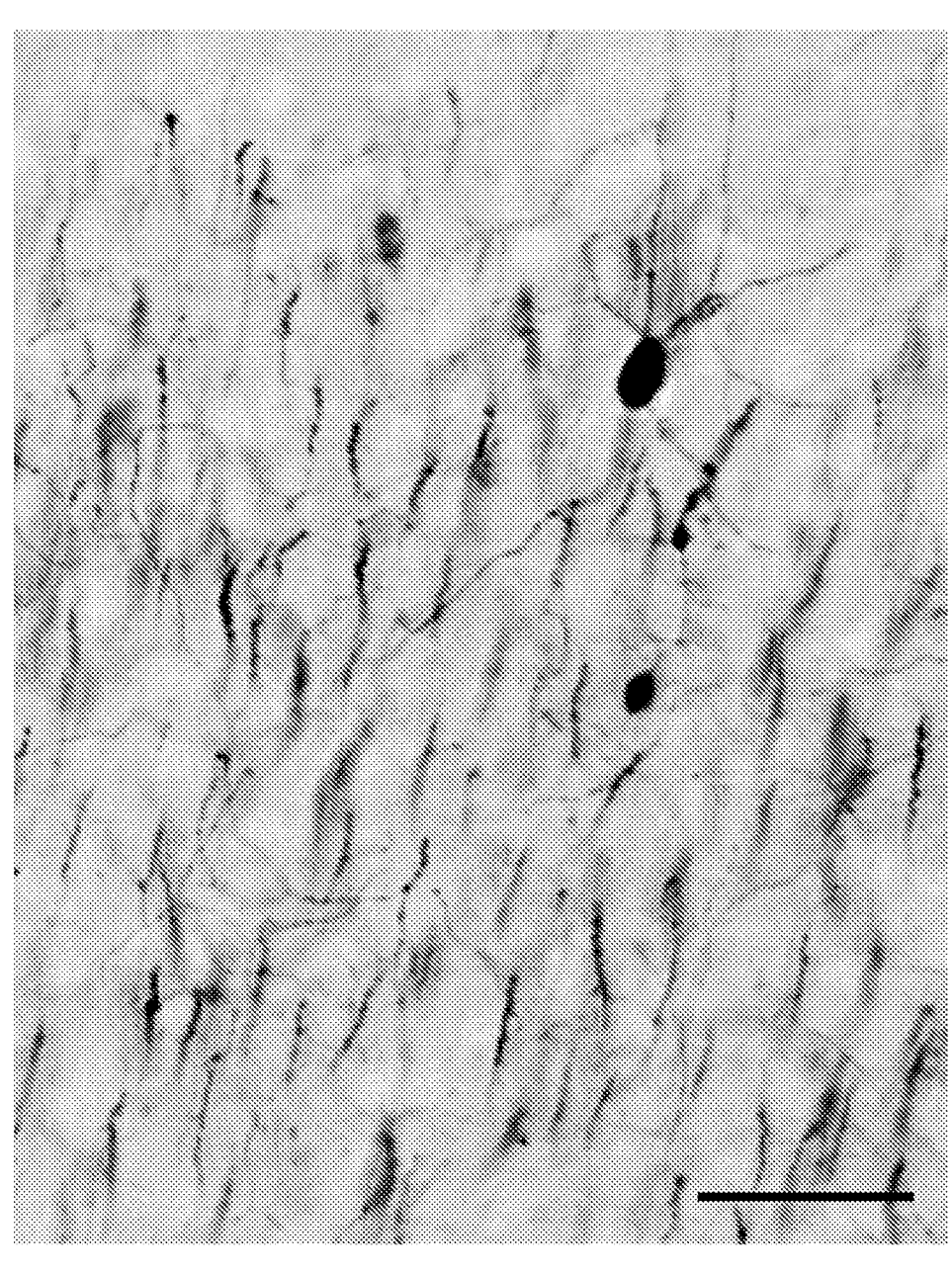
Figure 6A:
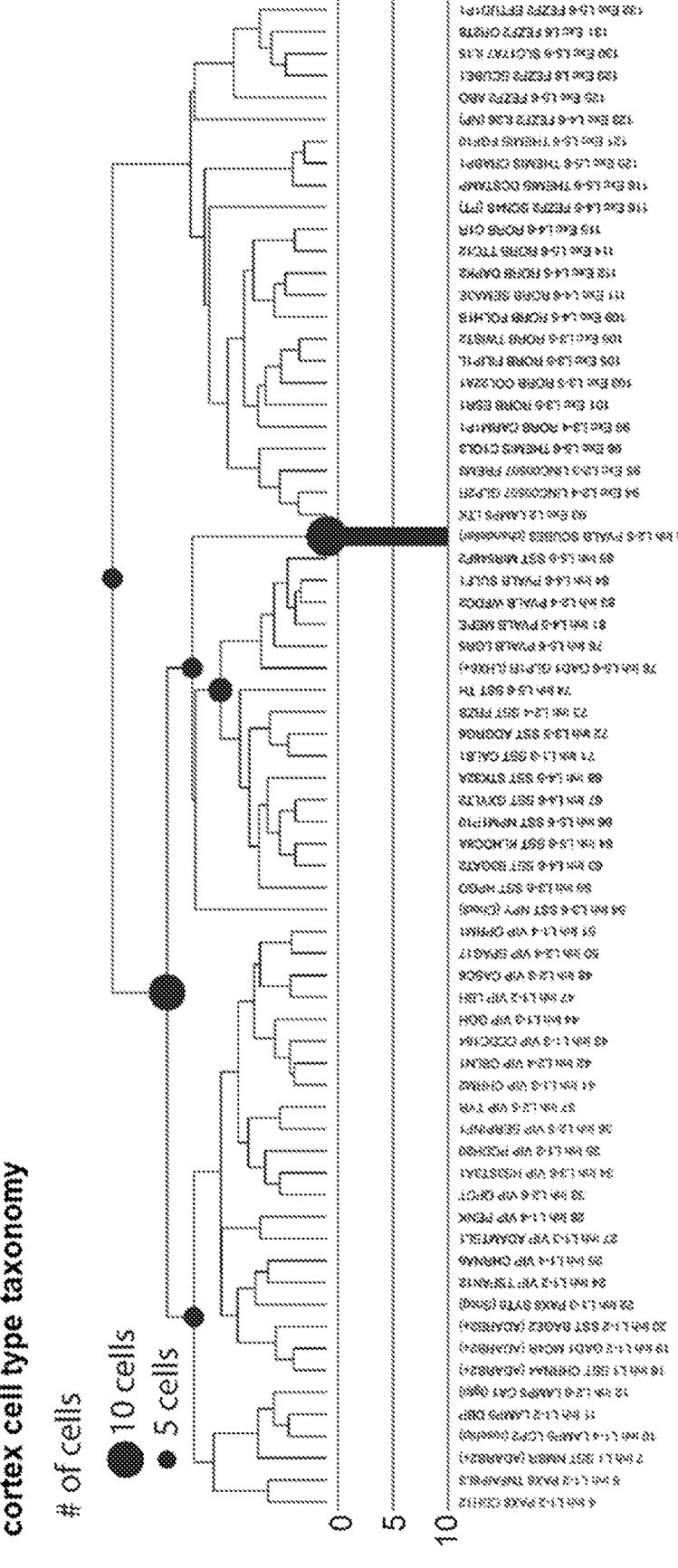
FIGS. 6A-6C. CN2320 (eHGT_475m) in macaque frontal cortex. (6A) Mapping of single cell transcriptomic profiles of SYPF2+ cells recorded using the Patch-seq technique (patch-clamp electrophysiology recording with nucleus extraction and post-hoc single nucleus RNA sequencing) from the frontal cortex region of the macaque cortex after in vivo stereotaxic injection of CN2320 virus packaged with the PHP.eB capsid. Experiments were conducted for two injected macaque monkeys and pooled. Number of cells mapped to the final leaf are shown on the bar plot below the dendrogram. Transcriptomic cell types of the human middle temporal gyrus are shown on the bottom. This data shows eHGT_475m enhancer-driven reporter expression is highly specific to primate chandelier cells (PVALB SCUBE3 type) in neocortex. (6B) Exemplary Patch-seq recorded neuron showing individual cell RNA-seq mapping with high confidence to the chandelier cell type PVALB SCUBE3, as well as (6C) the signature firing pattern in response to current injection step (top) and the cell morphology from biocytin fill and reaction (bottom). Scale bar in FIG. 6C (bottom): 20 microns. The text at the bottom of FIGS. 6A and 6B read (from left to right): 4 Inh L1-2 PAX6 CH12, 5 Inh L1-2 PAX6 TNFAIP8L3, 7 Inh L1-2 SST NMBR (ADARB2+), 10 Inh L1-4 LAMP5 LCP2 (rosehip), 11 Inh L1-2 LAMP5 DBP, 12 Inh L2-6 LAMP5 CA1 (Igtp), 18 Inh L1 SST CHRNA4 (ADARB2+), 19 Inh L1-2 GAD1 MC4R (ADARB2+), 20 Inh L1-2 SST BAGE2 (ADARB2+), 22 Inh L1-3 PAX6 SYT6 (Sncg), 24 Inh L1-2 VIP TSPAN12, 25 Inh L1-4 VIP CHRNA6, 27 Inh L1-3 VIP ADAMTSL1, 28 Inh L1-4 VIP PENK, 33 Inh L2-6 VIP QPCT, 34 Inh L3-6 VIP HS3ST3A1, 35 Inh L1-2 VIP PCDH20, 36 Inh L2-5 VIP SERPINF1, 37 Inh L2-5 VIP TYR, 41 Inh L1-3 VIP CHRM2, 42 Inh L2-4 VIP CBLN1, 43 Inh L1-3 VIP CCDC184, 44 Inh L1-3 VIP GGH, 47 Inh L1-2 VIP LHB, 48 Inh L2-3 VIPCASC6, 50 Inh L2-4 VIP SPAG17, 51 Inh L1-4 VIP OPRM1, 54 Inh L3-6 SST NPY (ChodI), 59 Inh L3-6 SST HPGD, 63 Inh L4-6 SST B3GAT2, 64 Inh L5-6 SST KLHDC8A, 66 Inh L5-6 SST NPM1P10, 67 Inh L4-6 SST GXYLT2, 68 Inh L4-5 SST STK32A, 71 Inh L1-3 SST CALB1, 72 Inh L3-5 SST ADGRG6, 73 Inh L2-4 SST FRZB, 74 Inh L5-6 SST TH, 76 Inh L5-6 GAD1 GLP1R (LHX6+), 78 Inh L5-6 PVALB LGR5, 81 Inh L4-5 PVALB MEPE, 83 Inh L2-4 PVALB WFDC2, 84 Inh L4-6 PVALB SULF1, 85 Inh L5-6 SST MIR548F2, 86 Inh L2-5 PVALB SCUBE3 (chandelier), 93 Exc L2 LAMP5 LTK, 94 Exc L2-4 LINC00507 GLP2R, 95 Exc L2-3 LINC00507 FREM3, 96 Exc L5-6 THEMIS C1QL3, 99 Exc L3-4 RORB CARM1P1, 101 Exc L3-5 RORB ESR1, 103 Exc L3-5 RORB COL22A1, 105 Exc L3-5 RORB FILIP1L, 106 Exc L3-5 RORB TWIST2, 109 Exc L4-5 RORB FOLH1B, 111 Exc L4-6 RORB SEMA3E, 112 Exc L4-5 RORB DAPK2, 114 Exc L5-6 RORB TTC12, 115 Exc L4-6 RORB C1R, 116 Exc L4-5 FEZF2 SCN4B (PT), 118 Exc L5-6 THEMIS DCSTAMP, 120 Exc L5-6 THEMIS CRABP1, 121 Exc L5-6 THEMIS FGF10, 123 Exc L4-6 FEZF2 IL26 (NP), 125 Exc L5-6 FEZF2 ABO, 129 Exc L6 FEZF2 SCUBE1, 130 Exc L5-6 SLC17A7 IL15, 131 Exc L6 FEZF2 OR2T8, and 132 Exc L5-6 FEZF2 EFTUD1P1.
Figure 6B:
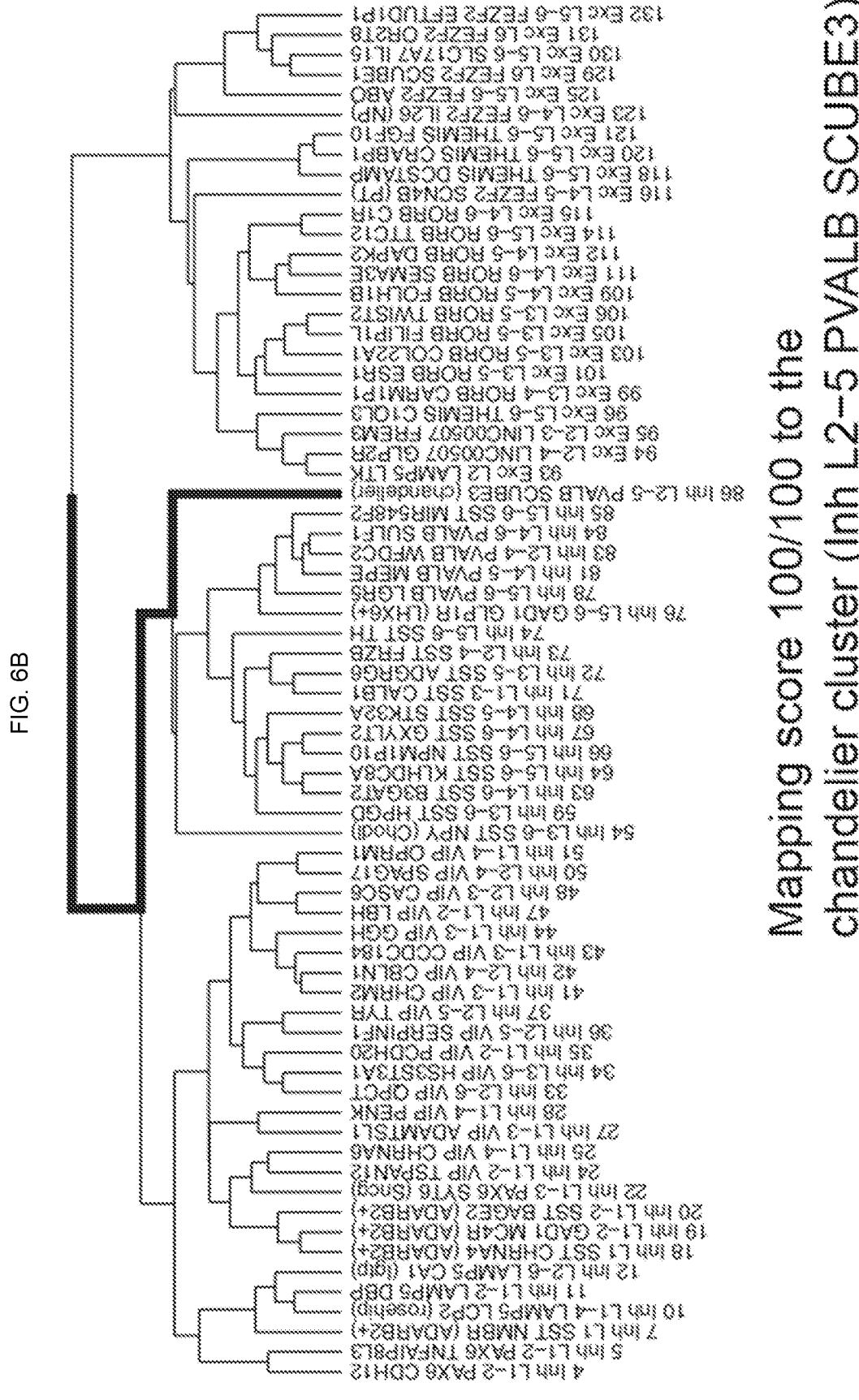
Figure 6C:
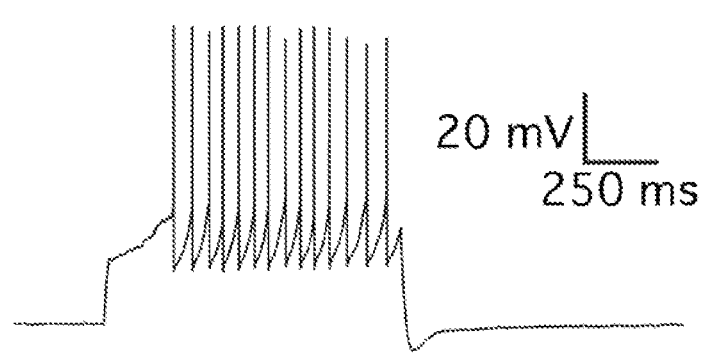
Figure 6C:
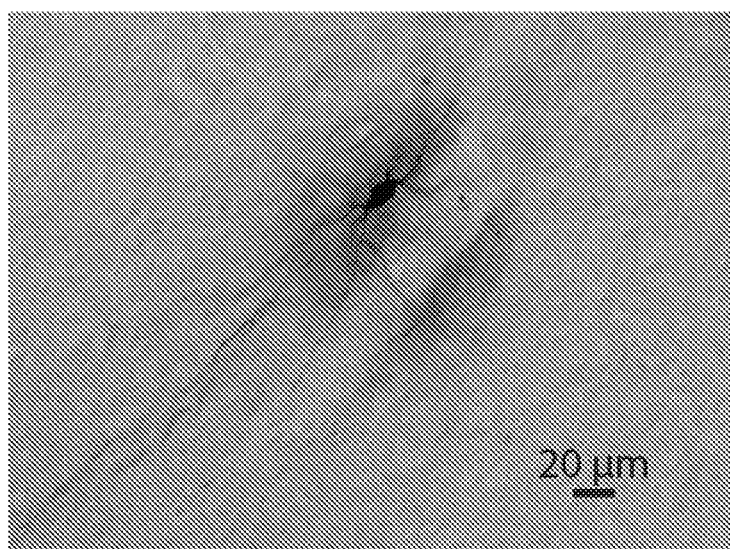
Figure 7A:
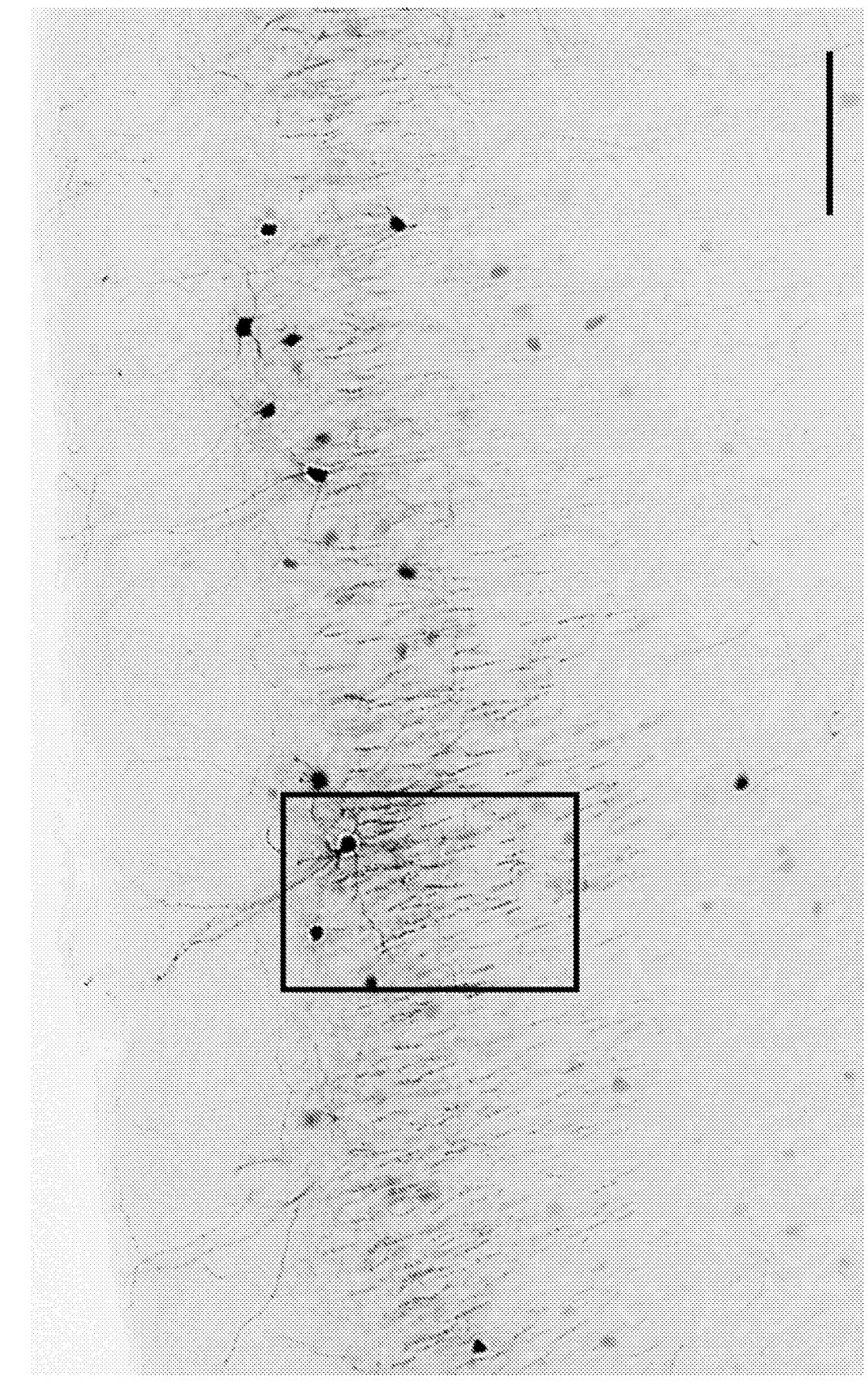
FIGS. 7A, 7B. CN2321 (eHGT_476m) in mouse neocortex. (7A) Epifluorescence micrograph image (inverted) showing native SYFP2 expression in the neocortex 42 days after retro-orbital delivery of 5.48E11 viral genome copies of AAV vector #CN2321 (eHGT_476m). Scale bar: 100 microns. (7B) Higher magnification view showing a sparse cell bodies and signature chandelier cell axon cartridges. Scale bar: 50 microns.
Figure 7B:
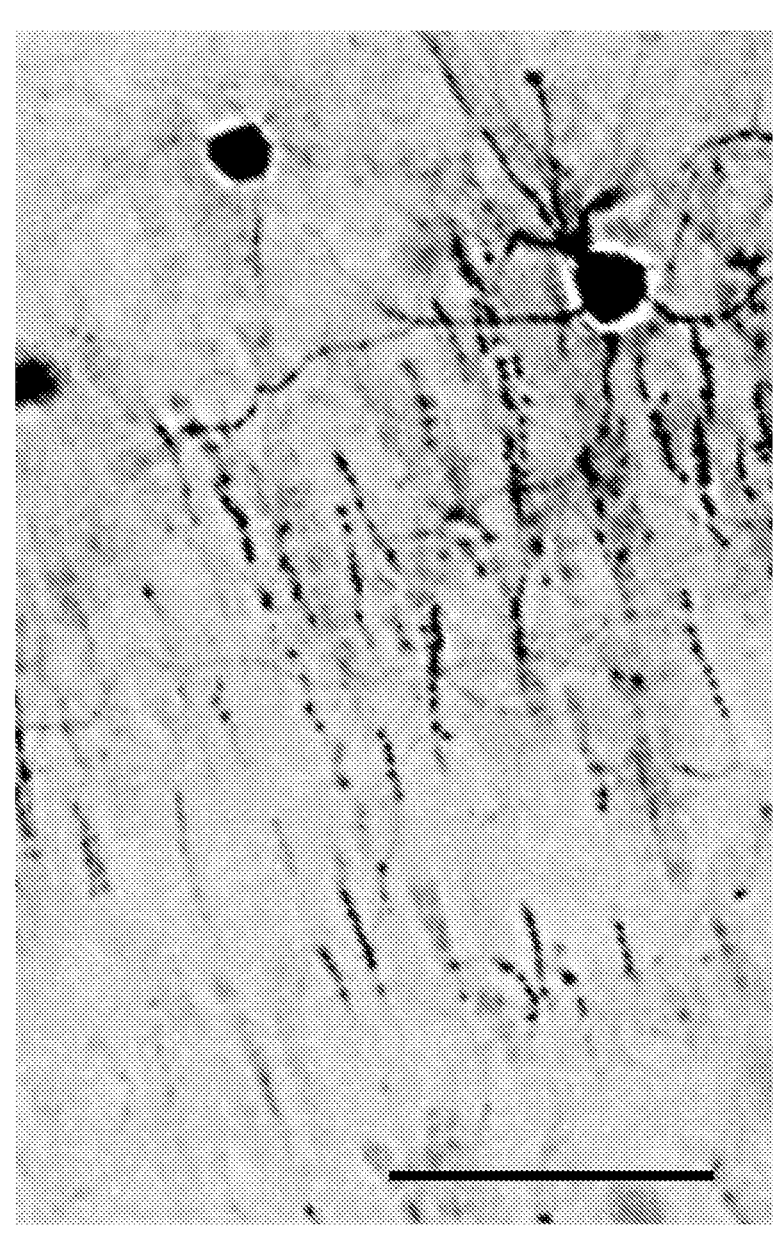
Figure 8:
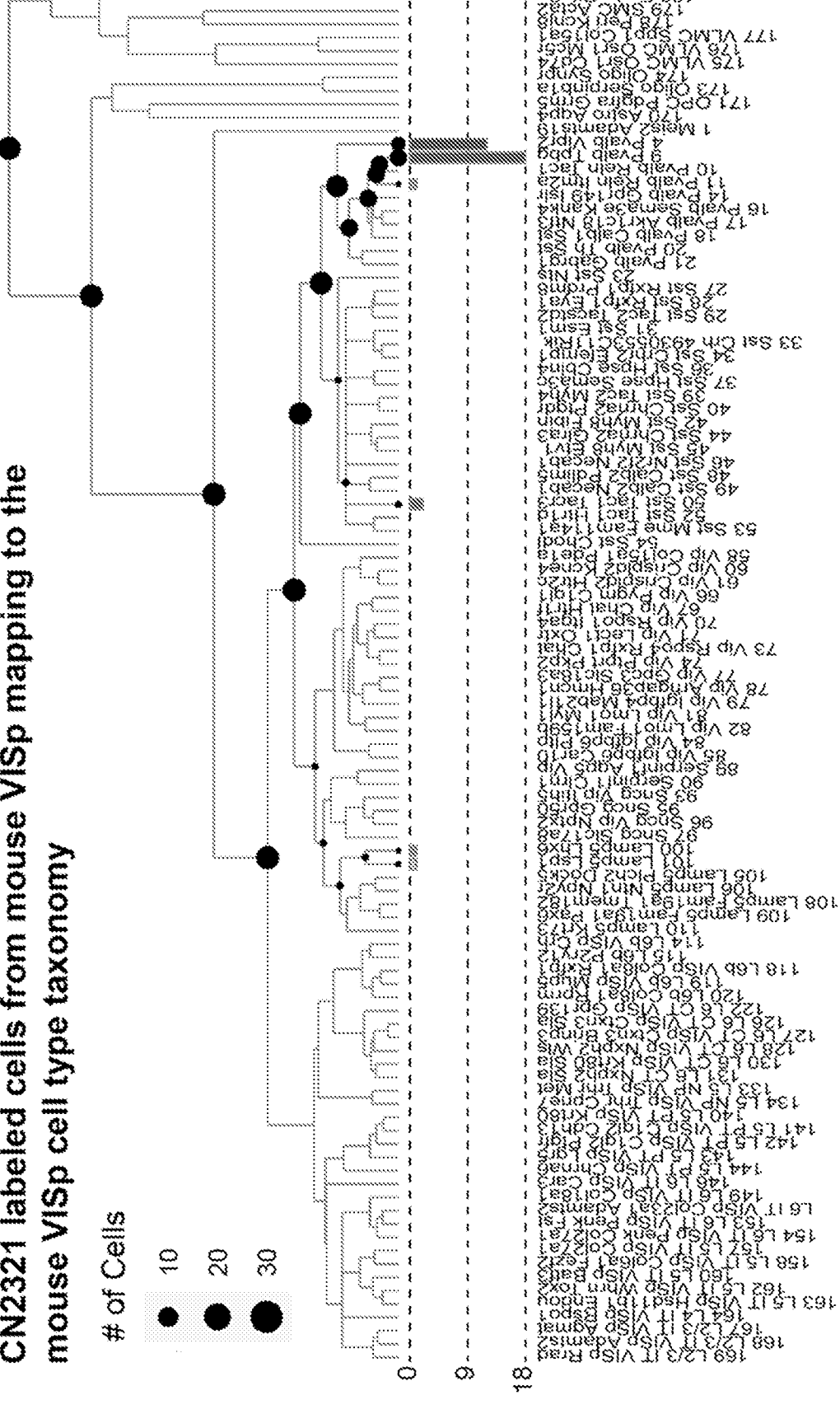
FIG. 8. CN2321 (eHGT_476m) in 569787 animal VISp. Mapping of single cell transcriptomic profiles of SYPF2+ cells sorted from the VISp region of the mouse neocortex after retro-orbital injection of CN2321 virus packaged with the PHP.eB capsid. Number of cells mapped to the final leaf are shown on the bar plot below the dendrogram. Transcriptomic cell types are shown on the bottom. This data shows eHGT_476m enhancer-driven reporter expression is enriched in chandelier cells (Pvalb Vipr2 cells) and Pvalb Tpbg cells when mouse VISp is evaluated. The text at the bottom of the figure from left to right reads the same as that described in FIG. 3.
Figure 9A:
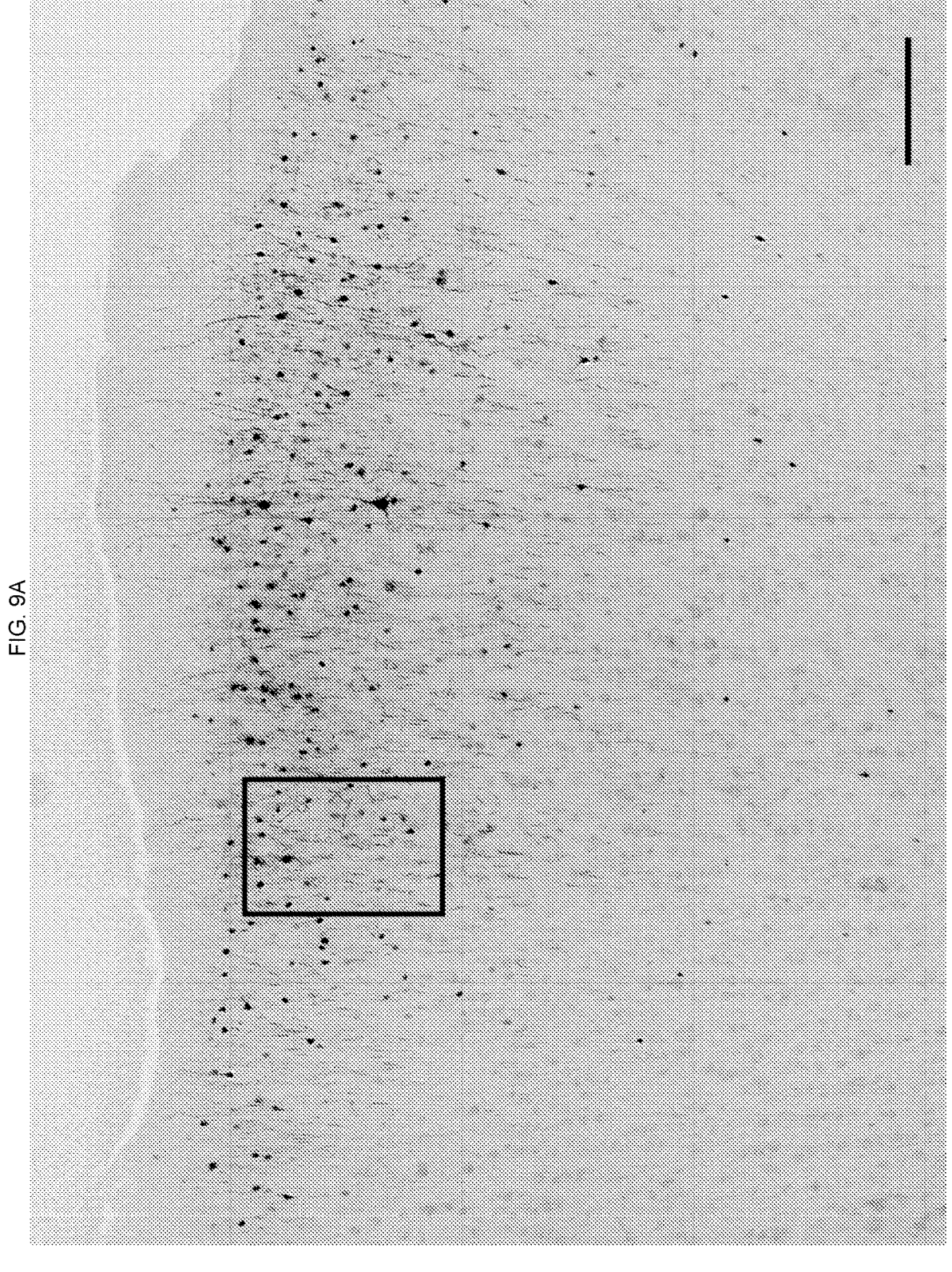
FIGS. 9A, 9B. CN2321 (eHGT_476m) in macaque frontal cortex. (9A) Epifluorescence micrograph image (inverted) showing native SYFP2 expression in the superior frontal cortex region 43 days after stereotaxic injection of 9.59E10 viral genome copies of AAV vector #CN2321 (eHGT_476m) in adult macaque in vivo. Scale bar: 200 microns. (9B) Higher magnification view showing a cell body and signature chandelier cell axon cartridges. Scale bar: 100 microns.
Figure 9B:
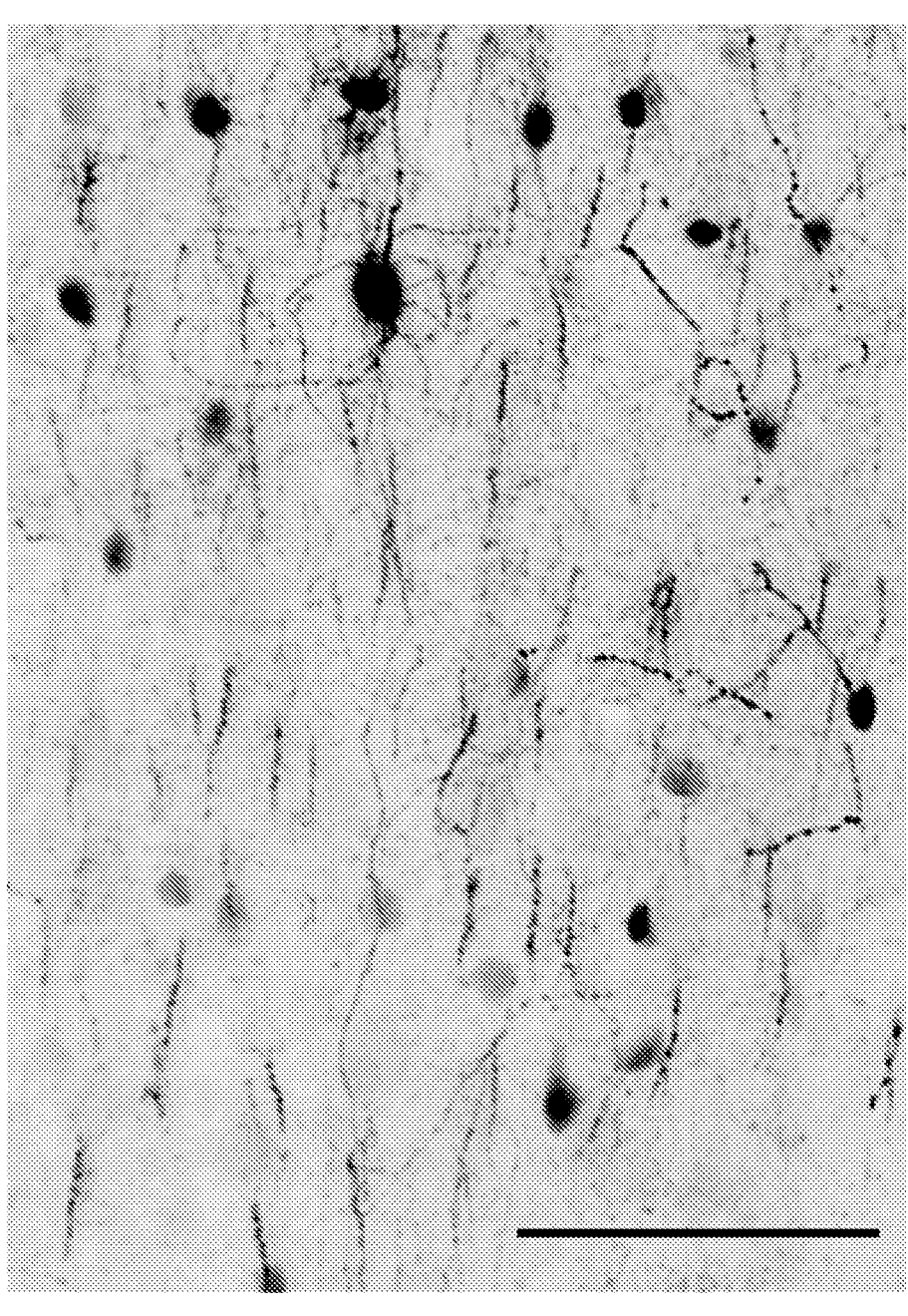
Figure 10A:
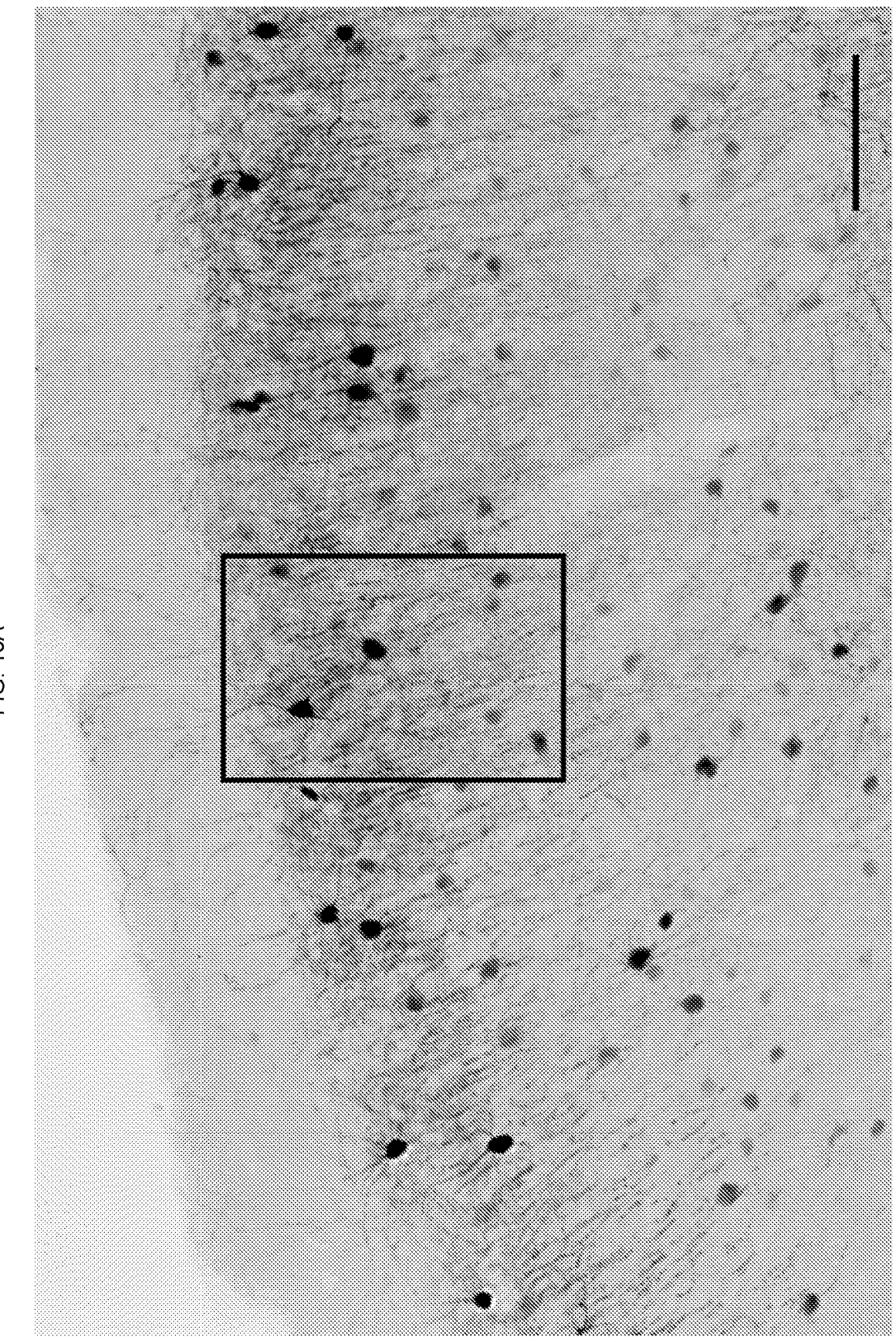
FIGS. 10A, 10B. CN2782 (3×Core-eHGT_476m) in mouse neocortex. (10A) Epifluorescence micrograph image (inverted) showing native SYFP2 expression in the neocortex 42 days after retro-orbital delivery of 4.48E11 viral genome copies of AAV vector #CN2782 (3×Core-eHGT_476m). Scale bar: 100 microns. (10B) Higher magnification view showing a sparse cell bodies and signature chandelier cell axon cartridges. Scale bar: 50 microns.
Figure 10B:
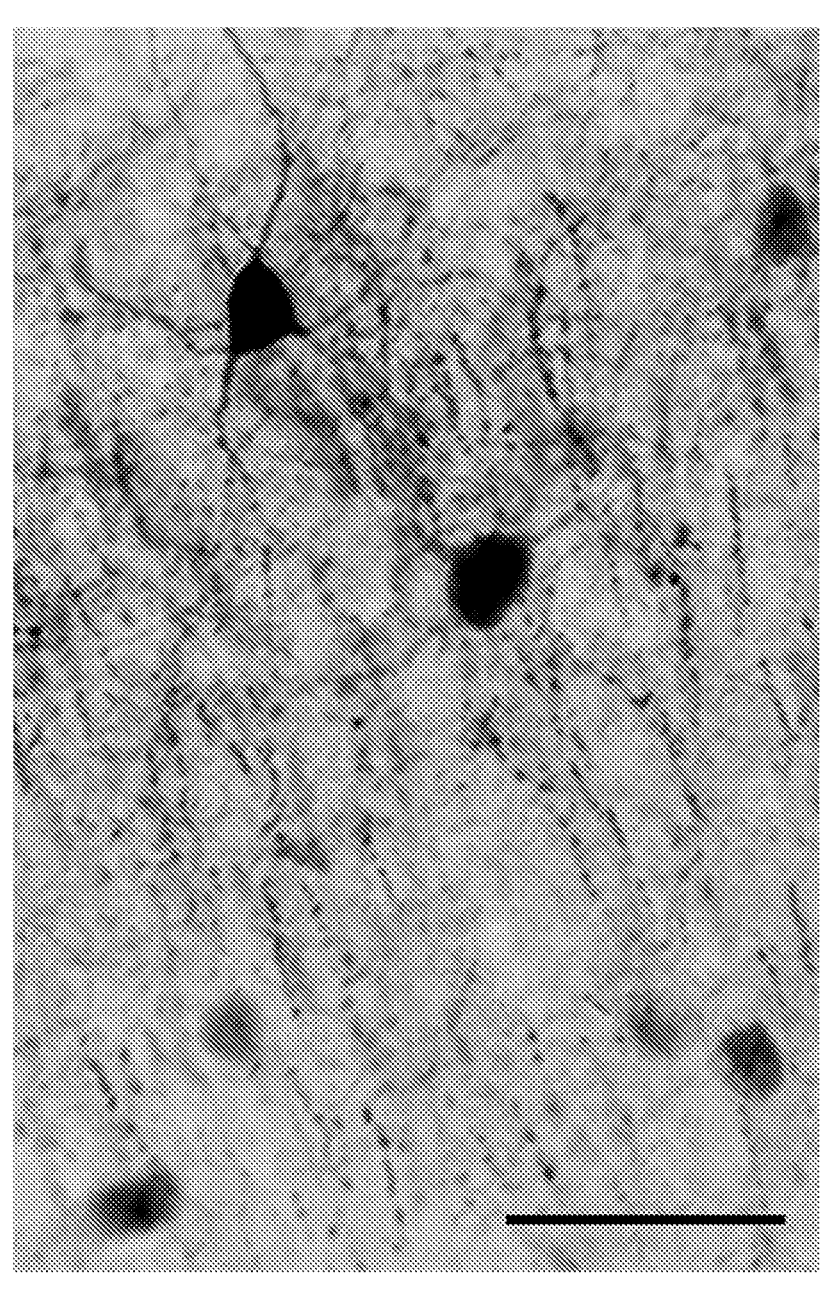
Figure 11A:
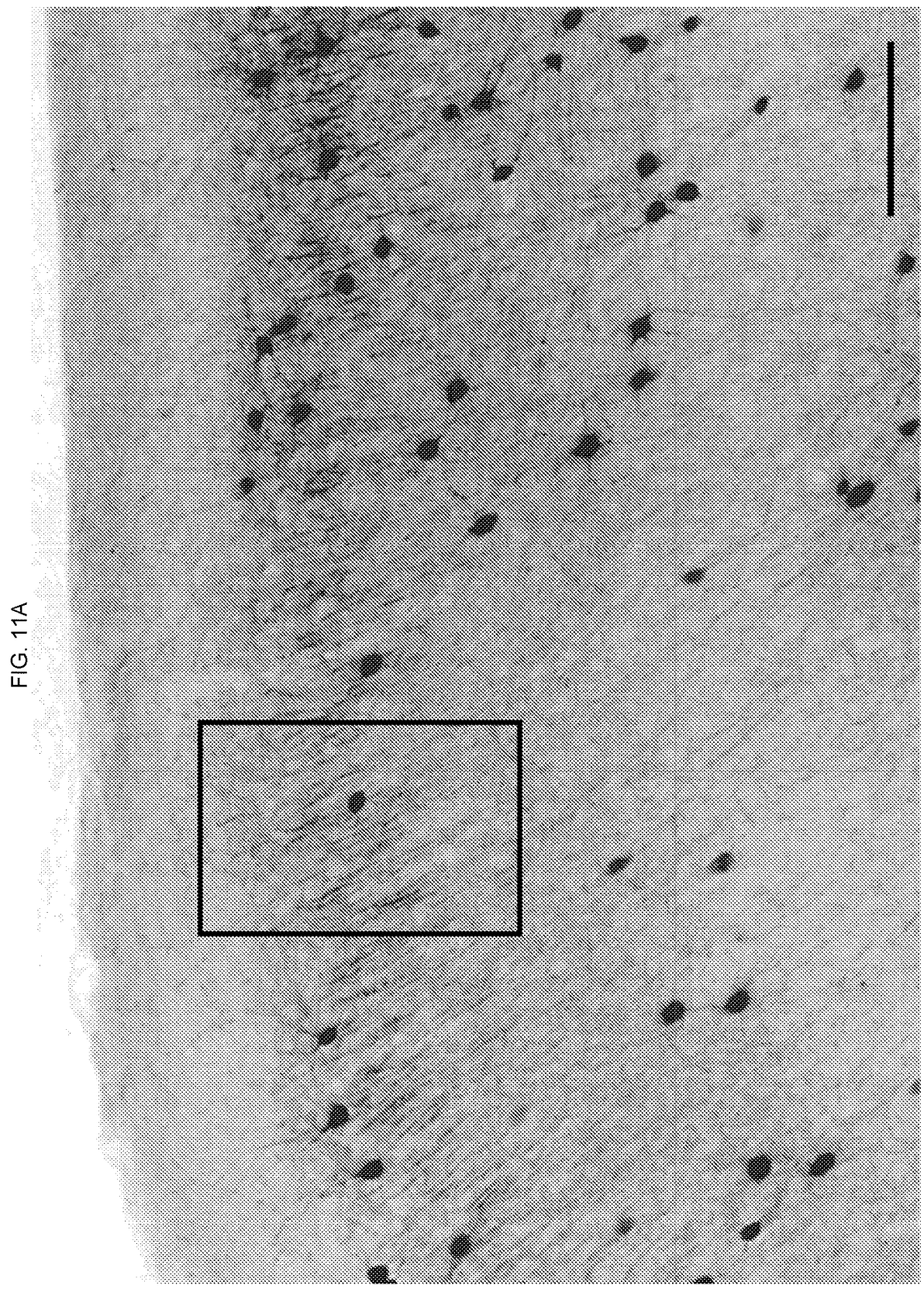
FIGS. 11A, 11B. CN2580 (eHGT_476m) in Ai14 mouse neocortex. (11A) Epifluorescence micrograph image (inverted) showing native SYFP2 expression in the neocortex 29 days after retro-orbital delivery of 1.0E11 viral genome copies of AAV vector #CN2580 (eHGT_476m) into Ai14 Cre-dependent reporter mouse line. Scale bar: 100 microns. (11B) Higher magnification view showing a sparse cell bodies and signature chandelier cell axon cartridges. Scale bar: 50 microns.
Figure 11B:
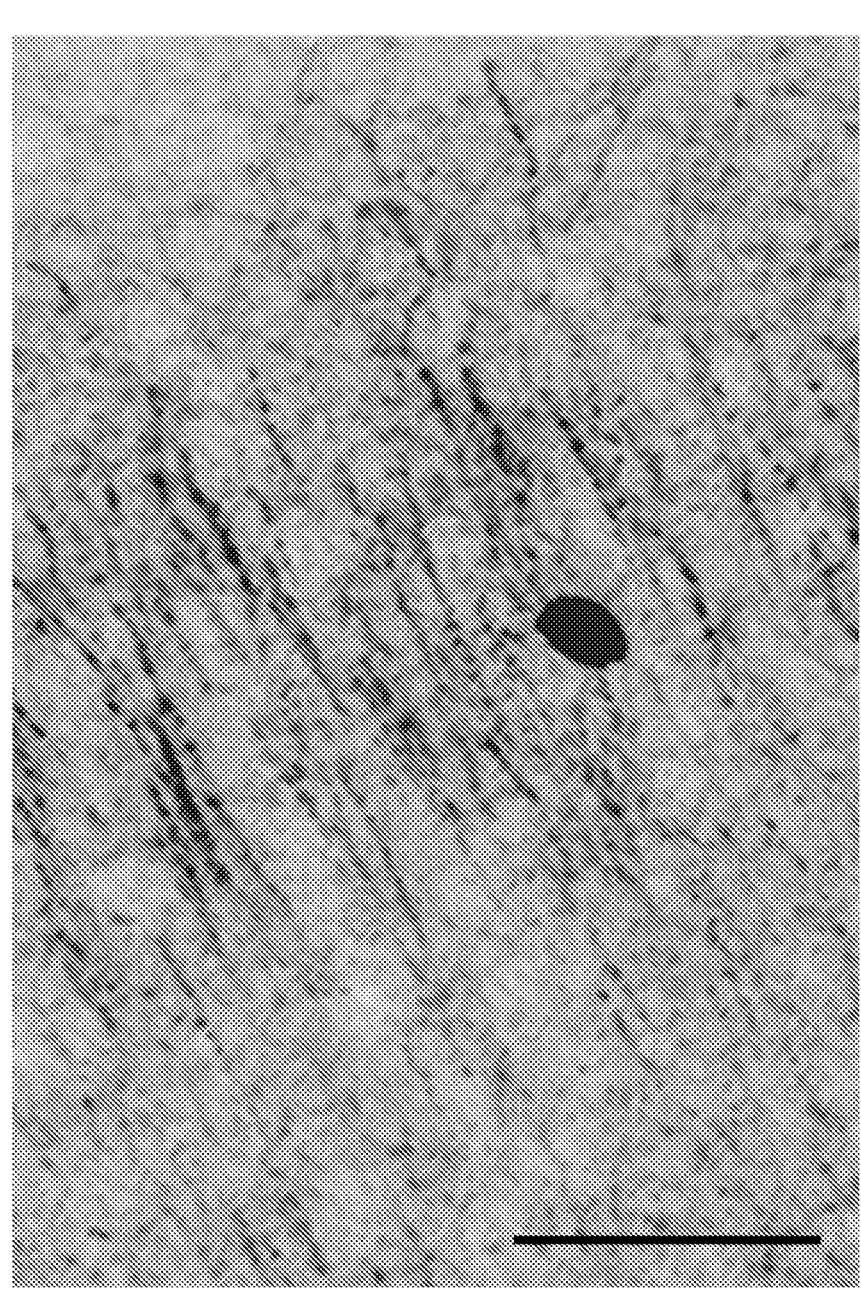
Figure 12A:
FIGS. 12A, 12B. CN2717 (eHGT_710m) in mouse neocortex. (12A) Epifluorescence micrograph image (inverted) showing native SYFP2 expression in the neocortex 40 days after retro-orbital delivery of 6.0E11 viral genome copies of AAV vector #CN2717 (eHGT_710m). Scale bar: 200 microns. (12B) Higher magnification view showing a sparse cell bodies and signature chandelier cell axon cartridges. Scale bar: 50 microns.
Figure 12B:
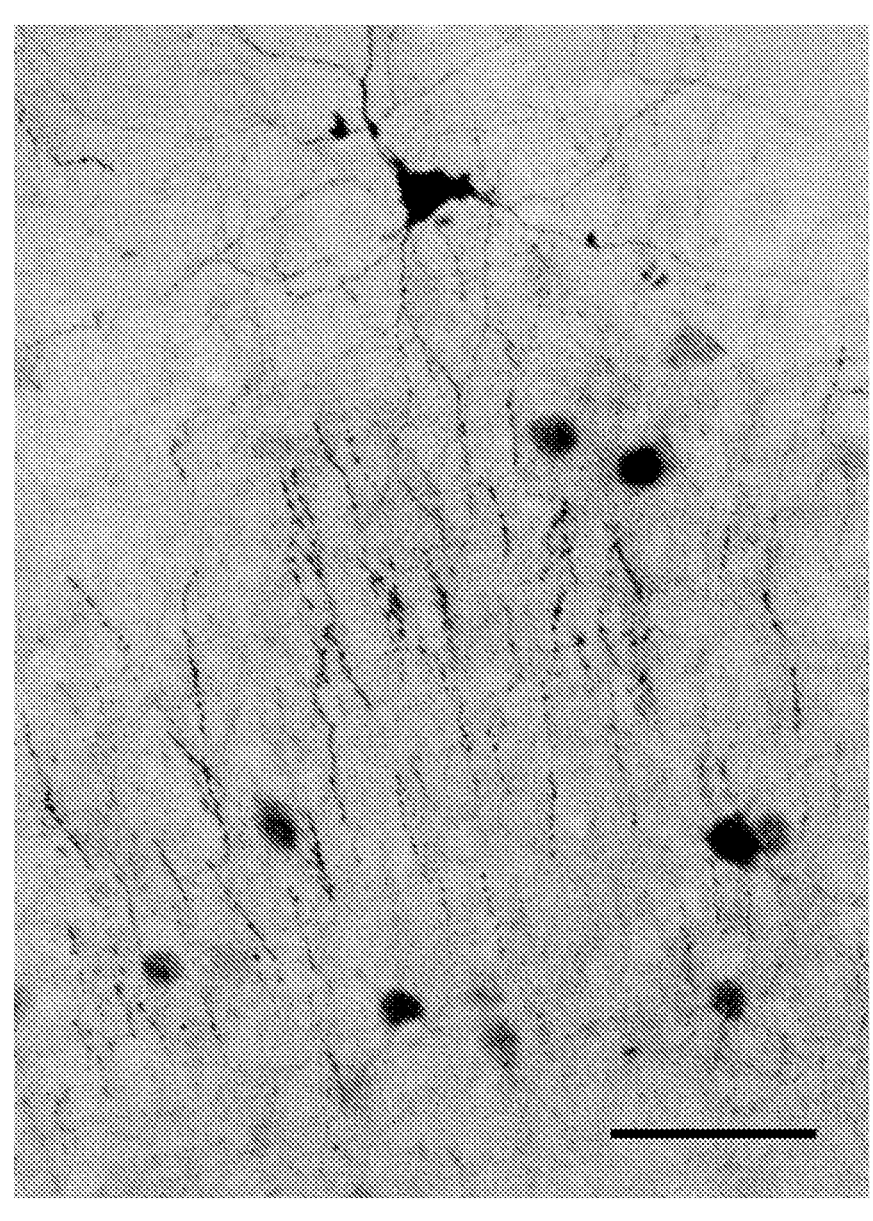
Figure 13A:
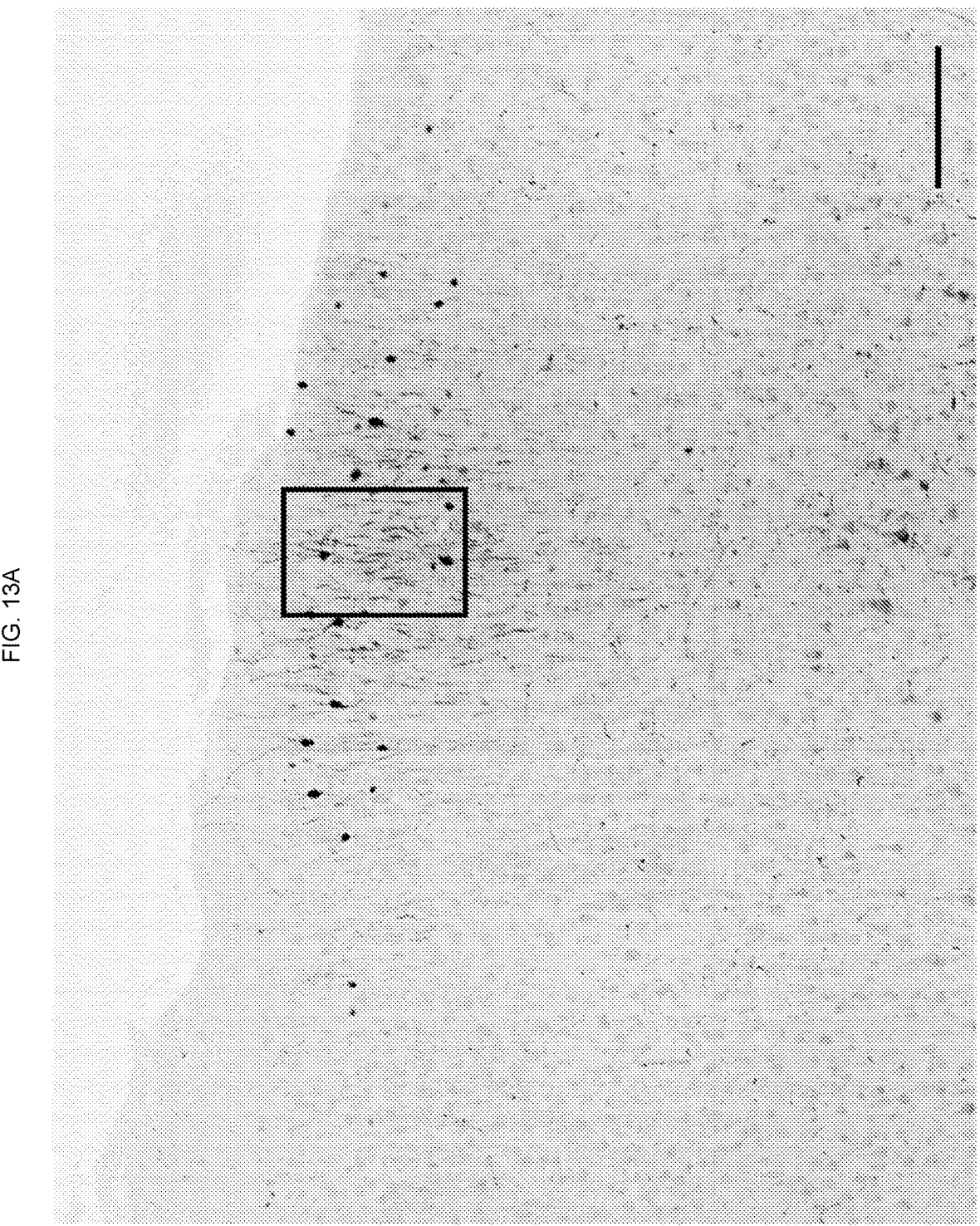
FIGS. 13A, 13B. CN2717 (eHGT_710m) in macaque frontal cortex. (13A) Epifluorescence micrograph image (inverted) showing native SYFP2 expression in the superior frontal cortex region 43 days after stereotaxic injection of 3.46E11 viral genome copies of AAV vector #CN2717 (eHGT_710m) in adult macaque in vivo. Scale bar: 200 microns. (13B) Higher magnification view showing a cell body and signature chandelier cell axon cartridges. Scale bar: 50 microns.
Figure 13B:

Subcomponent sequences within the larger vector sequences can be readily identified by one of ordinary skill in the art and based on the contents of the current disclosure (see FIG. 3). Nucleotides between identifiable and enumerated subcomponents reflect restriction enzyme recognition sites used in assembly (cloning) of the constructs, and in some cases, additional nucleotides do not convey any identifiable function. These segments of complete vector sequences can be adjusted based on use of different cloning strategies and/or vectors. In general, short 6-nucleotide palindromic sequences reflect vector construction artifacts that are not important to vector function.

In particular embodiments vectors (e.g., AAV) with capsids that cross the blood-brain barrier (BBB) are selected. In particular embodiments, vectors are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1 (Marchio et al., EMBO Mol Med. 2016; 8(6): 592), AAV-PHP.S (Chan et al., Nat Neurosci. 2017; 20(8): 1172), AAV-PHP.B (Deverman et al., Nat Biotechnol. 2016; 34(2): 204), AAV-PPS (Chen et al., Nat Med. 2009; 15: 1215), and PHP.eB. In particular embodiments, the PHP.eB capsid differs from AAV9 such that, using AAV9 as a reference, amino acids starting at residue 586: S-AQ-A (SEQ ID NO: 117) are changed to S-DGTLAVPFK-A (SEQ ID NO: 118). In particular embodiments, PHP.eb refers to SEQ ID NO: 59.

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to clinical trials for the treatment of spinal muscular atrophy (SMA) syndrome by AveXis (AVXS-101, NCT03505099) and the treatment of CLN3 gene-Related Neuronal Ceroid-Lipofuscinosis (NCT03770572).

AAVrh.10, was originally isolated from rhesus macaques and shows low seropositivity in humans when compared with other common serotypes used for gene delivery applications (Selot et al., Front Pharmacol. 2017; 8: 441) and has been evaluated in clinical trials LYS-SAF302, LYSOGENE, and NCT03612869.

AAV1R6 and AAV1R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 119) epitope that was isolated during in vivo screening of a random AAV display peptide library. It shows high specificity accompanied by high transgene expression in the brain with minimal off-target affinity (including for the liver) (Körbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 120), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 121). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 122) epitope into the capsid of AAV2, shows a dramatically improved brain tropism relative to AAV2.

For additional information regarding capsids that cross the blood brain barrier, see Chan et al., Nat. Neurosci. 2017 August: 20(8): 1172-1179.

(ii) Compositions for Administration

Artificial expression constructs and vectors of the present disclosure (referred to herein as physiologically active components) can be formulated with a carrier that is suitable for administration to a cell, tissue slice, animal (e.g., mouse, non-human primate, rat), or human. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously (e.g. at the retro-orbital plexus).

In particular embodiments, compositions can be formulated for intravenous, intraparenchymal, intraocular, intravitreal, parenteral, subcutaneous, intracerebro-ventricular, intramuscular, intrathecal, intraspinal, intraperitoneal, oral or nasal inhalation, or by direct injection in or application to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

The disclosure also provides for pharmaceutically acceptable nanocapsule formulations of the physiologically active components. Nanocapsules can generally entrap compounds in a stable and reproducible way (Quintanar-Guerrero et al., *Drug Dev Ind Pharm* 24(12):1113-1128, 1998; Quintanar-Guerrero et al., *Pharm Res.* 15(7):1056-1062, 1998; Quintanar-Guerrero et al., *J. Microencapsul.* 15(1):107-119, 1998; Douglas et al., *Crit Rev Ther Drug Carrier Syst* 3(3):233-261, 1987). To avoid side effects due to intracellular polymeric overloading, such ultrafine particles can be designed using polymers able to be degraded in vivo. Biodegradable polyalkyl-cyanoacrylate nanoparticles that meet these requirements are contemplated for use in the present disclosure. Such particles can be easily made, as described in Couvreur et al., *J Pharm Sci* 69(2):199-202, 1980; Couvreur et al., *Crit Rev Ther Drug Carrier Syst.* 5(1)1-20, 1988; zur Muhlen et al., *Eur J Pharm Biopharm*, 45(2):149-155, 1998; Zambaux et al., *J Control Release* 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res*, 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

(iii) Cell Lines Including Artificial Expression Constructs

The present disclosure includes cells including an artificial expression construct described herein. A cell that has been transformed with an artificial expression construct can be used for many purposes, including in neuroanatomical studies, assessments of functioning and/or non-functioning proteins, and drug screens that assess the regulatory properties of enhancers.

A variety of host cell lines can be used, but in particular embodiments, the cell is a mammalian cell. In particular embodiments, the artificial express construct includes an enhancer and/or a vector sequence of eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, eHGT_503m, CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and/or CN3752, and the cell line is a human, primate, or murine cell. Cell lines which can be utilized for transgenesis in the present disclosure also include primary cell lines derived from living tissue such as rat or mouse brains and organotypic cell cultures, including brain slices from animals such as rats or mice. The PC12 cell line (available from the American Type Culture Collection, ATCC, Manassas, VA) has been shown to express a number of neuronal marker proteins in response to Neuronal Growth Factor (NGF). The PC12 cell line is considered to be a neuronal cell line and is applicable for use with this disclosure. JAR cells (available from ATCC) are a platelet derived cell-line that express some neuronal genes, such as the serotonin transporter gene, and may be used with embodiments described herein.

WO 91/13150 describes a variety of cell lines, including neuronal cell lines, and methods of producing them. Similarly, WO 97/39117 describes a neuronal cell line and methods of producing such cell lines. The neuronal cell lines disclosed in these patent applications are applicable for use in the present disclosure.

In particular embodiments, "neuronal" describes something that is of, related to, or includes, neuronal cells. Neuronal cells are defined by the presence of an axon and dendrites. The term "neuronal-specific" refers to something that is found, or an activity that occurs, in neuronal cells or cells derived from neuronal cells, but is not found in or occur in, or is not found substantially in or occur substantially in, non-neuronal cells or cells not derived from neuronal cells, for example glial cells such as astrocytes or oligodendrocytes.

In particular embodiments, non-neuronal cell lines may be used, including mouse embryonic stem cells. Cultured mouse embryonic stem cells can be used to analyze expression of genetic constructs using transient transfection with plasmid constructs. Mouse embryonic stem cells are pluripotent and undifferentiated. These cells can be maintained in this undifferentiated state by Leukemia Inhibitory Factor (LIF). Withdrawal of LIF induces differentiation of the embryonic stem cells. In culture, the stem cells form a variety of differentiated cell types. Differentiation is caused by the expression of tissue specific transcription factors, allowing the function of an enhancer sequence to be evaluated. (See for example Fiskerstrand et al., *FEBS Lett* 458: 171-174, 1999).

Methods to differentiate stem cells into neuronal cells include replacing a stem cell culture media with a media including basic fibroblast growth factor (bFGF) heparin, an N2 supplement (e.g., transferrin, insulin, progesterone, putrescine, and selenite), laminin and polyornithine. A process to produce myelinating oligodendrocytes from stem cells is described in Hu, et al., 2009, *Nat. Protoc.* 4:1614-22. Bibel, et al., 2007, *Nat. Protoc.* 2:1034-43 describes a protocol to produce glutamatergic neurons from stem cells while Chatzi, et al., 2009, *Exp. Neurol.* 217:407-16 describes a procedure to produce GABAergic neurons. This procedure includes exposing stem cells to all-trans-RA for three days. After subsequent culture in serum-free neuronal induction medium including Neurobasal medium supplemented with B27, bFGF and EGF, 95% GABA neurons develop U.S. Publication No. 2012/0329714 describes use of prolactin to increase neural stem cell numbers while U.S. Publication No. 2012/0308530 describes a culture surface with amino groups that promotes neuronal differentiation into neurons, astrocytes and oligodendrocytes. Thus, the fate of neural stem cells can be controlled by a variety of extracellular factors. Commonly used factors include brain derived growth factor (BDNF; Shetty and Turner, 1998, *J. Neurobiol.* 35:395-425); fibroblast growth factor (bFGF; U.S. Pat. No. 5,766,948; FGF-1, FGF-2); Neurotrophin-3 (NT-3) and Neurotrophin-4 (NT-4); Caldwell, et al., 2001, *Nat. Biotechnol.* 1; 19:475-9); ciliary neurotrophic factor (CNTF); BMP-2 (U.S. Pat. Nos. 5,948,428 and 6,001,654); isobutyl 3-methylxanthine; leukemia inhibitory growth factor (LIF; U.S. Pat. No. 6,103,530); somatostatin; amphiregulin; neurotrophins (e.g., cyclic adenosine monophosphate; epidermal growth factor (EGF); dexamethasone (glucocorticoid hormone); forskolin; GDNF family receptor ligands; potassium; retinoic acid (U.S. Pat. No. 6,395,546); tetanus toxin; and transforming growth factor-α and TGF-β (U.S. Pat. Nos. 5,851,832 and 5,753,506).

In particular embodiments, yeast one-hybrid systems may also be used to identify compounds that inhibit specific protein/DNA interactions, such as transcription factors for eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, and/or eHGT_503m.

Transgenic animals are described below. Cell lines may also be derived from such transgenic animals. For example, primary tissue culture from transgenic mice (e.g., also as described below) can provide cell lines with the artificial expression construct already integrated into the genome. (for an example see MacKenzie & Quinn, *Proc Natl Acad Sci USA* 96: 15251-15255, 1999).

(iv) Transgenic Animals

Another aspect of the disclosure includes transgenic animals, the genome of which contains an artificial expression construct including eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, and/or eHGT_503m operatively linked to a heterologous coding sequence. In particular embodiments, the genome of a transgenic animal includes CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and/or CN3752.

In particular embodiments, when a non-integrating vector is utilized, a transgenic animal includes an artificial expression construct including eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, eHGT_503m, CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and/or CN3752 within one or more of its cells.

Detailed methods for producing transgenic animals are described in U.S. Pat. No. 4,736,866. Transgenic animals may be of any nonhuman species, but preferably include nonhuman primates (NHPs), sheep, horses, cattle, pigs, goats, dogs, cats, rabbits, chickens, and rodents such as guinea pigs, hamsters, gerbils, rats, mice, and ferrets.

In particular embodiments, construction of a transgenic animal results in an organism that has an engineered construct present in all cells in the same genomic integration site. Thus, cell lines derived from such transgenic animals will be consistent in as much as the engineered construct will be in the same genomic integration site in all cells and hence will suffer the same position effect variegation. In contrast, introducing genes into cell lines or primary cell cultures can give rise to heterologous expression of the construct. A disadvantage of this approach is that the expression of the introduced DNA may be affected by the specific genetic background of the host animal.

As indicated above in relation to cell lines, the artificial expression constructs of this disclosure can be used to genetically modify mouse embryonic stem cells using techniques known in the art. Typically, the artificial expression construct is introduced into cultured murine embryonic stem cells. Transformed ES cells are then injected into a blastocyst from a host mother and the host embryo re-implanted into the mother. This results in a chimeric mouse whose tissues are composed of cells derived from both the embryonic stem cells present in the cultured cell line and the embryonic stem cells present in the host embryo. Usually the mice from which the cultured ES cells used for transgenesis are derived are chosen to have a different coat color from the host mouse into whose embryos the transformed cells are to be injected. Chimeric mice will then have a variegated coat color. As long as the germ-line tissue is derived, at least in part, from the genetically modified cells, then the chimeric mice crossed with an appropriate strain can produce offspring that will carry the transgene.

In addition to the methods of delivery described above, the following techniques are also contemplated as alternative methods of delivering artificial expression constructs to target cells or targeted tissues and organs of an animal, and in particular, to cells, organs, or tissues of a vertebrate mammal: sonophoresis (e.g., ultrasound, as described in U.S. Pat. No. 5,656,016); intraosseous injection (U.S. Pat. No. 5,779,708); microchip devices (U.S. Pat. No. 5,797, 898); ophthalmic formulations (Bourlais et al., *Prog Retin Eye Res,* 17(1):33-58, 1998); transdermal matrices (U.S. Pat. Nos. 5,770,219 and 5,783,208); feedback-controlled delivery (U.S. Pat. No. 5,697,899), and any other delivery method available and/or described elsewhere in the disclosure.

(v) Methods of Use

In particular embodiments, a composition including a physiologically active component described herein is administered to a subject to result in a physiological effect.

In particular embodiments, the disclosure includes the use of the artificial expression constructs described herein to modulate expression of a heterologous gene which is either partially or wholly encoded in a location downstream to that enhancer in an engineered sequence. Thus, there are provided herein methods of use of the disclosed artificial expression constructs in the research, study, and potential development of medicaments for preventing, treating or ameliorating the symptoms of a disease, dysfunction, or disorder.

Particular embodiments include methods of administering to a subject an artificial expression construct that includes eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, eHGT_503m, CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, and/or CN3752 as described herein to drive expression of a gene in a targeted cell type. The subject can be an isolated cell, a network of cells, a tissue slice, an experimental animal, a veterinary animal, or a human.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from 105 to $10^{100}$ copies of an artificial expression construct of the disclosure. In particular embodiments, a patient receiving intravenous, intraparenchymal, intraspinal, retro-orbital, or intrathecal administration can be infused with from $10^6$ to $10^{22}$ copies of the artificial expression construct.

An "effective amount" is the amount of a composition necessary to result in a desired physiological change in the subject. Effective amounts are often administered for research purposes. Effective amounts disclosed herein can cause a statistically-significant effect in an animal model or in vitro assay.

The amount of expression constructs and time of administration of such compositions will be within the purview of the skilled artisan having benefit of the present teachings. It is likely, however, that the administration of effective amounts of the disclosed compositions may be achieved by a single administration, such as for example, a single injection of sufficient numbers of infectious particles to provide an effect in the subject. Alternatively, in some circumstances, it may be desirable to provide multiple, or successive administrations of the artificial expression construct compositions or other genetic constructs, either over a relatively short, or a relatively prolonged period of time, as may be determined by the individual overseeing the administration of such compositions. For example, the number of infectious particles administered to a mammal may be $10^7$, $10^8$, $10^9$, $10^{10}$, $10^{11}$, $10^{12}$, $10^{13}$, or even higher, infectious particles/ml given either as a single dose or divided into two or more administrations as may be required to achieve an intended effect. In fact, in certain embodiments, it may be desirable to administer two or more different expression constructs in combination to achieve a desired effect.

In certain circumstances it will be desirable to deliver the artificial expression construct in suitably formulated compositions disclosed herein either by pipette, retro-orbital injection, subcutaneously, intraocularly, intravitreally, parenterally, subcutaneously, intravenously, intraparenchymally, intracerebro-ventricularly, intramuscularly, intrathecally, intraspinally, intraperitoneally, by oral or nasal inhalation, or by direct application or injection to one or more cells, tissues, or organs. The methods of administration may also include those modalities as described in U.S. Pat. Nos. 5,543,158; 5,641,515 and 5,399,363.

(vi) Kits and Commercial Packages

Kits and commercial packages contain an artificial expression construct described herein. The artificial expression construct can be isolated. In particular embodiments, the components of an expression product can be isolated from each other. In particular embodiments, the expression product can be within a vector, within a viral vector, within a cell, within a tissue slice or sample, and/or within a transgenic animal. Such kits may further include one or more reagents, restriction enzymes, peptides, therapeutics, pharmaceutical compounds, or means for delivery of the compositions such as syringes, injectables, and the like.

Embodiments of a kit or commercial package will also contain instructions regarding use of the included components, for example, in basic research, electrophysiological research, neuroanatomical research, and/or the research and/or treatment of a disorder, disease or condition.

The Exemplary Embodiments below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(vii) Exemplary Embodiments

1. A concatemer including a core of eHGT_476m.
2. The concatemer of embodiment 1, wherein the core of eHGT_476m includes the sequence as set forth in SEQ ID NO: 8.
3. The concatemer of embodiment 1 or 2, wherein the concatemer includes 2, 3, 4, 5, 6, 7, 8, 9, or 10 copies of the core of eHGT_476m.
4. The concatemer of any of embodiments 1-3, wherein the concatemer includes the sequence as set forth in SEQ ID NO: 9.
5. An artificial expression construct including (i) an enhancer including eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, and/or eHGT_503m; (ii) a promoter; and (iii) a heterologous encoding sequence.
6. The artificial expression construct of embodiment 5, wherein the heterologous encoding sequence encodes an effector element or an expressible element.
7. The artificial expression construct of embodiment 6, wherein the effector element includes a reporter protein or a functional molecule.
8. The artificial expression construct of embodiment 7, wherein the reporter protein includes a fluorescent protein.
9. The artificial expression construct of embodiment 7 or 8, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a designer receptor exclusively activated by designer drug (DREADD).
10. The artificial expression construct of embodiment 6, wherein the expressible element includes a non-functional molecule.
11. The artificial expression construct of embodiment 10, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a DREADD.
12. The artificial expression construct of any of embodiments 5-11, wherein the artificial expression construct is associated with a capsid that crosses the blood brain barrier.
13. The artificial expression construct of embodiment 8, wherein the capsid includes PHP.eB, AAV-BR1, AAV-PHP.S, AAV-PHP.B, or AAV-PPS.
14. The artificial expression construct of any of embodiments 5-13, wherein the artificial expression construct includes or encodes a skipping element.
15. The artificial expression construct of embodiment 14, wherein the skipping element includes a 2A peptide and/or an internal ribosome entry site (IRES).
16. The artificial expression construct of embodiment 15, wherein the 2A peptide includes T2A, P2A, E2A, or F2A.
17. The artificial expression construct of any of embodiments 5-16, wherein the artificial expression construct encodes a linker.
18. The artificial expression construct of embodiment 17, wherein the linker has the sequence: set forth in SEQ ID NO: 102.

19. The artificial expression construct of embodiment 17, wherein the linker includes a Gly-Ser linker.

20. The artificial expression construct of any of embodiments 5-19, wherein the artificial expression construct encodes a nuclear localization protein.

21. The artificial expression construct of embodiment 20, wherein the nuclear localization protein includes Histone H1, Histone H2A, Histone H2B, Histone H3, Histone H4, and/or histone-like protein HPhA 22. The artificial expression construct of any of embodiments 5-21, wherein the artificial expression construct includes or encodes a set of features including: hsA2, eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, eHGT_503m, AAV, scAAV, rAAV, pAAV, minBglobin, CMV, minCMV, minRho, minRho*, fluorescent protein (e.g., EGFP, SYFP, GFP), Cre, iCre, dgCre, CreN-inteinN, inteinC-CreC, FlpO, tTA2, 3×FLAG, Histone H1, Histone H2A, Histone H2B, Histone H3, Histone H4, histone-like protein HPhA, a linker, SP10 insulator (e.g., 3×SP10ins), 10 amino acids (10 aa), 4×2C, P2A, WPRE, WPRE3, HGHpA, and/or BGHpA.

23. The artificial expression construct of any of embodiments 5-22, wherein the artificial expression construct includes or encodes a set of features including:

3×SP10ins-eHGT_297m-minRho*-[heterologous encoding sequence]-WPRE3-BGHpA;

3×SP10ins-eHGT_303m-minRho*-[heterologous encoding sequence]-WPRE3-BGHpA;

3×SP10ins-eHGT_307m-minRho*-[heterologous encoding sequence]-WPRE3-BGHpA;

3×SP10ins-eHGT_308m-minRho*-[heterologous encoding sequence]-WPRE3-BGHpA;

eHGT_472m-minBglobin-[heterologous encoding sequence]-WPRE3-BGHpA;

eHGT_475m-minBglobin-[heterologous encoding sequence]-WPRE3-BGHpA;

eHGT_476m-minBglobin-[heterologous encoding sequence]-WPRE3-BGHpA;

eHGT_503m-minBglobin-[heterologous encoding sequence]-WPRE3-BGHpA;

eHGT_571m-minBglobin-[heterologous encoding sequence]-WPRE3-BGHpA;

eHGT_706m-minBglobin-[heterologous encoding sequence]-WPRE3-BGHpA;

eHGT_710m-minBglobin-[heterologous encoding sequence]-WPRE3-BGHpA;

eHGT_296m-minBglobin-[heterologous encoding sequence]-WPRE-HGHpA;

eHGT_297m-minBglobin-[heterologous encoding sequence]-WPRE-HGHpA;

eHGT_299m-minBglobin-[heterologous encoding sequence]-WPRE-HGHpA;

eHGT_300m-minBglobin-[heterologous encoding sequence]-WPRE-HGHpA;

eHGT_306m-minBglobin-[heterologous encoding sequence]-WPRE-HGHpA;

eHGT_309m-minBglobin-[heterologous encoding sequence]-WPRE-HGHpA;

eHGT_310m-minBglobin-[heterologous encoding sequence]-WPRE-HGHpA;

eHGT_476m-minRho*-[heterologous encoding sequence]-WPRE3-BGHpA;

eHGT_3×_eHGT_476m-minBGlobin-[heterologous encoding sequence]-WPRE3-BGHpA;

eHGT_890m-minBGlobin-[heterologous encoding sequence]-WPRE3-BGHpA;

eHGT_891m-minBGlobin-[heterologous encoding sequence]-WPRE3-BGHpA;

eHGT_892m-minBGlobin-[heterologous encoding sequence]-WPRE3-BGHpA;

eHGT_1022m-minBGlobin-[heterologous encoding sequence]-WPRE3-BGHpA;

eHGT_1023m-minBGlobin-[heterologous encoding sequence]-WPRE3-BGHpA;

eHGT_1024m-minBGlobin-[heterologous encoding sequence]-WPRE3-BGHpA;

eHGT_475m-minBGlobin-[heterologous encoding sequence]-BGHpA;

3×SP10ins-eHGT_297m-[minimal promoter]-[heterologous encoding sequence]-WPRE3-BGHpA;

3×SP10ins-eHGT_303m-[minimal promoter]-[heterologous encoding sequence]-WPRE3-BGHpA;

3×SP10ins-eHGT_307m-[minimal promoter]-[heterologous encoding sequence]-WPRE3-BGHpA;

3×SP10ins-eHGT_308m-[minimal promoter]*-[heterologous encoding sequence]-WPRE3-BGHpA;

eHGT_472m-[minimal promoter]-[heterologous encoding sequence]-WPRE3-BGHpA;

eHGT_475m-[minimal promoter]-[heterologous encoding sequence]-WPRE3-BGHpA;

eHGT_476m-[minimal promoter]-[heterologous encoding sequence]-WPRE3-BGHpA;

eHGT_503m-[minimal promoter]-[heterologous encoding sequence]-WPRE3-BGHpA;

eHGT_571m-[minimal promoter]-[heterologous encoding sequence]-WPRE3-BGHpA;

eHGT_706m-[minimal promoter]-[heterologous encoding sequence]-WPRE3-BGHpA;

eHGT_710m-[minimal promoter]-[heterologous encoding sequence]-WPRE3-BGHpA;

eHGT_296m-[minimal promoter]-[heterologous encoding sequence]-WPRE-HGHpA;

eHGT_297m-[minimal promoter]-[heterologous encoding sequence]-WPRE-HGHpA;

eHGT_299m-[minimal promoter]-[heterologous encoding sequence]-WPRE-HGHpA;

eHGT_300m-[minimal promoter]-[heterologous encoding sequence]-WPRE-HGHpA;

eHGT_306m-[minimal promoter]-[heterologous encoding sequence]-WPRE-HGHpA;

eHGT_309m-[minimal promoter]-[heterologous encoding sequence]-WPRE-HGHpA;

eHGT_310m-[minimal promoter]-[heterologous encoding sequence]-WPRE-HGHpA;

eHGT_3×_eHGT_476m-[minimal promoter]-[heterologous encoding sequence]-WPRE3-BGHpA;

eHGT_890m-[minimal promoter]-[heterologous encoding sequence]-WPRE3-BGHpA;

eHGT_891m-[minimal promoter]-[heterologous encoding sequence]-WPRE3-BGHpA;

eHGT_892m-[minimal promoter]-[heterologous encoding sequence]-WPRE3-BGHpA;

eHGT_1022m-[minimal promoter]-[heterologous encoding sequence]-WPRE3-BGHpA;

eHGT_1023m-[minimal promoter]-[heterologous encoding sequence]-WPRE3-BGHpA;

eHGT_1024m-[minimal promoter]-[heterologous encoding sequence]-WPRE3-BGHpA; or eHGT_475m-[minimal promoter]-[heterologous encoding sequence]-BGHpA.

24. The artificial expression construct of embodiment 23, wherein the heterologous encoding sequence encodes a reporter protein.

25. The artificial expression construct of embodiment 24, wherein the heterologous encoding sequence further encodes a linker.

26. The artificial expression construct of embodiment 24 or 25, wherein the heterologous encoding sequence further encodes a nuclear localization protein.

27. A vector including an artificial expression construct of any of embodiments 5-26.

28. The vector of embodiment 27, wherein the vector includes a viral vector.

29. The vector of embodiment 27 or 28, wherein the viral vector includes a recombinant adeno-associated viral (AAV) vector.

30. An adeno-associated viral (AAV) vector including at least one heterologous encoding sequence, wherein the heterologous encoding sequence is under control of a promoter and an enhancer including eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, and/or eHGT_503m.

31. A transgenic cell including an expression construct or vector of any of the preceding embodiments.

32. The transgenic cell of embodiment 31, wherein the transgenic cell is a chandelier cell and optionally a vasoactive intestinal peptide (Vip) cell, a glutamatergic neuron in the thalamus, or a molecular layer GABAergic interneuron in the cerebellum.

33. A non-human transgenic animal including an artificial expression construct, vector, or transgenic cell of any of the preceding embodiments.

34. The non-human transgenic animal of embodiment 33, wherein the non-human transgenic animal is a mouse, a rat, or a non-human primate.

35. An administrable composition including an artificial expression construct, vector, or transgenic cell of any of the preceding embodiments.

36. A kit including an artificial expression construct, vector, transgenic cell, transgenic animal, and/or administrable compositions of any of the preceding embodiments.

37. A method for expressing a heterologous gene within a targeted population of cells in vivo or in vitro, the method including providing the administrable composition of embodiment 35 in a sufficient dosage and for a sufficient time to a sample or subject including the targeted population of cells thereby expressing the gene within the targeted population of cells.

38. The method of embodiment 37, wherein the heterologous gene encodes an effector element or an expressible element.

39. The method of embodiment 38, wherein the effector element includes a reporter protein or a functional molecule.

40. The method of embodiment 39, wherein the reporter protein includes a fluorescent protein.

41. The method of embodiment 39, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a DREADD.

42. The method of embodiment 39, wherein the expressible element includes a non-functional molecule.

43. The method of embodiment 42, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or DREADD.

44. The method of any of embodiments 37-43, wherein the targeted population of cells includes a chandelier cell.

45. The method of any of embodiments 37-44, wherein the targeted population of cells includes a chandelier cell and optionally an additional cell type.

46. The method of embodiment 45, wherein the additional cell type includes a VIP cell.

47. The method of embodiment 45, wherein the additional cell type includes a glutamatergic neuron in the thalamus and a molecular layer GABAergic interneuron in the cerebellum.

48. The method of any of embodiments 37-44, wherein the targeted population of cells includes a selective population of cells including chandelier cells.

49. The method of any of embodiments 37-48, wherein the providing includes pipetting.

50. The method of embodiment 49, wherein the pipetting is to a brain slice.

51. The method of embodiment 50, wherein the brain slice includes a chandelier cell.

52. The method of embodiments 50 or 51, wherein the brain slice includes a VIP cell.

53. The method of any embodiments 50-52, wherein the brain slice includes a glutamatergic neuron in the thalamus.

54. The method of any of embodiments 50-53, wherein the brain slice includes a molecular layer GABAergic interneuron in the cerebellum.

55. The method of any of embodiments 50-54, wherein the brain slice is murine, human, or non-human primate.

56. The method of any of embodiments 37-55, wherein the providing includes administering to a living subject.

57. The method of embodiment 56, wherein the living subject is a human, a non-human primate, a rat, or a mouse.

58. The method of embodiments 56 or 57, wherein the administering to a living subject is through injection.

59. The method of embodiment 58, wherein the injection includes intravenous injection, intraparenchymal injection into brain tissue, intracerebroventricular (ICV) injection, intra-cisterna magna (ICM) injection, or intrathecal injection.

60. An artificial expression construct including CN1917, CN2047, CN2048, CN2049, CN2427, CN2320, CN2321, CN2719, CN2707, CN2713, CN2717, AiP1104, AiP1089, AiP1105, AiP1090, AiP1106, AiP1091, AiP1092, CN2581, CN2782, CN3407, CN3408, CN3409, CN2580, CN2825, CN3270, CN3316, CN3271, CN3793, CN3794, CN3795, CN3790, CN3751, or CN3752.

(viii) Closing Paragraphs

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in nonessential regions of a polypeptide do not substantially alter biological activity (see, e.g., Watson et a1. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (lie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, lie, Phe, Met, and Trp; Group 11 (aliphatic): Gly, Ala, Val, Leu, and lie; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in targeted expression in chandelier cells using enhancer eHGT_297m, eHGT_303m, eHGT_307m, eHGT_308m, eHGT_472m, eHGT_475m, eHGT_476m, a core of eHGT_476m, a concatemer of the core of eHGT_476m, eHGT_571m, eHGT_706m, eHGT_710m, eHGT_296m, eHGT_299m, eHGT_300m, eHGT_306m, eHGT_309m, eHGT_310m, eHGT_890m, eHGT_891m, eHGT_892m, eHGT_1022m, eHGT_1023m, eHGT_1024m, or a statistically significant reduction in expression in chandelier cells and VIP cells using enhancer eHGT_503m.

In particular embodiments, artificial means not naturally occurring.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; ±15% of the stated value; 14% of the stated value; ±13% of the stated value; 12% of the stated value; 11% of the stated value; 10% of the stated value; 9% of the stated value; 8% of the stated value; 7% of the stated value; ±6% of the stated value; 5% of the stated value; 4% of the stated value; ±3% of the stated value; 2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A concatemer having 2, 3, 4, 5, 6, 7, 8, 9, or 10 copies of a sequence as set forth in SEQ ID NO: 8.

2. The concatemer of claim 1, wherein the concatemer has a sequence as set forth in SEQ ID NO: 9 or a sequence having at least 98% sequence identity to the sequence as set forth in SEQ ID NO: 9.

3. An artificial expression construct comprising:
   (i) the concatemer of claim 1; (ii) a promoter; and (iii) a heterologous encoding sequence.

4. The artificial expression construct of claim 3, wherein the heterologous encoding sequence encodes a fluorescent protein.

5. The artificial expression construct of claim 3, wherein the heterologous encoding sequence encodes a neurotransmitter.

6. The artificial expression construct of claim 3, wherein the artificial expression construct is associated with a capsid that crosses the blood brain barrier.

7. The artificial expression construct of claim 6, wherein the capsid comprises PHP.eB, AAV-BR1, AAV-PHP.S, AAV-PHP.B, AAV9, AAVrh.10, or AAV-PPS.

8. The artificial expression construct of claim 3, wherein the artificial expression construct comprises or encodes a skipping element.

9. The artificial expression construct of claim 8, wherein the skipping element comprises a T2A, P2A, E2A, or F2A peptide and/or an internal ribosome entry site (IRES).

10. The artificial expression construct of claim 3, wherein the artificial expression construct encodes a Gly-Ser linker.

11. The artificial expression construct of claim 3, wherein the artificial expression construct encodes a nuclear localization protein comprising Histone H1, Histone H2A, Histone H2B, Histone H3, Histone H4, and/or histone-like protein HPhA.

12. The artificial expression construct of claim 3, wherein the artificial expression construct is within a viral vector.

\* \* \* \* \*

SEQUENCE LISTING

```
<160> NUMBER OF SEQ ID NOS: 137

<210> SEQ ID NO 1
<211> LENGTH: 907
<212> TYPE: DNA
<213> ORGANISM: Artificial Sequence
<220> FEATURE:
<223> OTHER INFORMATION: eHGT_297m

<400> SEQUENCE: 1
actattccag ccacgaggta taaacactgg gaaggaaagt cctggctctg tattgtccac      60
aaagacccga agctgcagca aagttggcaa aagagaaaca aaaagagcag agaaggctca     120
gctttcaaca gctaggctca cccaaacatc aagaggtgga caaatattta cagtgtgaac     180
cttaacccaa agaacggcag tgcggtcatg ctgcacagag tcaacttcag aaccaagact     240
gtgaccaggg ctggagcaag agacacttca cgctaataaa taggccactt aatcaagaag     300
ctgtcacagt cctaaatatg tatgcaccga gcattagcac ttccaagtag agtggaacag     360
ctaaagatag aggcaagaag caagcagaca aatcttcggt gattgttgga aatcacagca     420
tttctctcag caattgtcag gacacagaaa atcagcgaga agacagaaga gtctcacaat     480
agtccccatc aacttgacct aattgacatt tatggagctt ggcatccaac agccgtggag     540
cgcatgcgct ctttaaggca gaatacagac catcaaacaa aaccagggag accaaagtca     600
cagaaaatat gctctgtgaa catgacataa taaagtggaa atcgataaca gagagatcgc     660
tgcaaaatcc cccaagtgat tggtaattaa atgctctact cctgaatgaa tgatgggcga     720
gaaaggaaag ccacgggga aagcagattt ctgcgttgaa agagcatgga gacagacttc     780
gtcaagatga gagagcacgt ggggctggag ggatggctca gcacttcaga ggcactcacg     840
ctcttccata ggacctaggt tcacttctca gcacacacat ggcaactcac acctgtgatg     900
cagagaa                                                             907

<210> SEQ ID NO 2
<211> LENGTH: 392
<212> TYPE: DNA
<213> ORGANISM: Artificial Sequence
<220> FEATURE:
<223> OTHER INFORMATION: eHGT_303m

<400> SEQUENCE: 2
```

-continued

```
tccttctcag aacctaggta aggtaagttc ctttcaaggc tggctatata aataatcatc        60
tcagttagga tgcttggtgg gaccaaagaa ccaaaactgc cgagcaggca tgatctgact       120
tggagtggtt ccaggacctt cctgtgaatg ctggagtcat tcagtgtaga gctctcctct       180
gtgactgggt caaggttgcc ccactgtaaa cccaggaag ctagcccagc cttcctctca        240
gggaatgtgt atgcttccct tacacctgac cctggcacag acctggtggt tgttttcag        300 aagcatcagt gtctttgcct taggcatttg tcctcaaagg gcagcgacac tgtctactga       360
ctgctttgta cagggtaact gcttaactaa tt                                      392
```

```
<210> SEQ ID NO 3
<211> LENGTH: 339
<212> TYPE: DNA
<213> ORGANISM: Artificial Sequence
<220> FEATURE:
<223> OTHER INFORMATION: eHGT_307m

<400> SEQUENCE: 3
aaatggagac tgccaagggc tgaaacgggg tgcgggaacc agggaccgag cccccccct        60 ccccacatga gaatctgtca cattgctgct ccagtggcct gaaagaccag cacagcccca       120
gctggagcct ctcccctctg gatcttgtca atgtggcttt gctttgctgc ttgggcagcc       180
gggagtggtg acaagcaggg agagagcgcc caaggcatct ggctgtgcca ctccagcctg       240
actgccagct cacccatcag tgcccatctc atcatcgaga gggacccaga tgagaccggg       300
gatcagcact gtccttacct tgaagggacg tgtcaggaa                              339
```

```
<210> SEQ ID NO 4
<211> LENGTH: 408
<212> TYPE: DNA
<213> ORGANISM: Artificial Sequence
<220> FEATURE:
<223> OTHER INFORMATION: eHGT_308m

<400> SEQUENCE: 4
tctgctttct cttcccttgg cctcctgctg ggatagaagg ggttggtgtg agtgtgtatg        60
gtggggtgct gtgagattaa ttagcagccg tgccaggcag caggcggtgg ggtgcagagt       120
aggctggctt tccctgctat agatccatgc tctctgggag aggcactagc cggctgcttt       180
gggctctggc tcagctattt taggaatatt cttaacccct ccagaaccgc tgccattgcc       240
agatctctct cccagaacac aggccagctc cagattgccc ctcctttctg cccccgccct       300
gcaccccacc tagcctctgc tcttcctccc tacaagttga gaaggtcaag gtttgacttt       360
taccaaagaa aactcctggc tcctgatccc actctctgtg ctttacct                    408
```

```
<210> SEQ ID NO 5
<211> LENGTH: 713
<212> TYPE: DNA
<213> ORGANISM: Artificial Sequence
<220> FEATURE:
<223> OTHER INFORMATION: eHGT_472m

<400> SEQUENCE: 5
gggatgcgat gcagtggcat ggtaaaaatg ccgtacctaa tgatgcagtt tcagccatca        60
tgacgtatgg atggaatgaa aagatgacaa agctactagc ggatctgttc acaaaggaaa       120
agaggctcag tttccaacag tctctggcat ttcatctttg gaaaacttgt caaagctaag       180
atgatttgtg agagtcctaa ctcattttcc taaatatgaa gtcgctatta tggataaaga       240
```

```
aaggttacaa tggagcatcc atttccactc tagtcattct gcttgattgc accaattagc      300
cctgcattca ctgtgcattt taacttcata atggtctatt atttggacca ctgaccataa      360
tgatgcaatt ctttccttga cgaaaataaa tgcttagtga taaataagta atcataatta      420
aagctttcat agtacttata gtaccacaat tggtatttag cccattgatt ataatttaaa      480
cacattttaa ttaatatgta actatattac ttccctattt ttcttttctt tcctccaaaa      540
tgcctcatgt ctccttctat caacacccccc cataccccccc agacactcct tgtcaaattg      600
atggcctttt aaaattatta ttattgtaac atgaagaaat agttgaacaa atatataaat      660
acagtacaat gagtctgttt atggtggctc ctatgggtat gatttggggg cct            713

<210> SEQ ID NO 6
<211> LENGTH: 627
<212> TYPE: DNA
<213> ORGANISM: Artificial Sequence
<220> FEATURE:
<223> OTHER INFORMATION: eHGT_475m

<400> SEQUENCE: 6
tatcttagag tgggaagatt tgagaagtgc catggttaat atgactgact ttttattctt       60
atttctttta atttcatggt tctaaatccg aatttaatca tagtacccag aaaagcagag      120
gtgtagaggt tcacagtggg agttgtaatc tagccctatt cattttgacc tcaaaaccca      180
aattatttat aacaaattat ttcctattct ttccttcact attcaggaac atctgtccac      240
cacttacatg atcacttatc ttgctattgt gtcattttga tgaaaaagaa ttttttctaa      300
atatctaaat acaaggcccc atattaacag tgctttttaa atccccacag atgtgggaga      360
tgaccccttt ccatccctga agattgtaat tgggccagtc tttagtacag tttgttccaa      420
taaagagata caattttatt cattaatttg tgtattcatt tagcaaatca ctttagagtc      480
ttattatatc aggattttgg ggtctatttt agtatatctt tttgtatttc ttggaacctc      540
tccaattatt ctagactctt tcaaaggttg gtgatcaata ttagacatta ttatgaaaag      600
aatcttactt gctaaaaggg ttagatg                                          627

<210> SEQ ID NO 7
<211> LENGTH: 486
<212> TYPE: DNA
<213> ORGANISM: Artificial Sequence
<220> FEATURE:
<223> OTHER INFORMATION: eHGT_476m

<400> SEQUENCE: 7
tatgatgtgc caggcttggg agaaacacca caagcaaagc caaaataggt ggcctagaac       60
ttccagcttg aaatatggga gagaatgagg gaggcactgt agagcagctg ccgggtgccg      120
catgagaaca attctccctg ctcataatta atcctaccta tttctgatga cagctggctc      180
ttcactttga acaagctagt taacaacttt cttctcacat tgagcaaata attcatattt      240
aattacttaa ccaccagtta caaatgagaa tcatcaagg aatcacaatt aatttgctat       300
tgacaaactc atactttttag caggctgatt tctactttat acttagattg gtaatgaaaa      360
atgaagctta ttttagttga ttggttggac ttgtgtatga atattatcta ttatttgaaa      420
agccaaactt gaatgcaaaa aaatattgaa tatgaaaaga aaacatttg cagtaaagct       480 tgttct                                                                 486

<210> SEQ ID NO 8
<211> LENGTH: 439
```

<212> TYPE: DNA
<213> ORGANISM: Artificial Sequence
<220> FEATURE:
<223> OTHER INFORMATION: eHGT_476m core

<400> SEQUENCE: 8
agaaacacca caagcaaagc caaaataggt ggcctagaac ttccagcttg aaatatggga        60
gagaatgagg gaggcactgt agagcagctg ccgggtgccg catgagaaca attctccctg       120
ctcataatta atcctaccta tttctgatga cagctggctc ttcactttga acaagctagt       180
taacaacttt cttctcacat tgagcaaata attcatattt aattacttaa ccaccagtta       240
caaaatgaga atcatcaagg aatcacaatt aatttgctat tgacaaactc atactttttag      300 caggctgatt tctactttat acttagattg gtaatgaaaa atgaagctta ttttagttga       360
ttggttggac ttgtgtatga atattatcta ttatttgaaa agccaaactt gaatgcaaaa      420
aaatattgaa tatgaaaag                                                   439

<210> SEQ ID NO 9
<211> LENGTH: 1316
<212> TYPE: DNA
<213> ORGANISM: Artificial Sequence
<220> FEATURE:
<223> OTHER INFORMATION: 3x_eHGT_476m core

<400> SEQUENCE: 9
agaaacacca caagcaaagc caaaataggt ggcctagaac ttccagcttg aaatatggga        60
gagaatgagg gaggcactgt agagcagctg ccgggtgccg catgagaaca attctccctg       120
ctcataatta atcctaccta tttctgatga cagctggctc ttcactttga acaagctagt       180
taacaacttt cttctcacat tgagcaaata attcatattt aattacttaa ccaccagtta       240
caaaatgaga atcatcaagg aatcacaatt aatttgctat tgacaaactc atactttttag      300 caggctgatt tctactttat acttagattg gtaatgaaaa atgaagctta ttttagttga       360
ttggttggac ttgtgtatga atattatcta ttatttgaaa agccaaactt gaatgcaaaa      420
aaatattgaa tatgaaaaga gaaacaccac aagcaaagcc aaaataggtg cctagaact       480 tccagcttga aatatgggag agaatgaggg aggcactgta gagcagctgc cgggtgccgc       540
atgagaacaa ttctccctgc tcataattaa tcctacctat tttctgatgac agctggctct       600 tcactttgaa caagctagtt aacaactttc ttctcacatt gagcaaataa ttcatattta       660
attacttaac caccagttac aaaatgagaa tcatcaagga atcacaatta atttgctatt       720
gacaaactca tactttttagc aggctgattt ctactttata cttagattgg taatgaaaaa       780
tgaagcttat tttagttgat tggttggact tgtgtatgaa tattatctat tatttgaaaa       840
gccaaacttg aatgcaaaaa aatattgaat atgaaaagag aaacaccaca agcaaagcca       900
aaataggtgg cctagaactt ccagcttgaa atatgggaga gaatgaggga ggcactgtag       960
agcagctgcc gggtgccgca tgagaacaat tctccctgct cataattaat cctacctatt      1020
tctgatgaca gctggctctt cactttgaac aagctagtta acaactttct tctcacattg      1080
agcaaataat tcatatttaa ttacttaacc accagttaca aaatgagaat catcaaggaa      1140
tcacaattaa tttgctattg acaaactcat actttttagca ggctgatttc tactttatac      1200
ttagattggt aatgaaaaat gaagcttatt ttagttgatt ggttggactt gtgtatgaat      1260
attatctatt atttgaaaag ccaaacttga atgcaaaaaa atattgaata tgaaaa          1316

<210> SEQ ID NO 10

-continued

```
<211> LENGTH: 988
<212> TYPE: DNA
<213> ORGANISM: Artificial Sequence
<220> FEATURE:
<223> OTHER INFORMATION: eHGT_503m

<400> SEQUENCE: 10
aaagctacat ctctgggctc cattattaaa gctgctttcc ttcctttctc tctctctcgc       60
tctctctctc tctctctttc tttctttctt tttcctgaga tgggtctcat gtagcccagg      120
ctggcctcaa gcttgccaca tagccaagga gccaaggatg gcattgaact cctagatcct      180
ccagcctctg cctcctgtta ggattagagg tgagctacaa tcccaagggc ctttagtgta      240
acagtcaaaa gctactggga gtcaggcaat tggctcagta taaccctgat tctccttttg      300
tgcccaggca cgttggtcag gagtctgtct tcagcctgtc atggcagcag ctcagcttca      360
gtgaccaatc tatactcact cacaggagac tctgaaatcc cagattctgt gctataaagt      420
ccccgctcga gtgagtcgtg actgctccaa acagcctggg cagctgcgaa ccctcatggc      480
atctaggtga ccctgttcat cctacagctg ttctcactga ggggagggga gcttttgagt      540
gagccagtca aaactctgtg ctcggtgatc ctgtgaggct cggaacggtg gcacccgaag      600
ccatgggtgc acacacaaac agggctctaa tcggtgggat cacaatccat gaacaagcat      660
gagacctccc ttcttctcac acacacacac acacacacac acacacacac actcactcac      720
atacatgagc tggtttccac aactgtgggg ttagcctgga aggtgtctgt cctatatagt      780
actccagtac cagtgttgca gactctaggc ccaggaaaag gttttttgatg tttgctggtg      840 tttttgatga ccttcatcgt gggtagagca ggctgcgctg gttcataaag agaagacaag      900
acctagagtg ctgtgaccct ttaaggcatc atggtgtgat gacccccaac cataaagtta      960
ttttcgctgc tgctttgtaa ctgtaagt                                         988

<210> SEQ ID NO 11
<211> LENGTH: 428
<212> TYPE: DNA
<213> ORGANISM: Artificial Sequence
<220> FEATURE:
<223> OTHER INFORMATION: eHGT_571m

<400> SEQUENCE: 11
tgaatcttca tggagaaaac atcatgaata gagaatgaag aagtaaagat gaacaagtga       60
gaattcagat catcagaggg ttttctagga tttctgtaaa tttctctgtg ttttggaatg      120
caataggaat gccagcccaa agccatatag gtcacagctg cccaagaaca gttaccaata      180
cagtataaat aacgtcctaa acttagaata ttgtgaaatt cttttttataa ctcagccatt      240 taattcttga gtgtaaattt tgtagatgga gtcatgttgt aatgttagac acatttgcta      300
gtgatgtgac aacataatat tcccatgaac tgatgtcaaa tgttgtattg tactttgacc      360
aggtatataa ggtttattat cttcttgacc ttggagtaat ttcagtccca acttaaatcc      420
ctagtggt                                                               428

<210> SEQ ID NO 12
<211> LENGTH: 352
<212> TYPE: DNA
<213> ORGANISM: Artificial Sequence
<220> FEATURE:
<223> OTHER INFORMATION: eHGT_706m

<400> SEQUENCE: 12
tatgtagata caggtcatag aacttgccct ggggaatggc tccatttggt accaacaggc       60
```

-continued

```
tgaccccctag ggaggaagga aggctatcag caagaggagg aggaggtagc agagatgaga      120
aagatggggt agactctggc tccaacctag ggaagggaaa gactctagac tcggggtat       180 gggggtggat agatacaggg agcacacagg ctacttggcc tggtctgccc atgaatacag       240
ggggcctcta acattgctgg ggtaggaggg tcagaatgct ccagtgctag ccctcatgct       300
ggctcaggac aggactctga aaagccacca gctgccactt tcacaagctg ag              352

<210> SEQ ID NO 13
<211> LENGTH: 382
<212> TYPE: DNA
<213> ORGANISM: Artificial Sequence
<220> FEATURE:
<223> OTHER INFORMATION: eHGT_710m

<400> SEQUENCE: 13
agtgacttgg tgctatgagc catattttgc tgttgctgtt gttactggta gtttttgtaa       60 ttctgggggct aaaacttggg gtctggtatg ctgtcattta ccagtgagct ataccctgga     120
tattatgatt tagatgaatg tgaaatatca ccccagacat acatatacta aacacttggc      180
ccttggccca tgatgctaaa tggaggagat agaagctttt ggggcacagc ctagtggaag      240
gaaatgaggt caaatgacat gtactctgaa aggaatatgg gtattctggg cttgcgttat      300
tctctctctc cctctctctc cctctctctc cctctccctc tctctttctc ctttttctctt     360 tctctcctcg ccttgtttttc ca                                              382

<210> SEQ ID NO 14
<211> LENGTH: 912
<212> TYPE: DNA
<213> ORGANISM: Artificial Sequence
<220> FEATURE:
<223> OTHER INFORMATION: eHGT_296m

<400> SEQUENCE: 14
tccagctacc accagcctgt ccaaaagggg acaccaaagg agaggaggaa gtctgagaga       60
cacctctctg caccatggcc atcttagtag tcagacccag aacaaaactc tctgatgagt      120
gtgcggagcg tcgcttctgg tctttgctca aactattcac tgaagattta aagcaatccc      180
gtgagtgata catttgggtg aatttgttct ctagaaggta tcacagaaat ctggtcactg      240
ggccacccga gacatcctga taggccctct ggtaacccat cacatgctgc agactgactc      300
tgggggccta gaacccagat cagaagcaac cttgaccccg gcccacccgc cacggaagca      360
ccatcatctc tctgattaaa aacctcgatc acggacccgg gggcgtgccc ggaagagcta      420
agataatcag cgtcagcact ttgccttcgc cgtccaagac tgcagacggc cttcatttga      480
cctgattcgt ggtgttaatg acagcagagc aattttgaga ggcagcttgc tctcggcatc      540
tataaggaga ggaaaagcac tgagggctgg ggaccaagct ccttgcagag gcggcagctg      600
cagtcaccct cccctccac ccctgcccct ccctcccct ccagaggcac tttgagtaag        660
tgctgccctc cgatctgccc tgatacgatg ggagaaagct gatgtgaggg ctggagccag      720
agtgtgcaag gggacagtgt gtgcatgtgc gtgtgtcggg gagaggtacc cgtgctatac      780
ctgagaacat tgctgggtga acacagcctt ggacctggaa gagcgcatag cttacttaga      840
ggcatgggct gcacatgagc tgcccattta cctgctcatt tagaagctac tatgaaggct      900
ggtgagatgg ct                                                         912

<210> SEQ ID NO 15
```

<210> LENGTH: 481
<212> TYPE: DNA
<213> ORGANISM: Artificial Sequence
<220> FEATURE:
<223> OTHER INFORMATION: eHGT_299m

<400> SEQUENCE: 15
accagaagtt cagtgagcag aagatgggct aaaatgaaaa gggtactgtc ttgaactgaa        60
gatggaatcc tgcagcttca ttctggccaa aagaagatct attcccagga ggagggtaaa       120
ggctttgttc ttaagagatg ctgaggctgg ccctgtgaat ctgatgtcaa gatgtccctt       180
gtcactctgc agaagcgtat gtctcttgca tttccttctt atttccttgg gtgaaattgc       240
tgtggcattg tgtcactcat cctaatgggt catgtctaac atctgcgtgc ttacaaatca       300
ggcatgctca tttctgggct tatggagctt gtataacacc aggacaggca agacatgttg       360
cccactcagg aagaatagaa gctgggcaca gctggagtgc aaagtaggtc agttcagaga       420
gcaaagggag ttgatggagc aatgagttgt tagtgggaaa gttctaacca actgtcccag       480
a                                                                       481

<210> SEQ ID NO 16
<211> LENGTH: 990
<212> TYPE: DNA
<213> ORGANISM: Artificial Sequence
<220> FEATURE:
<223> OTHER INFORMATION: eHGT_300m

<400> SEQUENCE: 16
tgtcttagac tgagttgctg taacaaaaat ctgggatgag gtcatttcta aagcacagca        60
atttatttcc cacagtctga aggctgcaga ttccaagatc actggcaaga tcagttgtaa       120
aggcttcgtc ctccagaggc ggggatgctg catactccct gggcagagag acaggaaaac       180
tccgtaactg catgtgtcct tcctgatgcc tcttctatat aggcctggat cccaatcacc       240
ctgtgaacct ctccctgctt cgtggcccc acctcttaac actaccacat ggcaactcc        300 tgaaatttga aggggacaca ctgaaccatg gcacaacagc tttctgactg atgcagtaac       360
ccaatggcag tgcagaaggg gccagctaaa agcccaaatg gttagctcaa aattcgctgt       420
ctcttccgag tgtctgaacc cttagtcctg gtatgtaaag acatcagaac atttcccctt       480
gtgtccatca gatttctgtc tagtgaaacg atgacactgt aacctccaag atctcacacg       540
aaatgatctt ttctcctttg tggaaggaaa ccagcattta gctcatctct ccttcgtagc       600
agctcagaat gtccacagtg acccagttac catagctaaa ggcttccttt tcaaaacaca       660
gagcagaggc agccaattca gtatgtgctg ctgccatcct ctgattcttt cctgcttcca       720
tagacaccaa ctctattgta actaagcctt atacattgtg tcttcctcct ttacattagc       780
ttgtgctggg gtggttcatg aggcccgctg agtagtttca gtgacagcct atccctctgc       840
cagtgctgct ttgagccatc ttattggtga ggctgtaaga gaagcctgaa gtcacagggt       900
aaagctatgt tgaaggcagc cccagaacca agtttcccta tttctatctc cttacgctgt       960
ttgagcctca ggggtagatc aggtgcctgt                                        990

<210> SEQ ID NO 17
<211> LENGTH: 860
<212> TYPE: DNA
<213> ORGANISM: Artificial Sequence
<220> FEATURE:
<223> OTHER INFORMATION: eHGT_306m

<400> SEQUENCE: 17

-continued

```
agatgagtct gcagctgggt acagtgacct ttcagtccat gtttatttgg aaatgacctt      60
taagcagcaa tcagcaagaa taaaatgctt caaaggaata cattagataa tgcagaagtc     120
ccccagaggt aagttacacc caaggcaccc agctgacaat gaaagtggcc ctgccctggg     180
aagccaagga ctaggccacc cattagacta acaagtgaac acagggtccc cagagtttgg     240
tctaatagac aatggggagt ctgaagacag ggtgacctgg gcaagacaca agagcagttc     300
caaaattaaa cctctgtcgt aatgaaggat gcctagttgt gctttttcca tcctaggatg     360
gggaatcctc aagggcaggg cacagctgtg ccaggggaac tgtacgggct ccatcctgcc     420
tccctcccat ggggtgagct gatagtcttc ctcatactga gctcttgtct ctgctgtgtg     480
ctggggagtc tgaaatgcta gagaaactaa gccttcccac tcaaagacag agaaagagct     540
ggcccatggc tccgtgccct ctcctctctc tgtgcgtgtc tttaactctg tatgttctat     600
tttcccccct ctcgtcccct gcttcgcgct cacagagtca ctcctagtag caccaaagag     660
agatgcttgg cagttcacta accccttgag ctgaaataga aataaatatc ccaaaagaga     720
aatcagaaaa gcagggtgtc gcgctggaga agaggcagga agatcagaaa tacaaggtca     780
tctgtggcta cacatctagt ccaagtccca gcctgggcta tgtgagatgg aggggaatcg     840
ctcagaaaca aggctgtaca                                                  860
```

```
<210> SEQ ID NO 18
<211> LENGTH: 778
<212> TYPE: DNA
<213> ORGANISM: Artificial Sequence
<220> FEATURE:
<223> OTHER INFORMATION: eHGT_309m

<400> SEQUENCE: 18
ttcacccacc tgacacttgg gttagacctg aatgtcgttt ctttaactca cactgctcat      60
cccactggcc tttgctgtgc ttctctgtgc ctcctcagag atacatgaaa ctgtcccatc     120
cccctaacga tgctggatgg atggctccaa cagctcactg ctctcacctt gacacaaagt     180
cctagcgtct gcatctgtga dacaagttgg aatttatata tttccagtgg agattaataa     240
ttcattagat gctgaagtag aaaaacaaag taccgattaa tcaaggctct gctgaggcct     300
gctttgcagc caccagtctg tggggattgg cagtgctttt acactggaag taggtcagga     360
ccacagaaaa gcagctctca tgcactagca tctgttcgca ctaatcactg tacacagctt     420
tgggtcttac tatagttttt attagttatc ccagctggga tttatgtctc aggaataaag     480
agccaagaat gggaggagtt accctcgaaa gatccaggtc atgtggtgca gggcagggaa     540
tatggctgac tcaatctctt tgcccataga gcctcagagt atcagatctt agcactctaa     600
ggagggagac tcagagggta caagtcttag aagtctccct agggcttggt gcccagcaaa     660
tatatgctgt ttgtgacttc cctaatacca ggtacaggcc aacacaaagg acctgtccaa     720
gggaaactca cggctcagac ctgatctatt tacaggttga gtttgggtga agccaaga     778
```

```
<210> SEQ ID NO 19
<211> LENGTH: 549
<212> TYPE: DNA
<213> ORGANISM: Artificial Sequence
<220> FEATURE:
<223> OTHER INFORMATION: eHGT_310m

<400> SEQUENCE: 19
atccctggag atgaggagtc ctctctggca gggtcccctc actctagagc agccctatc       60
```

```
ccaggcccc  taggagtctc  taattaaagg  gccggcacgc  ccctctggga  ctcattaggc      120
ccgctgtgca  gagaacattt  aatcattgct  cagagcatcg  attggaaaat  caatttcttt      180
gtctcttcgc  acgaggcgcg  ctggagaagt  gggggggagtg  ctgacctcct  tctgctgccg      240
tgtaaagcgc  tgcacattta  atcagggaac  agaaatcaat  tagccactta  cgaggttggc      300
tttagttacc  gagtcggcaa  ggcccgcgcc  acagctcagc  cgctgacagt  agcgaatctc      360
ctcctctcgg  ccctgctgca  tggctctgtc  tccctccctg  tatctctctg  gcttccttct      420
ttcccagagt  gctctgggtt  ctcaccatct  tggcagatcc  tcacagaact  ccaaacaagt      480
cccgagaagc  cttcctaatg  cccagtctcc  tcggccacct  tcttgttctc  agctctagac      540
gtttcaaga                                                                  549

<210> SEQ ID NO 20
<211> LENGTH: 575
<212> TYPE: DNA
<213> ORGANISM: Artificial Sequence
<220> FEATURE:
<223> OTHER INFORMATION: eHGT_890m

<400> SEQUENCE: 20
tgagcttcaa  ccaaatcagg  cattgatgga  ttttatagtt  tgattaacaa  agataatagc       60
aaaccccaga  tttagtttaa  acataaaaag  tattaaggtt  gtatcctgct  tgtatagcat      120
atgcaaatga  cctcgtttct  gctactgcat  ttggaaatgt  agcagaagaa  aaaaaaaagg      180
cacttcaatt  gcagctctca  tcagttattc  actgtatcca  ggcctctcaa  ttgtgttctt      240
ttctttaatg  caatagcaag  cagcaatcac  ccagctgtgc  ttggtagagt  gaactatata      300
cacatctata  ttgagatttc  atacacacat  aacataaaag  cgagagaaaa  agcctcaaga      360
atgtttggcc  cattgcaaat  cacacaaaag  gactaatgaa  tctctctcca  aatggatctg      420
tagtgaccat  ctgtaagcct  tgattgattc  atattccata  acggtatcag  catccaggaa      480
gtgattactt  caaggtgcaa  cacaacttcc  cctatgaaag  ctcagtctct  ttaatcatac      540
ctagtcagta  tctgtcacgg  ggataaacta  aggca                                  575

<210> SEQ ID NO 21
<211> LENGTH: 611
<212> TYPE: DNA
<213> ORGANISM: Artificial Sequence
<220> FEATURE:
<223> OTHER INFORMATION: eHGT_891m

<400> SEQUENCE: 21
acatttgcag  taaagcttgt  tcttttttctt  gaagtatatt  ttaagatttt  gagttctact       60
atcattaaag  acagataatt  aatagtttat  ttttatttac  ttttgttagt  agtgacttgg      120
tgctatgagc  catattttgc  tgttgctgtt  gttactggta  gttttgtaa   ttctggggct      180 aaaacttggg  gtctggtatg  ctgtcattta  ccagtgagct  ataccctgga  tattatgatt      240
tagatgaatg  tgaaatatca  ccccagacat  acatatacta  aacacttggc  ccttggccca      300
tgatgctaaa  tggaggagat  agaagctttt  ggggcacagc  ctagtggaag  gaaatgaggt      360
caaatgacat  gtactctgaa  aggaatatgg  gtattctggg  cttgcgttat  tctctctctc      420
cctctctctc  cctctctctc  cctctccctc  tctctttctc  cttttctctt  tctctcctcg      480
ccttgttttc  cagctgccag  aaggtaggcc  tcttctctgc  tgaatatctg  tgtcatgtta      540
tgcaccaaca  cagtactaac  tgtcatgtta  tacctagtgg  ccaggtaacc  atggaccaaa      600
atggcagagc  a                                                              611
```

```
<210> SEQ ID NO 22
<211> LENGTH: 661
<212> TYPE: DNA
<213> ORGANISM: Artificial Sequence
<220> FEATURE:
<223> OTHER INFORMATION: eHGT_892m

<400> SEQUENCE: 22
tgcaaaataa agatttcttg ggatacagag aaaaaaacaa atctgacagg agaggaagaa      60
gcacccggtg ggctataacg gtgcaattca gctgattata tgttacaagt aacaaggacg     120
agaaaaaatg ttatttcttt gaaaataaaa ctaaccaggc catacatatt taacaggact     180
gcatgagaga agaagaagcc agctgcagga gtgactgtgg gggggagggg gaacttgaca     240
aaaaaagcaa aatggcagtc ctgcttccaa agtcctcaag gtcacagtta tttgggcatt     300
cttgcgggca ctgcttatac aagaatgtgc tttcagtcaa ggctttctaa tagattctca     360
aaatttggga caaatgttat ttttgtatct gtagaaatgt actgattcag aaagatcttt     420
gagcaataca gatgttaaaa catttaagtc acaaatgggt ctatttaat caatgcgact      480 agtttggaac attattcaaa ctgccagaaa tacaatgtaa atgaaacctc aggccaatat     540
tttggagccc taaaagattt gatggctaat tttatcgtag acactaatta taaataggag     600
accccaggat gggactagaa aaccaagcca gctttttaat ttacccctcc aggactttgc     660
t                                                                     661

<210> SEQ ID NO 23
<211> LENGTH: 1316
<212> TYPE: DNA
<213> ORGANISM: Artificial Sequence
<220> FEATURE:
<223> OTHER INFORMATION: eHGT_476m

<400> SEQUENCE: 23
agaaacacca caagcaaagc caaaataggt ggcctagaac ttccagcttg aaatatggga      60
gagaatgagg gaggcactgt agagcagctg ccgggtgccg catgagaaca attctccctg     120
ctcataatta atcctaccta tttctgatga cagctggctc ttcactttga acaagctagt     180
taacaacttt cttctcacat tgagcaaata attcatattt aattacttaa ccaccagtta     240
caaaatgaga atcatcaagg aatcacaatt aatttgctat tgacaaactc atacttttag     300
caggctgatt tctactttat acttagattg gtaatgaaaa atgaagctta ttttagttga     360
ttggttggac ttgtgtatga atattatcta ttatttgaaa agccaaactt gaatgcaaaa     420
aaatattgaa tatgaaaga gaaacaccac aagcaaagcc aaaataggtg gcctagaact      480
tccagcttga aatatgggag agaatgaggg aggcactgta gagcagctgc cgggtgccgc     540
atgagaacaa ttctccctgc tcataattaa tcctacctat ttctgatgac agctggctct     600
tcactttgaa caagctagtt aacaactttc ttctcacatt gagcaaataa ttcatattta     660
attacttaac caccagttac aaaatgagaa tcatcaagga atcacaatta atttgctatt     720
gacaaactca tacttttagc aggctgattt ctactttata cttagattgg taatgaaaaa     780
tgaagcttat tttagttgat tggttggact tgtgtatgaa tattatctat tatttgaaaa     840
gccaaacttg aatgcaaaaa aatattgaat atgaaaagag aaacaccaca agcaaagcca     900
aaataggtgg cctagaactt ccagcttgaa atatgggaga gaatgaggga ggcactgtag     960
agcagctgcc gggtgccgca tgagaacaat tctccctgct cataattaat cctacctatt    1020
```

```
tctgatgaca gctggctctt cactttgaac aagctagtta acaactttct tctcacattg     1080
agcaaataat tcatatttaa ttacttaacc accagttaca aaatgagaat catcaaggaa     1140
tcacaattaa tttgctattg acaaactcat acttttagca ggctgatttc tactttatac     1200
ttagattggt aatgaaaaat gaagcttatt ttagttgatt ggttggactt gtgtatgaat     1260
attatctatt atttgaaaag ccaaacttga atgcaaaaaa atattgaata tgaaaa        1316

<210> SEQ ID NO 24
<211> LENGTH: 505
<212> TYPE: DNA
<213> ORGANISM: Artificial Sequence
<220> FEATURE:
<223> OTHER INFORMATION: eHGT_1022m

<400> SEQUENCE: 24
cagtttccag cgtggttgtt gatgaggctc agagaaaaga ctctaaagtt atgatgggaa       60
attaccatgc cattcatcat catacacatt cacctcacac tttctgagtc tcctatacaa      120
agtcagttct ctgccaaggg catggaagag cgaggaacag gatgttagga agggctgaca      180
gcgctgtttt agcctgacag gcagatttac aacaggagaa tgaatgtacc acttgtataa      240
gaaggccatg cggcactgct aatgcacaag ttggcagtac atcaacatct ctatcgtcct      300
catattcatg aagcagagaa cggaaatggc acactgcttg taccggcgaa taaccaaagt      360
gaacgcccta cggctgccat tcactgtgtc cttccaaaag cattttttcta ctgagctctt      420 cccagagatt tagggtttgc ttagacaggt cttatgacgc cacgtgatag gtcattcttc      480
tgttctgagg agcttggaga agatc                                            505

<210> SEQ ID NO 25
<211> LENGTH: 439
<212> TYPE: DNA
<213> ORGANISM: Artificial Sequence
<220> FEATURE:
<223> OTHER INFORMATION: eHGT_1023m

<400> SEQUENCE: 25
gtagaacata cttattaaca cattcgtaca taaaataaaa ttctactctc ccgacctttt       60
cctcaccatc ttgcttttca acgtatggcg ttagacctaa cagcgagtcc acttcttccc      120
ctttcattct gtagcaagaa cacacggctc actgtaacag ggactggct gtgggttgca       180 gactggcttc ctgctgcctc cacttgagcc ccacacagct gtggctttgt gtttacaacc      240
ctccaggctg ccattcattc ggtgctgtgg gctcatgtac tggaagacag cttccatcac      300
aaccttcccg tcccagcagg agaactccct tgcttccttg gggaacattt gcttgctcct      360
gctgcttggc tcttcccact tttgcctcac tctggagttt ctctctcccg ttttgaattc      420
tagtagtaaa cacatggcc                                                   439

<210> SEQ ID NO 26
<211> LENGTH: 507
<212> TYPE: DNA
<213> ORGANISM: Artificial Sequence
<220> FEATURE:
<223> OTHER INFORMATION: eHGT_1024m

<400> SEQUENCE: 26
ccagtgagat cttccaccag cagaactcat ggacacaaac tagacagctc acttcttgcc       60
tgtattccag gagtggcttt ttctctactc ctgtactgat gccagtcatt cagagtgcac      120
tcaagacact tgacccacat cagttaagag aatgaaaatc aagctctgaa agccattagc      180
```

-continued

```
ttctattgca cacccagaaa acaggctcat caaacacctt cttatggtaa tgcctttgat        240
caaaaggagg gttaattcaa caaatggttt gcaccgtgac cccatcaaag cctgagcacc        300
agtgtcctca tttcctttcc cctggtgtat aatgagttgt tagtctggct caccttgtca        360
tccccatcat actgccataa tccacatctc taaagagtgg attacaacag tcccgtctgt        420
gacactcagg actggcatca aggttcccaa gctctagtct attgtgacat tgatacaaat        480
agggctcaga gtctcactga tcacacc                                           507

<210> SEQ ID NO 27
<211> LENGTH: 53
<212> TYPE: DNA
<213> ORGANISM: Artificial Sequence
<220> FEATURE:
<223> OTHER INFORMATION: minBGlobin promoter

<400> SEQUENCE: 27
gggctgggca taaaagtcag ggcagagcca tctattgctt acatttgctt ctg              53

<210> SEQ ID NO 28
<211> LENGTH: 68
<212> TYPE: DNA
<213> ORGANISM: Artificial Sequence
<220> FEATURE:
<223> OTHER INFORMATION: minCMV promoter

<400> SEQUENCE: 28
gaggtaggcg tgtacggtgg gaggcctata taagcagagc tcgtttagtg aaccgtcaga       60
tcgcctgg                                                                68

<210> SEQ ID NO 29
<211> LENGTH: 68
<212> TYPE: DNA
<213> ORGANISM: Artificial Sequence
<220> FEATURE:
<223> OTHER INFORMATION: mutate minCMV promoter

<400> SEQUENCE: 29
gaggtaggcg tgtacggtgg gaggcctata taagcagagc tggtttagtg aaccgtcaga       60
tcgcctgg                                                                68

<210> SEQ ID NO 30
<211> LENGTH: 120
<212> TYPE: DNA
<213> ORGANISM: Artificial Sequence
<220> FEATURE:
<223> OTHER INFORMATION: minRho promoter

<400> SEQUENCE: 30
gattcagccg ggagcttagg gaggggaggt cacttcataa gggcctgggg ggggagttgg       60
agccacgagt cgtccagccg gagccccgtg tggctgagct ccggcctcag aagcatcccc      120

<210> SEQ ID NO 31
<211> LENGTH: 120
<212> TYPE: DNA
<213> ORGANISM: Artificial Sequence
<220> FEATURE:
<223> OTHER INFORMATION: minRho* promoter

<400> SEQUENCE: 31
gattcagccg ggagcttagg gaggggaggt cacttcataa gggcttgggg ggggagttgg       60
```

-continued

```
agccacgagt cgtccagccg gagccccgtg tggctgtgct ccggcctcag aagcatcccc      120

<210> SEQ ID NO 32
<211> LENGTH: 867
<212> TYPE: DNA
<213> ORGANISM: Artificial Sequence
<220> FEATURE:
<223> OTHER INFORMATION: Hsp68 minimal promoter (proHsp68)

<400> SEQUENCE: 32
caggaacatc caaactgagc agccggggtc ccccccaccc cccaccccgc cccacgcggc       60
aactttgagc ctgtgctggg acagagcctc tagttcctaa attagtccat gaggtcagag      120
gcagcactgc cattgtaacg cgattggaga ggatcacgtc accggacacg cccccaggca      180
tctccctggg tctcctaaac ttggcggggga gaagtttttag cccttaagtt ttagcccttta      240 accccccatat tcagaactgt gcgagttggc gaaaccccac aaatcacaac aaactgtaca      300
caacaccgag ctagaggtga tctttcttgt ccattccaca caggccttag taatgcgtcg      360
ccatagcaac agtgtcacta gtagcaccag cacttcccca caccctcccc ctcaggaatc      420
cgtactctcc agtgaacccc agaaacctct ggagagttct ggacaagggc ggaacccaca      480
actccgatta ctcaagggag gcggggaagc tccaccagac gcgaaactgc tggaagattc      540
ctggccccaa ggcctcctcc ggctcgctga ttggcccagc ggagagtggg cggggccggt      600
gaagactcct taaaggcgca gggcggcgag caggtcacca gacgctgaca gctactcaga      660
accaaatctg gttccatcca gagacaagcg aagacaagag aagcagagcg agcggcgcgt      720
tcccgatcct cggccaggac cagccttccc cagagcatcc ctgccgcgga gcgcaacctt      780
cccaggagca tccctgccgc ggagcgcaac tttccccgga gcatccacgc cgcggagcgc      840
agccttccag aagcagagcg cggcgcc                                         867

<210> SEQ ID NO 33
<211> LENGTH: 720
<212> TYPE: DNA
<213> ORGANISM: Artificial Sequence
<220> FEATURE:
<223> OTHER INFORMATION: SYFP2

<400> SEQUENCE: 33
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagct gatctgcacc accggcaagc tgcccgtgcc ctggcccacc      180
ctcgtgacca ccctgggcta cggcgtgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca ccgccgacaa gcagaagaac      480
ggcatcaagg ccaacttcaa gatccgccac aacatcgagg acggcggcgt gcagctcgcc      540
gaccactacc agcagaacac ccccatcggc gacggccccg tgctgctgcc cgacaaccac      600
tacctgagct accagtccaa gctgagcaaa gaccccaacg agaagcgcga tcacatggtc      660
ctgctggagt tcgtgaccgc cgccgggatc actctcggca tggacgagct gtacaagtaa      720

<210> SEQ ID NO 34
<211> LENGTH: 720
```

```
<212> TYPE: DNA
<213> ORGANISM: Artificial Sequence
<220> FEATURE:
<223> OTHER INFORMATION: EGFP

<400> SEQUENCE: 34
atggtgagca aggGcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720

<210> SEQ ID NO 35
<211> LENGTH: 1299
<212> TYPE: DNA
<213> ORGANISM: Artificial Sequence
<220> FEATURE:
<223> OTHER INFORMATION: Optimized Flp recombinase (FlpO)

<400> SEQUENCE: 35
atggctccta agaagaagag gaaggtgatg agccagttcg acatcctgtg caagaccccc       60
cccaaggtgc tggtgcggca gttcgtggag agattcgaga ggcccagcgg cgagaagatc      120
gccagctgtg ccgccgagct gacctacctg tgctggatga tcacccacaa cggcaccgcc      180
atcaagaggg ccaccttcat gagctacaac accatcatca gcaacagcct gagcttcgac      240
atcgtgaaca gagagcctgca gttcaagtac aagacccaga aggccaccat cctggaggcc      300
agcctgaaga agctgatccc cgcctgggag ttcaccatca tcccttacaa cggccagaag      360
caccagagcg acatcaccga catcgtgtcc agcctgcagc tgcagttcga gagcagcgag      420
gaggccgaca agggcaacag ccacagcaag aagatgctga aggccctgct gtccgagggc      480
gagagcatct gggagatcac cgagaagatc ctgaacagct tcgagtacac cagcaggttc      540
accaagacca gaccctgta ccagttcctg ttcctggcca cattcatcaa ctgcggcagg      600
ttcagcgaca tcaagaacgt ggaccccaag agcttcaagc tggtgcagaa caagtacctg      660
ggcgtgatca ttcagtgcct ggtgaccgag accaagacaa gcgtgtccag gcacatctac      720
tttttcagcg ccagaggcag gatcgacccc ctggtgtacc tggacgagtt cctgaggaac      780
agcgagcccg tgctgaagag agtgaacagg accggcaaca gcagcagcaa caagcaggag      840
taccagctgc tgaaggacaa cctggtgcgc agctacaaca ggccctgaa gaagaacgcc      900 ccctacccca tcttcgctat caagaacggc cctaagagcc acatcggcag gcacctgatg      960
accagctttc tgagcatgaa gggcctgacc gagctgacaa acgtggtggg caactggagc     1020
gacaagaggg cctccgccgt ggccaggacc acctacaccc accagatcac cgccatcccc     1080
gaccactact cgccctggt gtccaggtac tacgcctacg accccatcag caaggagatg     1140
```

-continued

```
atcgccctga aggacgagac caaccccatc gaggagtggc agcacatcga gcagctgaag      1200
ggcagcgccg agggcagcat cagataccccc gcctggaacg gcatcatcag ccaggaggtg      1260
ctggactacc tgagcagcta catcaacagg cggatctga                              1299

<210> SEQ ID NO 36
<211> LENGTH: 1056
<212> TYPE: DNA
<213> ORGANISM: Artificial Sequence
<220> FEATURE:
<223> OTHER INFORMATION: improved Cre recombinase (iCre)

<400> SEQUENCE: 36
atggtgccca agaagaagag gaaagtctcc aacctgctga ctgtgcacca aaacctgcct        60
gccctccctg tggatgccac ctctgatgaa gtcaggaaga acctgatgga catgttcagg       120
gacaggcagg ccttctctga acacacctgg aagatgctcc tgtctgtgtg cagatcctgg       180 gctgctggt gcaagctgaa caacaggaaa tggttccctg ctgaacctga ggatgtgagg        240
gactacctcc tgtacctgca agccagaggc ctggctgtga agaccatcca acagcacctg       300
ggccagctca acatgctgca caggagatct ggcctgcctc gcccttctga ctccaatgct       360
gtgtccctgg tgatgaggag aatcagaaag gagaatgtgg atgctgggga gagagccaag       420
caggccctgg cctttgaacg cactgacttt gaccaagtca gatccctgat ggagaactct       480
gacagatgcc aggacatcag gaacctggcc ttcctgggca ttgcctacaa caccctgctg       540
cgcattgccg aaattgccag aatcagagtg aaggacatct cccgcaccga tggtgggaga       600
atgctgatcc acattggcag gaccaagacc ctggtgtcca gctggtgt ggagaaggcc         660 ctgtccctgg gggttaccaa gctggtggag agatggatct ctgtgtctgg tgtggctgat       720 gacccccaaca actacctgtt ctgccgggtc agaaagaatg gtgtggctgc cccttctgcc      780
acctcccaac tgtccacccg ggccctggaa gggatctttg aggccaccca ccgcctgatc       840
tatggtgcca aggatgactc tgggcagaga tacctggcct ggtctggcca ctctgccaga       900
gtgggtgctg ccagggacat ggccagggct ggtgtgtcca tccctgaaat catgcaggct       960
ggtggctgga ccaatgtgaa cattgtgatg aactacatca gaaacctgga ctctgagact      1020
ggggccatgg tgaggctgct cgaggatggg gactaa                               1056

<210> SEQ ID NO 37
<211> LENGTH: 1056
<212> TYPE: DNA
<213> ORGANISM: Artificial Sequence
<220> FEATURE:
<223> OTHER INFORMATION: iCre(R297T)

<400> SEQUENCE: 37
atggtgccca agaagaagag gaaagtctcc aacctgctga ctgtgcacca aaacctgcct        60
gccctccctg tggatgccac ctctgatgaa gtcaggaaga acctgatgga catgttcagg       120
gacaggcagg ccttctctga acacacctgg aagatgctcc tgtctgtgtg cagatcctgg       180 gctgctggt gcaagctgaa caacaggaaa tggttccctg ctgaacctga ggatgtgagg        240
gactacctcc tgtacctgca agccagaggc ctggctgtga agaccatcca acagcacctg       300
ggccagctca acatgctgca caggagatct ggcctgcctc gcccttctga ctccaatgct       360
gtgtccctgg tgatgaggag aatcagaaag gagaatgtgg atgctgggga gagagccaag       420
caggccctgg cctttgaacg cactgacttt gaccaagtca gatccctgat ggagaactct       480
gacagatgcc aggacatcag gaacctggcc ttcctgggca ttgcctacaa caccctgctg       540
```

-continued

```
cgcattgccg aaattgccag aatcagagtg aaggacatct cccgcaccga tggtgggaga      600
atgctgatcc acattggcag gaccaagacc ctggtgtcca cagctggtgt ggagaaggcc      660
ctgtccctgg gggttaccaa gctggtggag agatggatct ctgtgtctgg tgtggctgat      720
gaccccaaca actacctgtt ctgccgggtc agaaagaatg tgtggctgc cccttctgcc        780 acctcccaac tgtccacccg ggccctggaa gggatctttg aggccaccca ccgcctgatc      840
tatggtgcca aggatgactc tgggcagaga tacctggcct ggtctggcca ctctgccaga      900
gtgggtgctg ccaccgacat ggccagggct ggtgtgtcca tccctgaaat catgcaggct      960
ggtggctgga ccaatgtgaa cattgtgatg aactacatca gaaacctgga ctctgagact     1020
ggggccatgg tgaggctgct cgaagatggg gactga                               1056
```

```
<210> SEQ ID NO 38
<211> LENGTH: 513
<212> TYPE: DNA
<213> ORGANISM: Artificial Sequence
<220> FEATURE:
<223> OTHER INFORMATION: CreN-inteinN

<400> SEQUENCE: 38
atgacgagtg atgaggttcg caagaacctg atggacatgt tcagggatcg ccaggcgttt       60
tctgagcata cctggaaaat gcttctgtcc gtttgccggt cgtgggcggc atggtgcaag      120
ttgaataaat ttgcggaata ttgcctcagt tttggcaccg aaattttaac cgttgagtac      180
ggcccattgc ccattggcaa aattgtgagt gaagaaatta attgttctgt gtacagtgtt      240
gatccagaag ggagagttta cacccaggcg atcgcccaat ggcatgaccg gggagagcag      300
gaagtattgg aatatgaatt ggaagatggt tcagtaatcc gagctacctc tgaccaccgc      360 ttttttaacca ccgattatca actgttggcg atcgaagaaa tttttgctag gcaactggac      420
ttgttgactt tagaaaatat taagcaaact gaagaagctc ttgacaacca tcgtcttccc      480
tttccattac ttgacgctgg gacaattaaa taa                                   513
```

```
<210> SEQ ID NO 39
<211> LENGTH: 978
<212> TYPE: DNA
<213> ORGANISM: Artificial Sequence
<220> FEATURE:
<223> OTHER INFORMATION: inteinC-CreC

<400> SEQUENCE: 39
atggttaaag ttatcggtcg tcgttccctc ggagtgcaaa gaatatttga tattggtctt       60
ccccaagacc ataattttct gctagccaat ggggcgatcg ccgccaattg ttttaacaaa      120
tccaaccgga aatggtttcc cgcagaacct gaagatgttc gcgattatct tctatatctt      180
caggcgcgcg gtctggcagt aaaaactatc cagcaacatt tgggccagct aaacatgctt      240
catcgtcggt ccgggctgcc acgaccaagt gacagcaatg ctgtttcact ggttatgcgg      300
cggatccgaa aagaaaacgt tgatgccggt gaacgtgcaa acaggctct agcgttcgaa       360 cgcactgatt tcgaccaggt tcgttcactc atggaaaata gcgatcgctg ccaggatata      420
cgtaatctgg catttctggg gattgcttat aacaccctgt tacgtatagc cgaaattgcc      480
aggatcaggg ttaaagatat ctcacgtact gacggtggga aatgttaat ccatattggc        540 agaacgaaaa cgctggttag caccgcaggt gtagagaagg cacttagcct gggggtaact      600
aaactggtcg agcgatggat ttccgtctct ggtgtagctg atgatccgaa taactacctg      660
```

-continued

```
ttttgccggg tcagaaaaaa tggtgttgcc gcgccatctg ccaccagcca gctatcaact      720
cgcgccctgg aagggatttt tgaagcaact catcgattga tttacggcgc taaggatgac      780
tctggtcaga gatacctggc ctggtctgga cacagtgccc gtgtcggagc cgcgcgagat      840
atggcccgcg ctggagtttc aataccggag atcatgcaag ctggtggctg gaccaatgta      900
aatattgtca tgaactatat ccgtaacctg gatagtgaaa caggggcaat ggtgcgcctg      960
ctggaagatg gcgattag                                                    978
```

<210> SEQ ID NO 40
<211> LENGTH: 50
<212> TYPE: DNA
<213> ORGANISM: Artificial Sequence
<220> FEATURE:
<223> OTHER INFORMATION: SP10 insulator (SP10ins)

<400> SEQUENCE: 40

```
gaagctaccc ctaacacact attctacaca cagaaaatgc tcttcactag                  50
```

<210> SEQ ID NO 41
<211> LENGTH: 150
<212> TYPE: DNA
<213> ORGANISM: Artificial Sequence
<220> FEATURE:
<223> OTHER INFORMATION: 3x SP10ins

<400> SEQUENCE: 41

```
gaagctaccc ctaacacact attctacaca cagaaaatgc tcttcactag gaagctaccc      60
ctaacacact attctacaca cagaaaatgc tcttcactag gaagctaccc ctaacacact     120
attctacaca cagaaaatgc tcttcactag                                      150
```

<210> SEQ ID NO 42
<211> LENGTH: 228
<212> TYPE: DNA
<213> ORGANISM: Artificial Sequence
<220> FEATURE:
<223> OTHER INFORMATION: 4X2C

<400> SEQUENCE: 42

```
gcggccttaa agagaccggt tcactgtgac agtaaaagag accggttcac tgtgagaatg      60
aaagagaccg gttcactgtg atcggaaaag agaccggttc actgtgagcg gccttgaaac     120
ccagcagaca atgtagctca gtagaaaccc agcagacaat gtagctgaat ggaaacccag     180
cagacaatgt agcttcggag aaacccagca gacaatgtag ctgtcgac                  228
```

<210> SEQ ID NO 43
<211> LENGTH: 66
<212> TYPE: DNA
<213> ORGANISM: Artificial Sequence
<220> FEATURE:
<223> OTHER INFORMATION: 3XFLAG

<400> SEQUENCE: 43

```
gactacaaag accatgacgg agattataaa gatcatgaca tcgattacaa ggatgacgat      60
gacaag                                                                 66
```

<210> SEQ ID NO 44
<211> LENGTH: 30
<212> TYPE: DNA
<213> ORGANISM: Artificial Sequence
<220> FEATURE:
<223> OTHER INFORMATION: 10aa

<400> SEQUENCE: 44
tccggactca gatctggagg ctccggaggc                                         30

<210> SEQ ID NO 45
<211> LENGTH: 378
<212> TYPE: DNA
<213> ORGANISM: Artificial Sequence
<220> FEATURE:
<223> OTHER INFORMATION: H2B

<400> SEQUENCE: 45
ccagagccag cgaagtctgc tcccgccccg aaaaagggct ccaagaaggc ggtgactaag       60
gcgcagaaga aaggcggcaa gaagcgcaag cgcagccgca aggagagcta ttccatctat      120
gtgtacaagt tctctgaagca ggtccaccct gacaccggca tttcgtccaa ggccatgggc      180
atcatgaatt cgtttgtgaa cgacattttc gagcgcatcg caggagaggc ttccgcctg       240 gcgcattaca caagcgctc gaccatcacc tcccgggaga tccagacggc cgtgcgcctg       300
ctgctgcctg gggagttggc caagcacgcc gtgtccgagg gtactaaggc catcaccaag      360
tacaccagcg ctaagtaa                                                    378

<210> SEQ ID NO 46
<211> LENGTH: 246
<212> TYPE: DNA
<213> ORGANISM: Artificial Sequence
<220> FEATURE:
<223> OTHER INFORMATION: WPRE3

<400> SEQUENCE: 46
ataatcaacc tctggattac aaaatttgtg aaagattgac tggtattctt aactatgttg       60 ctcctttttac gctatgtgga tacgctgctt taatgccttt gtatcatgct attgcttccc      120
gtatggcttt cattttctcc tccttgtata aatcctggtt agttcttgcc acggcggaac      180
tcatcgccgc ctgccttgcc cgctgctgga caggggctcg gctgttgggc actgacaatt      240
ccgtgg                                                                 246

<210> SEQ ID NO 47
<211> LENGTH: 609
<212> TYPE: DNA
<213> ORGANISM: Artificial Sequence
<220> FEATURE:
<223> OTHER INFORMATION: WPRE

<400> SEQUENCE: 47
gcttatcgat aatcaacctc tggattacaa aatttgtgaa agattgactg gtattcttaa       60
ctatgttgct cctttttacgc tatgtggata cgctgcttta atgcctttgt atcatgctat      120
tgcttcccgt atggctttca ttttctcctc cttgtataaa tcctggttgc tgtctcttta      180
tgaggagttg tggcccgttg tcaggcaacg tggcgtggtg tgcactgtgt ttgctgacgc      240
aacccccact ggttggggca ttgccaccac ctgtcagctc ctttccggga ctttcgcttt      300 cccctccct attgccacgg cggaactcat cgccgcctgc cttgcccgct gctggacagg       360
ggctcggctg ttgggcactg acaattccgt ggtgttgtcg gggaaatcat cgtcctttcc      420
ttggctgctc gcctatgttg ccacctggat tctgcgcggg acgtccttct gctacgtccc      480
ttcggccctc aatccagcgg accttccttc ccgcggcctg ctgccggctc tgcggcctct      540
tccgcgtctt cgccttcgcc ctcagacgag tcggatctcc ctttgggccg cctccccgca      600

-continued

```
tcgataccg                                                         609

<210> SEQ ID NO 48
<211> LENGTH: 204
<212> TYPE: DNA
<213> ORGANISM: Artificial Sequence
<220> FEATURE:
<223> OTHER INFORMATION: BGHpA

<400> SEQUENCE: 48
cgactgtgcc ttctagttgc cagccatctg ttgtttgccc ctcccccgtg ccttccttga     60
ccctggaagg tgccactccc actgtccttt cctaataaaa tgaggaaatt gcatcgcatt    120
gtctgagtag gtgtcattct attctggggg gtggggtggg gcaggacagc aaggggagg    180 attgggaaga caatagcagg catg                                          204

<210> SEQ ID NO 49
<211> LENGTH: 479
<212> TYPE: DNA
<213> ORGANISM: Artificial Sequence
<220> FEATURE:
<223> OTHER INFORMATION: HGHpA

<400> SEQUENCE: 49
acgggtggca tccctgtgac ccctccccag tgcctctcct ggccctggaa gttgccactc     60
cagtgcccac cagccttgtc ctaataaaat taagttgcat cattttgtct gactaggtgt    120
ccttctataa tattatgggg tggagggggg tggtatggag caaggggcaa gttgggaaga    180
caacctgtag ggcctgcggg gtctattggg aaccaagctg gagtgcagtg gcacaatctt    240
ggctcactgc aatctccgcc tcctgggttc aagcgattct cctgcctcag cctcccgagt    300
tgttgggatt ccaggcatgc atgaccaggc tcagctaatt tttgtttttt tggtagagac    360
ggggtttcac catattggcc aggctggtct ccaactccta atctcaggtg atctacccac    420
cttggcctcc caaattgctg ggattacagg cgtgaaccac tgctcccttc cctgtcctt    479

<210> SEQ ID NO 50
<211> LENGTH: 78
<212> TYPE: DNA
<213> ORGANISM: Artificial Sequence
<220> FEATURE:
<223> OTHER INFORMATION: P2A

<400> SEQUENCE: 50
ggcagcggcg ccaccaactt cagcctgctg aagcaggccg gcgacgtgga ggagaacccc     60
ggccccggag ctagcgga                                                  78

<210> SEQ ID NO 51
<211> LENGTH: 78
<212> TYPE: DNA
<213> ORGANISM: Artificial Sequence
<220> FEATURE:
<223> OTHER INFORMATION: P2A

<400> SEQUENCE: 51
ggctctggtg ctaccaactt ctcactgttg aaacaggcag gggatgtaga ggagaatcca     60
gggcctggtg ctagtgga                                                  78

<210> SEQ ID NO 52
<211> LENGTH: 21
<212> TYPE: PRT
<213> ORGANISM: Artificial Sequence
```

```
<220> FEATURE:
<223> OTHER INFORMATION: T2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 52

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 53
<211> LENGTH: 24
<212> TYPE: PRT
<213> ORGANISM: Artificial Sequence
<220> FEATURE:
<223> OTHER INFORMATION: E2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 53

Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 54
<211> LENGTH: 25
<212> TYPE: PRT
<213> ORGANISM: Artificial Sequence
<220> FEATURE:
<223> OTHER INFORMATION: F2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 54

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 55
<211> LENGTH: 130
<212> TYPE: DNA
<213> ORGANISM: Artificial Sequence
<220> FEATURE:
<223> OTHER INFORMATION: Exemplary plasmid backbone left ITR

<400> SEQUENCE: 55
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 56
<211> LENGTH: 141
<212> TYPE: DNA
<213> ORGANISM: Artificial Sequence
```

-continued

```
<220> FEATURE:
<223> OTHER INFORMATION: Exemplary plasmid backbone right ITR

<400> SEQUENCE: 56
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggg.gttcc t                                              141

<210> SEQ ID NO 57
<211> LENGTH: 146
<212> TYPE: DNA
<213> ORGANISM: Artificial Sequence
<220> FEATURE:
<223> OTHER INFORMATION: Exemplary plasmid backbone left ITR

<400> SEQUENCE: 57
catgtcctgc aggcagctgc gcgctcgctc gctcactgag gccgcccggg caaagcccgg      60
gcgtcgggcg acctttggtc gcccggcctc agtgagcgag cgagcgcgca gagagggagt     120
ggccaactcc atcactaggg gttcct                                         146

<210> SEQ ID NO 58
<211> LENGTH: 149
<212> TYPE: DNA
<213> ORGANISM: Artificial Sequence
<220> FEATURE:
<223> OTHER INFORMATION: Exemplary plasmid backbone right ITR

<400> SEQUENCE: 58
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc     120 gagcgcgcag ctgcctgcag gggcgcctg                                      149

<210> SEQ ID NO 59
<211> LENGTH: 743
<212> TYPE: PRT
<213> ORGANISM: Artificial Sequence
<220> FEATURE:
<223> OTHER INFORMATION: PHP.eB capsid

<400> SEQUENCE: 59

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560
```

-continued

```
Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
            645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
            725                 730                 735

Arg Tyr Leu Thr Arg Asn Leu
            740
```

```
<210> SEQ ID NO 60
<211> LENGTH: 736
<212> TYPE: PRT
<213> ORGANISM: Adeno-associated virus

<400> SEQUENCE: 60

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190
```

-continued

```
Ala Ala Pro Ser Gly Val Gly Ser Leu Thr Met Ala Ser Gly Gly Gly
        195             200             205

Ala Pro Val Ala Asp Asn Asn Glu Gly Ala Asp Gly Val Gly Ser Ser
        210             215             220

Ser Gly Asn Trp His Cys Asp Ser Gln Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Asn Ser Thr Ser Gly Gly Ser Ser Asn Asp Asn
            260             265             270

Ala Tyr Phe Gly Tyr Ser Thr Pro Trp Gly Tyr Phe Asp Phe Asn Arg
        275             280             285

Phe His Cys His Phe Ser Pro Arg Asp Trp Gln Arg Leu Ile Asn Asn
        290             295             300

Asn Trp Gly Phe Arg Pro Lys Arg Leu Asn Phe Lys Leu Phe Asn Ile
305             310             315             320

Gln Val Lys Glu Val Thr Asp Asn Asn Gly Val Lys Thr Ile Ala Asn
            325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
        370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
        435             440             445

Lys Thr Ile Asn Gly Ser Gly Gln Asn Gln Gln Thr Leu Lys Phe Ser
        450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
        515             520             525

Glu Gly Glu Asp Arg Phe Phe Pro Leu Ser Gly Ser Leu Ile Phe Gly
        530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Ala Gln Ala Gln
            580             585             590

Thr Gly Trp Val Gln Asn Gln Gly Ile Leu Pro Gly Met Val Trp Gln
        595             600             605
```

-continued

```
Asp Arg Asp Val Tyr Leu Gln Gly Pro Ile Trp Ala Lys Ile Pro His
    610             615                 620

Thr Asp Gly Asn Phe His Pro Ser Pro Leu Met Gly Gly Phe Gly Met
625             630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705             710                 715                 720

Tyr Ser Glu Pro Arg Pro Ile Gly Thr Arg Tyr Leu Thr Arg Asn Leu
                725                 730                 735
```

```
<210> SEQ ID NO 61
<211> LENGTH: 747
<212> TYPE: DNA
<213> ORGANISM: Artificial Sequence
<220> FEATURE:
<223> OTHER INFORMATION: tet-Transactivator version 2 (tTA2)

<400> SEQUENCE: 61
atgtctagac tggacaagag caaagtcata aactctgctc tggaattact caatgaagtc     60
ggtatcgaag gcctgacgac aaggaaactc gctcaaaagc tgggagttga gcagcctacc    120
ctgtactggc acgtgaagaa caagcgggcc ctgctcgatg ccctggcaat cgagatgctg    180
gacaggcatc atacccactt ctgccccctg gaaggcgagt catggcaaga ctttctgcgg    240
aacaacgcca agtcattccg ctgtgctctc ctctcacatc gcgacggggc taaagtgcat    300
ctcggcaccc gcccaacaga gaaacagtac gaaaccctgg aaaatcagct cgcgttcctg    360
tgtcagcaag gcttctccct ggagaacgca ctgtacgctc tgtccgccgt gggccacttt    420
acactgggct gcgtattgga ggatcaggag catcaagtag caaaagagga agagagagaca   480 cctaccaccg attctatgcc cccacttctg agacaagcaa ttgagctgtt cgaccatcag    540
ggagccgaac ctgccttcct tttcggcctg gaactaatca tatgtggcct ggagaaacag    600
ctaaagtgcg aaagcggcgg gccggccgac gcccttgacg attttgactt agacatgctc    660
ccagccgatg cccttgacga ctttgacctt gatatgctgc ctgctgacgc tcttgacgat    720
tttgaccttg acatgctccc cgggtaa                                        747
```

```
<210> SEQ ID NO 62
<211> LENGTH: 189
<212> TYPE: PRT
<213> ORGANISM: Homo sapiens

<400> SEQUENCE: 62
```

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60
```

-continued

```
Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

```
<210> SEQ ID NO 63
<211> LENGTH: 11
<212> TYPE: PRT
<213> ORGANISM: Homo sapiens

<400> SEQUENCE: 63

Arg Pro Lys Pro Gln Gln Phe Phe Gly Leu Met
1               5                   10
```

```
<210> SEQ ID NO 64
<211> LENGTH: 9
<212> TYPE: PRT
<213> ORGANISM: Homo sapiens

<400> SEQUENCE: 64

Cys Tyr Ile Gln Asn Cys Pro Leu Gly
1               5
```

```
<210> SEQ ID NO 65
<211> LENGTH: 1353
<212> TYPE: DNA
<213> ORGANISM: Artificial Sequence
<220> FEATURE:
<223> OTHER INFORMATION: GCaMP6m

<400> SEQUENCE: 65
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag tcggctgag ctcactcgag      180 aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg      420
atcactctcg gcatggacga gctgtacaag ggcggtaccg gagggagcat ggtgagcaag     480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
```

-continued

```
ctgacctacg gcgtgcagtg cttcagccgc taccccgacc acatgaagca gcacgacttc      720
ttcaagtccg ccatgcccga aggctacatc caggagcgca ccatcttctt caaggacgac      780
ggcaactaca agacccgcgc cgaggtgaag ttcgagggcg acaccctggt gaaccgcatc      840
gagctgaagg gcatcgactt caaggaggac ggcaacatcc tggggcacaa gctggagtac      900
aacctgccgg accaactgac tgaagagcag atcgcagaat ttaaagaggc tttctcccta      960
tttgacaagg acggggatgg gacaataaca accaaggagc tggggacggt gatgcggtct     1020
ctggggcaga accccacaga agcagagctg caggacatga tcaatgaagt agatgccgac     1080
ggtgacggca caatcgactt ccctgagttc ctgacaatga tggcaagaaa agggagctac     1140
agggacacgg aagaagaaat tagagaagcg ttcggtgtgt ttgataagga tggcaatggc     1200
tacatcagtg cagcagagct tcgccacgtg atgacaaacc ttggagagaa gttaacagat     1260
gaagaggttg atgaaatgat cagggaagca gacatcgatg gggatggtca ggtaaactac     1320
gaagagtttg tacaaatgat gacagcgaag tga                                  1353
```

```
<210> SEQ ID NO 66
<211> LENGTH: 1353
<212> TYPE: DNA
<213> ORGANISM: Artificial Sequence
<220> FEATURE:
<223> OTHER INFORMATION: GCaMP6s
```

```
<400> SEQUENCE: 66
```

```
atgggttctc atcatcatca tcatcatggt atggctagca tgactggtgg acagcaaatg       60
ggtcgggatc tgtacgacga tgacgataag gatctcgcca ccatggtcga ctcatcacgt      120
cgtaagtgga ataagacagg tcacgcagtc agagctatag gtcggctgag ctcactcgag      180
aacgtctata tcaaggccga caagcagaag aacggcatca aggcgaactt ccacatccgc      240
cacaacatcg aggacggcgg cgtgcagctc gcctaccact accagcagaa caccccatc      300 ggcgacggcc ccgtgctgct gcccgacaac cactacctga gcgtgcagtc caaacttcg       360 aaagacccca cgagaagcg cgatcacatg gtcctgctgg agttcgtgac cgccgccggg      420
atcactctcg gcatggacga gctgtacaag ggcggtaccg gagggagcat ggtgagcaag      480
ggcgaggagc tgttcaccgg ggtggtgccc atcctggtcg agctggacgg cgacgtaaac      540
ggccacaagt tcagcgtgtc cggcgagggt gagggcgatg ccacctacgg caagctgacc      600
ctgaagttca tctgcaccac cggcaagctg cccgtgccct ggcccaccct cgtgaccacc      660
ctgacctacg gcgtgcagtg cttcagccgc taccccgacc acatgaagca gcacgacttc      720
ttcaagtccg ccatgcccga aggctacatc caggagcgca ccatcttctt caaggacgac      780
ggcaactaca agacccgcgc cgaggtgaag ttcgagggcg acaccctggt gaaccgcatc      840
gagctgaagg gcatcgactt caaggaggac ggcaacatcc tggggcacaa gctggagtac      900
aacctgccgg accaactgac tgaagagcag atcgcagaat ttaaagaggc tttctcccta      960
tttgacaagg acggggatgg gacaataaca accaaggagc tggggacggt gatgcggtct     1020
ctggggcaga accccacaga agcagagctg caggacatga tcaatgaagt agatgccgac     1080
ggtgacggca caatcgactt ccctgagttc ctgacaatga tggcaagaaa aatgaaatac     1140
agggacacgg aagaagaaat tagagaagcg ttcggtgtgt ttgataagga tggcaatggc     1200
tacatcagtg cagcagagct tcgccacgtg atgacaaacc ttggagagaa gttaacagat     1260
gaagaggttg atgaaatgat cagggaagca gacatcgatg gggatggtca ggtaaactac     1320
gaagagtttg tacaaatgat gacagcgaag tga                                  1353
```

<210> SEQ ID NO 67
<211> LENGTH: 1353
<212> TYPE: DNA
<213> ORGANISM: Artificial Sequence
<220> FEATURE:
<223> OTHER INFORMATION: GCaMP6f

<400> SEQUENCE: 67
atgggttctc atcatcatca tcatcatggt atggctagca tgactggtgg acagcaaatg        60
ggtcgggatc tgtacgacga tgacgataag gatctcgcca ccatggtcga ctcatcacgt       120
cgtaagtgga ataagacagg tcacgcagtc agagctatag gtcggctgag ctcactcgag       180
aacgtctata tcaaggccga caagcagaag aacggcatca aggcgaactt caagatccgc       240
cacaacatcg aggacggcgg cgtgcagctc gcctaccact accagcagaa cacccccatc       300
ggcgacggcc ccgtgctgct gcccgacaac cactacctga gcgtgcagtc caaactttcg       360
aaagacccca cgagaagcg cgatcacatg gtcctgctgg agttcgtgac cgccgccggg       420
atcactctcg gcatggacga gctgtacaag ggcggtaccg agggagcat ggtgagcaag        480 ggcgaggagc tgttcaccgg ggtggtgccc atcctggtcg agctggacgg cgacgtaaac       540
ggccacaagt tcagcgtgtc cggcgagggt gagggcgatg ccacctacgg caagctgacc       600
ctgaagttca tctgcaccac cggcaagctg cccgtgccct ggcccaccct cgtgaccacc       660
ctgacctacg gcgtgcagtg cttcagccgc taccccgacc acatgaagca gcacgacttc       720
ttcaagtccg ccatgcccga aggctacatc caggagcgca ccatcttctt caaggacgac       780
ggcaactaca agacccgcgc cgaggtgaag ttcgagggcg acaccctggt gaaccgcatc       840
gagctgaagg gcatcgactt caaggaggac ggcaacatcc tggggcacaa gctggagtac       900
aacctgccgg accaactgac tgaagagcag atcgcagaat ttaaagagga attctcccta       960
tttgacaagg acgggggatgg gacaataaca accaaggagc tggggacggt gatgcggtct      1020
ctggggcaga accccacaga agcagagctg caggacatga tcaatgaagt agatgccgac      1080
ggtgacggca caatcgactt ccctgagttc ctgacaatga tggcaagaaa aatgaaatac      1140
agggacacgg aagaagaaat tagagaagcg ttcggtgtgt ttgataagga tggcaatggc      1200
tacatcagtg cagcagagct tcgccacgtg atgacaaacc ttggagagaa gttaacagat      1260
gaagaggttg atgaaatgat cagggaagca gacatcgatg gggatggtca ggtaaactac      1320
gaagagtttg tacaaatgat gacagcgaag tga                                    1353

<210> SEQ ID NO 68
<211> LENGTH: 2495
<212> TYPE: DNA
<213> ORGANISM: Artificial Sequence
<220> FEATURE:
<223> OTHER INFORMATION: CN1917

<400> SEQUENCE: 68
gcggccgcac gcgccggtac cgaagctacc cctaacacac tattctacac acagaaaatg        60
ctcttcacta ggaagctacc cctaacacac tattctacac acagaaaatg ctcttcacta       120
ggaagctacc cctaacacac tattctacac acagaaaatg ctcttcacta gacgcgtact       180
attccagcca cgaggtataa acactgggaa ggaaagtcct ggctctgtat tgtccacaaa       240
gacccgaagc tgcagcaaag ttggcaaaag agaaacaaaa agagcagaga aggctcagct       300
ttcaacagct aggctcaccc aaacatcaag aggtggacaa atatttacag tgtgaacctt       360

-continued

```
aacccaaaga acggcagtgc ggtcatgctg cacagagtca acttcagaac caagactgtg      420
accagggctg gagcaagaga cacttcacgc taataaatag gccacttaat caagaagctg      480
tcacagtcct aaatatgtat gcaccgagca ttagcacttc caagtagagt ggaacagcta      540
aagatagagg caagaagcaa gcagacaaat cttcggtgat tgttggaaat cacagcattt      600
ctctcagcaa ttgtcaggac acagaaaatc agcgagaaga cagaagagtc tcacaatagt      660
ccccatcaac ttgacctaat tgacatttat ggagcttggc atccaacagc cgtggagcgc      720
atgcgctctt taaggcagaa tacagaccat caaacaaaac cagggagacc aaagtcacag      780
aaaatatgct ctgtgaacat gacataataa agtggaaatc gataacagag agatcgctgc      840
aaaatccccc aagtgattgg taattaaatg ctctactcct gaatgaatga tgggcgagaa      900
aggaaagcca cggggggaaag cagatttctg cgttgaaaga gcatggagac agacttcgtc      960
aagatgagag agcacgtggg gctggaggga tggctcagca cttcagaggc actcacgctc     1020
ttccatagga cctaggttca cttctcagca cacacatggc aactcacacc tgtgatgcag     1080
agaagagctc gattcagccg ggagcttagg gaggggaggt cacttcataa gggcttgggg     1140
ggggagttgg agccacgagt cgtccagccg gagccccgtg tggctgtgct ccggcctcag     1200
aagcatcccc ggatccagat cttcgaagc tagcgctacc ggtcgccacc atggtgagca     1260
agggcgagga gctgttcacc ggggtggtgc ccatcctggt cgagctggac ggcgacgtaa     1320
acggccacaa gttcagcgtg tccggcgagg gcgaggcga tgccacctac ggcaagctga     1380
ccctgaagct gatctgcacc accggcaagc tgcccgtgcc ctggcccacc ctcgtgacca     1440
ccctgggcta cggcgtgcag tgcttcgccc gctaccccga ccacatgaag cagcacgact     1500
tcttcaagtc cgccatgccc gaaggctacg tccaggagcg caccatcttc ttcaaggacg     1560
acggcaacta caagacccgc gccgaggtga agttcgaggg cgacaccctg gtgaaccgca     1620
tcgagctgaa gggcatcgac ttcaaggagg acggcaacat cctggggcac aagctggagt     1680
acaactacaa cagccacaac gtctatatca ccgccgacaa gcagaagaac ggcatcaagg     1740
ccaacttcaa gatccgccac aacatcgagg acggcggcgt gcagctcgcc gaccactacc     1800
agcagaacac ccccatcggc gacggccccg tgctgctgcc cgacaaccac tacctgagct     1860
accagtccaa gctgagcaaa gaccccaacg agaagcgcga tcacatggtc ctgctggagt     1920
tcgtgaccgc cgccgggatc actctcggca tggacgagct gtacaagtaa gtcgacggcg     1980
cgccgcggcc gcgaattcga tatcataatc aacctctgga ttacaaaatt tgtgaaagat     2040
tgactggtat tcttaactat gttgctcctt ttacgctatg tggatacgct gctttaatgc     2100
ctttgtatca tgctattgct tcccgtatgg ctttcatttt ctcctccttg tataaatcct     2160
ggttagttct tgccacggcg gaactcatcg ccgcctgcct tgcccgctgc tggacagggg     2220
ctcggctgtt gggcactgac aattccgtgg ctcgagagat cttcgactgt gccttctagt     2280
tgccagccat ctgttgtttg cccctccccc gtgccttcct tgaccctgga aggtgccact     2340
cccactgtcc tttcctaata aaatgaggaa attgcatcgc attgtctgag taggtgtcat     2400
tctattctgg ggggtggggt ggggcaggac agcaaggggg aggattggga agacaatagc     2460
aggcatgaga tctcacgtgc ggaccgagcg gccgc                                2495
```

<210> SEQ ID NO 69
<211> LENGTH: 1986
<212> TYPE: DNA
<213> ORGANISM: Artificial Sequence
<220> FEATURE:
<223> OTHER INFORMATION: CN2047

<400> SEQUENCE: 69

```
gcggccgcac gcgccggtac cgaagctacc cctaacacac tattctacac acagaaaatg      60
ctcttcacta ggaagctacc cctaacacac tattctacac acagaaaatg ctcttcacta     120
ggaagctacc cctaacacac tattctacac acagaaaatg ctcttcacta gacgcgttcc     180
ttctcagaac ctaggtaagg taagttcctt tcaaggctgg ctatataaat aatcatctca     240
gttaggatgc ttggtgggac caaagaacca aaactgccga gcaggcatga tctgacttgg     300
agtggttcca ggaccttcct gtgaatgctg gagtcattca gtgtagagct ctcctctgtg     360
actgggtcaa ggttgcccca ctgtaaaccc agggaagcta gcccagcctt cctctcaggg     420
aatgtgtatg cttcccttac acctgaccct ggcacagacc tggtggttgt ttttcagaag     480
catcagtgtc tttgccttag gcatttgtcc tcaaagggca gcgacactgt ctactgactg     540
ctttgtacag ggtaactgct taactaattc ttaaggagct cgattcagcc gggagcttag     600
ggaggggagg tcacttcata agggcttggg ggggagttg gagccacgag tcgtccagcc     660
ggagccccgt gtggctgtgc tccggcctca gaagcatccc cggatccaga tctttcgaag     720
ctagcgctac cggtcgccac catggtgagc aagggcgagg agctgttcac cggggtggtg     780
cccatcctgg tcgagctgga cggcgacgta aacggccaca agttcagcgt gtccggcgag     840
ggcgagggcg atgccaccta cggcaagctg accctgaagc tgatctgcac caccggcaag     900
ctgcccgtgc cctggcccac cctcgtgacc accctgggct acggcgtgca gtgcttcgcc     960 cgctacccccg accacatgaa gcagcacgac ttcttcaagt ccgccatgcc cgaaggctac    1020
gtccaggagc gcaccatctt cttcaaggac gacggcaact acaagacccg cgccgaggtg    1080
aagttcgagg gcgacaccct ggtgaaccgc atcgagctga agggcatcga cttcaaggag    1140
gacggcaaca tcctggggca caagctggag tacaactaca acagccacaa cgtctatatc    1200
accgccgaca gcagaagaa cggcatcaag gccaacttca agatccgcca caacatcgag    1260
gacggcggcg tgcagctcgc cgaccactac cagcagaaca cccccatcgg cgacggcccc    1320
gtgctgctgc ccgacaacca ctacctgagc taccagtcca agctgagcaa agaccccaac    1380
gagaagcgcg atcacatggt cctgctggag ttcgtgaccg ccgccgggat cactctcggc    1440
atggacgagc tgtacaagta agtcgacggc gcgccgcggc cgcgaattcg atatcataat    1500
caacctctgg attacaaaat ttgtgaaaga ttgactggta ttcttaacta tgttgctcct    1560
tttacgctat gtggatacgc tgctttaatg cctttgtatc atgctattgc ttcccgtatg    1620
gctttcattt tctcctcctt gtataaatcc tggttagttc ttgccacggc ggaactcatc    1680
gccgcctgcc ttgcccgctg ctggacaggg gctcggctgt tgggcactga caattccgtg    1740
gctcgagaga tcttcgactg tgccttctag ttgccagcca tctgttgttt gcccctcccc    1800
cgtgccttcc ttgaccctgg aaggtgccac tcccactgtc ctttcctaat aaaatgagga    1860
aattgcatcg cattgtctga gtaggtgtca ttctattctg ggggtgggg tggggcagga    1920 cagcaagggg gaggattggg aagacaatag caggcatgag atctcacgtg cggaccgagc    1980
ggccgc                                                                1986
```

<210> SEQ ID NO 70
<211> LENGTH: 1927
<212> TYPE: DNA
<213> ORGANISM: Artificial Sequence
<220> FEATURE:
<223> OTHER INFORMATION: CN20478

```
<400> SEQUENCE: 70
gcggccgcac gcgccggtac cgaagctacc cctaacacac tattctacac acagaaaatg      60
ctcttcacta ggaagctacc cctaacacac tattctacac acagaaaatg ctcttcacta     120
ggaagctacc cctaacacac tattctacac acagaaaatg ctcttcacta gacgcgtaaa     180
tggagactgc caagggctga aacggggtgc gggaaccagg gaccgagccc ccccctccc      240 cacatgagaa tctgtcacat tgctgctcca gtggcctgaa agaccagcac agccccagct     300
ggagcctctc ccctctggat cttgtcaatg tggctttgct ttgctgcttg ggcagccggg     360
agtggtgaca agcagggaga gagcgcccaa ggcatctggc tgtgccactc cagcctgact     420
gccagctcac ccatcagtgc ccatctcatc atcgagaggg acccagatga gaccgggggat    480 cagcactgtc cttaccttga agggacgtgt caggaagagc tcgattcagc cgggagctta     540
gggaggggag gtcacttcat aagggcttgg ggggggagtt ggagccacga gtcgtccagc     600
cggagccccg tgtggctgtg ctccggcctc agaagcatcc ccggatccag atctttcgaa     660
gctagcgcta ccggtcgcca ccatggtgag caagggcgag gagctgttca ccggggtggt     720
gcccatcctg gtcgagctgg acggcgacgt aaacggccac aagttcagcg tgtccggcga     780
gggcgagggc gatgccacct acggcaagct gaccctgaag ctgatctgca ccaccggcaa     840
gctgcccgtg ccctggccca cccctcgtgac caccctgggc tacggcgtgc agtgcttcgc     900
ccgctacccc gaccacatga gcagcacga  cttcttcaag tccgccatgc ccgaaggcta     960
cgtccaggag cgcaccatct tcttcaagga cgacggcaac tacaagaccc gcgccgaggt    1020
gaagttcgag ggcgacaccc tggtgaaccg catcgagctg aagggcatcg acttcaagga    1080
ggacggcaac atcctggggc acaagctgga gtacaactac aacagccaca cgtctatat     1140 caccgccgac aagcagaaga acggcatcaa ggccaacttc aagatccgcc acaacatcga    1200
ggacggcggc gtgcagctcg ccgaccacta ccagcagaac acccccatcg cgacggccc     1260 cgtgctgctg cccgacaacc actacctgag ctaccagtcc aagctgagca aagaccccaa    1320
cgagaagcgc gatcacatgg tcctgctgga gttcgtgacc gccgccggga tcactctcgg    1380
catggacgag ctgtacaagt aagtcgacgg cgcgccgcgg ccgcgaattc gatatcataa    1440
tcaacctctg gattacaaaa tttgtgaaag attgactggt attcttaact atgttgctcc    1500
ttttacgcta tgtggatacg ctgctttaat gcctttgtat catgctattg cttcccgtat    1560
ggctttcatt ttctcctcct tgtataaatc ctggttagtt cttgccacgg cggaactcat    1620
cgccgcctgc cttgcccgct gctggacagg ggctcggctg ttgggcactg acaattccgt    1680
ggctcgagag atcttcgact gtgccttcta gttgccagcc atctgttgtt tgcccctccc    1740
ccgtgccttc cttgaccctg gaaggtgcca ctcccactgt cctttcctaa taaaatgagg    1800
aaattgcatc gcattgtctg agtaggtgtc attctattct ggggggtggg gtggggcagg    1860
acagcaaggg ggaggattgg gaagacaata gcaggcatga gatctcacgt gcggaccgag    1920
cggccgc                                                              1927

<210> SEQ ID NO 71
<211> LENGTH: 1996
<212> TYPE: DNA
<213> ORGANISM: Artificial Sequence
<220> FEATURE:
<223> OTHER INFORMATION: CN2049

<400> SEQUENCE: 71
gcggccgcac gcgccggtac cgaagctacc cctaacacac tattctacac acagaaaatg      60
```

-continued

```
ctcttcacta ggaagctacc cctaacacac tattctacac acagaaaatg ctcttcacta        120
ggaagctacc cctaacacac tattctacac acagaaaatg ctcttcacta gacgcgttct        180
gctttctctt cccttggcct cctgctggga tagaaggggt tggtgtgagt gtgtatggtg        240
gggtgctgtg agattaatta gcagccgtgc caggcagcag gcggtggggt gcagagtagg        300
ctggctttcc ctgctataga tccatgctct ctgggagagg cactagccgg ctgctttggg        360
ctctggctca gctattttag gaatattctt aaccccttcca gaaccgctgc cattgccaga        420
tctctctccc agaacacagg ccagctccag attgcccctc ctttctgccc ccgccctgca        480
ccccacctag cctctgctct tcctccctac aagttgagaa ggtcaaggtt tgacttttac        540
caaagaaaac tcctggctcc tgatcccact ctctgtgctt tacctgagct cgattcagcc        600
gggagcttag ggaggggagg tcacttcata agggcttggg gggggagttg gagccacgag        660
tcgtccagcc ggagccccgt gtggctgtgc tccggcctca gaagcatccc cggatccaga        720
tctttcgaag ctagcgctac cggtcgccac catggtgagc aagggcgagg agctgttcac        780
cggggtggtg cccatcctgg tcgagctgga cggcgacgta aacggccaca agttcagcgt        840
gtccggcgag ggcgagggcg atgccaccta cggcaagctg accctgaagc tgatctgcac        900
caccggcaag ctgcccgtgc cctggcccac cctcgtgacc accctgggct acggcgtgca        960
gtgcttcgcc cgctacccc g accacatgaa gcagcacgac ttcttcaagt ccgccatgcc       1020
cgaaggctac gtccaggagc gcaccatctt cttcaaggac gacggcaact acaagacccg       1080
cgccgaggtg aagttcgagg gcgacaccct ggtgaaccgc atcgagctga agggcatcga       1140
cttcaaggag gacggcaaca tcctggggca caagctggag tacaactaca acagccacaa       1200
cgtctatatc accgccgaca gcagaagaa c cggcatcaag gccaacttca gatccgcca        1260 caacatcgag gacggcggcg tgcagctcgc cgaccactac cagcagaaca cccccatcgg       1320
cgacggcccc gtgctgctgc ccgacaacca ctacctgagc taccagtcca gctgagcaa        1380 agaccccaac gagaagcgcg atcacatggt cctgctggag ttcgtgaccg ccgccgggat       1440
cactctcggc atggacgagc tgtacaagta agtcgacggc gcgccgcggc cgcgaattcg       1500
atatcataat caacctctgg attacaaaat ttgtgaaaga ttgactggta ttcttaacta       1560
tgttgctcct tttacgctat gtggatacgc tgctttaatg cctttgtatc atgctattgc       1620
ttcccgtatg gctttcattt tctcctcctt gtataaatcc tggttagttc ttgccacggc       1680
ggaactcatc gccgcctgcc ttgcccgctg ctggacaggg gctcggctgt tgggcactga       1740
caattccgtg gctcgagaga tcttcgactg tgccttctag ttgccagcca tctgttgttt       1800
gcccctcccc cgtgccttcc ttgaccctgg aaggtgccac tcccactgtc ctttcctaat       1860
aaaatgagga aattgcatcg cattgtctga gtaggtgtca ttctattctg ggggtgggg        1920 tggggcagga cagcaagggg gaggattggg aagacaatag caggcatgag atctcacgtg       1980
cggaccgagc ggccgc                                                       1996
```

```
<210> SEQ ID NO 72
<211> LENGTH: 2071
<212> TYPE: DNA
<213> ORGANISM: Artificial Sequence
<220> FEATURE:
<223> OTHER INFORMATION: CN2427

<400> SEQUENCE: 72
gcggccgcac gcgtgggatg cgatgcagtg gcatggtaaa aatgccgtac ctaatgatgc        60
```

-continued

```
agtttcagcc atcatgacgt atggatggaa tgaaaagatg acaaagctac tagcggatct      120
gttcacaaag gaaaagaggc tcagtttcca acagtctctg gcatttcatc tttggaaaac      180
ttgtcaaagc taagatgatt tgtgagagtc ctaactcatt ttcctaaata tgaagtcgct      240
attatggata aagaaaggtt acaatggagc atccatttcc actctagtca ttctgcttga      300
ttgcaccaat tagccctgca ttcactgtgc attttaactt cataatggtc tattatttgg      360
accactgacc ataatgatgc aattctttcc ttgacgaaaa taaatgctta gtgataaata      420
agtaatcata attaaagctt tcatagtact tatagtacca caattggtat ttagcccatt      480
gattataatt taaacacatt ttaattaata tgtaactata ttacttccct atttttcttt      540
tctttcctcc aaaatgcctc atgtctcctt ctatcaacac cccccatacc ccccagacac      600
tccttgtcaa attgatggcc ttttaaaatt attattattg taacatgaag aaatagttga      660
acaaatatat aaatacagta caatgagtct gtttatggtg gctcctatgg gtatgatttg      720
ggggcctgag ctcgggctgg gcataaaagt cagggcagag ccatctattg cttacatttg      780
cttctgggat ccagatcttt cgaagctagc gctaccggtc gccaccatgg tgagcaaggg      840
cgaggagctg ttcaccgggg tggtgcccat cctggtcgag ctggacggcg acgtaaacgg      900
ccacaagttc agcgtgtccg gcgagggcga gggcgatgcc acctacggca agctgaccct      960
gaagctgatc tgcaccaccg gcaagctgcc cgtgccctgg cccaccctcg tgaccaccct     1020
gggctacggc gtgcagtgct tcgcccgcta ccccgaccac atgaagcagc acgacttctt     1080
caagtccgcc atgcccgaag ctacgtccca ggagcgcacc atcttcttca aggacgacgg     1140
caactacaag acccgcgccg aggtgaagtt cgagggcgac accctggtga accgcatcga     1200
gctgaagggc atcgacttca aggaggacgg caacatcctg gggcacaagc tggagtacaa     1260
ctacaacagc cacaacgtct atatcaccgc cgacaagcag aagaacggca tcaaggccaa     1320
cttcaagatc cgccacaaca tcgaggacgg cggcgtgcag ctcgccgacc actaccagca     1380 gaacacccccc atcggcgacg gccccgtgct gctgcccgac aaccactacc tgagctacca     1440
gtccaagctg agcaaagacc ccaacgagaa gcgcgatcac atggtcctgc tggagttcgt     1500
gaccgccgcc gggatcactc tcggcatgga cgagctgtac aagtaagtcg acggcgcgcc     1560
gcggccgcga attcgatatc ataatcaacc tctggattac aaaatttgtg aaagattgac     1620
tggtattctt aactatgttg ctccttttac gctatgtgga tacgctgctt taatgccttt     1680
gtatcatgct attgcttccc gtatggcttt cattttctcc tccttgtata aatcctggtt     1740
agttcttgcc acggcggaac tcatcgccgc ctgccttgcc cgctgctgga caggggctcg     1800
gctgttgggc actgacaatt ccgtggctcg agagatcttc gactgtgcct tctagttgcc     1860
agccatctgt tgtttgcccc tcccccgtgc cttccttgac cctggaaggt gccactccca     1920
ctgtcctttc ctaataaaat gaggaaattg catcgcattg tctgagtagg tgtcattcta     1980 ttctggggggg tggggtgggg caggacagca aggggaggga ttgggaagac aatagcaggc     2040
atgagatctc acgtgcggac cgagcggccg c                                     2071
```

```
<210> SEQ ID NO 73
<211> LENGTH: 1985
<212> TYPE: DNA
<213> ORGANISM: Artificial Sequence
<220> FEATURE:
<223> OTHER INFORMATION: CN2320

<400> SEQUENCE: 73
gcggccgcac gcgttatctt agagtgggaa gatttgagaa gtgccatggt taatatgact      60
```

```
gactttttat tcttatttct tttaattttca tggttctaaa tccgaattta atcatagtac      120
ccagaaaagc agaggtgtag aggttcacag tgggagttgt aatctagccc tattcatttt      180
gacctcaaaa cccaaattat ttataacaaa ttatttccta ttctttcctt cactattcag      240
gaacatctgt ccaccactta catgatcact tatcttgcta ttgtgtcatt ttgatgaaaa      300
agaatttttt ctaaatatct aaatacaagg ccccatatta acagtgcttt ttaaatcccc      360
acagatgtgg gagatgaccc ctttccatcc ctgaagattg taattgggcc agtctttagt      420
acagtttgtt ccaataaaga gatacaattt tattcattaa tttgtgtatt catttagcaa      480
atcactttag agtcttatta tatcaggatt ttggggtcta ttttagtata tctttttgta      540
tttcttggaa cctctccaat tattctagac tctttcaaag gttggtgatc aatattagac      600
attattatga aaagaatctt acttgctaaa agggttagat ggagctcggg ctgggcataa      660
aagtcagggc agagccatct attgcttaca tttgcttctg ggatccagat ctttcgaagc      720
tagcgctacc ggtcgccacc atggtgagca agggcgagga gctgttcacc ggggtggtgc      780
ccatcctggt cgagctggac ggcgacgtaa acggccacaa gttcagcgtg tccggcgagg      840
gcgagggcga tgccacctac ggcaagctga ccctgaagct gatctgcacc accggcaagc      900
tgcccgtgcc ctggcccacc ctcgtgacca ccctgggcta cggcgtgcag tgcttcgccc      960
gctaccccga ccacatgaag cagcacgact tcttcaagtc cgccatgccc gaaggctacg     1020
tccaggagcg caccatcttc ttcaaggacg acggcaacta caagacccgc gccgaggtga     1080
agttcgaggg cgacaccctg gtgaaccgca tcgagctgaa gggcatcgac ttcaaggagg     1140
acggcaacat cctggggcac aagctggagt acaactacaa cagccacaac gtctatatca     1200
ccgccgacaa gcagaagaac ggcatcaagg ccaacttcaa gatccgccac aacatcgagg     1260
acggcggcgt gcagctcgcc gaccactacc agcagaacac ccccatcggc gacggccccg     1320
tgctgctgcc cgacaaccac tacctgagct accagtccaa gctgagcaaa gaccccaacg     1380
agaagcgcga tcacatggtc ctgctggagt tcgtgaccgc cgccgggatc actctcggca     1440
tggacgagct gtacaagtaa gtcgacggcg cgccgcggcc gcgaattcga tatcataatc     1500
aacctctgga ttacaaaatt tgtgaaagat tgactggtat tcttaactat gttgctcctt     1560
ttacgctatg tggatacgct gctttaatgc ctttgtatca tgctattgct tcccgtatgg     1620
ctttcatttt ctcctccttg tataaatcct ggttagttct tgccacggcg gaactcatcg     1680
ccgcctgcct tgcccgctgc tggacagggg ctcggctgtt gggcactgac aattccgtgg     1740
ctcgagagat cttcgactgt gccttctagt tgccagccat ctgttgtttg cccctcccc     1800 gtgccttcct tgaccctgga aggtgccact cccactgtcc tttcctaata aaatgaggaa     1860
attgcatcgc attgtctgag taggtgtcat tctattctgg ggggtggggt ggggcaggac     1920
agcaaggggg aggattggga agacaatagc aggcatgaga tctcacgtgc ggaccgagcg     1980
gccgc                                                                 1985
```

```
<210> SEQ ID NO 74
<211> LENGTH: 1844
<212> TYPE: DNA
<213> ORGANISM: Artificial Sequence
<220> FEATURE:
<223> OTHER INFORMATION: CN2321

<400> SEQUENCE: 74
gcggccgcac gcgttatgat gtgccaggct tgggagaaac accacaagca aagccaaaat       60
```

```
aggtggccta gaacttccag cttgaaatat gggagagaat gagggaggca ctgtagagca      120
gctgccgggt gccgcatgag aacaattctc cctgctcata attaatccta cctatttctg      180
atgacagctg gctcttcact ttgaacaagc tagttaacaa ctttcttctc acattgagca      240
aataattcat atttaattac ttaaccacca gttacaaaat gagaatcatc aaggaatcac      300
aattaatttg ctattgacaa actcatactt ttagcaggct gatttctact ttatacttag      360
attggtaatg aaaaatgaag cttattttag ttgattggtt ggacttgtgt atgaatatta      420
tctattattt gaaaagccaa acttgaatgc aaaaaaatat tgaatatgaa aagaaaaaca      480
tttgcagtaa agcttgttct gagctcgggc tgggcataaa agtcagggca gagccatcta      540
ttgcttacat ttgcttctgg gatccagatc tttcgaagct agcgctaccg gtcgccacca      600
tggtgagcaa gggcgaggag ctgttcaccg gggtggtgcc catcctggtc gagctggacg      660
gcgacgtaaa cggccacaag ttcagcgtgt ccggcgaggg cgagggcgat gccacctacg      720
gcaagctgac cctgaagctg atctgcacca ccggcaagct gcccgtgccc tggcccaccc      780
tcgtgaccac cctgggctac ggcgtgcagt gcttcgcccg ctaccccgac cacatgaagc      840
agcacgactt cttcaagtcc gccatgcccg aaggctacgt ccaggagcgc accatcttct      900
tcaaggacga cggcaactac aagacccgcg ccgaggtgaa gttcgagggc gacaccctgg      960
tgaaccgcat cgagctgaag ggcatcgact tcaaggagga cggcaacatc ctggggcaca     1020
agctggagta caactacaac agccacaacg tctatatcac cgccgacaag cagaagaacg     1080
gcatcaaggc caacttcaag atccgccaca acatcgagga cggcggcgtg cagctcgccg     1140
accactacca gcagaacacc cccatcggcg acggccccgt gctgctgccc gacaaccact     1200
acctgagcta ccagtccaag ctgagcaaag accccaacga gaagcgcgat cacatggtcc     1260
tgctggagtt cgtgaccgcc gccgggatca ctctcggcat ggacgagctg tacaagtaag     1320
tcgacggcgc gccgcggccg cgaattcgat atcataatca acctctggat tacaaaattt     1380
gtgaaagatt gactggtatt cttaactatg ttgctccttt tacgctatgt ggatacgctg     1440
ctttaatgcc tttgtatcat gctattgctt cccgtatggc tttcattttc tcctccttgt     1500
ataaatcctg gttagttctt gccacggcgg aactcatcgc cgcctgcctt gcccgctgct     1560
ggacaggggc tcggctgttg ggcactgaca attccgtggc tcgagagatc ttcgactgtg     1620
ccttctagtt gccagccatc tgttgtttgc ccctcccccg tgccttcctt gaccctggaa     1680
ggtgccactc ccactgtcct ttcctaataa aatgaggaaa ttgcatcgca ttgtctgagt     1740
aggtgtcatt ctattctggg gggtggggtg gggcaggaca gcaaggggga ggattgggaa     1800
gacaatagca ggcatgagat ctcacgtgcg gaccgagcgg ccgc                      1844
```

```
<210> SEQ ID NO 75
<211> LENGTH: 2346
<212> TYPE: DNA
<213> ORGANISM: Artificial Sequence
<220> FEATURE:
<223> OTHER INFORMATION: CN2719

<400> SEQUENCE: 75
gcggccgcac gcgtaaagct acatctctgg gctccattat taaagctgct ttccttcctt       60
tctctctctc tcgctctctc tctctctctc tttctttctt tcttttttcct gagatgggtc      120 tcatgtagcc caggctggcc tcaagcttgc cacatagcca aggagccaag gatggcattg      180
aactcctaga tcctccagcc tctgcctcct gttaggatta gaggtgagct acaatcccaa      240
gggcctttag tgtaacagtc aaaagctact gggagtcagg caattggctc agtataaccc      300
```

-continued

```
tgattctcct tttgtgccca ggcacgttgg tcaggagtct gtcttcagcc tgtcatggca    360
gcagctcagc ttcagtgacc aatctatact cactcacagg agactctgaa atcccagatt    420
ctgtgctata aagtccccgc tcgagtgagt cgtgactgct ccaaacagcc tgggcagctg    480
cgaaccctca tggcatctag gtgaccctgt tcatcctaca gctgttctca ctgaggggag    540
gggagctttt gagtgagcca gtcaaaactc tgtgctcggt gatcctgtga ggctcggaac    600
ggtggcaccc gaagccatgg gtgcacacac aaacagggct ctaatcggtg ggatcacaat    660
ccatgaacaa gcatgagacc tcccttcttc tcacacacac acacacacac acacacacac    720
acacactcac tcacatacat gagctggttt ccacaactgt ggggttagcc tggaaggtgt    780
ctgtcctata tagtactcca gtaccagtgt tgcagactct aggcccagga aaaggtttt    840 gatgtttgct ggtgtttttg atgaccttca tcgtgggtag agcaggctgc gctggttcat    900
aaagagaaga caagacctag agtgctgtga cccttttaagg catcatggtg tgatgacccc    960
caaccataaa gttattttcg ctgctgcttt gtaactgtaa gtgagctcgg gctgggcata   1020
aaagtcaggg cagagccatc tattgcttac atttgcttct gggatccaga tctttcgaag   1080
ctagcgctac cggtcgccac catggtgagc aagggcgagg agctgttcac cggggtggtg   1140
cccatcctgg tcgagctgga cggcgacgta aacggccaca agttcagcgt gtccggcgag   1200
ggcgagggcg atgccaccta cggcaagctg accctgaagc tgatctgcac caccggcaag   1260
ctgcccgtgc cctggcccac cctcgtgacc accctgggct acggcgtgca gtgcttcgcc   1320
cgctaccccg accacatgaa gcagcacgac ttcttcaagt ccgccatgcc cgaaggctac   1380
gtccaggagc gcaccatctt cttcaaggac gacggcaact acaagacccg cgccgaggtg   1440
aagttcgagg gcgacaccct ggtgaaccgc atcgagctga agggcatcga cttcaaggag   1500
gacggcaaca tcctggggca caagctggag tacaactaca acagccacaa cgtctatatc   1560
accgccgaca gcagaagaa cggcatcaag gccaacttca agatccgcca caacatcgag    1620
gacggcggcg tgcagctcgc cgaccactac cagcagaaca cccccatcgg cgacggcccc   1680
gtgctgctgc ccgacaacca ctacctgagc taccagtcca agctgagcaa agaccccaac   1740
gagaagcgcg atcacatggt cctgctggag ttcgtgaccg ccgccgggat cactctcggc   1800
atggacgagc tgtacaagta agtcgacggc gcgccgcggc cgcgaattcg atatcataat   1860
caacctctgg attacaaaat ttgtgaaaga ttgactggta ttcttaacta tgttgctcct   1920
tttacgctat gtggatacgc tgctttaatg cctttgtatc atgctattgc ttcccgtatg   1980
gctttcattt tctcctcctt gtataaatcc tggttagttc ttgccacggc ggaactcatc   2040
gccgcctgcc ttgcccgctg ctggacaggg gctcggctgt tgggcactga caattccgtg   2100
gctcgagaga tcttcgactg tgccttctag ttgccagcca tctgttgttt gcccctcccc   2160
cgtgccttcc ttgaccctgg aaggtgccac tcccactgtc ctttcctaat aaaatgagga   2220
aattgcatcg cattgtctga gtaggtgtca ttctattctg gggggtgggg tggggcagga   2280
cagcaagggg gaggattggg aagacaatag caggcatgag atctcacgtg cggaccgagc   2340
ggccgc                                                             2346
```

<210> SEQ ID NO 76
<211> LENGTH: 1786
<212> TYPE: DNA
<213> ORGANISM: Artificial Sequence
<220> FEATURE:
<223> OTHER INFORMATION: CN2707

```
<400> SEQUENCE: 76
gcggccgcac gcgttgaatc ttcatggaga aaacatcatg aatagagaat gaagaagtaa        60
agatgaacaa gtgagaattc agatcatcag agggttttct aggatttctg taaatttctc       120
tgtgttttgg aatgcaatag gaatgccagc ccaaagccat ataggtcaca gctgcccaag       180
aacagttacc aatacagtat aaataacgtc ctaaacttag aatattgtga aattcttttt       240
ataactcagc catttaattc ttgagtgtaa attttgtaga tggagtcatg ttgtaatgtt       300
agacacattt gctagtgatg tgacaacata atattcccat gaactgatgt caaatgttgt       360
attgtacttt gaccaggtat ataaggttta ttatcttctt gaccttggag taatttcagt       420
cccaacttaa atccctagtg gtgagctcgg gctgggcata aaagtcaggg cagagccatc       480
tattgcttac atttgcttct gggatccaga tctttcgaag ctagcgctac cggtcgccac       540
catggtgagc aagggcgagg agctgttcac cggggtggtg cccatcctgg tcgagctgga       600
cggcgacgta aacggccaca gttcagcgt gtccggcgag ggcgagggcg atgccaccta       660
cggcaagctg accctgaagc tgatctgcac caccggcaag ctgcccgtgc cctggcccac       720
cctcgtgacc accctgggct acggcgtgca gtgcttcgcc cgctacccg accacatgaa       780 gcagcacgac ttcttcaagt ccgccatgcc cgaaggctac gtccaggagc gcaccatctt       840
cttcaaggac gacggcaact acaagacccg cgccgaggtg aagttcgagg gcgacaccct       900
ggtgaaccgc atcgagctga agggcatcga cttcaaggag gacggcaaca tcctggggca       960
caagctggag tacaactaca acagccacaa cgtctatatc accgccgaca gcagaagaa       1020 cggcatcaag gccaacttca gatccgcca aacatcgag gacggcggcg tgcagctcgc       1080
cgaccactac cagcagaaca ccccccatcgg cgacggcccc gtgctgctgc ccgacaacca       1140
ctacctgagc taccagtcca agctgagcaa agaccccaac gagaagcgcg atcacatggt       1200
cctgctggag ttcgtgaccg ccgccgggat cactctcggc atggacgagc tgtacaagta       1260
agtcgacggc gcgccgcggc cgcgaattcg atatcataat caacctctgg attacaaaat       1320
ttgtgaaaga ttgactggta ttcttaacta tgttgctcct tttacgctat gtggatacgc       1380
tgctttaatg cctttgtatc atgctattgc ttcccgtatg ctttcattt tctcctcctt       1440 gtataaatcc tggttagttc ttgccacggc ggaactcatc gccgcctgcc ttgcccgctg       1500
ctggacaggg gctcggctgt tgggcactga caattccgtg gctcgagaga tcttcgactg       1560
tgccttctag ttgccagcca tctgttgttt gcccctcccc cgtgccttcc ttgaccctgg       1620
aaggtgccac tcccactgtc ctttcctaat aaaatgagga aattgcatcg cattgtctga       1680
gtaggtgtca ttctattctg ggggtgggg tggggcagga cagcaagggg gaggattggg       1740
aagacaatag caggcatgag atctcacgtg cggaccgagc ggccgc                    1786

<210> SEQ ID NO 77
<211> LENGTH: 1710
<212> TYPE: DNA
<213> ORGANISM: Artificial Sequence
<220> FEATURE:
<223> OTHER INFORMATION: CN2713

<400> SEQUENCE: 77
gcggccgcac gcgttatgta gatacaggtc atagaacttg ccctggggaa tggctccatt        60
tggtaccaac aggctgaccc ctagggagga aggaaggcta tcagcaagag gaggaggagg       120
tagcagagat gagaaagatg gggtagactc tggctccaac ctagggaagg gaaagactct       180
agactcgggg gtatgggggt ggatagatac agggagcaca caggctactt ggcctggtct       240
```

-continued

```
gcccatgaat acagggggcc tctaacattg ctggggtagg agggtcagaa tgctccagtg     300
ctagccctca tgctggctca ggacaggact ctgaaaagcc accagctgcc actttcacaa     360
gctgaggagc tcgggctggg cataaaagtc agggcagagc catctattgc ttacatttgc     420
ttctgggatc cagatctttc gaagctagcg ctaccggtcg ccaccatggt gagcaagggc     480
gaggagctgt tcaccggggt ggtgcccatc ctggtcgagc tggacggcga cgtaaacggc     540
cacaagttca gcgtgtccgg cgagggcgag ggcgatgcca cctacggcaa gctgaccctg     600
aagctgatct gcaccaccgg caagctgccc gtgccctggc ccaccctcgt gaccaccctg     660
ggctacggcg tgcagtgctt cgcccgctac cccgaccaca tgaagcagca cgacttcttc     720
aagtccgcca tgcccgaagg ctacgtccag gagcgcacca tcttcttcaa ggacgacggc     780
aactacaaga cccgcgccga ggtgaagttc gagggcgaca ccctggtgaa ccgcatcgag     840
ctgaagggca tcgacttcaa ggaggacggc aacatcctgg ggcacaagct ggagtacaac     900
tacaacagcc acaacgtcta tatcaccgcc gacaagcaga gaaacggcat caaggccaac     960
ttcaagatcc gccacaacat cgaggacggc ggcgtgcagc tcgccgacca ctaccagcag    1020 aacacccca tcggcgacgg ccccgtgctg ctgcccgaca ccactacct gagctaccag    1080 tccaagctga gcaaagaccc caacgagaag cgcgatcaca tggtcctgct ggagttcgtg    1140
accgccgccg ggatcactct cggcatggac gagctgtaca agtaagtcga cggcgcgccg    1200
cggccgcgaa ttcgatatca taatcaacct ctggattaca aaatttgtga agattgact     1260 ggtattctta actatgttgc tccttttacg ctatgtggat acgctgcttt aatgcctttg    1320
tatcatgcta ttgcttcccg tatggctttc attttctcct ccttgtataa atcctggtta    1380
gttcttgcca cggcggaact catcgccgcc tgccttgccc gctgctggac aggggctcgg    1440
ctgttgggca ctgacaattc cgtggctcga gagatcttcg actgtgcctt ctagttgcca    1500
gccatctgtt gtttgcccct ccccgtgcc ttccttgacc ctggaaggtg ccactcccac    1560
tgtcctttcc taataaaatg aggaaattgc atcgcattgt ctgagtaggt gtcattctat    1620
tctggggggt ggggtggggc aggacagcaa gggggaggat tgggaagaca atagcaggca    1680
tgagatctca cgtgcggacc gagcggccgc                                     1710
```

```
<210> SEQ ID NO 78
<211> LENGTH: 1740
<212> TYPE: DNA
<213> ORGANISM: Artificial Sequence
<220> FEATURE:
<223> OTHER INFORMATION: CN2717

<400> SEQUENCE: 78
gcggccgcac gcgtagtgac ttggtgctat gagccatatt ttgctgttgc tgttgttact      60
ggtagttttt gtaattctgg ggctaaaact tggggtctgg tatgctgtca tttaccagtg     120 agctatacccc tggatattat gatttagatg aatgtgaaat atcaccccag acatacatat     180
actaaacact tggcccttgg cccatgatgc taaatggagg agatagaagc ttttggggca     240
cagcctagtg gaaggaaatg aggtcaaatg acatgtactc tgaaaggaat atgggtattc     300
tgggcttgcg ttattctctc tctccctctc tctccctctc tctccctctc cctctctctt     360 tctcctttc tctttctctc ctcgccttgt tttccagagc tcgggctggg cataaaagtc     420
agggcagagc catctattgc ttacatttgc ttctgggatc cagatctttc gaagctagcg     480
ctaccggtcg ccaccatggt gagcaagggc gaggagctgt tcaccggggt ggtgcccatc     540
```

-continued

```
ctggtcgagc tggacggcga cgtaaacggc cacaagttca gcgtgtccgg cgagggcgag      600
ggcgatgcca cctacggcaa gctgaccctg aagctgatct gcaccaccgg caagctgccc      660
gtgccctggc ccaccctcgt gaccaccctg ggctacggcg tgcagtgctt cgcccgctac      720
cccgaccaca tgaagcagca cgacttcttc aagtccgcca tgcccgaagg ctacgtccag      780
gagcgcacca tcttcttcaa ggacgacggc aactacaaga cccgcgccga ggtgaagttc      840
gagggcgaca ccctggtgaa ccgcatcgag ctgaagggca tcgacttcaa ggaggacggc      900
aacatcctgg ggcacaagct ggagtacaac tacaacagcc acaacgtcta tatcaccgcc      960
gacaagcaga agaacggcat caaggccaac ttcaagatcc gccacaacat cgaggacggc     1020
ggcgtgcagc tcgccgacca ctaccagcag aacacccca tcggcgacgg ccccgtgctg     1080
ctgcccgaca accactacct gagctaccag tccaagctga gcaaagaccc caacgagaag     1140
cgcgatcaca tggtcctgct ggagttcgtg accgccgccg ggatcactct cggcatggac     1200
gagctgtaca gtaagtcga cggcgcgccg cggccgcgaa ttcgatatca taatcaacct     1260
ctggattaca aaatttgtga agattgact ggtattctta actatgttgc tcctttacg     1320 ctatgtggat acgctgcttt aatgcctttg tatcatgcta ttgcttcccg tatggctttc     1380
attttctcct ccttgtataa atcctggtta gttcttgcca cggcggaact catcgccgcc     1440
tgccttgccc gctgctggac aggggctcgg ctgttgggca ctgacaattc cgtggctcga     1500
gagatcttcg actgtgcctt ctagttgcca gccatctgtt gtttgcccct cccccgtgcc     1560
ttccttgacc ctggaaggtg ccactcccac tgtcctttcc taataaaatg aggaaattgc     1620
atcgcattgt ctgagtaggt gtcattctat tctgggtggt ggggtggggc aggacagcaa     1680
gggggaggat tgggaagaca atagcaggca tgagatctca cgtgcggacc gagcggccgc     1740
```

```
<210> SEQ ID NO 79
<211> LENGTH: 3455
<212> TYPE: DNA
<213> ORGANISM: Artificial Sequence
<220> FEATURE:
<223> OTHER INFORMATION: AiP1104

<400> SEQUENCE: 79
```

```
gcggccgcac gcgttccagc taccaccagc ctgtccaaaa ggggacacca aaggagagga       60
ggaagtctga gagacacctc tctgcaccat ggccatctta gtagtcagac ccagaacaaa      120
actctctgat gagtgtgcgg agcgtcgctt ctggtctttg ctcaaactat tcactgaaga      180
tttaaagcaa tcccgtgagt gatacatttg ggtgaatttg ttctctagaa ggtatcacag      240
aaatctggtc actgggccac ccgagacatc ctgataggcc ctctggtaac ccatcacatg      300
ctgcagactg actctggggg cctagaaccc agatcagaag caaccttgac cccggcccac      360
ccgccacgga agcaccatca tctctctgat taaaaacctc gatcacggac ccggggggcgt      420 gcccggaaga gctaagataa tcagcgtcag cactttgcct tcgccgtcca agactgcaga      480
cggccttcat ttgacctgat tcgtggtgtt aatgacagca gagcaatttt gagaggcagc      540
ttgctctcgg catctataag gagaggaaaa gcactgaggg ctggggacca agctccttgc      600
agaggcggca gctgcagtca ccctccccct ccaccctgc ccctcccctc ccctccagag      660
gcactttgag taagtgctgc cctccgatct gccctgatac gatgggagaa agctgatgtg      720
agggctggag ccagagtgtg caaggggaca gtgtgtgcat gtgcgtgtgt cggggagagg      780
tacccgtgct atacctgaga acattgctgg gtgaacacag ccttggacct ggaagagcgc      840
atagcttact tagaggcatg ggctgcacat gagctgccca tttacctgct catttagaag      900
```

```
ctactatgaa ggctggtgag atggctgagc tcgggctggg cataaaagtc agggcagagc     960
catctattgc ttacatttgc ttctggcgtg gccaccatgg ctcctaagaa gaagaggaag    1020
gtgatgagcc agttcgacat cctgtgcaag accccccca  aggtgctggt gcggcagttc    1080
gtggagagat tcgagaggcc cagcggcgag aagatcgcca gctgtgccgc cgagctgacc    1140
tacctgtgct ggatgatcac ccacaacggc accgccatca agagggccac cttcatgagc    1200
tacaacacca tcatcagcaa cagcctgagc ttcgacatcg tgaacaagag cctgcagttc    1260
aagtacaaga cccagaaggc caccatcctg gaggccagcc tgaagaagct gatccccgcc    1320
tgggagttca ccatcatccc ttacaacggc cagaagcacc agagcgacat caccgacatc    1380
gtgtccagcc tgcagctgca gttcgagagc agcgaggagg ccgacaaggg caacagccac    1440
agcaagaaga tgctgaaggc cctgctgtcc gagggcgaga gcatctggga gatcaccgag    1500
aagatcctga acagcttcga gtacaccagc aggttcacca agaccaagac cctgtaccag    1560
ttcctgttcc tggccacatt catcaactgc ggcaggttca gcgacatcaa gaacgtggac    1620
cccaagagct tcaagctggt gcagaacaag tacctgggcg tgatcattca gtgcctggtg    1680
accgagacca agacaagcgt gtccaggcac atctacttt  tcagcgccag aggcaggatc    1740
gaccccctgg tgtacctgga cgagttcctg aggaacagcg agcccgtgct gaagagagtg    1800
aacaggaccg gcaacagcag cagcaacaag caggagtacc agctgctgaa ggacaacctg    1860
gtgcgcagct acaacaaggc cctgaagaag aacgcccct  accccatctt cgctatcaag    1920
aacgccccta agagccacat cggcaggcac ctgatgacca gctttctgag catgaagggc    1980
ctgaccgagc tgacaaacgt ggtgggcaac tggagcgaca agagggcctc cgccgtggcc    2040
aggaccacct acacccacca gatcaccgcc atccccgacc actacttcgc cctggtgtcc    2100
aggtactacg cctacgaccc catcagcaag gagatgatcg ccctgaagga cgagaccaac    2160
cccatcgagg agtggcagca catcgagcag ctgaagggca cgccgaggg  cagcatcaga    2220 tacccccgcct ggaacggcat catcagccag gaggtgctgg actacctgag cagctacatc    2280
aacaggcgga tctgagaatt cgatatcaag cttatcgata atcaacctct ggattacaaa    2340
atttgtgaaa gattgactgg tattcttaac tatgttgctc ctttacgct  atgtggatac    2400 gctgctttaa tgcctttgta tcatgctatt gcttcccgta tggctttcat tttctcctcc    2460
ttgtataaat cctggttgct gtctctttat gaggagttgt ggcccgttgt caggcaacgt    2520
ggcgtggtgt gcactgtgtt tgctgacgca accccactg  gttggggcat tgccaccacc    2580
tgtcagctcc tttccgggac tttcgctttc cccctcccta ttgccacggc ggaactcatc    2640
gccgcctgcc ttgcccgctg ctggacaggg gctcggctgt tgggcactga caattccgtg    2700
gtgttgtcgg ggaaatcatc gtcctttcct tggctgctcg cctatgttgc cacctggatt    2760
ctgcgcggga cgtccttctg ctacgtccct tcggccctca atccagcgga ccttccttcc    2820
cgcggcctgc tgccggctct gcggcctctt ccgcgtcttc gccttcgccc tcagacgagt    2880
cggatctccc tttgggccgc ctccccgcat cgataccgag cgctgctcga gagatctacg    2940
ggtggcatcc ctgtgacccc tccccagtgc ctctcctggc cctggaagtt gccactccag    3000
tgcccaccag ccttgtccta ataaaattaa gttgcatcat tttgtctgac taggtgtcct    3060
tctataatat tatggggtgg aggggggtgg tatggagcaa ggggcaagtt gggaagacaa    3120
cctgtagggc ctgcggggtc tattgggaac caagctggag tgcagtggca caatcttggc    3180
tcactgcaat ctccgcctcc tgggttcaag cgattctcct gcctcagcct cccgagttgt    3240
```

-continued

```
tgggattcca ggcatgcatg accaggctca gctaattttt gttttttttgg tagagacggg    3300 gtttcaccat attggccagg ctggtctcca actcctaatc tcaggtgatc tacccaccttt   3360 ggcctcccaa attgctggga ttacaggcgt gaaccactgc tcccttccct gtccttctga    3420
ttttgtaggt aaccacgtgc ggaccgagcg gccgc                               3455

<210> SEQ ID NO 80
<211> LENGTH: 3450
<212> TYPE: DNA
<213> ORGANISM: Artificial Sequence
<220> FEATURE:
<223> OTHER INFORMATION: AiP1089

<400> SEQUENCE: 80
gcggccgcac gcgtactatt ccagccacga ggtataaaca ctgggaagga aagtcctggc      60
tctgtattgt ccacaaagac ccgaagctgc agcaaagttg gcaaaagaga aacaaaaaga     120
gcagagaagg ctcagctttc aacagctagg ctcacccaaa catcaagagg tggacaaata     180
tttacagtgt gaaccttaac ccaaagaacg gcagtgcggt catgctgcac agagtcaact     240
tcagaaccaa gactgtgacc agggctggag caagagacac ttcacgctaa taaataggcc     300
acttaatcaa gaagctgtca cagtcctaaa tatgtatgca ccgagcatta gcacttccaa     360
gtagagtgga acagctaaag atagaggcaa gaagcaagca gacaaatctt cggtgattgt     420
tggaaatcac agcatttctc tcagcaattg tcaggacaca gaaaatcagc gagaagacag     480
aagagtctca caatagtccc catcaacttg acctaattga catttatgga gcttggcatc     540
caacagccgt ggagcgcatg cgctctttaa ggcagaatac agaccatcaa acaaaaccag     600
ggagaccaaa gtcacagaaa atatgctctg tgaacatgac ataataaagt ggaaatcgat     660
aacagagaga tcgctgcaaa atcccccaag tgattggtaa ttaaatgctc tactcctgaa     720
tgaatgatgg gcgagaaagg aaagccacgg gggaaagcag atttctgcgt tgaaagagca     780
tggagacaga cttcgtcaag atgagagagc acgtggggct ggagggatgg ctcagcactt     840
cagaggcact cacgctcttc cataggacct aggttcactt ctcagcacac acatggcaac     900
tcacacctgt gatgcagaga agagctcggg ctgggcataa aagtcagggc agagccatct     960
attgcttaca tttgcttctg gcgtggccac catggctcct aagaagaaga ggaaggtgat    1020
gagccagttc gacatcctgt gcaagacccc ccccaaggtg ctggtgcggc agttcgtgga    1080
gagattcgag aggcccagcg gcgagaagat cgccagctgt gccgccgagc tgacctacct    1140
gtgctggatg atcacccaca acggcaccgc catcaagagg gccaccttca tgagctacaa    1200
caccatcatc agcaacagcc tgagcttcga catcgtgaac aagagcctgc agttcaagta    1260
caagacccag aaggccacca tcctggagga cagcctgaag aagctgatcc ccgcctggga    1320
gttcaccatc atcccttaca cggccagaa gcaccagagc gacatcaccg acatcgtgtc    1380
cagcctgcag ctgcagttcg agagcagcga ggaggccgac aagggcaaca gccacagcaa    1440
gaagatgctg aaggccctgc tgtccgaggg cgagagcatc tgggagatca ccgagaagat    1500
cctgaacagc ttcgagtaca ccagcaggtt caccaagacc aagaccctgt accagttcct    1560
gttcctggcc acattcatca actgcggcag gttcagcgac atcaagaacg tggaccccaa    1620
gagcttcaag ctggtgcaga caagtacct gggcgtgatc attcagtgcc tggtgaccga    1680
gaccaagaca agcgtgtcca ggcacatcta cttttttcagc gccagaggca ggatcgaccc    1740
cctggtgtac ctggacgagt tcctgaggaa cagcgagccc gtgctgaaga gagtgaacag    1800
gaccggcaac agcagcagca acaagcagga gtaccagctg ctgaaggaca acctggtgcg    1860
```

```
cagctacaac aaggccctga agaagaacgc cccctacccc atcttcgcta tcaagaacgg   1920
ccctaagagc cacatcggca ggcacctgat gaccagcttt ctgagcatga agggcctgac   1980
cgagctgaca aacgtggtgg gcaactggag cgacaagagg gcctccgccg tggccaggac   2040
cacctacacc caccagatca ccgccatccc cgaccactac ttcgccctgg tgtccaggta   2100
ctacgcctac gaccccatca gcaaggagat gatcgccctg aaggacgaga ccaaccccat   2160
cgaggagtgg cagcacatcg agcagctgaa gggcagcgcc gagggcagca tcagatcccc   2220
cgcctggaac ggcatcatca gccaggaggt gctggactac ctgagcagct acatcaacag   2280
gcggatctga gaattcgata tcaagcttat cgataatcaa cctctggatt acaaaatttg   2340
tgaaagattg actggtattc ttaactatgt tgctcctttt acgctatgtg gatacgctgc   2400
tttaatgcct ttgtatcatg ctattgcttc ccgtatggct ttcattttct cctccttgta   2460
taaatcctgg ttgctgtctc tttatgagga gttgtggccc gttgtcaggc aacgtggcgt   2520
ggtgtgcact gtgtttgctg acgcaacccc cactggttgg ggcattgcca ccacctgtca   2580
gctcctttcc gggactttcg ctttcccact cctattgcc acggcggaac tcatcgccgc    2640
ctgccttgcc cgctgctgga caggggctcg gctgttgggc actgacaatt ccgtggtgtt   2700
gtcggggaaa tcatcgtcct tccttggct gctcgcctat gttgccacct ggattctgcg    2760
cgggacgtcc ttctgctacg tcccttcggc cctcaatcca gcggaccttc cttcccgcgg   2820
cctgctgccg gctctgcggc ctcttccgcg tcttcgcctt cgccctcaga cgagtcggat   2880
ctcccttggg gccgcctccc cgcatcgata ccgagcgctg ctcgagagat ctacgggtgg   2940
catccctgtg acccctcccc agtgcctctc ctggccctgg aagttgccac tccagtgccc   3000
accagccttg tcctaataaa attaagttgc atcattttgt ctgactaggt gtccttctat   3060
aatattatgg ggtggagggg ggtggtatgg agcaaggggc aagttgggaa gacaacctgt   3120
agggcctgcg gggtctattg ggaaccaagc tggagtgcag tggcacaatc ttggctcact   3180
gcaatctccg cctcctgggt tcaagcgatt ctcctgcctc agcctcccga gttgttggga   3240
ttccaggcat gcatgaccag gctcagctaa tttttgtttt tttggtagag acggggtttc   3300
accatattgg ccaggctggt ctccaactcc taatctcagg tgatctaccc accttggcct   3360
cccaaattgc tgggattaca ggcgtgaacc actgctccct tccctgtcct tctgattttg   3420
taggtaacca cgtgcggacc gagcggccgc                                   3450
```

```
<210> SEQ ID NO 81
<211> LENGTH: 3024
<212> TYPE: DNA
<213> ORGANISM: Artificial Sequence
<220> FEATURE:
<223> OTHER INFORMATION: AiP1105

<400> SEQUENCE: 81
gcggccgcac gcgtaccaga agttcagtga gcagaagatg ggctaaaatg aaaagggtac     60
tgtcttgaac tgaagatgga atcctgcagc ttcattctgg ccaaaagaag atctattccc   120
aggaggaggg taaaggcttt gttcttaaga gatgctgagg ctggccctgt gaatctgatg   180
tcaagatgtc ccttgtcact ctgcagaagc gtatgtctct tgcatttcct tcttatttcc   240
ttgggtgaaa ttgctgtggc attgtgtcac tcatcctaat gggtcatgtc taacatctgc   300
gtgcttacaa atcaggcatg ctcatttctg ggcttatgga gcttgtataa caccaggaca   360
ggcaagacat gttgcccact caggaagaat agaagctggg cacagctgga gtgcaaagta   420
```

-continued

```
ggtcagttca gagagcaaag ggagttgatg gagcaatgag ttgttagtgg gaaagttcta      480
accaactgtc ccagagagct cgggctgggc ataaaagtca gggcagagcc atctattgct      540
tacatttgct tctggcgtgg ccaccatggc tcctaagaag aagaggaagg tgatgagcca      600
gttcgacatc ctgtgcaaga cccccccaa ggtgctggtg cggcagttcg tggagagatt      660
cgagaggccc agcggcgaga agatcgccag ctgtgccgcc gagctgacct acctgtgctg      720
gatgatcacc cacaacggca ccgccatcaa gagggccacc ttcatgagct acaacaccat      780
catcagcaac agcctgagct tcgacatcgt gaacaagagc ctgcagttca agtacaagac      840
ccagaaggcc accatcctgg aggccagcct gaagaagctg atccccgcct gggagttcac      900
catcatccct tacaacggcc agaagcacca gagcgacatc accgacatcg tgtccagcct      960
gcagctgcag ttcgagagca gcgaggaggc cgacaagggc aacagccaca gcaagaagat     1020
gctgaaggcc ctgctgtccg agggcgagag catctgggag atcaccgaga agatcctgaa     1080
cagcttcgag tacaccagca ggttcaccaa gaccaagacc ctgtaccagt tcctgttcct     1140
ggccacattc atcaactgcg gcaggttcag cgacatcaag aacgtggacc ccaagagctt     1200
caagctggtg cagaacaagt acctgggcgt gatcattcag tgcctggtga ccgagaccaa     1260
gacaagcgtg tccaggcaca tctacttttt cagcgccaga ggcaggatcg accccctggt     1320
gtacctggac gagttcctga ggaacagcga gcccgtgctg aagagagtga acaggaccgg     1380
caacagcagc agcaacaagc aggagtacca gctgctgaag gacaacctgg tgcgcagcta     1440
caacaaggcc ctgaagaaga cgcccccta ccccatcttc gctatcaaga acggccctaa     1500
gagccacatc ggcaggcacc tgatgaccag ctttctgagc atgaagggcc tgaccgagct     1560
gacaaacgtg gtgggcaact ggagcgacaa gagggcctcc gccgtggcca ggaccaccta     1620
cacccaccag atcaccgcca tccccgacca ctacttcgcc ctggtgtcca ggtactacgc     1680
ctacgacccc atcagcaagg agatgatcgc cctgaaggac gagaccaacc ccatcgagga     1740
gtggcagcac atcgagcagc tgaagggcag cgccgagggc agcatcagat accccgcctg     1800
gaacggcatc atcagccagg aggtgctgga ctacctgagc agctacatca caggcggat     1860 ctgagaattc gatatcaagc ttatcgataa tcaacctctg gattacaaaa tttgtgaaag     1920
attgactggt attcttaact atgttgctcc ttttacgcta tgtggatacg ctgctttaat     1980
gcctttgtat catgctattg cttcccgtat ggctttcatt ttctcctcct tgtataaatc     2040
ctggttgctg tctctttatg aggagttgtg gcccgttgtc aggcaacgtg gcgtggtgtg     2100
cactgtgttt gctgacgcaa cccccactgg ttggggcatt gccaccacct gtcagctcct     2160
ttccgggact ttcgctttcc ccctccctat tgccacggcg gaactcatcg ccgcctgcct     2220
tgcccgctgc tggacagggg ctcggctgtt gggcactgac aattccgtgg tgttgtcggg     2280
gaaatcatcg tcctttcctt ggctgctcgc ctatgttgcc acctggattc tgcgcgggac     2340
gtccttctgc tacgtccctt cggccctcaa tccagcggac cttccttccc gcggcctgct     2400
gccggctctg cggcctcttc cgcgtcttcg ccttcgccct cagacgagtc ggatctcct     2460 ttgggccgcc tccccgcatc gataccgagc gctgctcgag agatctacgg gtggcatccc     2520
tgtgacccct ccccagtgcc tctcctggcc ctggaagttg ccactccagt gcccaccagc     2580
cttgtcctaa taaaattaag ttgcatcatt ttgtctgact aggtgtcctt ctataatatt     2640
atggggtgga ggggggtggt atggagcaag ggcaagttg ggaagacaac ctgtagggcc     2700
tgcggggtct attgggaacc aagctggagt gcagtggcac aatcttggct cactgcaatc     2760
tccgcctcct gggttcaagc gattctcctg cctcagcctc ccgagttgtt gggattccag     2820
```

-continued

```
gcatgcatga ccaggctcag ctaatttttg tttttttggt agagacgggg tttcaccata    2880
ttggccaggc tggtctccaa ctcctaatct caggtgatct acccaccttg gcctcccaaa    2940
ttgctgggat tacaggcgtg aaccactgct cccttccctg tccttctgat tttgtaggta    3000
accacgtgcg gaccgagcgg ccgc                                          3024

<210> SEQ ID NO 82
<211> LENGTH: 3533
<212> TYPE: DNA
<213> ORGANISM: Artificial Sequence
<220> FEATURE:
<223> OTHER INFORMATION: AiP1090

<400> SEQUENCE: 82
gcggccgcac gcgttgtctt agactgagtt gctgtaacaa aaatctggga tgaggtcatt      60
tctaaagcac agcaatttat ttcccacagt ctgaaggctg cagattccaa gatcactggc     120
aagatcagtt gtaaaggctt cgtcctccag aggcggggat gctgcatact ccctgggcag     180
agagacagga aaactccgta actgcatgtg tccttcctga tgcctcttct atataggcct     240
ggatcccaat caccctgtga acctctccct gcttcgtggc ccccacctct taacactacc     300
acattggcaa ctcctgaaat ttgaagggga cacactgaac catggcacaa cagctttctg     360
actgatgcag taacccaatg gcagtgcaga aggggccagc taaaagccca aatggttagc     420
tcaaaattcg ctgtctcttc cgagtgtctg aacccttagt cctggtatgt aaagacatca     480
gaacatttcc ccttgtgtcc atcagatttc tgtctagtga aacgatgaca ctgtaacctc     540
caagatctca cacgaaatga tcttttctcc tttgtggaag gaaaccagca tttagctcat     600
ctctccttcg tagcagctca gaatgtccac agtgacccag ttaccatagc taaaggcttc     660
cttttcaaaa cacagagcag aggcagccaa ttcagtatgt gctgctgcca tcctctgatt     720
ctttcctgct tccatagaca ccaactctat tgtaactaag ccttatacat tgtgtcttcc     780
tcctttacat tagcttgtgc tggggtggtt catgaggccc gctgagtagt ttcagtgaca     840
gcctatccct ctgccagtgc tgctttgagc catcttattg gtgaggctgt aagagaagcc     900
tgaagtcaca gggtaaagct atgttgaagg cagccccaga accaagtttc cctatttcta     960
tctccttacg ctgtttgagc ctcaggggta gatcaggtgc ctgtgagctc gggctgggca    1020
taaaagtcag ggcagagcca tctattgctt acatttgctt ctggcgtggc caccatggct    1080
cctaagaaga gaggaaggt gatgagccag ttcgacatcc tgtgcaagac ccccccaag     1140 gtgctggtgc ggcagttcgt ggagagattc gagaggccca gcggcgagaa gatcgccagc    1200
tgtgccgccg agctgaccta cctgtgctgg atgatcaccc acaacggcac cgccatcaag    1260
agggccacct tcatgagcta caacaccatc atcagcaaca gcctgagctt cgacatcgtg    1320
aacaagagcc tgcagttcaa gtacaagacc cagaaggcca ccatcctgga ggccagcctg    1380
aagaagctga tccccgcctg ggagttcacc atcatccctt acaacggcca gaagcaccag    1440
agcgacatca ccgacatcgt gtccagcctg cagctgcagt tcgagagcag cgaggaggcc    1500
gacaagggca acagccacag caagaagatg ctgaaggccc tgctgtccga gggcgagagc    1560
atctgggaga tcaccgagaa gatcctgaac agcttcgagt acaccagcag gttcaccaag    1620
accaagaccc tgtaccagtt cctgttcctg gccacattca tcaactgcgg caggttcagc    1680
gacatcaaga cgtggacccc caagagcttc aagctggtgc agaacaagta cctgggcgtg    1740
atcattcagt gcctggtgac cgagaccaag acaagcgtgt ccaggcacat ctactttttc    1800
```

-continued

```
agcgccagag gcaggatcga ccccctggtg tacctggacg agttcctgag gaacagcgag    1860
cccgtgctga agagagtgaa caggaccggc aacagcagca gcaacaagca ggagtaccag    1920
ctgctgaagg acaacctggt gcgcagctac aacaaggccc tgaagaagaa cgccccctac    1980
cccatcttcg ctatcaagaa cggccctaag agccacatcg gcaggcacct gatgaccagc    2040
tttctgagca tgaagggcct gaccgagctg acaaacgtgg tgggcaactg gagcgacaag    2100
agggcctccg ccgtggccag gaccacctac acccaccaga tcaccgccat ccccgaccac    2160
tacttcgccc tggtgtccag gtactacgcc tacgacccca tcagcaagga gatgatcgcc    2220
ctgaaggacg agaccaaccc catcgaggag tggcagcaca tcgagcagct gaagggcagc    2280
gccgagggca gcatcagata ccccgcctgg aacggcatca tcagccagga ggtgctggac    2340
tacctgagca gctacatcaa caggcggatc tgagaattcg atatcaagct tatcgataat    2400
caacctctgg attacaaaat ttgtgaaaga ttgactggta ttcttaacta tgttgctcct    2460
tttacgctat gtggatacgc tgctttaatg cctttgtatc atgctattgc ttcccgtatg    2520
gctttcattt tctcctcctt gtataaatcc tggttgctgt ctctttatga ggagttgtgg    2580
cccgttgtca ggcaacgtgg cgtggtgtgc actgtgtttg ctgacgcaac ccccactggt    2640
tggggcattg ccaccacctg tcagctcctt ccgggacttt cgctttccc cctccctatt    2700 gccacggcgg aactcatcgc cgcctgcctt gcccgctgct ggacaggggc tcggctgttg    2760
ggcactgaca attccgtggt gttgtcgggg aaatcatcgt cctttccttg gctgctcgcc    2820
tatgttgcca cctggattct gcgcgggacg tccttctgct acgtcccttc ggccctcaat    2880
ccagcggacc ttccttcccg cggcctgctg ccggctctgc ggcctcttcc gcgtcttcgc    2940
cttcgccctc agacgagtcg gatctccctt tgggccgcct ccccgcatcg ataccgagcg    3000
ctgctcgaga gatctacggg tggcatccct gtgacccctc cccagtgcct cctggccc     3060 tggaagttgc cactccagtg cccaccagcc ttgtcctaat aaaattaagt tgcatcattt    3120
tgtctgacta ggtgtccttc tataatatta tggggtggag gggggtggta tggagcaagg    3180
ggcaagttgg gaagacaacc tgtagggcct gcggggtcta ttgggaacca agctggagtg    3240
cagtggcaca tcttggctc actgcaatct ccgcctcctg ggttcaagcg attctcctgc    3300
ctcagcctcc cgagttgttg ggattccagg catgcatgac caggctcagc taatttttgt    3360
ttttttggta gagacggggt ttcaccatat tggccaggct ggtctccaac tcctaatctc    3420
aggtgatcta cccaccttgg cctcccaaat tgctgggatt acaggcgtga accactgctc    3480
ccttccctgt ccttctgatt ttgtaggtaa ccacgtgcgg accgagcggc cgc           3533
```

<210> SEQ ID NO 83
<211> LENGTH: 3409
<212> TYPE: DNA
<213> ORGANISM: Artificial Sequence
<220> FEATURE:
<223> OTHER INFORMATION: AiP1106

<400> SEQUENCE: 83

```
gcggccgcac gcgtagatga gtctgcagct gggtacagtg acctttcagt ccatgtttat      60
ttggaaatga cctttaagca gcaatcagca agaataaaat gcttcaaagg aatacattag     120
ataatgcaga agtcccccag aggtaagtta cacccaaggc acccagctga caatgaaagt     180
ggccctgccc tgggaagcca aggactaggc cacccattag actaacaagt gaacacaggg     240
tccccagagt ttggtctaat agacaatggg gagtctgaag acagggtgac ctgggcaaga     300
cacaagagca gttccaaaat taaacctctg tcgtaatgaa ggatgcctag ttgtgctttt     360
```

-continued

```
tccatcctag gatggggaat cctcaagggc agggcacagc tgtgccaggg gaactgtacg    420
ggctccatcc tgcctccctc ccatggggtg agctgatagt cttcctcata ctgagctctt    480
gtctctgctg tgtgctgggg agtctgaaat gctagagaaa ctaagccttc ccactcaaag    540
acagagaaag agctggccca tggctccgtg ccctctcctc tctctgtgcg tgtctttaac    600
tctgtatgtt ctattttccc cctcctcgtc ccctgcttcg cgctcacaga gtcactccta    660
gtagcaccaa agagagatgc ttggcagttc actaacccct tgagctgaaa tagaaataaa    720
tatcccaaaa gagaaatcag aaaagcaggg tgtcgcgctg gagaagaggc aggaagatca    780
gaaatacaag gtcatctgtg gctacacatc tagtccaagt cccagcctgg gctatgtgag    840
atggagggga atcgctcaga aacaaggctg tacacttaag gagctcgggc tgggcataaa    900
agtcagggca gagccatcta ttgcttacat ttgcttctgg cgtggccacc atggctccta    960
agaagaagag gaaggtgatg agccagttcg acatcctgtg caagacccccc cccaaggtgc   1020 tggtgcggca gttcgtggag agattcgaga ggcccagcgg cgagaagatc gccagctgtg   1080
ccgccgagct gacctacctg tgctggatga tcacccacaa cggcaccgcc atcaagaggg   1140
ccaccttcat gagctacaac accatcatca gcaacagcct gagcttcgac atcgtgaaca   1200
agagcctgca gttcaagtac aagacccaga aggccaccat cctggaggcc agcctgaaga   1260
agctgatccc cgcctgggag ttcaccatca tcccttacaa cggccagaag caccagagcg   1320
acatcaccga catcgtgtcc agcctgcagc tgcagttcga gagcagcgag gaggccgaca   1380
agggcaacag ccacagcaag aagatgctga aggccctgct gtccgagggc gagagcatct   1440
gggagatcac cgagaagatc ctgaacagct tcgagtacac cagcaggttc accaagacca   1500
agaccctgta ccagttcctg ttcctggcca cattcatcaa ctgcggcagg ttcagcgaca   1560
tcaagaacgt ggaccccaag agcttcaagc tggtgcagaa caagtacctg ggcgtgatca   1620
ttcagtgcct ggtgaccgag accaagacaa gcgtgtccag gcacatctac ttttttcagcg   1680 ccagaggcag gatcgacccc ctggtgtacc tggacgagtt cctgaggaac agcgagcccg   1740
tgctgaagag agtgaacagg accggcaaca gcagcagcaa caagcaggag taccagctgc   1800
tgaaggacaa cctggtgcgc agctacaaca aggccctgaa gaagaacgcc ccctacccca   1860
tcttcgctat caagaacggc cctaagagcc acatcggcag gcacctgatg accagctttc   1920
tgagcatgaa gggcctgacc gagctgacaa acgtggtggg caactggagc gacaagaggg   1980
cctccgccgt ggccaggacc acctacaccc accagatcac cgccatcccc gaccactact   2040
tcgccctggt gtccaggtac tacgcctacg accccatcag caaggagatg atcgccctga   2100
aggacgagac caaccccatc gaggagtggc agcacatcga gcagctgaag ggcagcgccg   2160
agggcagcat cagataccccc gcctggaacg gcatcatcag ccaggaggtg ctggactacc   2220
tgagcagcta catcaacagg cggatctgag aattcgatat caagcttatc gataatcaac   2280
ctctggatta caaaatttgt gaaagattga ctggtattct taactatgtt gctcctttta   2340
cgctatgtgg atacgctgct ttaatgcctt tgtatcatgc tattgcttcc cgtatggctt   2400
tcattttctc ctccttgtat aaatcctggt tgctgtctct ttatgaggag ttgtggcccg   2460
ttgtcaggca acgtggcgtg gtgtgcactg tgtttgctga cgcaaccccc actggttggg   2520
gcattgccac cacctgtcag ctcctttccg ggactttcgc tttccccctc cctattgcca   2580
cggcggaact catcgccgcc tgccttgccc gctgctggac aggggctcgg ctgttgggca   2640
ctgacaattc cgtggtgttg tcggggaaat catcgtcctt ccttggctg ctcgcctatg   2700
```

```
ttgccacctg gattctgcgc gggacgtcct tctgctacgt cccttcggcc ctcaatccag       2760
cggaccttcc ttcccgcggc ctgctgccgg ctctgcggcc tcttccgcgt cttcgccttc       2820
gccctcagac gagtcggatc tccctttggg ccgcctcccc gcatcgatac cgagcgctgc       2880
tcgagagatc tacgggtggc atccctgtga cccctcccca gtgcctctcc tggccctgga       2940
agttgccact ccagtgccca ccagccttgt cctaataaaa ttaagttgca tcattttgtc       3000
tgactaggtg tccttctata atattatggg gtggaggggg gtggtatgga gcaaggggca       3060
agttgggaag acaacctgta gggcctgcgg ggtctattgg gaaccaagct ggagtgcagt       3120
ggcacaatct tggctcactg caatctccgc ctcctgggtt caagcgattc tcctgcctca       3180
gcctcccgag ttgttgggat tccaggcatg catgaccagg ctcagctaat ttttgttttt       3240
ttggtagaga cggggtttca ccatattggc caggctggtc tccaactcct aatctcaggt       3300
gatctaccca ccttggcctc ccaaattgct gggattacag gcgtgaacca ctgctccctt       3360
ccctgtcctt ctgattttgt aggtaaccac gtgcggaccg agcggccgc                  3409
```

<210> SEQ ID NO 84
<211> LENGTH: 3320
<212> TYPE: DNA
<213> ORGANISM: Artificial Sequence
<220> FEATURE:
<223> OTHER INFORMATION: AiP1091

<400> SEQUENCE: 84

```
gcggccgcac gcgtttcacc cacctgacac ttgggttaga cctgaatgtc gtttctttaa        60
ctcacactgc tcatcccact ggcctttgct gtgcttctct gtgcctcctc agagatacat       120
gaaactgtcc catcccccta acgatgctgg atggatggct ccaacagctc actgctctca       180
ccttgacaca aagtcctagc gtctgcatct gtgagacaag ttggaattta tatatttcca       240
gtggagatta ataattcatt agatgctgaa gtagaaaaac aaagtaccga ttaatcaagg       300
ctctgctgag gcctgctttg cagccaccag tctgtgggga ttggcagtgc ttttacactg       360
gaagtaggtc aggaccacag aaaagcagct ctcatgcact agcatctgtt cgcactaatc       420
actgtacaca gctttgggtc ttactatagt ttttattagt tatcccagct gggatttatg       480
tctcaggaat aaagagccaa gaatgggagg agttaccctc gaaagatcca ggtcatgtgg       540
tgcagggcag ggaatatggc tgactcaatc tctttgccca tagagcctca gagtatcaga       600
tcttagcact ctaaggaggg agactcagag ggtacaagtc ttagaagtct ccctagggct       660
tggtgcccag caaatatatg ctgtttgtga cttccctaat accaggtaca ggccaacaca       720
aaggacctgt ccaagggaaa ctcacggctc agacctgatc tatttacagg ttgagtttgg       780
gtgaagccaa gagagctcgg gctgggcata aaagtcaggg cagagccatc tattgcttac       840
atttgcttct ggcgtggcca ccatggctcc taagaagaag aggaaggtga tgagccagtt       900
cgacatcctg tgcaagaccc cccccaaggt gctggtgcgg cagttcgtgg agagattcga       960
gaggcccagc ggcgagaaga tcgccagctg tgccgccgag ctgacctacc tgtgctggat      1020
gatcacccac aacggcaccg ccatcaagag ggccaccttc atgagctaca acaccatcat      1080
cagcaacagc ctgagcttcg acatcgtgaa caagagcctg cagttcaagt acaagaccca      1140
gaaggccacc atcctggagg ccagcctgaa gaagctgatc cccgcctggg agttcaccat      1200
catcccttac aacggccaga agcaccagag cgacatcacc gacatcgtgt ccagcctgca      1260
gctgcagttc gagagcagcg aggaggccga caagggcaac agccacagca agaagatgct      1320
gaaggccctg ctgtccgagg gcgagagcat ctgggagatc accgagaaga tcctgaacag      1380
```

-continued

```
cttcgagtac accagcaggt tcaccaagac caagaccctg taccagttcc tgttcctggc       1440
cacattcatc aactgcggca ggttcagcga catcaagaac gtggacccca agagcttcaa       1500
gctggtgcag aacaagtacc tgggcgtgat cattcagtgc ctggtgaccg agaccaagac       1560
aagcgtgtcc aggcacatct actttttcag cgccagaggc aggatcgacc ccctggtgta       1620
cctggacgag ttcctgagga acagcgagcc cgtgctgaag agagtgaaca ggaccggcaa       1680
cagcagcagc aacaagcagg agtaccagct gctgaaggac aacctggtgc gcagctacaa       1740
caaggccctg aagaagaacg cccctaccc catcttcgct atcaagaacg ccctaagag        1800 ccacatcggc aggcacctga tgaccagctt tctgagcatg aagggcctga ccgagctgac      1860
aaacgtggtg ggcaactgga gcgacaagag ggcctccgcc gtggccagga ccacctacac      1920
ccaccagatc accgccatcc ccgaccacta cttcgccctg gtgtccaggt actacgccta      1980
cgaccccatc agcaaggaga tgatcgccct gaaggacgag accaacccca tcgaggagtg      2040
gcagcacatc gagcagctga agggcagcgc cgagggcagc atcagatacc ccgcctggaa      2100
cggcatcatc agccaggagg tgctggacta cctgagcagc tacatcaaca ggcggatctg      2160
agaattcgat atcaagctta tcgataatca acctctggat tacaaaattt gtgaaagatt     2220
gactggtatt cttaactatg ttgctccttt tacgctatgt ggatacgctg ctttaatgcc     2280
tttgtatcat gctattgctt cccgtatggc tttcattttc tcctccttgt ataaatcctg     2340
gttgctgtct ctttatgagg agttgtggcc cgttgtcagg caacgtggcg tggtgtgcac     2400
tgtgtttgct gacgcaaccc ccactggttg gggcattgcc accacctgtc agctcctttc     2460
cgggactttc gctttccccc tccctattgc cacggcggaa ctcatcgccg cctgccttgc     2520
ccgctgctgg acaggggctc ggctgttggg cactgacaat tccgtggtgt tgtcggggaa     2580
atcatcgtcc tttccttggc tgctcgccta tgttgccacc tggattctgc gcgggacgtc     2640
cttctgctac gtcccttcgg ccctcaatcc agcggacctt ccttcccgcg gcctgctgcc     2700
ggctctgcgg cctcttccgc gtcttcgcct tcgccctcag acgagtcgga tctccctttg     2760
ggccgcctcc ccgcatcgat accgagcgct gctcgagaga tctacgggtg gcatccctgt     2820
gacccctccc cagtgcctct cctggccctg gaagttgcca ctccagtgcc caccagcctt     2880
gtcctaataa aattaagttg catcattttg tctgactagg tgtccttcta taatattatg     2940
gggtggaggg gggtggtatg gagcaagggg caagttggga agacaacctg tagggcctgc     3000
ggggtctatt gggaaccaag ctggagtgca gtggcacaat cttggctcac tgcaatctcc     3060
gcctcctggg ttcaagcgat tctcctgcct cagcctcccg agttgttggg attccaggca     3120
tgcatgacca ggctcagcta attttgtttt tttggtaga gacggggttt caccatattg     3180
gccaggctgg tctccaactc ctaatctcag gtgatctacc caccttggcc tcccaaattg     3240
ctgggattac aggcgtgaac cactgctccc ttccctgtcc ttctgatttt gtaggtaacc     3300
acgtgcggac cgagcggccg                                                 3320
```

<210> SEQ ID NO 85
<211> LENGTH: 3092
<212> TYPE: DNA
<213> ORGANISM: Artificial Sequence
<220> FEATURE:
<223> OTHER INFORMATION: AiP1092

<400> SEQUENCE: 85

```
gcggccgcac gcgtatccct ggagatgagg agtcctctct ggcagggtcc cctcactcta        60
```

-continued

```
gagcagcccc tatcccaggc cccctaggag tctctaatta aagggccggc acgcccctct      120
gggactcatt aggcccgctg tgcagagaac atttaatcat tgctcagagc atcgattgga      180
aaatcaattt ctttgtctct tcgcacgagg cgcgctggag aagtggggggg agtgctgacc     240 tccttctgct gccgtgtaaa gcgctgcaca tttaatcagg gaacagaaat caattagcca      300
cttacgaggt tggctttagt taccgagtcg gcaaggcccg cgccacagct cagccgctga      360
cagtagcgaa tctcctcctc tcggccctgc tgcatggctc tgtctccctc cctgtatctc      420
tctggcttcc ttctttccca gagtgctctg ggttctcacc atcttggcag atcctcacag      480
aactccaaac aagtcccgag aagccttcct aatgcccagt ctcctcggcc accttcttgt      540
tctcagctct agacgtttca agagagctcg ggctgggcat aaaagtcagg gcagagccat      600
ctattgctta catttgcttc tggcgtggcc accatggctc ctaagaagaa gaggaaggtg      660
atgagccagt tcgacatcct gtgcaagacc ccccccaagg tgctggtgcg gcagttcgtg      720
gagagattcg agaggcccag cggcgagaag atcgccagct gtgccgccga gctgacctac      780
ctgtgctgga tgatcaccca caacggcacc gccatcaaga gggccacctt catgagctac      840
aacaccatca tcagcaacag cctgagcttc gacatcgtga acaagagcct gcagttcaag      900
tacaagaccc agaaggccac catcctggag gccagcctga agaagctgat ccccgcctgg      960
gagttcacca tcatcccctta caacggccag aagcaccaga gcgacatcac cgacatcgtg     1020
tccagcctgc agctgcagtt cgagagcagc gaggaggccg acaagggcaa cagccacagc     1080
aagaagatgc tgaaggccct gctgtccgag ggcgagagca tctgggagat caccgagaag     1140
atcctgaaca gcttcgagta caccagcagg ttcaccaaga ccaagaccct gtaccagttc     1200
ctgttcctgg ccacattcat caactgcggc aggttcagcg acatcaagaa cgtggacccc     1260
aagagcttca gctggtgca gaacaagtac ctgggcgtga tcattcagtg cctggtgacc     1320
gagaccaaga caagcgtgtc caggcacatc tacttttttca gcgccagagg caggatcgac     1380
cccctggtgt acctggacga gttcctgagg aacagcgagc ccgtgctgaa gagagtgaac     1440
aggaccggca acagcagcag caacaagcag gagtaccagc tgctgaagga caacctggtg     1500
cgcagctaca caaggccct gaagaagaac gccccctacc ccatcttcgc tatcaagaac      1560
ggccctaaga gccacatcgg caggcacctg atgaccagct ttctgagcat gaagggcctg     1620
accgagctga caaacgtggt gggcaactgg agcgacaaga gggcctccgc cgtggccagg     1680
accacctaca cccaccagat caccgccatc cccgaccact acttcgccct ggtgtccagg     1740
tactacgcct acgaccccat cagcaaggag atgatcgccc tgaaggacga gaccaacccc     1800
atcgaggagt ggcagcacat cgagcagctg aagggcagcg ccgagggcag catcagatac     1860
cccgcctgga acggcatcat cagccaggag gtgctggact acctgagcag ctacatcaac     1920
aggcggatct gagaattcga tatcaagctt atcgataatc aacctctgga ttacaaaatt     1980
tgtgaaagat tgactggtat tcttaactat gttgctcctt ttacgctatg tggatacgct     2040
gctttaatgc ctttgtatca tgctattgct tcccgtatgg ctttcatttt ctcctccttg     2100
tataaatcct ggttgctgtc tctttatgag gagttgtggc ccgttgtcag gcaacgtggc     2160
gtggtgtgca ctgtgtttgc tgacgcaacc cccactggtt ggggcattgc caccacctgt     2220
cagctccttt ccgggacttt cgctttcccc ctccctattg ccacggcgga actcatcgcc     2280
gcctgccttg cccgctgctg gacaggggct cggctgttgg gcactgacaa ttccgtggtg     2340
ttgtcgggga aatcatcgtc ctttccttgg ctgctcgcct atgttgccac ctggattctg     2400
cgcgggacgt ccttctgcta cgtcccttcg gccctcaatc cagcggacct tccttcccgc     2460
```

```
ggcctgctgc cggctctgcg gcctcttccg cgtcttcgcc ttcgccctca gacgagtcgg     2520
atctcccttt gggccgcctc cccgcatcga taccgagcgc tgctcgagag atctacgggt     2580
ggcatccctg tgacccctcc ccagtgcctc tcctggccct ggaagttgcc actccagtgc     2640
ccaccagcct tgtcctaata aaattaagtt gcatcatttt gtctgactag gtgtccttct     2700
ataatattat ggggtggagg ggggtggtat ggagcaaggg gcaagttggg aagacaacct     2760
gtagggcctg cggggtctat tgggaaccaa gctggagtgc agtggcacaa tcttggctca     2820
ctgcaatctc cgcctcctgg gttcaagcga ttctcctgcc tcagcctccc gagttgttgg     2880
gattccaggc atgcatgacc aggctcagct aattttttgtt tttttggtag agacggggtt     2940
tcaccatatt ggccaggctg tctccaact cctaatctca ggtgatctac ccaccttggc     3000
ctcccaaatt gctgggatta caggcgtgaa ccactgctcc cttccctgtc cttctgattt     3060
tgtaggtaac cacgtgcgga ccgagcggcc gc     3092
```

<210> SEQ ID NO 86
<211> LENGTH: 2307
<212> TYPE: DNA
<213> ORGANISM: Artificial Sequence
<220> FEATURE:
<223> OTHER INFORMATION: CN2581

<400> SEQUENCE: 86

```
gcggccgcac gcgttatgat gtgccaggct tgggagaaac accacaagca aagccaaaat      60
aggtggccta gaacttccag cttgaaatat gggagagaat gagggaggca ctgtagagca     120
gctgccgggt gccgcatgag aacaattctc cctgctcata attaatccta cctatttctg     180 atgcagctg gctcttcact ttgaacaagc tagttaacaa ctttcttctc acattgagca     240
aataattcat atttaattac ttaaccacca gttacaaat gagaatcatc aaggaatcac     300
aattaatttg ctattgacaa actcatactt ttagcaggct gatttctact ttatacttag     360
attggtaatg aaaaatgaag cttattttag ttgattggtt ggacttgtgt atgaatatta     420
tctattattt gaaaagccaa acttgaatgc aaaaaaatat tgaatatgaa aagaaaaaca     480
tttgcagtaa agcttgttct gagctcgatt cagccgggag cttagggagg ggaggtcact     540
tcataagggc ttggggggggg agttggagcc acgagtcgtc cagccggagc cccgtgtggc     600
tgtgctccgg cctcagaagc atccccggat ccttcgaagc tagcgctacc ggtcgccacc     660
atggtgagca agggcgagga gctgttcacc ggggtggtgc ccatcctggt cgagctggac     720
ggcgacgtaa acggccacaa gttcagcgtg tccggcgagg gcgagggcga tgccacctac     780
ggcaagctga ccctgaagct gatctgcacc accggcaagc tgcccgtgcc ctggcccacc     840
ctcgtgacca ccctgggcta cggcgtgcag tgcttcgccc gctaccccga ccacatgaag     900
cagcacgact tcttcaagtc cgccatgccc gaaggctacg tccaggagcg caccatcttc     960
ttcaaggacg acggcaacta caagacccgc gccgaggtga agttcgaggg cgacaccctg    1020
gtgaaccgca tcgagctgaa gggcatcgac ttcaaggagg acggcaacat cctggggcac    1080
aagctggagt acaactacaa cagccacaac gtctatatca ccgccgacaa gcagaagaac    1140
ggcatcaagg ccaacttcaa gatccgccac aacatcgagg acggcggcgt gcagctcgcc    1200
gaccactacc agcagaacac ccccatcggc gacggccccg tgctgctgcc cgacaaccac    1260
tacctgagct accagtccaa gctgagcaaa gaccccaacg agaagcgcga tcacatggtc    1320
ctgctggagt tcgtgaccgc cgccgggatc actctcggca tggacgagct gtacaagtcc    1380
```

```
ggactcagat ctggaggctc cggaggccca gagccagcga agtctgctcc cgccccgaaa    1440
aagggctcca agaaggcggt gactaaggcg cagaagaaag gcggcaagaa gcgcaagcgc    1500
agccgcaagg agagctattc catctatgtg tataaggttc tgaagcaggt ccaccctgac    1560
accggcattt cgtccaaggc catgggcatc atgaactcgt ttgtgaacga cattttcgag    1620
cgcatcgcag gtgaggcttc ccgcctggcg cattacaaca agcgctcgac catcacctcc    1680
agggagatcc agacggccgt gcgcctgctg ctgcctgggg agttggccaa gcacgccgtg    1740
tccgagggta ctaaggccat caccaagtac accagcgcta agtaatgagt cgacggcgcg    1800
cccctgcagg gaattcgata tcataatcaa cctctggatt acaaaatttg tgaaagattg    1860
actggtattc ttaactatgt tgctcctttt acgctatgtg gatacgctgc tttaatgcct    1920
ttgtatcatg ctattgcttc ccgtatggct ttcattttct cctccttgta taaatcctgg    1980
ttagttcttg ccacggcgga actcatcgcc gcctgccttg cccgctgctg gacaggggct    2040
cggctgttgg gcactgacaa ttccgtggct cgagagatct tcgactgtgc cttctagttg    2100
ccagccatct gttgtttgcc cctcccccgt gccttccttg accctggaag gtgccactcc    2160
cactgtcctt tcctaataaa atgaggaaat tgcatcgcat tgtctgagta ggtgtcattc    2220
tattctgggg ggtggggtgg ggcaggacag caagggggag gattgggaag acaatagcag    2280
gcatgcacgt gcggaccgag cggccgc                                       2307
```

<210> SEQ ID NO 87
<211> LENGTH: 2675
<212> TYPE: DNA
<213> ORGANISM: Artificial Sequence
<220> FEATURE:
<223> OTHER INFORMATION: CN2782

<400> SEQUENCE: 87

```
gcggccgcac gcgtagaaac accacaagca aagccaaaat aggtggccta gaacttccag      60
cttgaaatat gggagagaat gagggaggca ctgtagagca gctgccgggt gccgcatgag     120
aacaattctc cctgctcata attaatccta cctatttctg atgacagctg gctcttcact     180
ttgaacaagc tagttaacaa ctttcttctc acattgagca ataattcat atttaattac     240 ttaaccacca gttacaaaat gagaatcatc aaggaatcac aattaatttg ctattgacaa     300
actcatactt ttagcaggct gatttctact ttatacttag attggtaatg aaaaatgaag     360
cttattttag ttgattggtt ggacttgtgt atgaatatta tctattattt gaaaagccaa     420
acttgaatgc aaaaaaatat tgaatatgaa aagagaaaca ccacaagcaa agccaaaata     480
ggtggcctag aacttccagc ttgaaatatg ggagagaatg agggaggcac tgtagagcag     540
ctgccgggtg ccgcatgaga acaattctcc ctgctcataa ttaatcctac ctatttctga     600
tgacagctgg ctcttcactt tgaacaagct agttaacaac tttcttctca cattgagcaa     660
ataattcata tttaattact taaccaccag ttacaaaatg agaatcatca aggaatcaca     720
attaatttgc tattgacaaa ctcatacttt tagcaggctg atttctactt tatacttaga     780
ttggtaatga aaaatgaagc ttattttagt tgattggttg gacttgtgta tgaatattat     840
ctattatttg aaaagccaaa cttgaatgca aaaaaatatt gaatatgaaa agagaaacac     900
cacaagcaaa gccaaaatag gtggcctaga acttccagct tgaaatatgg gagagaatga     960
gggaggcact gtagagcagc tgccgggtgc cgcatgagaa caattctccc tgctcataat    1020
taatcctacc tatttctgat gacagctggc tcttcacttt gaacaagcta gttaacaact    1080
ttcttctcac attgagcaaa taattcatat ttaattactt aaccaccagt tacaaaatga    1140
```

```
gaatcatcaa ggaatcacaa ttaatttgct attgacaaac tcatacttt agcaggctga     1200 tttctacttt atacttagat tggtaatgaa aaatgaagct tattttagtt gattggttgg     1260
acttgtgtat gaatattatc tattatttga aaagccaaac ttgaatgcaa aaaaatattg     1320
aatatgaaaa ggagctcggg ctgggcataa aagtcagggc agagccatct attgcttaca     1380
tttgcttctg ggatccagat ctttcgaagc tagcgctacc ggtcgccacc atggtgagca     1440
agggcgagga gctgttcacc ggggtggtgc ccatcctggt cgagctggac ggcgacgtaa     1500
acggccacaa gttcagcgtg tccggcgagg gcgagggcga tgccacctac ggcaagctga     1560
ccctgaagct gatctgcacc accggcaagc tgcccgtgcc ctggcccacc ctcgtgacca     1620
ccctgggcta cggcgtgcag tgcttcgccc gctaccccga ccacatgaag cagcacgact     1680
tcttcaagtc cgccatgccc gaaggctacg tccaggagcg caccatcttc ttcaaggacg     1740
acggcaacta caagacccgc gccgaggtga agttcgaggg cgacaccctg gtgaaccgca     1800
tcgagctgaa gggcatcgac ttcaaggagg acggcaacat cctggggcac aagctggagt     1860
acaactacaa cagccacaac gtctatatca ccgccgacaa gcagaagaac ggcatcaagg     1920
ccaacttcaa gatccgccac aacatcgagg acggcggcgt gcagctcgcc gaccactacc     1980
agcagaacac ccccatcggc gacggccccg tgctgctgcc cgacaaccac tacctgagct     2040
accagtccaa gctgagcaaa gaccccaacg agaagcgcga tcacatggtc ctgctggagt     2100
tcgtgaccgc cgccgggatc actctcggca tggacgagct gtacaagtaa gtcgacggcg     2160
cgccgcggcc gcgaattcga tatcataatc aacctctgga ttacaaaatt tgtgaaagat     2220
tgactggtat tcttaactat gttgctcctt ttacgctatg tggatacgct gctttaatgc     2280
ctttgtatca tgctattgct tcccgtatgg ctttcatttt ctcctccttg tataaatcct     2340
ggttagttct tgccacggcg gaactcatcg ccgcctgcct tgcccgctgc tggacagggg     2400
ctcggctgtt gggcactgac aattccgtgg ctcgagagat cttcgactgt gccttctagt     2460
tgccagccat ctgttgtttg cccctccccc gtgccttcct tgaccctgga aggtgccact     2520
cccactgtcc tttcctaata aaatgaggaa attgcatcgc attgtctgag taggtgtcat     2580
tctattctgg ggggtggggt ggggcaggac agcaagggg  aggattggga agacaatagc     2640
aggcatgaga tctcacgtgc ggaccgagcg gccgc                                2675
```

```
<210> SEQ ID NO 88
<211> LENGTH: 2479
<212> TYPE: DNA
<213> ORGANISM: Artificial Sequence
<220> FEATURE:
<223> OTHER INFORMATION: CN3407

<400> SEQUENCE: 88
gcggccgcac gcgttgagct tcaaccaaat caggcattga tggattttat agtttgatta      60
acaaagataa tagcaaaccc cagatttagt ttaaacataa aaagtattaa ggttgtatcc     120
tgcttgtata gcatatgcaa atgacctcgt ttctgctact gcatttggaa atgtagcaga     180
agaaaaaaaa aaggcacttc aattgcagct ctcatcagtt attcactgta tccaggcctc     240
tcaattgtgt tctttctttt aatgcaatag caagcagcaa tcacccagct gtgcttggta     300
gagtgaacta tatacacatc tatattgaga tttcatacac acataacata aaagcgagag     360
aaaaagcctc aagaatgttt ggcccattgc aaatcacaca aaaggactaa tgaatctctc     420
tccaaatgga tctgtagtga ccatctgtaa gccttgattg attcatattc cataacggta     480
```

-continued

```
tcagcatcca ggaagtgatt acttcaaggt gcaacacaac ttcccctatg aaagctcagt    540
ctctttaatc atacctagtc agtatctgtc acggggataa actaaggcag agctcgggct    600
gggcataaaa gtcagggcag agccatctat tgcttacatt tgcttctggg atccagatct    660
ttcgaagcta cgcgctaccgg tcgccaccat ggtctccaag ggcgaggagc tgttcaccgg    720
ggtggtgccc atcctggtcg agctggacgg cgatgtcaac ggccacaagt tcagcgtgtc    780
cggcgagggc gagggcgatg ccacctacgg caagctgacc ctgaagctga tctgcaccac    840
cggcaagctg cccgtgccct ggcccaccct cgtgaccacc ctgggctacg gcgtgcagtg    900
cttcgcccgc tacccgacc acatgaagca gcacgacttc ttcaagtccg ccatgcccga    960
aggctacgtc caggagcgca ccatcttctt caaagacgac ggcaactaca gacccgcgc   1020 cgaggtgaag ttcgagggcg acaccctggt gaaccgcatc gagctgaagg gcatcgactt   1080
caaggaggac ggcaacatcc tggggcacaa gctggagtac aactacaaca gccacaacgt   1140
ctatatcacc gccgacaagc agaagaacgg catcaaggcc aacttcaaga tccgccacaa   1200
catcgaggac ggcggcgtgc agctcgccga ccactaccag cagaacaccc ccatcggcga   1260
cggccccgtg ctgctgcccg acaaccacta cctgagctac cagtccaagc tgagcaaaga   1320
ccccaacgag aagcgcgatc acatggtcct gctggagttc gtgaccgccg ccgggatcac   1380
tctcggcatg gacgagctgt acaagggctc tggtgctacc aacttctcac tgttgaaaca   1440
ggcaggggat gtagaggaga tccagggcc tggtgctagt ggagactaca agaccatga   1500 cggagattat aaagatcatg acatcgatta caaggatgac gatgacaagt ccggactcag   1560
atctggaggc tccggaggcc cagagccagc gaagtctgct cccgccccga aaaagggctc   1620
caagaaggcg gtgactaagg cgcagaagaa aggcggcaag aagcgcaagc gcagccgcaa   1680
ggagagctat tccatctatg tgtacaaggt tctgaagcag gtccaccctg acaccggcat   1740
ttcgtccaag gccatgggca tcatgaattc gtttgtgaac gacatttcg agcgcatcgc   1800 aggagaggct tcccgcctgg cgcattacaa caagcgctcg accatcacct cccgggagat   1860
ccagacggcc gtgcgcctgc tgctgcctgg ggagttggcc aagcacgccg tgtccgaggg   1920
tactaaggcc atcaccaagt acaccagcgc taagtaatga ggcgcgccgc ggccgcgaat   1980
tcgatatcat aatcaacctc tggattacaa aatttgtgaa agattgactg gtattcttaa   2040
ctatgttgct ccttttacgc tatgtggata cgctgcttta atgcctttgt atcatgctat   2100
tgcttcccgt atggctttca ttttctcctc cttgtataaa tcctggttag ttcttgccac   2160
ggcggaactc atcgccgcct gccttgcccg ctgctggaca ggggctcggc tgttgggcac   2220
tgacaattcc gtggctcgag agatcttcga ctgtgccttc tagttgccag ccatctgttg   2280
tttgcccctc ccccgtgcct tccttgaccc tggaaggtgc cactcccact gtcctttcct   2340
aataaaatga ggaaattgca tcgcattgtc tgagtaggtg tcattctatt ctggggggtg   2400
gggtggggca ggacagcaag ggggaggatt gggaagacaa tagcaggcat gagatctcac   2460
gtgcggaccg agcggccgc                                                2479
```

<210> SEQ ID NO 89
<211> LENGTH: 2515
<212> TYPE: DNA
<213> ORGANISM: Artificial Sequence
<220> FEATURE:
<223> OTHER INFORMATION: CN3408

<400> SEQUENCE: 89

```
gcggccgcac gcgtacattt gcagtaaagc ttgttctttt tcttgaagta tattttaaga     60
```

-continued

```
ttttgagttc tactatcatt aaagacagat aattaatagt ttatttttat ttacttttgt      120
tagtagtgac ttggtgctat gagccatatt ttgctgttgc tgttgttact ggtagttttt      180
gtaattctgg ggctaaaact tggggtctgg tatgctgtca tttaccagtg agctataccc      240
tggatattat gatttagatg aatgtgaaat atcaccccag acatacatat actaaacact      300
tggcccttgg cccatgatgc taaatggagg agatagaagc ttttggggca cagcctagtg      360
gaaggaaatg aggtcaaatg acatgtactc tgaaaggaat atgggtattc tgggcttgcg      420
ttattctctc tctccctctc tctccctctc tctccctctc cctctctctt tctccttttc      480
tctttctctc ctcgccttgt tttccagctg ccagaaggta ggcctcttct ctgctgaata      540
tctgtgtcat gttatgcacc aacacagtac taactgtcat gttataccta gtggccaggt      600
aaccatggac caaaatggca gagcagagct cgggctgggc ataaaagtca gggcagagcc      660
atctattgct tacatttgct tctgggatcc agatctttcg aagctagcgc taccggtcgc      720
caccatggtc tccaagggcg aggagctgtt caccggggtg gtgcccatcc tggtcgagct      780
ggacggcgat gtcaacggcc acaagttcag cgtgtccggc gagggcgagg gcgatgccac      840
ctacggcaag ctgaccctga agctgatctg caccaccggc aagctgcccg tgccctggcc      900
caccctcgtg accaccctgg ctacggcgt gcagtgcttc gcccgctacc ccgaccacat      960
gaagcagcac gacttcttca gtccgccat gcccgaaggc tacgtccagg agcgcaccat     1020
cttcttcaaa gacgacggca actacaagac ccgcgccgag gtgaagttcg agggcgacac     1080
cctggtgaac cgcatcgagc tgaagggcat cgacttcaag gaggacggca acatcctggg     1140
gcacaagctg gagtacaact acaacagcca caacgtctat atcaccgccg acaagcagaa     1200
gaacggcatc aaggccaact tcaagatccg ccacaacatc gaggacggcg cgtgcagct     1260 cgccgaccac taccagcaga acacccccat cggcgacggc cccgtgctgc tgcccgacaa     1320
ccactacctg agctaccagt ccaagctgag caaagacccc aacgagaagc gcgatcacat     1380
ggtcctgctg gagttcgtga ccgccgccgg gatcactctc ggcatggacg agctgtacaa     1440
gggctctggt gctaccaact ctcactgtt gaaacaggca ggggatgtag aggagaatcc     1500
agggcctggt gctagtggag actacaaaga ccatgacgga gattataaag atcatgacat     1560
cgattacaag gatgacgatg acaagtccgg actcagatct ggaggctccg gaggcccaga     1620
gccagcgaag tctgctcccg ccccgaaaaa gggctccaag aaggcggtga ctaaggcgca     1680
gaagaaaggc ggcaagaagc gcaagcgcag ccgcaaggag agctattcca tctatgtgta     1740
caaggttctg aagcaggtcc accctgacac cggcatttcg tccaaggcca tgggcatcat     1800
gaattcgttt gtgaacgaca ttttcgagcg catcgcagga gaggcttccc gcctggcgca     1860
ttacaacaag cgctcgacca tcacctcccg ggagatccag acggccgtgc gcctgctgct     1920
gcctggggag ttggccaagc acgccgtgtc cgagggtact aaggccatca ccaagtacac     1980
cagcgctaag taatgaggcg cgccgcggcc gcgaattcga tatcataatc aacctctgga     2040
ttacaaaatt tgtgaaagat tgactggtat tcttaactat gttgctcctt ttacgctatg     2100
tggatacgct gctttaatgc ctttgtatca tgctattgct tcccgtatgg ctttcatttt     2160
ctcctccttg tataaatcct ggttagttct tgccacggcg gaactcatcg ccgcctgcct     2220
tgcccgctgc tggacagggg ctcggctgtt gggcactgac aattccgtgg ctcgagagat     2280
cttcgactgt gccttctagt tgccagccat ctgttgtttg cccctccccc gtgccttcct     2340
tgaccctgga aggtgccact cccactgtcc tttcctaata aaatgaggaa attgcatcgc     2400
```

-continued

```
attgtctgag taggtgtcat tctattctgg ggggtggggt ggggcaggac agcaaggggg    2460
aggattggga agacaatagc aggcatgaga tctcacgtgc ggaccgagcg gccgc        2515

<210> SEQ ID NO 90
<211> LENGTH: 2565
<212> TYPE: DNA
<213> ORGANISM: Artificial Sequence
<220> FEATURE:
<223> OTHER INFORMATION: CN3409

<400> SEQUENCE: 90
gcggccgcac gcgttgcaaa ataaagattt cttgggatac agagaaaaaa acaaatctga      60
caggagagga agaagcaccc ggtgggctat aacggtgcaa ttcagctgat tatatgttac     120
aagtaacaag gacgagaaaa aatgttattt ctttgaaaat aaaactaacc aggccataca     180
tatttaacag gactgcatga gagaagaaga agccagctgc aggagtgact gtggggggga     240
gggggaactt gacaaaaaaa gcaaaatggc agtcctgctt ccaaagtcct caaggtcaca     300
gttatttggg cattcttgcg ggcactgctt atacaagaat gtgctttcag tcaaggcttt     360
ctaatagatt ctcaaaattt gggacaaatg ttatttttgt atctgtagaa atgtactgat     420
tcagaaagat ctttgagcaa tacagatgtt aaaacattta agtcacaaaa tgggtctatt     480
taatcaatgc gactagtttg gaacattatt caaactgcca gaaatacaat gtaaatgaaa     540
cctcaggcca atattttgga gccctaaaag atttgatggc taattttatc gtagacacta     600
attataaata ggagacccca ggatgggact agaaaccaa gccagctttt taatttaccc      660
ctccaggact ttgctgagct cgggctgggc ataaaagtca gggcagagcc atctattgct     720
tacatttgct tctgggatcc agatctttcg aagctagcgc taccggtcgc caccatggtc     780
tccaagggcg aggagctgtt caccggggtg gtgcccatcc tggtcgagct ggacggcgat     840
gtcaacggcc acaagttcag cgtgtccggc gagggcgagg gcgatgccac ctacggcaag     900
ctgaccctga agctgatctg caccaccggc aagctgcccg tgccctggcc caccctcgtg     960
accaccctgg gctacggcgt gcagtgcttc gcccgctacc ccgaccacat gaagcagcac    1020
gacttcttca gtccgccat gcccgaaggc tacgtccagg agcgcaccat cttcttcaaa     1080
gacgacggca actacaagac ccgcgccgag gtgaagttcg agggcgacac cctggtgaac    1140
cgcatcgagc tgaagggcat cgacttcaag gaggacggca acatcctggg gcacaagctg    1200
gagtacaact acaacagcca caacgtctat atcaccgccg acaagcagaa gaacggcatc    1260
aaggccaact tcaagatccg ccacaacatc gaggacggcg cgtgcagct cgccgaccac    1320 taccagcaga acacccccat cggcgacggc cccgtgctgc tgcccgacaa ccactacctg    1380
agctaccagt ccaagctgag caaagacccc aacgagaagc gcgatcacat ggtcctgctg    1440
gagttcgtga ccgccgccgg gatcactctc ggcatggacg agctgtacaa gggctctggt    1500
gctaccaact ctcactgtt gaaacaggca ggggatgtag aggagaatcc agggcctggt    1560
gctagtggag actacaaaga ccatgacgga gattataaag atcatgacat cgattacaag    1620
gatgacgatg acaagtccgg actcagatct ggaggctccg gaggcccaga gccagcgaag    1680
tctgctcccg ccccgaaaaa gggctccaag aaggcggtga ctaaggcgca gaagaaaggc    1740
ggcaagaagc gcaagcgcag ccgcaaggag agctattcca tctatgtgta caaggttctg    1800
aagcaggtcc accctgacac cggcatttcg tccaaggcca tgggcatcat gaattcgttt    1860
gtgaacgaca ttttcgagcg catcgcagga gaggcttccc gcctggcgca ttacaacaag    1920
cgctcgacca tcacctcccg ggagatccag acggccgtgc gcctgctgct gcctggggag    1980
```

-continued

```
ttggccaagc acgccgtgtc cgagggtact aaggccatca ccaagtacac cagcgctaag    2040
taatgaggcg cgccgcggcc gcgaattcga tatcataatc aacctctgga ttacaaaatt    2100
tgtgaaagat tgactggtat tcttaactat gttgctcctt ttacgctatg tggatacgct    2160
gctttaatgc ctttgtatca tgctattgct tcccgtatgg ctttcatttt ctcctccttg    2220
tataaatcct ggttagttct tgccacggcg gaactcatcg ccgcctgcct tgcccgctgc    2280
tggacagggg ctcggctgtt gggcactgac aattccgtgg ctcgagagat cttcgactgt    2340
gccttctagt tgccagccat ctgttgtttg cccctccccc gtgccttcct tgaccctgga    2400
aggtgccact cccactgtcc tttcctaata aaatgaggaa attgcatcgc attgtctgag    2460
taggtgtcat tctattctgg ggggtggggt ggggcaggac agcaaggggg aggattggga    2520
agacaatagc aggcatgaga tctcacgtgc ggaccgagcg gccgc                    2565
```

<210> SEQ ID NO 91
<211> LENGTH: 2378
<212> TYPE: DNA
<213> ORGANISM: Artificial Sequence
<220> FEATURE:
<223> OTHER INFORMATION: CN2580

<400> SEQUENCE: 91

```
gcggccgcac gcgttatgat gtgccaggct tgggagaaac accacaagca aagccaaat     60 aggtggccta gaacttccag cttgaaatat gggagagaat gagggaggca ctgtagagca    120
gctgccgggt gccgcatgag aacaattctc cctgctcata attaatccta cctatttctg    180
atgacagctg gctcttcact ttgaacaagc tagttaacaa cttttcttctc acattgagca    240 aataattcat atttaattac ttaaccacca gttacaaaat gagaatcatc aaggaatcac    300
aattaatttg ctattgacaa actcatactt ttagcaggct gatttctact ttatacttag    360
attggtaatg aaaaatgaag cttattttag ttgattggtt ggacttgtgt atgaatatta    420
tctattattt gaaaagccaa acttgaatgc aaaaaaatat tgaatatgaa aagaaaaca     480 tttgcagtaa agcttgttct gagctcgggc tgggcataaa agtcagggca gagccatcta    540
ttgcttacat ttgcttctgg gatccagatc tttcgaagct agcaccatgg tgcccaagaa    600
gaagaggaaa gtctccaacc tgctgactgt gcaccaaaac ctgcctgccc tccctgtgga    660
tgccacctct gatgaagtca ggaagaacct gatggacatg ttcagggaca ggcaggcctt    720
ctctgaacac acctggaaga tgctcctgtc tgtgtgcaga tcctgggctg cctggtgcaa    780
gctgaacaac aggaaatggt tccctgctga acctgaggat gtgagggact acctcctgta    840
cctgcaagcc agaggcctgg ctgtgaagac catccaacag cacctgggcc agctcaacat    900
gctgcacagg agatctggcc tgcctcgccc ttctgactcc aatgctgtgt ccctggtgat    960
gaggagaatc agaaaggaga tgtggatgc tggggagaga gccaagcagg ccctggcctt    1020
tgaacgcact gactttgacc aagtcagatc cctgatggag aactctgaca gatgccagga    1080
catcaggaac ctggccttcc tgggcattgc ctacaacacc ctgctgcgca ttgccgaaat    1140
tgccagaatc agagtgaagg acatctcccg caccgatggt gggagaatgc tgatccacat    1200
tggcaggacc aagaccctgg tgtccacagc tggtgtggag aaggccctgt ccctgggggt    1260
taccaagctg gtggagagat ggatctctgt gtctggtgtg gctgatgacc ccaacaacta    1320
cctgttctgc cgggtcagaa agaatggtgt ggctgcccct tctgccacct cccaactgtc    1380
cacccgggcc ctggaaggga tctttgaggc cacccaccgc ctgatctatg gtgccaagga    1440
```

-continued

```
tgactctggg cagagatacc tggcctggtc tggccactct gccagagtgg gtgctgccag      1500
ggacatggcc agggctggtg tgtccatccc tgaaatcatg caggctggtg gctggaccaa      1560
tgtgaacatt gtgatgaact acatcagaaa cctggactct gagactgggg ccatggtgag      1620
gctgctcgag gatggggact aatgaggcgc gccgcggcct aaagagacc ggttcactgt       1680 gacagtaaaa gagaccggtt cactgtgaga atgaaagaga ccggttcact gtgatcggaa      1740
aagagaccgg ttcactgtga gcggccttga aacccagcag acaatgtagc tcagtagaaa      1800
cccagcagac aatgtagctg aatggaaacc cagcagacaa tgtagcttcg agaaaccca       1860 gcagacaatg tagctgtcga cgaattcgat atcataatca acctctggat tacaaaattt      1920
gtgaaagatt gactggtatt cttaactatg ttgctccttt tacgctatgt ggatacgctg      1980
ctttaatgcc tttgtatcat gctattgctt cccgtatggc tttcattttc tcctccttgt      2040
ataaatcctg gttagttctt gccacggcgg aactcatcgc cgcctgcctt gcccgctgct      2100
ggacaggggc tcggctgttg ggcactgaca attccgtggc tcgagagatc ttcgactgtg      2160
ccttctagtt gccagccatc tgttgtttgc ccctcccccg tgccttcctt gaccctggaa      2220
ggtgccactc ccactgtcct ttcctaataa aatgaggaaa ttgcatcgca ttgtctgagt      2280
aggtgtcatt ctattctggg gggtggggtg ggcaggaca gcaggggga ggattgggaa        2340 gacaatagca ggcatgcacg tgcggaccga gcggccgc                             2378
```

<210> SEQ ID NO 92
<211> LENGTH: 2625
<212> TYPE: DNA
<213> ORGANISM: Artificial Sequence
<220> FEATURE:
<223> OTHER INFORMATION: CN2825

<400> SEQUENCE: 92

```
gcggccgcac gcgttatgat gtgccaggct tgggagaaac accacaagca aagccaaaat       60
aggtggccta gaacttccag cttgaaatat gggagagaat gagggaggca ctgtagagca      120
gctgccgggt gccgcatgag aacaattctc cctgctcata attaatccta cctatttctg      180
atgacagctg gctcttcact ttgaacaagc tagttaacaa ctttcttctc acattgagca      240
aataattcat atttaattac ttaaccacca gttacaaaat gagaatcatc aaggaatcac      300
aattaatttg ctattgacaa actcatactt ttagcaggct gatttctact ttatacttag      360
attggtaatg aaaaatgaag cttatttttag ttgattggtt ggacttgtgt atgaatatta     420
tctattattt gaaaagccaa acttgaatgc aaaaaaatat tgaatatgaa aagaaaaaca      480
tttgcagtaa agcttgttct gagctcgggc tgggcataaa agtcagggca gagccatcta      540
ttgcttacat ttgcttctgg gatccagatc tttcgaagct agccaccatg gctcctaaga      600
agaagaggaa ggtgatgagc cagttcgaca tcctgtgcaa gacccccccc aaggtgctgg      660
tgcggcagtt cgtggagaga ttcgagaggc cagcggcga aagatcgcc agctgtgccg        720 ccgagctgac ctacctgtgc tggatgatca cccacaacgg caccgccatc aagagggcca      780
ccttcatgag ctacaacacc atcatcagca acagcctgag cttcgacatc gtgaacaaga      840
gcctgcagtt caagtacaag acccagaagg ccaccatcct ggaggccagc ctgaagaagc      900
tgatccccgc ctgggagttc accatcatcc cttacaacgg ccagaagcac cagagcgaca      960
tcaccgacat cgtgtccagc ctgcagctgc agttcgagag cagcgaggag gccgacaagg     1020
gcaacagcca cagcaagaag atgctgaagg ccctgctgtc cgagggcgag agcatctggg     1080
agatcaccga gaagatcctg aacagcttcg agtacaccag caggttcacc aagaccaaga     1140
```

-continued

```
ccctgtacca gttcctgttc ctggccacat tcatcaactg cggcaggttc agcgacatca      1200
agaacgtgga ccccaagagc ttcaagctgg tgcagaacaa gtacctgggc gtgatcattc      1260
agtgcctggt gaccgagacc aagacaagcg tgtccaggca catctacttt ttcagcgcca      1320
gaggcaggat cgaccccctg gtgtacctgg acgagttcct gaggaacagc gagcccgtgc      1380
tgaagagagt gaacaggacc ggcaacagca gcagcaacaa gcaggagtac cagctgctga      1440
aggacaacct ggtgcgcagc tacaacaagg ccctgaagaa gaacgccccc tacccatct       1500 tcgctatcaa gaacggccct aagagccaca tcggcaggca cctgatgacc agctttctga      1560
gcatgaaggg cctgaccgag ctgacaaacg tggtgggcaa ctggagcgac aagagggcct      1620
ccgccgtggc caggaccacc tacacccacc agatcaccgc catccccgac cactacttcg      1680
ccctggtgtc caggtactac gcctacgacc ccatcagcaa ggagatgatc gccctgaagg      1740
acgagaccaa ccccatcgag gagtggcagc acatcgagca gctgaagggc agcgccgagg      1800
gcagcatcag ataccccgcc tggaacggca tcatcagcca ggaggtgctg gactacctga      1860
gcagctacat caacaggcgg atctgagtcg acggcgcgcc gcggccttaa agagaccggt      1920
tcactgtgac agtaaaagag accggttcac tgtgagaatg aaagagaccg gttcactgtg      1980
atcggaaaag agaccggttc actgtgagcg gccttgaaac ccagcagaca atgtagctca      2040
gtagaaaccc agcagacaat gtagctgaat ggaaacccag cagacaatgt agcttcggag      2100
aaacccagca gacaatgtag ctgtcgacga attcgatatc ataatcaacc tctggattac      2160
aaaatttgtg aaagattgac tggtattctt aactatgttg ctcctttttac gctatgtgga      2220 tacgctgctt taatgccttt gtatcatgct attgcttccc gtatggcttt catttttctcc      2280 tccttgtata aatcctggtt agttcttgcc acggcggaac tcatcgccgc ctgccttgcc      2340
cgctgctgga caggggctcg gctgttgggc actgacaatt ccgtggctcg agagatcttc      2400
gactgtgcct tctagttgcc agccatctgt tgtttgcccc tccccgtgc cttccttgac       2460 cctggaaggt gccactccca ctgtcctttc ctaataaaat gaggaaattg catcgcattg      2520
tctgagtagg tgtcattcta ttctgggggg tggggtgggg caggacagca aggggggagga     2580 ttgggaagac aatagcaggc atgcacgtgc ggaccgagcg ccgc                        2625
```

```
<210> SEQ ID NO 93
<211> LENGTH: 2205
<212> TYPE: DNA
<213> ORGANISM: Artificial Sequence
<220> FEATURE:
<223> OTHER INFORMATION: CN3270

<400> SEQUENCE: 93
```

```
gcggccgcac gcgttatctt agagtgggaa gatttgagaa gtgccatggt taatatgact       60
gactttttat tcttatttct tttaatttca tggttctaaa tccgaattta atcatagtac      120
ccagaaaagc agaggtgtag aggttcacag tgggagttgt aatctagccc tattcatttt      180
gacctcaaaa cccaaattat ttataacaaa ttatttccta ttctttcctt cactattcag      240
gaacatctgt ccaccactta catgatcact tatcttgcta ttgtgtcatt ttgatgaaaa      300 agaattttt ctaaatatct aaatacaagg ccccatatta acagtgcttt ttaaatcccc       360
acagatgtgg gagatgaccc ctttccatcc ctgaagattg taattgggcc agtctttagt      420
acagtttgtt ccaataaaga gatacaattt tattcattaa tttgtgtatt catttagcaa      480
atcactttag agtcttatta tatcaggatt ttggggtcta ttttagtata tcttttgta       540
```

```
tttcttggaa cctctccaat tattctagac tctttcaaag gttggtgatc aatattagac      600
attattatga aaagaatctt acttgctaaa agggttagat ggagctcggg ctgggcataa      660
aagtcagggc agagccatct attgcttaca tttgcttctg ggatccagat ctttcgaagc      720
tagcgctacc ggtcgccacc atggtgagca agggcgagga gctgttcacc ggggtggtgc      780
ccatcctggt cgagctggac ggcgacgtaa acggccacaa gttcagcgtg tccggcgagg      840
gcgagggcga tgccacctac ggcaagctga ccctgaagct gatctgcacc accggcaagc      900
tgcccgtgcc ctggcccacc ctcgtgacca ccctgggcta cggcgtgcag tgcttcgccc      960
gctaccccga ccacatgaag cagcacgact tcttcaagtc cgccatgccc gaaggctacg     1020
tccaggagcg caccatcttc ttcaaggacg acggcaacta caagacccgc gccgaggtga     1080
agttcgaggg cgacaccctg gtgaaccgca tcgagctgaa gggcatcgac ttcaaggagg     1140
acggcaacat cctggggcac aagctggagt acaactacaa cagccacaac gtctatatca     1200
ccgccgacaa gcagaagaac ggcatcaagg ccaacttcaa gatccgccac aacatcgagg     1260
acggcggcgt gcagctcgcc gaccactacc agcagaacac ccccatcggc gacggccccg     1320
tgctgctgcc cgacaaccac tacctgagct accagtccaa gctgagcaaa gaccccaacg     1380
agaagcgcga tcacatggtc ctgctggagt tcgtgaccgc cgccgggatc actctcggca     1440
tggacgagct gtacaagtaa gtcgacggcg cgccgcggcc ttaaagagac cggttcactg     1500
tgacagtaaa agagaccggt tcactgtgag aatgaaagag accggttcac tgtgatcgga     1560
aaagagaccg gttcactgtg agcggccttg aaacccagca gacaatgtag ctcagtagaa     1620
acccagcaga caatgtagct gaatggaaac ccagcagaca atgtagcttc ggagaaaccc     1680
agcagacaat gtagctgtcg acgaattcga tatcataatc aacctctgga ttacaaaatt     1740
tgtgaaagat tgactggtat tcttaactat gttgctcctt ttacgctatg tggatacgct     1800
gctttaatgc ctttgtatca tgctattgct tcccgtatgg ctttcatttt ctcctccttg     1860
tataaatcct ggttagttct tgccacggcg gaactcatcg ccgcctgcct tgcccgctgc     1920
tggacagggg ctcggctgtt gggcactgac aattccgtgg ctcgagagat cttcgactgt     1980
gccttctagt tgccagccat ctgttgtttg cccctccccc gtgccttcct tgaccctgga     2040
aggtgccact cccactgtcc tttcctaata aaatgaggaa attgcatcgc attgtctgag     2100
taggtgtcat tctattctgg ggggtggggt ggggcaggac agcaaggggg aggattggga     2160
agacaatagc aggcatgaga tctcacgtgc ggaccgagcg ccgc                      2205
```

```
<210> SEQ ID NO 94
<211> LENGTH: 1960
<212> TYPE: DNA
<213> ORGANISM: Artificial Sequence
<220> FEATURE:
<223> OTHER INFORMATION: CN3316

<400> SEQUENCE: 94
```

```
gcggccgcac gcgtagtgac ttggtgctat gagccatatt ttgctgttgc tgttgttact       60
ggtagttttt gtaattctgg ggctaaaact tggggtctgg tatgctgtca tttaccagtg      120
agctataccc tggatattat gatttagatg aatgtgaaat atcaccccag acatacatat      180
actaaacact tggcccttgg cccatgatgc taaatggagg agatagaagc ttttggggca      240
cagcctagtg gaaggaaatg aggtcaaatg acatgtactc tgaaaggaat atgggtattc      300
tgggcttgcg ttattctctc tctccctctc tctccctctc tctccctctc cctctctctt      360
tctccttttc tctttctctc ctcgccttgt tttccagagc tcgggctggg cataaaagtc      420
```

```
agggcagagc catctattgc ttacatttgc ttctgggatc cagatctttc gaagctagcg      480
ctaccggtcg ccaccatggt gagcaagggc gaggagctgt tcaccggggt ggtgcccatc      540
ctggtcgagc tggacggcga cgtaaacggc cacaagttca gcgtgtccgg cgagggcgag      600
ggcgatgcca cctacggcaa gctgaccctg aagctgatct gcaccaccgg caagctgccc      660
gtgccctggc ccaccctcgt gaccaccctg ggctacggcg tgcagtgctt cgcccgctac      720
cccgaccaca tgaagcagca cgacttcttc aagtccgcca tgcccgaagg ctacgtccag      780
gagcgcacca tcttcttcaa ggacgacggc aactacaaga cccgcgccga ggtgaagttc      840
gagggcgaca ccctggtgaa ccgcatcgag ctgaagggca tcgacttcaa ggaggacggc      900
aacatcctgg ggcacaagct ggagtacaac tacaacagcc acaacgtcta tatcaccgcc      960
gacaagcaga agaacggcat caaggccaac ttcaagatcc gccacaacat cgaggacggc     1020
ggcgtgcagc tcgccgacca ctaccagcag aacacccocca tcggcgacgg ccccgtgctg     1080
ctgcccgaca accactacct gagctaccag tccaagctga gcaaagaccc caacgagaag     1140
cgcgatcaca tggtcctgct ggagttcgtg accgccgccg ggatcactct cggcatggac     1200
gagctgtaca agtaagtcga cggcgcgccg cggccttaaa gagaccggtt cactgtgaca     1260
gtaaaagaga ccggttcact gtgagaatga aagagaccgg ttcactgtga tcggaaaaga     1320
gaccggttca ctgtgagcgg ccttgaaacc cagcagacaa tgtagctcag tagaaaccca     1380
gcagacaatg tagctgaatg gaaacccagc agacaatgta gcttcggaga aacccagcag     1440
acaatgtagc tgtcgacgaa ttcgatatca taatcaacct ctggattaca aaatttgtga     1500
aagattgact ggtattctta actatgttgc tccttttacg ctatgtggat acgctgcttt     1560
aatgcctttg tatcatgcta ttgcttcccg tatggctttc attttctcct ccttgtataa     1620
atcctggtta gttcttgcca cggcggaact catcgccgcc tgccttgccc gctgctggac     1680
aggggctcgg ctgttgggca ctgacaattc cgtggctcga gagatcttcg actgtgcctt     1740
ctagttgcca gccatctgtt gtttgcccct ccccgtgcc ttccttgacc ctggaaggtg     1800
ccactcccac tgtcctttcc taataaaatg aggaaattgc atcgcattgt ctgagtaggt     1860
gtcattctat tctggggggt ggggtggggc aggacagcaa gggggaggat tgggaagaca     1920
atagcaggca tgagatctca cgtgcggacc gagcggccgc                          1960
```

<210> SEQ ID NO 95
<211> LENGTH: 2895
<212> TYPE: DNA
<213> ORGANISM: Artificial Sequence
<220> FEATURE:
<223> OTHER INFORMATION: CN3271

<400> SEQUENCE: 95

```
gcggccgcac gcgtagaaac accacaagca aagccaaaat aggtggccta gaacttccag       60
cttgaaatat gggagagaat gagggaggca ctgtagagca gctgccgggt gccgcatgag      120
aacaattctc cctgctcata attaatccta cctatttctg atgacagctg gctcttcact      180
ttgaacaagc tagttaacaa ctttcttctc acattgagca aataattcat atttaattac      240
ttaaccacca gttacaaaat gagaatcatc aaggaatcac aattaatttg ctattgacaa      300
actcatactt ttagcaggct gatttctact ttatacttag attggtaatg aaaaatgaag      360
cttattttag ttgattggtt ggacttgtgt atgaatatta tctattattt gaaaagccaa      420
acttgaatgc aaaaaaatat tgaatatgaa aagagaaaca ccacaagcaa agccaaaata      480
```

-continued

```
ggtggcctag aacttccagc ttgaaatatg ggagagaatg agggaggcac tgtagagcag      540
ctgccgggtg ccgcatgaga acaattctcc ctgctcataa ttaatcctac ctatttctga      600
tgacagctgg ctcttcactt tgaacaagct agttaacaac tttcttctca cattgagcaa      660
ataattcata tttaattact taaccaccag ttacaaaatg agaatcatca aggaatcaca      720
attaatttgc tattgacaaa ctcatacttt tagcaggctg atttctactt tatacttaga      780
ttggtaatga aaaatgaagc ttattttagt tgattggttg acttgtgta tgaatattat      840 ctattatttg aaaagccaaa cttgaatgca aaaaaatatt gaatatgaaa agagaaacac      900
cacaagcaaa gccaaaatag gtggcctaga acttccagct tgaaatatgg gagagaatga      960
gggaggcact gtagagcagc tgccgggtgc cgcatgagaa caattctccc tgctcataat     1020
taatcctacc tatttctgat gacagctggc tcttcacttt gaacaagcta gttaacaact     1080
ttcttctcac attgagcaaa taattcatat ttaattactt aaccaccagt tacaaaatga     1140
gaatcatcaa ggaatcacaa ttaatttgct attgacaaac tcatacttttt agcaggctga     1200 tttctacttt atacttagat tggtaatgaa aaatgaagct tattttagtt gattggttgg     1260
acttgtgtat gaatattatc tattatttga aaagccaaac ttgaatgcaa aaaatattg      1320 aatatgaaaa ggagctcggg ctgggcataa aagtcagggc agagccatct attgcttaca     1380
tttgcttctg ggatccagat ctttcgaagc tagcgctacc ggtcgccacc atggtgagca     1440
agggcgagga gctgttcacc ggggtggtgc ccatcctggt cgagctggac ggcgacgtaa     1500
acggccacaa gttcagcgtg tccggcgagg gcgagggcga tgccacctac ggcaagctga     1560
ccctgaagct gatctgcacc accggcaagc tgcccgtgcc ctggcccacc ctcgtgacca     1620
ccctgggcta cggcgtgcag tgcttcgccc gctaccccga ccacatgaag cagcacgact     1680
tcttcaagtc cgccatgccc gaaggctacg tccaggagcg caccatcttc ttcaaggacg     1740
acggcaacta caagacccgc gccgaggtga agttcgaggg cgacaccctg gtgaaccgca     1800
tcgagctgaa gggcatcgac ttcaaggagg acggcaacat cctggggcac aagctggagt     1860
acaactacaa cagccacaac gtctatatca ccgccgacaa gcagaagaac ggcatcaagg     1920
ccaacttcaa gatccgccac aacatcgagg acggcggcgt gcagctcgcc gaccactacc     1980
agcagaacac ccccatcggc gacggccccg tgctgctgcc cgacaaccac tacctgagct     2040
accagtccaa gctgagcaaa gaccccaacg agaagcgcga tcacatggtc ctgctggagt     2100
tcgtgaccgc cgccgggatc actctcggca tggacgagct gtacaagtaa gtcgacggcg     2160
cgccgcggcc ttaaagagac cggttcactg tgacagtaaa agagaccggt tcactgtgag     2220
aatgaaagag accggttcac tgtgatcgga aaagagaccg gttcactgtg agcggccttg     2280
aaacccagca gacaatgtag ctcagtagaa acccagcaga caatgtagct gaatggaaac     2340
ccagcagaca atgtagcttc ggagaaaccc agcagacaat gtagctgtcg acgaattcga     2400
tatcataatc aacctctgga ttacaaaatt tgtgaaagat tgactggtat cttaactat     2460 gttgctcctt ttacgctatg tggatacgct gctttaatgc ctttgtatca tgctattgct     2520
tcccgtatgg ctttcatttt ctcctccttg tataaatcct ggttagttct tgccacggcg     2580
gaactcatcg ccgcctgcct tgcccgctgc tggacagggg ctcggctgtt gggcactgac     2640
aattccgtgg ctcgagagat cttcgactgt gccttctagt tgccagccat ctgttgtttg     2700
cccctccccc gtgccttcct tgaccctgga aggtgccact cccactgtcc tttcctaata     2760
aaatgaggaa attgcatcgc attgtctgag taggtgtcat tctattctgg ggggtggggt     2820
ggggcaggac agcaagggtg aggattggga agacaatagc aggcatgaga tctcacgtgc     2880
```
ggaccgagcg gccgc                                                           2895

<210> SEQ ID NO 96
<211> LENGTH: 2409
<212> TYPE: DNA
<213> ORGANISM: Artificial Sequence
<220> FEATURE:
<223> OTHER INFORMATION: CN3793

<400> SEQUENCE: 96
gcggccgcac gcgtcagttt ccagcgtggt tgttgatgag gctcagagaa aagactctaa      60
agttatgatg ggaaattacc atgccattca tcatcataca cattcacctc acactttctg     120
agtctcctat acaaagtcag ttctctgcca agggcatgga agagcgagga acaggatgtt     180
aggaagggct gacagcgctg ttttagcctg acaggcagat ttacaacagg agaatgaatg     240
taccacttgt ataagaaggc catgcggcac tgctaatgca caagttggca gtacatcaac     300
atctctatcg tcctcatatt catgaagcag agaacggaaa tggcacactg cttgtaccgg     360
cgaataacca aagtgaacgc cctacggctg ccattcactg tgtccttcca aaagcatttt     420
tctactgagc tcttcccaga gatttagggt ttgcttagac aggtcttatg acgccacgtg     480
ataggtcatt cttctgttct gaggagcttg agaagatcg agctcgggct gggcataaaa     540
gtcagggcag agccatctat tgcttacatt tgcttctggg atccagatct ttcgaagcta     600
gcgctaccgg tcgccaccat ggtctccaag ggcgaggagc tgttcaccgg ggtggtgccc     660
atcctggtcg agctggacgg cgatgtcaac ggccacaagt tcagcgtgtc cggcgagggc     720
gagggcgatg ccacctacgg caagctgacc ctgaagctga tctgcaccac cggcaagctg     780
cccgtgccct ggcccaccct cgtgaccacc ctgggctacg gcgtgcagtg cttcgcccgc     840
taccccgacc acatgaagca gcacgacttc ttcaagtccg ccatgcccga aggctacgtc     900
caggagcgca ccatcttctt caaagacgac ggcaactaca agacccgcgc cgaggtgaag     960
ttcgagggcg acaccctggt gaaccgcatc gagctgaagg gcatcgactt caaggaggac    1020
ggcaacatcc tggggcacaa gctggagtac aactacaaca gccacaacgt ctatatcacc    1080
gccgacaagc agaagaacgg catcaaggcc aacttcaaga tccgccacaa catcgaggac    1140
ggcggcgtgc agctcgccga ccactaccag cagaacaccc ccatcggcga cggccccgtg    1200
ctgctgcccg acaaccacta cctgagctac cagtccaagc tgagcaaaga ccccaacgag    1260
aagcgcgatc acatggtcct gctggagttc gtgaccgccg ccgggatcac tctcggcatg    1320
gacgagctgt acaagggctc tggtgctacc aacttctcac tgttgaaaca ggcaggggat    1380
gtagaggaga tccagggcc tggtgctagt ggagactaca agaccatga cggagattat    1440 aaagatcatg acatcgatta caaggatgac gatgacaagt ccggactcag atctggaggc    1500
tccggaggcc cagagccagc gaagtctgct cccgccccga aaaagggctc caagaaggcg    1560
gtgactaagg cgcagaagaa aggcggcaag aagcgcaagc gcagccgcaa ggagagctat    1620
tccatctatg tgtacaaggt tctgaagcag gtccaccctg acaccggcat ttcgtccaag    1680
gccatgggca tcatgaattc gtttgtgaac gacattttcg agcgcatcgc aggagaggct    1740 tccgcctgg cgcattacaa caagcgctcg accatcacct cccgggagat ccagacggcc    1800
gtgcgcctgc tgctgcctgg ggagttggcc aagcacgccg tgtccgaggg tactaaggcc    1860
atcaccaagt acaccagcgc taagtaatga ggcgcgccgc ggccgcgaat cgatatcat    1920 aatcaacctc tggattacaa aatttgtgaa agattgactg gtattcttaa ctatgttgct    1980

```
ccttttacgc tatgtggata cgctgcttta atgcctttgt atcatgctat tgcttcccgt      2040
atggctttca ttttctcctc cttgtataaa tcctggttag ttcttgccac ggcggaactc      2100
atcgccgcct gccttgcccg ctgctggaca ggggctcggc tgttgggcac tgacaattcc      2160
gtggctcgag agatcttcga ctgtgccttc tagttgccag ccatctgttg tttgcccctc      2220
ccccgtgcct tccttgaccc tggaaggtgc cactcccact gtcctttcct aataaaatga      2280
ggaaattgca tcgcattgtc tgagtaggtg tcattctatt ctggggggtg gggtggggca      2340
ggacagcaag ggggaggatt gggaagacaa tagcaggcat gagatctcac gtgcggaccg      2400
agcggccgc                                                              2409

<210> SEQ ID NO 97
<211> LENGTH: 2343
<212> TYPE: DNA
<213> ORGANISM: Artificial Sequence
<220> FEATURE:
<223> OTHER INFORMATION: CN3794

<400> SEQUENCE: 97
gcggccgcac gcgtgtagaa catacttatt aacacattcg tacataaaat aaaattctac        60
tctcccgacc ttttcctcac catcttgctt ttcaacgtat ggcgttagac ctaacagcga       120
gtccacttct tcccctttca ttctgtagca agaacacacg gctcactgta acagggactt       180
ggctgtgggt tgcagactgg cttcctgctg cctccacttg agccccacac agctgtggct       240
ttgtgtttac aaccctccag gctgccattc attcggtgct gtgggctcat gtactggaag       300
acagcttcca tcacaacctt cccgtcccag caggagaact cccttgcttc cttggggaac       360
atttgcttgc tcctgctgct tggctcttcc cacttttgcc tcactctgga gtttctctct       420 cccgtttga attctagtag taaacacatg gccgagctcg ggctgggcat aaaagtcagg        480
gcagagccat ctattgctta catttgcttc tgggatccag atctttcgaa gctagcgcta       540
ccggtcgcca ccatggtctc caagggcgag gagctgttca ccggggtggt gcccatcctg       600
gtcgagctgg acggcgatgt caacggccac aagttcagcg tgtccggcga gggcgagggc       660
gatgccacct acggcaagct gaccctgaag ctgatctgca ccaccggcaa gctgcccgtg       720
ccctggccca ccctcgtgac caccctgggc tacggcgtgc agtgcttcgc ccgctacccc       780
gaccacatga gcagcacgag cttcttcaag tccgccatgc ccgaaggcta cgtccaggag       840
cgcaccatct tcttcaaaga cgacggcaac tacaagaccc gcgccgaggt gaagttcgag       900
ggcgacaccc tggtgaaccg catcgagctg aagggcatcg acttcaagga ggacggcaac       960
atcctggggc acaagctgga gtacaactac aacagccaca cgtctatat caccgccgac      1020 aagcagaaga acggcatcaa ggccaacttc aagatccgcc acaacatcga ggacggcggc      1080
gtgcagctcg ccgaccacta ccagcagaac acccccatcg gcgacggccc cgtgctgctg      1140
cccgacaacc actacctgag ctaccagtcc aagctgagca agacccccaa cgagaagcgc      1200
gatcacatgg tcctgctgga gttcgtgacc gccgccggga tcactctcgg catggacgag      1260
ctgtacaagg gctctggtgc taccaacttc tcactgttga acaggcagg ggatgtagag       1320 gagaatccag ggcctggtgc tagtggagac tacaaagacc atgacggaga ttataaagat      1380
catgacatcg attacaagga tgacgatgac aagtccggac tcagatctgg aggctccgga      1440
ggcccagagc cagcgaagtc tgctcccgcc ccgaaaaagg ctccaagaa ggcggtgact       1500 aaggcgcaga gagaaggcgg caagaagcgc aagcgcagcc gcaaggagag ctattccatc      1560
tatgtgtaca aggttctgaa gcaggtccac cctgacaccg gcatttcgtc caaggccatg      1620
```

-continued

```
ggcatcatga attcgtttgt gaacgacatt ttcgagcgca tcgcaggaga ggcttcccgc      1680
ctggcgcatt acaacaagcg ctcgaccatc acctcccggg agatccagac ggccgtgcgc      1740
ctgctgctgc ctggggagtt ggccaagcac gccgtgtccg agggtactaa ggccatcacc      1800
aagtacacca cgcgctaagta atgaggcgcg ccgcggccgc gaattcgata tcataatcaa      1860
cctctggatt acaaaatttg tgaaagattg actggtattc ttaactatgt tgctcctttt      1920
acgctatgtg gatacgctgc tttaatgcct ttgtatcatg ctattgcttc ccgtatggct      1980
ttcattttct cctccttgta taaatcctgg ttagttcttg ccacggcgga actcatcgcc      2040
gcctgccttg cccgctgctg gacaggggct cggctgttgg gcactgacaa ttccgtggct      2100
cgagagatct tcgactgtgc cttctagttg ccagccatct gttgtttgcc cctcccccgt      2160
gccttccttg accctggaag gtgccactcc cactgtcctt tcctaataaa atgaggaaat      2220
tgcatcgcat tgtctgagta ggtgtcattc tattctgggg ggtggggtgg ggcaggacag      2280 caaggggggag gattgggaag acaatagcag gcatgagatc tcacgtgcgg accgagcggc      2340
cgc                                                                     2343
```

<210> SEQ ID NO 98
<211> LENGTH: 2411
<212> TYPE: DNA
<213> ORGANISM: Artificial Sequence
<220> FEATURE:
<223> OTHER INFORMATION: CN3795

<400> SEQUENCE: 98

```
gcggccgcac gcgtccagtg agatcttcca ccagcagaac tcatggacac aaactagaca       60
gctcacttct tgcctgtatt ccaggagtgg cttttctct actcctgtac tgatgccagt       120
cattcagagt gcactcaaga cacttgaccc acatcagtta agagaatgaa aatcaagctc       180
tgaaagccat tagcttctat tgcacaccca gaaaacaggc tcatcaaaca ccttcttatg       240
gtaatgcctt tgatcaaaag gagggttaat tcaacaaatg gtttgcaccg tgaccccatc       300
aaagcctgag caccagtgtc ctcatttcct ttcccctggt gtataatgag ttgttagtct       360
ggctcacctt gtcatcccca tcatactgcc ataatccaca tctctaaaga gtggattaca       420
acagtcccgt ctgtgacact caggactggc atcaaggttc ccaagctcta gtctattgtg       480
acattgatac aaatagggct cagagtctca ctgatcacac cgagctcggg ctgggcataa       540
aagtcagggc agagccatct attgcttaca tttgcttctg ggatccagat ctttcgaagc       600
tagcgctacc ggtcgccacc atggtctcca agggcgagga gctgttcacc ggggtggtgc       660
ccatcctggt cgagctggac ggcgatgtca acggccacaa gttcagcgtg tccggcgagg       720
gcgagggcga tgccacctac ggcaagctga ccctgaagct gatctgcacc accggcaagc       780
tgcccgtgcc ctggcccacc ctcgtgacca ccctgggcta cggcgtgcag tgcttcgccc       840
gctaccccga ccacatgaag cagcacgact tcttcaagtc cgccatgccc gaaggctacg       900
tccaggagcg caccatcttc ttcaaagacg acggcaacta caagaccocgc gccgaggtga       960 agttcgaggg cgacacctg gtgaaccgca tcgagctgaa gggcatcgac ttcaaggagg      1020
acggcaacat cctggggcac aagctggagt acaactacaa cagccacaac gtctatatca      1080
ccgccgacaa gcagaagaac ggcatcaagg ccaacttcaa gatccgccac aacatcgagg      1140
acggcggcgt gcagctcgcc gaccactacc agcagaacac ccccatcggc gacggccccg      1200
tgctgctgcc cgacaaccac tacctgagct accagtccaa gctgagcaaa gaccccaacg      1260
```

```
agaagcgcga tcacatggtc ctgctggagt tcgtgaccgc cgccgggatc actctcggca    1320
tggacgagct gtacaagggc tctggtgcta ccaacttctc actgttgaaa caggcagggg    1380
atgtagagga gaatccaggg cctggtgcta gtggagacta caaagaccat gacggagatt    1440
ataaagatca tgacatcgat tacaaggatg acgatgacaa gtccggactc agatctggag    1500
gctccggagg cccagagcca gcgaagtctg ctcccgcccc gaaaaagggc tccaagaagg    1560
cggtgactaa ggcgcagaag aaaggcggca agaagcgcaa gcgcagccgc aaggagagct    1620
attccatcta tgtgtacaag gttctgaagc aggtccaccc tgacaccggc atttcgtcca    1680
aggccatggg catcatgaat tcgtttgtga acgacatttt cgagcgcatc gcaggagagg    1740
cttcccgcct ggcgcattac aacaagcgct cgaccatcac ctcccgggag atccagacgg    1800
ccgtgcgcct gctgctgcct ggggagttgg ccaagcacgc cgtgtccgag ggtactaagg    1860
ccatcaccaa gtacaccagc gctaagtaat gaggcgcgcc gcggccgcga attcgatatc    1920
ataatcaacc tctggattac aaaatttgtg aaagattgac tggtattctt aactatgttg    1980 ctcctttac gctatgtgga tacgctgctt taatgccttt gtatcatgct attgcttccc    2040
gtatggcttt cattttctcc tccttgtata atcctggtt agttcttgcc acggcggaac    2100
tcatcgccgc ctgccttgcc cgctgctgga caggggctcg gctgttgggc actgacaatt    2160
ccgtggctcg agagatcttc gactgtgcct ctagttgcc agccatctgt tgtttgcccc    2220 tccccgtgc cttccttgac cctggaaggt gccactccca ctgtcctttc ctaataaaat    2280
gaggaaattg catcgcattg tctgagtagg tgtcattcta ttctggggg tggggtgggg    2340 caggacagca aggggagga ttgggaagac aatagcaggc atgagatctc acgtgcggac    2400
cgagcggccg c                                                         2411
```

<210> SEQ ID NO 99
<211> LENGTH: 2043
<212> TYPE: DNA
<213> ORGANISM: Artificial Sequence
<220> FEATURE:
<223> OTHER INFORMATION: CN3790

<400> SEQUENCE: 99

```
gcggccgcac gcgttatctt agagtgggaa gatttgagaa gtgccatggt taatatgact      60 gacttttat tcttatttct tttaatttca tggttctaaa tccgaattta atcatagtac     120
ccagaaaagc agaggtgtag aggttcacag tgggagttgt aatctagccc tattcatttt     180
gacctcaaaa cccaaattat ttataacaaa ttatttccta ttctttcctt cactattcag     240
gaacatctgt ccaccactta catgatcact tatcttgcta ttgtgtcatt ttgatgaaaa     300 agaattttt ctaaatatct aaatacaagg ccccatatta acagtgcttt ttaaatcccc     360
acagatgtgg gagatgaccc ctttccatcc ctgaagattg taattgggcc agtctttagt     420
acagtttgtt ccaataaaga gatacaattt tattcattaa tttgtgtatt catttagcaa     480
atcactttag agtcttatta tatcaggatt ttggggtcta ttttagtata tcttttgta     540 tttcttggaa cctctccaat tattctagac tctttcaaag gttggtgatc aatattagac     600
attattatga aaagaatctt acttgctaaa agggttagat ggagctcggg ctgggcataa     660
aagtcagggc agagccatct attgcttaca tttgcttctg ggatccagat ctttccaagc     720
tagccaccat ggtgcccaag aagaagagga agtctccaa cctgctgact gtgcaccaaa     780
acctgcctgc cctccctgtg gatgccacct ctgatgaagt caggaagaac ctgatggaca     840
tgttcaggga caggcaggcc ttctctgaac acacctggaa gatgctcctg tctgtgtgca     900
```

-continued

```
gatcctgggc tgcctggtgc aagctgaaca acaggaaatg gttccctgct gaacctgagg      960
atgtgaggga ctacctcctg tacctgcaag ccagaggcct ggctgtgaag accatccaac     1020
agcacctggg ccagctcaac atgctgcaca ggagatctgg cctgcctcgc ccttctgact     1080
ccaatgctgt gtccctggtg atgaggagaa tcagaaagga gaatgtggat gctggggaga     1140
gagccaagca ggccctggcc tttgaacgca ctgactttga ccaagtcaga tccctgatgg     1200
agaactctga cagatgccag gacatcagga acctggcctt cctgggcatt gcctacaaca     1260
ccctgctgcg cattgccgaa attgccagaa tcagagtgaa ggacatctcc cgcaccgatg     1320
gtgggagaat gctgatccac attggcagga ccaagaccct ggtgtccaca gctggtgtgg     1380
agaaggccct gtccctgggg gttaccaagc tggtggagag atggatctct gtgtctggtg     1440
tggctgatga ccccaacaac tacctgttct gccgggtcag aaagaatggt gtggctgccc     1500
cttctgccac ctcccaactg tccacccggg ccctggaagg gatctttgag gccacccacc     1560
gcctgatcta tggtgccaag gatgactctg ggcagagata cctggcctgg tctgccact      1620 ctgccagagt gggtgctgcc accgacatgg ccagggctgg tgtgtccatc cctgaaatca     1680
tgcaggctgg tggctggacc aatgtgaaca ttgtgatgaa ctacatcaga aacctggact     1740
ctgagactgg ggccatggtg aggctgctcg aagatgggga ctgaggcgcg ccgaattcaa     1800
gcttctcgag atcttcga ctgtgccttc tagttgccag ccatctgttg tttgcccctc      1860
ccccgtgcct tccttgaccc tggaaggtgc cactcccact gtcctttcct aataaaatga     1920
ggaaattgca tcgcattgtc tgagtaggtg tcattctatt ctggggggtg gggtggggca     1980
ggacagcaag ggggaggatt gggaagacaa tagcaggcat gcacgtgcgg accgagcggc     2040
cgc                                                                  2043
```

<210> SEQ ID NO 100
<211> LENGTH: 1747
<212> TYPE: DNA
<213> ORGANISM: Artificial Sequence
<220> FEATURE:
<223> OTHER INFORMATION: CN3751

<400> SEQUENCE: 100

```
gcggccgcac gcgttatctt agagtgggaa gatttgagaa gtgccatggt taatatgact       60 gacttttat tcttatttct tttaatttca tggttctaaa tccgaattta atcatagtac      120
ccagaaaagc agaggtgtag aggttcacag tgggagttgt aatctagccc tattcatttt     180
gacctcaaaa cccaaattat ttataacaaa ttatttccta ttctttcctt cactattcag     240
gaacatctgt ccaccactta catgatcact tatcttgcta ttgtgtcatt ttgatgaaaa     300
agaatttttt ctaaatatct aaatacaagg ccccatatta acagtgcttt ttaaatcccc     360
acagatgtgg gagatgaccc ctttccatcc ctgaagattg taattgggcc agtctttagt     420
acagtttgtt ccaataaaga gatacaattt tattcattaa tttgtgtatt catttagcaa     480
atcactttag agtcttatta tatcaggatt ttggggtcta ttttagtata tcttttttgta    540 tttcttggaa cctctccaat tattctagac tctttcaaag gttggtgatc aatattagac     600
attattatga aaagaatctt acttgctaaa agggttagat ggagctcggg ctgggcataa     660
aagtcagggc agagccatct attgcttaca tttgcttctg ggatccagat ctttcgaagc     720
tagcaattcg ccaccatgac gagtgatgag gttcgcaaga acctgatgga catgttcagg     780
gatcgccagg cgttttctga gcatacctgg aaaatgcttc tgtccgtttg ccggtcgtgg     840
```

-continued

```
gcggcatggt gcaagttgaa taaatttgcg gaatattgcc tcagttttgg caccgaaatt     900
ttaaccgttg agtacggccc attgcccatt ggcaaaattg tgagtgaaga aattaattgt     960
tctgtgtaca gtgttgatcc agaagggaga gtttacaccc aggcgatcgc ccaatggcat    1020
gaccggggag agcaggaagt attggaatat gaattggaag atggttcagt aatccgagct    1080
acctctgacc accgcttttt aaccaccgat tatcaactgt tggcgatcga agaaatttt     1140 gctaggcaac tggacttgtt gactttagaa aatattaagc aaactgaaga agctcttgac    1200
aaccatcgtc ttccctttcc attacttgac gctgggacaa ttaaataact cgaatcataa    1260
tcaacctctg gattacaaaa tttgtgaaag attgactggt attcttaact atgttgctcc    1320
ttttacgcta tgtggatacg ctgctttaat gcctttgtat catgctattg cttcccgtat    1380
ggctttcatt ttctcctcct tgtataaatc ctggttagtt cttgccacgg cggaactcat    1440
cgccgcctgc cttgcccgct gctggacagg ggctcggctg ttgggcactg acaattccgt    1500
ggctcgagag atcttcgact gtgccttcta gttgccagcc atctgttgtt tgcccctccc    1560
ccgtgccttc cttgaccctg gaaggtgcca ctcccactgt cctttcctaa taaaatgagg    1620 aaaattgcatc gcattgtctg agtaggtgtc attctattct gggggggtggg gtggggcagg   1680 acagcaaggg ggaggattgg gaagacaata gcaggcatga gatctcacgt gcggaccgag    1740
cggccgc                                                              1747
```

<210> SEQ ID NO 101
<211> LENGTH: 2071
<212> TYPE: DNA
<213> ORGANISM: Artificial Sequence
<220> FEATURE:
<223> OTHER INFORMATION: CN3752

<400> SEQUENCE: 101

```
gcggccgcac gcgttatgat gtgccaggct tgggagaaac accacaagca aagccaaaat      60
aggtggccta gaacttccag cttgaaatat gggagagaat gagggaggca ctgtagagca     120
gctgccgggt gccgcatgag aacaattctc cctgctcata attaatccta cctatttctg     180
atgacagctg gctcttcact ttgaacaagc tagttaacaa ctttcttctc acattgagca     240
aataattcat atttaattac ttaaccacca gttacaaaat gagaatcatc aaggaatcac     300
aattaatttg ctattgacaa actcatactt ttagcaggct gatttctact ttatacttag     360
attggtaatg aaaaatgaag cttatttttag ttgattggtt ggacttgtgt atgaatatta    420
tctattattt gaaaagccaa acttgaatgc aaaaaaatat tgaatatgaa aagaaaaaca     480
tttgcagtaa agcttgttct gagctcgggc tgggcataaa agtcagggca gagccatcta     540
ttgcttacat ttgcttctgg gatccagatc tttcgaagct agcaattcgc caccatggtt     600
aaagttatcg gtcgtcgttc cctcggagtg caaagaatat ttgatattgg tcttccccaa     660
gaccataatt ttctgctagc caatggggcg atcgccgcca attgtttaa caaatccaac     720 cggaaatggt ttcccgcaga acctgaagat gttcgcgatt atcttctata tcttcaggcg     780
cgcggtctgg cagtaaaaac tatccagcaa catttgggcc agctaaacat gcttcatcgt     840
cggtccgggc tgccacgacc aagtgacagc aatgctgttt cactggttat gcggcggatc     900
cgaaaagaaa acgttgatgc cggtgaacgt gcaaacagg ctctagcgtt cgaacgcact     960
gatttcgacc aggttcgttc actcatggaa aatagcgatc gctgccagga tatacgtaat    1020
ctggcatttc tggggattgc ttataacacc ctgttacgta tagccgaaat tgccaggatc    1080
agggttaaag atatctcacg tactgacggt gggagaatgt taatccatat tggcagaacg    1140
```

```
aaaacgctgg ttagcaccgc aggtgtagag aaggcactta gcctgggggt aactaaactg      1200
gtcgagcgat ggatttccgt ctctggtgta gctgatgatc cgaataacta cctgtttgc       1260 cgggtcagaa aaaatggtgt tgccgcgcca tctgccacca gccagctatc aactcgcgcc      1320
ctggaaggga tttttgaagc aactcatcga ttgatttacg gcgctaagga tgactctggt      1380
cagagatacc tggcctggtc tggacacagt gcccgtgtcg gagccgcgcg agatatggcc      1440
cgcgctggag tttcaatacc ggagatcatg caagctggtg gctggaccaa tgtaaatatt      1500
gtcatgaact atatccgtaa cctggatagt gaaacagggg caatggtgcg cctgctggaa      1560
gatggcgatt agctcgaatc ataatcaacc tctggattac aaaatttgtg aaagattgac      1620
tggtattctt aactatgttg ctcctttac gctatgtgga tacgctgctt taatgccttt       1680
gtatcatgct attgcttccc gtatggcttt cattttctcc tccttgtata aatcctggtt      1740
agttcttgcc acggcggaac tcatcgccgc ctgccttgcc cgctgctgga cagggggctcg     1800 gctgttgggc actgacaatt ccgtggctcg agagatcttc gactgtgcct tctagttgcc      1860
agccatctgt tgtttgcccc tcccccgtgc cttccttgac cctggaaggt gccactccca      1920
ctgtcctttc ctaataaaat gaggaaattg catcgcattg tctgagtagg tgtcattcta      1980
ttctgggggg tggggtgggg caggacagca aggggggagga ttgggaagac aatagcaggc     2040
atgagatctc acgtgcggac cgagcggccg c                                     2071
```

```
<210> SEQ ID NO 102
<211> LENGTH: 10
<212> TYPE: PRT
<213> ORGANISM: Artificial Sequence
<220> FEATURE:
<223> OTHER INFORMATION: Linker

<400> SEQUENCE: 102

Ser Gly Leu Arg Ser Gly Gly Ser Gly Gly
1               5                   10

<210> SEQ ID NO 103
<211> LENGTH: 5
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(5)
<223> OTHER INFORMATION: GlyGlyGlyGlySer can be repeated n times wherein
      n is an integer of 1, 2, 3, 4, 5, 6, 7, 8, 9 or 10

<400> SEQUENCE: 103

Gly Gly Gly Gly Ser
1               5

<210> SEQ ID NO 104
<211> LENGTH: 9
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: GlyGlyGlySer can be repeated n times wherein n
      is an integer of 1, 2, 3, 4, 5, 6, 7, 8, 9 or 10
<220> FEATURE:
<221> NAME/KEY: MISC_FEATURE
<222> LOCATION: (5)..(9)
```

```
<223> OTHER INFORMATION: GlyGlyGlyGlySer can be repeated n times wherein
      n is an integer of 1, 2, 3, 4, 5, 6, 7, 8, 9 or 10

<400> SEQUENCE: 104

Gly Gly Gly Ser Gly Gly Gly Gly Ser
1               5

<210> SEQ ID NO 105
<211> LENGTH: 7
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: GlyGlyGlySer can be repeated n times wherein n
      is an integer of 1, 2, 3, 4, 5, 6, 7, 8, 9 or 10
<220> FEATURE:
<221> NAME/KEY: MISC_FEATURE
<222> LOCATION: (5)..(7)
<223> OTHER INFORMATION: GlyGlySer can be repeated n times wherein n is
      an integer of 1, 2, 3, 4, 5, 6, 7, 8, 9 or 10

<400> SEQUENCE: 105

Gly Gly Gly Ser Gly Gly Ser
1               5

<210> SEQ ID NO 106
<211> LENGTH: 9
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: GlyGlyGlySer can be repeated n times wherein n
      is an integer of 1, 2, 3, 4, 5, 6, 7, 8, 9 or 10

<400> SEQUENCE: 106

Gly Gly Gly Ser Gly Gly Gly Gly Ser
1               5

<210> SEQ ID NO 107
<211> LENGTH: 20
<212> TYPE: PRT
<213> ORGANISM: Artificial Sequence
<220> FEATURE:
<223> OTHER INFORMATION: GlySer linker

<400> SEQUENCE: 107

Gly Gly Gly Gly Ser Gly Gly Gly Gly Ser Gly Gly Gly Gly Ser Gly
1               5                   10                  15

Gly Gly Gly Ser
            20

<210> SEQ ID NO 108
<211> LENGTH: 15
<212> TYPE: PRT
<213> ORGANISM: Artificial Sequence
<220> FEATURE:
<223> OTHER INFORMATION: GlySer linker

<400> SEQUENCE: 108

Gly Gly Gly Gly Ser Gly Gly Gly Gly Ser Gly Gly Gly Gly Ser
1               5                   10                  15
```

-continued

```
<210> SEQ ID NO 109
<211> LENGTH: 10
<212> TYPE: PRT
<213> ORGANISM: Artificial Sequence
<220> FEATURE:
<223> OTHER INFORMATION: GlySer linker

<400> SEQUENCE: 109

Gly Gly Gly Gly Ser Gly Gly Gly Gly Ser
1               5                   10

<210> SEQ ID NO 110
<211> LENGTH: 5
<212> TYPE: PRT
<213> ORGANISM: Artificial Sequence
<220> FEATURE:
<223> OTHER INFORMATION: GlySer linker

<400> SEQUENCE: 110

Gly Gly Gly Gly Ser
1               5

<210> SEQ ID NO 111
<211> LENGTH: 8
<212> TYPE: PRT
<213> ORGANISM: Artificial Sequence
<220> FEATURE:
<223> OTHER INFORMATION: GlySer linker

<400> SEQUENCE: 111

Gly Gly Gly Ser Gly Gly Gly Ser
1               5

<210> SEQ ID NO 112
<211> LENGTH: 4
<212> TYPE: PRT
<213> ORGANISM: Artificial Sequence
<220> FEATURE:
<223> OTHER INFORMATION: GlySer linker

<400> SEQUENCE: 112

Gly Gly Gly Ser
1

<210> SEQ ID NO 113
<211> LENGTH: 6
<212> TYPE: PRT
<213> ORGANISM: Artificial Sequence
<220> FEATURE:
<223> OTHER INFORMATION: GlySer linker

<400> SEQUENCE: 113

Gly Gly Ser Gly Gly Ser
1               5

<210> SEQ ID NO 114
<211> LENGTH: 11
<212> TYPE: PRT
<213> ORGANISM: Artificial Sequence
<220> FEATURE:
<223> OTHER INFORMATION: GlySer linker

<400> SEQUENCE: 114

Gly Gly Ser Gly Gly Gly Ser Gly Gly Ser Gly
1               5                   10

<210> SEQ ID NO 115
```

```
<211> LENGTH: 10
<212> TYPE: PRT
<213> ORGANISM: Artificial Sequence
<220> FEATURE:
<223> OTHER INFORMATION: GlySer linker

<400> SEQUENCE: 115

Gly Gly Ser Gly Gly Gly Ser Gly Ser Gly
1               5                   10

<210> SEQ ID NO 116
<211> LENGTH: 8
<212> TYPE: PRT
<213> ORGANISM: Artificial Sequence
<220> FEATURE:
<223> OTHER INFORMATION: GlySer linker

<400> SEQUENCE: 116

Gly Gly Ser Gly Gly Gly Ser Gly
1               5

<210> SEQ ID NO 117
<211> LENGTH: 4
<212> TYPE: PRT
<213> ORGANISM: Artificial Sequence
<220> FEATURE:
<223> OTHER INFORMATION: PHP.eB at residue 586

<400> SEQUENCE: 117

Ser Ala Gln Ala
1

<210> SEQ ID NO 118
<211> LENGTH: 11
<212> TYPE: PRT
<213> ORGANISM: Artificial Sequence
<220> FEATURE:
<223> OTHER INFORMATION: AAV9 at residue 586

<400> SEQUENCE: 118

Ser Asp Gly Thr Leu Ala Val Pro Phe Lys Ala
1               5                   10

<210> SEQ ID NO 119
<211> LENGTH: 7
<212> TYPE: PRT
<213> ORGANISM: Artificial Sequence
<220> FEATURE:
<223> OTHER INFORMATION: AAV-BR1

<400> SEQUENCE: 119

Asn Arg Gly Thr Glu Trp Asp
1               5

<210> SEQ ID NO 120
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 120

Gln Ala Val Arg Thr Ser Leu
1               5

<210> SEQ ID NO 121
<211> LENGTH: 7
```

-continued

```
<212> TYPE: PRT
<213> ORGANISM: Artificial Sequence
<220> FEATURE:
<223> OTHER INFORMATION: AAV-PHP.B

<400> SEQUENCE: 121

Thr Leu Ala Val Pro Phe Lys
1               5

<210> SEQ ID NO 122
<211> LENGTH: 7
<212> TYPE: PRT
<213> ORGANISM: Artificial Sequence
<220> FEATURE:
<223> OTHER INFORMATION: AAV-PPS

<400> SEQUENCE: 122

Asp Ser Pro Ala His Pro Ser
1               5

<210> SEQ ID NO 123
<211> LENGTH: 6
<212> TYPE: PRT
<213> ORGANISM: Artificial Sequence
<220> FEATURE:
<223> OTHER INFORMATION: His tag

<400> SEQUENCE: 123

His His His His His His
1               5

<210> SEQ ID NO 124
<211> LENGTH: 8
<212> TYPE: PRT
<213> ORGANISM: Artificial Sequence
<220> FEATURE:
<223> OTHER INFORMATION: Flag tag

<400> SEQUENCE: 124

Asp Tyr Lys Asp Asp Asp Asp Lys
1               5

<210> SEQ ID NO 125
<211> LENGTH: 8
<212> TYPE: PRT
<213> ORGANISM: Artificial Sequence
<220> FEATURE:
<223> OTHER INFORMATION: Xpress tag

<400> SEQUENCE: 125

Asp Leu Tyr Asp Asp Asp Asp Lys
1               5

<210> SEQ ID NO 126
<211> LENGTH: 15
<212> TYPE: PRT
<213> ORGANISM: Artificial Sequence
<220> FEATURE:
<223> OTHER INFORMATION: Avi tag

<400> SEQUENCE: 126

Gly Leu Asn Asp Ile Phe Glu Ala Gln Lys Ile Glu Trp His Glu
1               5                   10                  15

<210> SEQ ID NO 127
<211> LENGTH: 26
<212> TYPE: PRT
```

<213> ORGANISM: Artificial Sequence
<220> FEATURE:
<223> OTHER INFORMATION: Calmodulin tag

<400> SEQUENCE: 127

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 128
<211> LENGTH: 9
<212> TYPE: PRT
<213> ORGANISM: Artificial Sequence
<220> FEATURE:
<223> OTHER INFORMATION: HA tag

<400> SEQUENCE: 128

Tyr Pro Tyr Asp Val Pro Asp Tyr Ala
1               5

<210> SEQ ID NO 129
<211> LENGTH: 10
<212> TYPE: PRT
<213> ORGANISM: Artificial Sequence
<220> FEATURE:
<223> OTHER INFORMATION: Myc tag

<400> SEQUENCE: 129

Glu Gln Lys Leu Ile Ser Glu Glu Asp Leu
1               5                   10

<210> SEQ ID NO 130
<211> LENGTH: 8
<212> TYPE: PRT
<213> ORGANISM: Artificial Sequence
<220> FEATURE:
<223> OTHER INFORMATION: Strep tag

<400> SEQUENCE: 130

Trp Arg His Pro Gln Phe Gly Gly
1               5

<210> SEQ ID NO 131
<211> LENGTH: 8
<212> TYPE: PRT
<213> ORGANISM: Artificial Sequence
<220> FEATURE:
<223> OTHER INFORMATION: Strep tag II

<400> SEQUENCE: 131

Trp Ser His Pro Gln Phe Glu Lys
1               5

<210> SEQ ID NO 132
<211> LENGTH: 13
<212> TYPE: PRT
<213> ORGANISM: Artificial Sequence
<220> FEATURE:
<223> OTHER INFORMATION: Softag 1

<400> SEQUENCE: 132

Ser Leu Ala Glu Leu Leu Asn Ala Gly Leu Gly Gly Ser
1               5                   10

<210> SEQ ID NO 133

```
<211> LENGTH: 8
<212> TYPE: PRT
<213> ORGANISM: Artificial Sequence
<220> FEATURE:
<223> OTHER INFORMATION: Softag 3

<400> SEQUENCE: 133

Thr Gln Asp Pro Ser Arg Val Gly
1               5

<210> SEQ ID NO 134
<211> LENGTH: 14
<212> TYPE: PRT
<213> ORGANISM: Artificial Sequence
<220> FEATURE:
<223> OTHER INFORMATION: V5 tag

<400> SEQUENCE: 134

Gly Lys Pro Ile Pro Asn Pro Leu Leu Gly Leu Asp Ser Thr
1               5                   10

<210> SEQ ID NO 135
<211> LENGTH: 381
<212> TYPE: DNA
<213> ORGANISM: Artificial Sequence
<220> FEATURE:
<223> OTHER INFORMATION: H2B

<400> SEQUENCE: 135
ccagagccag cgaagtctgc tcccgccccg aaaaagggct ccaagaaggc ggtgactaag      60
gcgcagaaga aaggcggcaa gaagcgcaag cgcagccgca aggagagcta ttccatctat     120
gtgtataagg ttctgaagca ggtccaccct gacaccggca tttcgtccaa ggccatgggc     180
atcatgaact cgtttgtgaa cgacattttc gagcgcatcg caggtgaggc ttcccgcctg     240
gcgcattaca acaagcgctc gaccatcacc tccagggaga tccagacggc cgtgcgcctg     300
ctgctgcctg gggagttggc caagcacgcc gtgtccgagg gtactaaggc catcaccaag     360
tacaccagcg ctaagtaatg a                                               381

<210> SEQ ID NO 136
<211> LENGTH: 21
<212> TYPE: DNA
<213> ORGANISM: Artificial Sequence
<220> FEATURE:
<223> OTHER INFORMATION: miR128 Recognition Sequence

<400> SEQUENCE: 136
aaagagaccg gttcactgtg a                                                21

<210> SEQ ID NO 137
<211> LENGTH: 23
<212> TYPE: DNA
<213> ORGANISM: Artificial Sequence
<220> FEATURE:
<223> OTHER INFORMATION: miR221 Recognition Sequence

<400> SEQUENCE: 137
gaaacccagc agacaatgta gct                                              23
```